(12) United States Patent
Li et al.

(10) Patent No.: US 10,889,611 B2
(45) Date of Patent: Jan. 12, 2021

(54) SIALYLTRANSFERASE INHIBITORS AND USES THEREOF

(71) Applicant: Academia Sinica, Taipei (TW)

(72) Inventors: Wen-Shan Li, Taipei (TW); Wen-Chun Hung, Kaohsiung (TW); Chia-Ning Shen, Keelung (TW)

(73) Assignee: Academia Sinica, Taipei (TW)

( * ) Notice: Subject to any disclaimer, the term of this patent is extended or adjusted under 35 U.S.C. 154(b) by 12 days.

(21) Appl. No.: 15/754,806

(22) PCT Filed: Aug. 26, 2016

(86) PCT No.: PCT/US2016/049084
§ 371 (c)(1),
(2) Date: Feb. 23, 2018

(87) PCT Pub. No.: WO2017/035501
PCT Pub. Date: Mar. 2, 2017

(65) Prior Publication Data
US 2018/0244713 A1    Aug. 30, 2018

Related U.S. Application Data

(60) Provisional application No. 62/210,975, filed on Aug. 27, 2015.

(51) Int. Cl.
| | |
|---|---|
| *A61P 35/00* | (2006.01) |
| *C07J 43/00* | (2006.01) |
| *C07J 9/00* | (2006.01) |
| *C07J 41/00* | (2006.01) |
| *C07J 73/00* | (2006.01) |
| *C07J 63/00* | (2006.01) |

(52) U.S. Cl.
CPC ............. *C07J 43/003* (2013.01); *A61P 35/00* (2018.01); *C07J 9/005* (2013.01); *C07J 41/0005* (2013.01); *C07J 41/0055* (2013.01); *C07J 63/00* (2013.01); *C07J 63/004* (2013.01); *C07J 73/003* (2013.01); *C07J 73/005* (2013.01)

(58) Field of Classification Search
CPC ...... C07J 43/003; C07J 9/005; C07J 41/0005; C07J 41/0055; C07J 63/00; C07J 63/004; C07J 73/003; C07J 73/005; A61P 35/00
See application file for complete search history.

(56) References Cited

U.S. PATENT DOCUMENTS

| | | | |
|---|---|---|---|
| 5,439,899 A | 8/1995 | Cushman et al. | |
| 2009/0181854 A1 | 7/2009 | Thorson et al. | |
| 2011/0311651 A1 | 12/2011 | Djaballah et al. | |
| 2013/0183250 A1 | 7/2013 | Friedman et al. | |
| 2018/0044373 A1* | 2/2018 | Finch | C07J 9/005 |

OTHER PUBLICATIONS

Huefner, 1(11) J. Am. Chem. Soc. 493 (1879) (CAS Abstract) (Year: 1879).*
Fischer, Hans, 73 Z. Physiol. Chem. 204-39 (1912) (Year: 1912).*
Sievanen et al., 46(4) Magnetic Resonance in Chem., 392-397 (2008) (CAS Abstract) (Year: 2008).*

* cited by examiner

*Primary Examiner* — Timothy R Rozof
(74) *Attorney, Agent, or Firm* — Muncy, Geissler, Olds & Lowe, P.C.

(57) ABSTRACT

Disclosed herein are novel sialyltransferase inhibitors, and compositions and methods for treating diseases and/or conditions associated with the activation of sialyltransferase, such as a cancer, an immune disease or an inflammatory disease.

24 Claims, 13 Drawing Sheets
Specification includes a Sequence Listing.

(A)

(B)

(C)

(A) (B) (C)

Liver Function — Inflammation marker (D) (E) (F)

Vascular Function — Kidney Function (G)

Stress/cancer marker (A)

(B)

(C)

(A)

(B)

(C)

(A)  (B)  (C)

(D)  (E)  (F)

(G)  (H)

(A)

(B)

(C)

Liver Function | Inflammation marker (D)

(E)

(F)

Vascular Function | Kidney Function (G)

Stress/cancer marker

SIALYLTRANSFERASE INHIBITORS AND USES THEREOF

CROSS-REFERENCE TO RELATED APPLICATIONS

This application claims priority to U.S. Provisional Patent Application No. 62/210,975, filed Aug. 27, 2015, which is incorporated herein by reference in its entirety.

BACKGROUNDS OF THE INVENTION

1. Field of the Invention

The present disclosure relates in general, to the field of sialyltransferase inhibitors. Compounds that inhibit sialyltransferase are provided. Also provided are methods for inhibiting sialyltransferase, and methods for treating diseases and/or conditions that involve sialylation.

2. Description of Related Art

Sialic acid containing epitopes are known to involve in various biological processes, such as adhesion and inflammation. There is also a correlation between sialyl content of glycoconjugates and the malignancy of tumor cells. Recently, sialylation and lymphocyte activation and immune function have also been reported.

Sialylglycoside are synthesized by sialyltransferase, which catalyzes the transfer of a sialic acid from a donor substrate, i.e., cytidine monophosphate (CMP)-sialic acid, to the subterminal sugars of glycoproteins or glycolipids via α2,6-bond to N-acetylgalactosamine (GalNAc) or N-acetylglucosamine (GlcNAc), an α2,3-bond to galactose (Gal) or through an α2,8-bond to another sialic acid, forming polysialic acid.

Due to the widely impact of sialyltransferase on various biological process (e.g., inflammation and cancer progression), it is highly desirable to develop efficient inhibitors of sialyltransferase. In the past, most efforts in developing sialyltransferase inhibitors focused on CMP-based donor and acceptor substrate analogues, however, few of them are cell permeable, and this lack of membrane permeability hampered their biological and clinical applications.

In view of the foregoing, there exists in this art a need of novel sialyltransferase inhibitors, which not only can suppress the activity of sialyltransferase, but also are membrane permeable; thus may be used as lead compounds for the development of medicaments for treating diseases and/or conditions that involve sialylation.

SUMMARY

The present disclosure is based, at least in part, unexpected discovery that certain lithocholic acid derivatives are effective in suppressing the activity of sialyltransferase, accordingly, these lithocholic acid derivatives are potential candidates that may act as lead compounds for the development of medicaments suitable for treating a disease and/or a condition associated with the activation of sialyltransferase, such as a cancer, an immune disease or an inflammatory disease.

Accordingly, it is the first aspect of the present disclosure to provide a compound having the structure of formula (1)

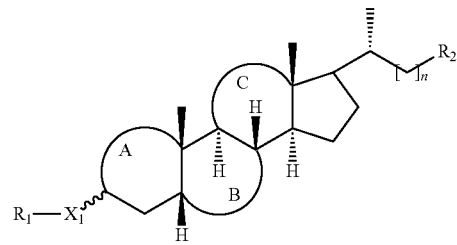

and pharmaceutically acceptable salts and solvates thereof, wherein, n is an integral from 1 to 4;

A, B, and C are independently a 6- or 7-membered saturated or unsaturated carbon cyclic ring, a homolactone or a homolactam, in which the saturated or unsaturated carbon cyclic ring, the homolactone or the homolactam is optionally substituted with one or more fluoro or hydroxy;

$X_1$ is O or N; or $X_1$ is fluoro, provided that $R_1$ is null;

$R_1$ is selected from the group consisting of null, H,

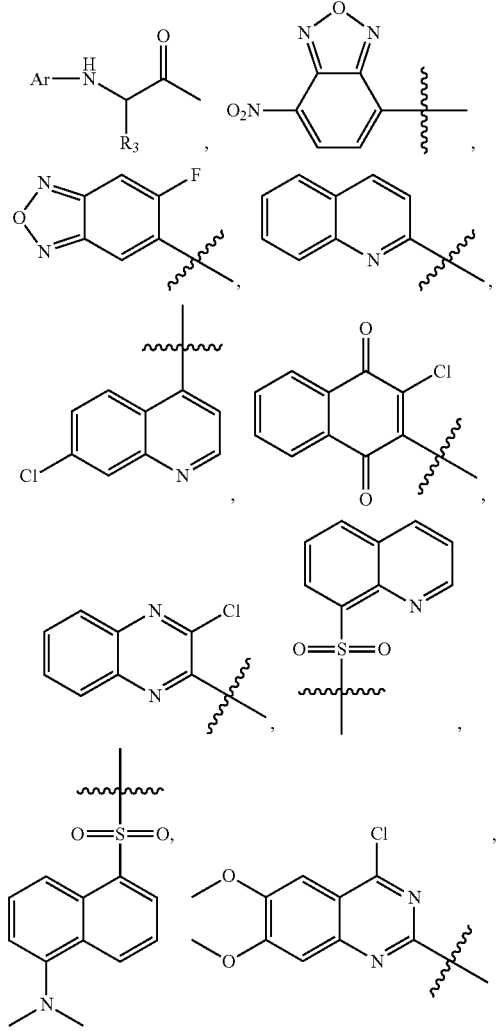

-continued

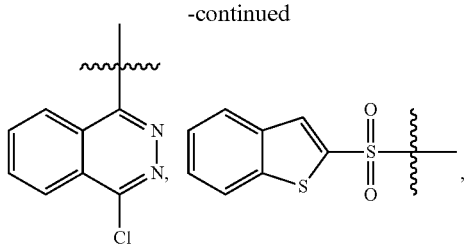

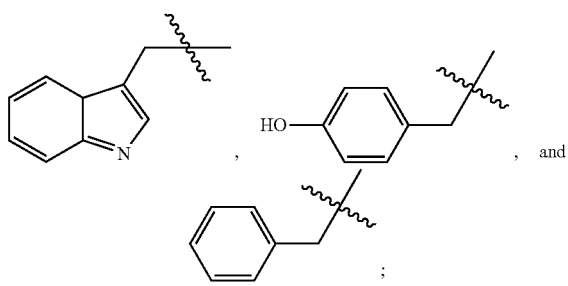

or

R₃ and the neighboring carbon and nitrogen atoms compounds are taken together to form a 5-membered heterocyclic ring;

$R_a$ and $R_b$ are independently H or $C_{1-6}$ alkyl;

$R_2$ is COOH, CH(COOH)COOH, or $COX_2(CH_2CH_2O)_mCH_2CH_2N_3$, $X_2$ is O or N, and m is an integral from 1 to 4; and
Ar is selected from the group consisting of, H,

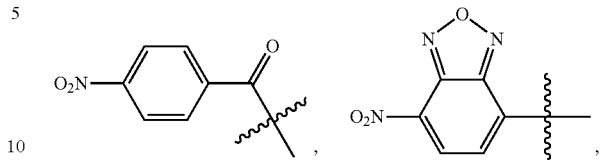

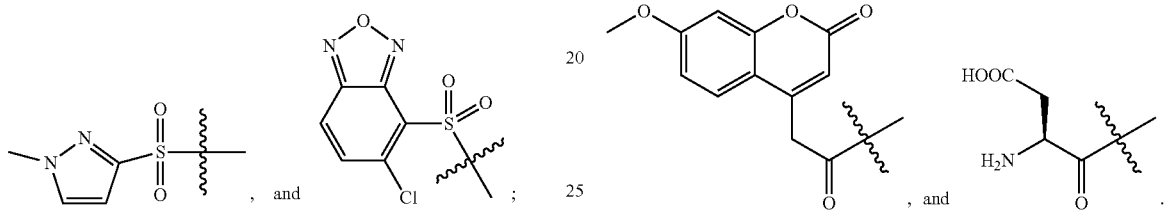

In some embodiments, particular compounds are of formula (1-1)

(1-1)

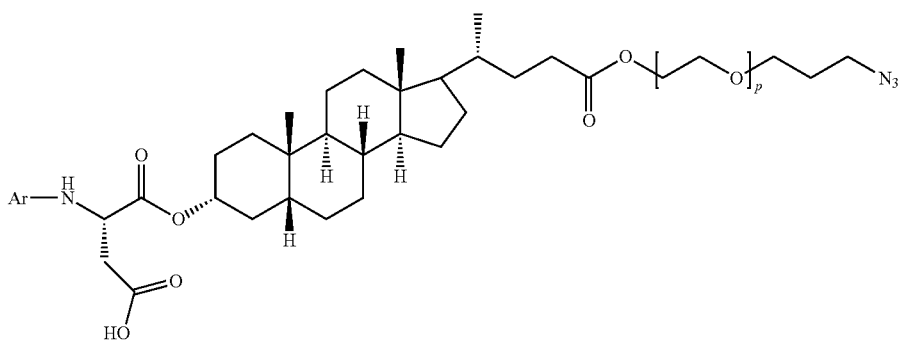

wherein,
p is an integral from 1 to 4; and
Ar is selected from the group consisting of,

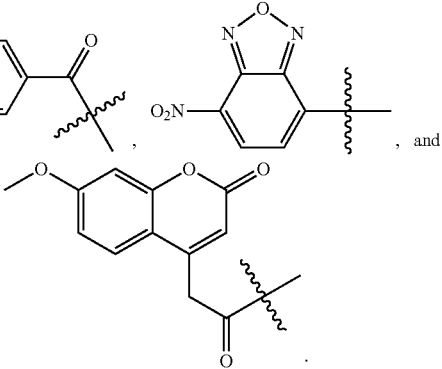

In other embodiments, particular compounds are of formula (1-2),

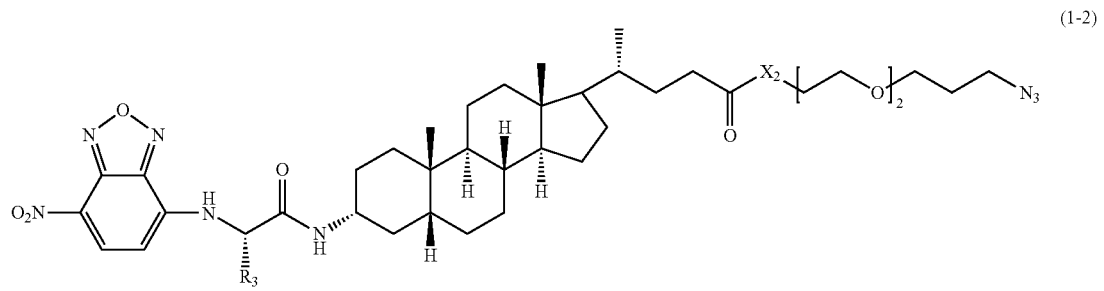
(1-2)

wherein, $X_2$ is O or N;

$R_3$ is selected from the group consisting of $CH_3$, $R_aCOOH$, $R_aNH_2$, $R_aNHC(NH_2)=NH$, $R_aSR_b$,

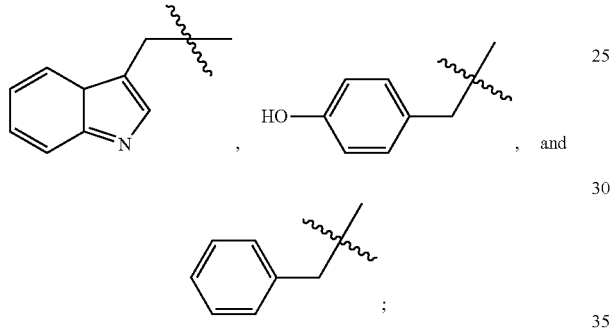
, and or $R_3$ and the neighboring carbon and nitrogen atoms are taken together to form a 5-membered heterocyclic ring; and $R_a$ and $R_b$ are independently H or $C_{1-6}$ alkyl.

In some embodiments, particular compounds are of formula (1-3),

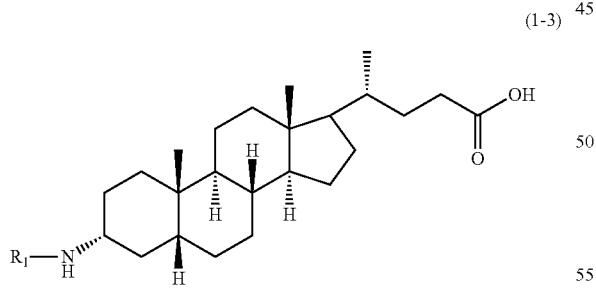
(1-3)

wherein, $R_1$ is selected from the group consisting of,

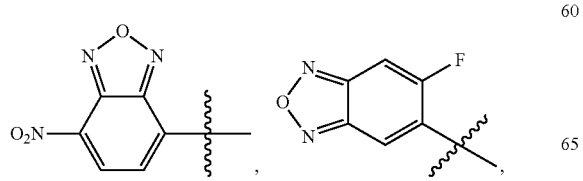

-continued

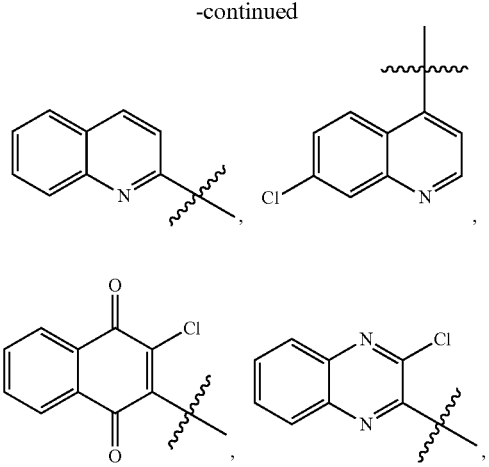

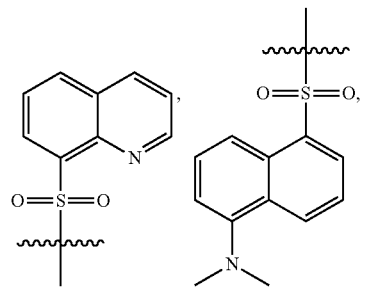

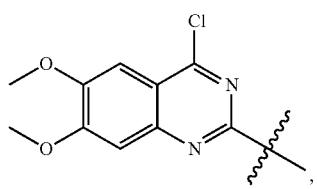

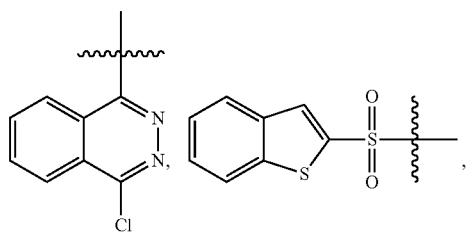

-continued

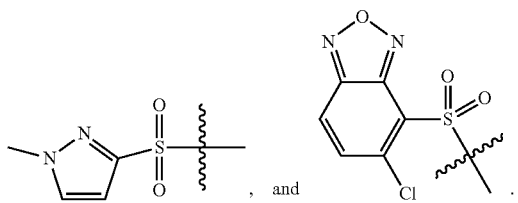, and

In further embodiments, particular compounds are of formula (1-4), (1-4)

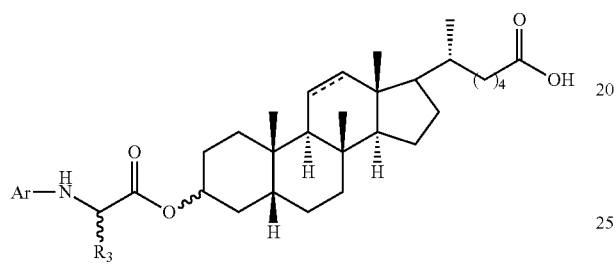

wherein, ===== is a single or a double bond;

R$_3$ is selected from the group consisting of, CH$_2$OH, R$_a$COOH, R$_a$NH$_2$, R$_a$NHC(NH$_2$)=NH, R$_a$SR$_b$,

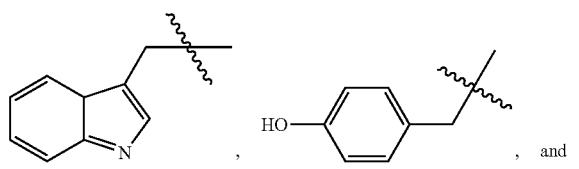, and

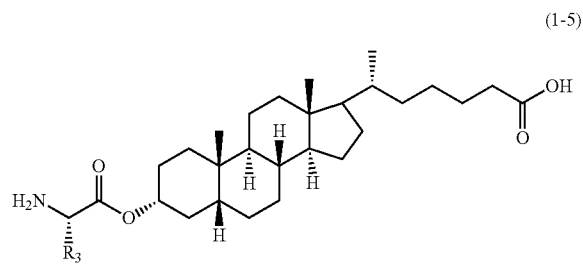

In some embodiments, particular compounds are of formula (1-5), (1-5)

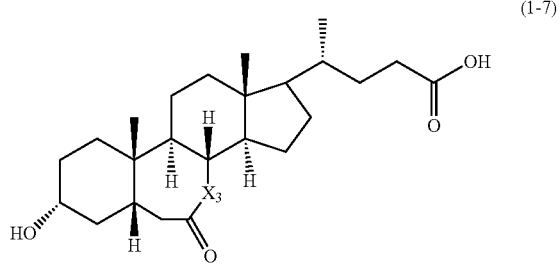

wherein, R$_3$ is CH$_2$COOH, or CH$_2$CH$_2$COOH.

In other embodiments, particular compounds are of formula (1-6), (1-6)

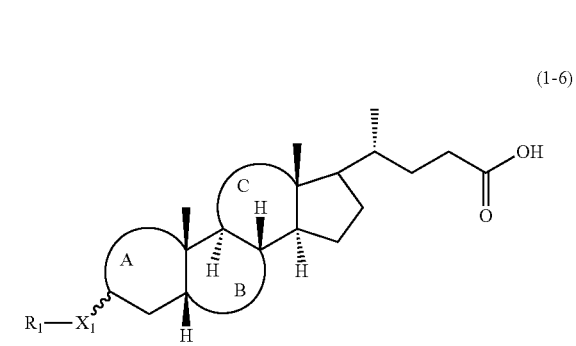

wherein, A, B, and C are independently a 6-membered saturated carbon cyclic ring substituted with at least one fluoro;

X$_1$ is H, O or fluoro, and in the case when X$_1$ is fluoro, then R$_1$ is null, H, or

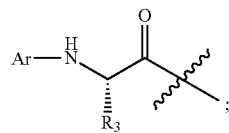;

and

R$_3$ is CH$_2$COOH or

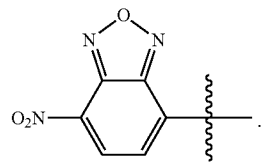.

In still further embodiments, particular compounds are of formula (1-7), (1-7)

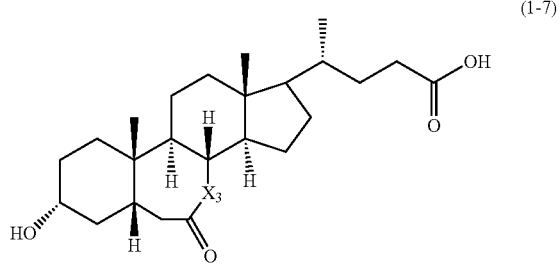

wherein, X$_3$ is O or N.

In some embodiments, particular compounds are of formula (1-8)

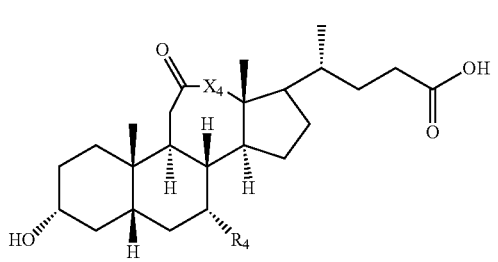

(1-8)

Wherein, $X_4$ is O or N; and $R_4$ is H or OH.

In still further embodiments, particular compound is of formula (1-9),

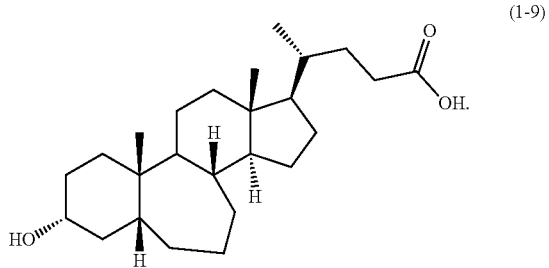

(1-9)

Accordingly, it is the second aspect of the present disclosure to provide a composition that suppresses the activity of sialyltransferase. The composition is therefore useful for treating a disease and/or a condition associated with the activation of sialyltransferase. The composition comprises an effective amount of the compound of formula (I), a salt or a solvate thereof; and a pharmaceutically acceptable excipient.

The compound of formula (I) is present in the composition about 0.1% to 99% by weight, based on the total amount of the composition. In certain embodiments, the compound of formula (1) is present in the composition at least about 1% by weight, based on the total amount of the composition. In other embodiments, the compound of formula (I) is present in the composition at least about 5% by weight, based on the total amount of the composition. In further embodiments, the compound of formula (1) is present in the composition at least about 10% by weight, based on the total amount of the composition. In still further embodiments, the compound of formula (I) is present in the composition at least about 25% by weight, based on the total amount of the composition.

According to some preferred embodiments, the composition further comprises a chemotherapeutic agent, an anti-inflammatory agent, or an immunosuppressive agent.

Accordingly, it is the third aspect of the present disclosure to provide a method of treating a disease and/or a condition associated with the activation of sialyltransferase. The method includes the step of, administering to the subject the composition of the present disclosure, so as to alleviate or ameliorate the symptoms related to the disease and/or condition.

According to some embodiments, the disease and/or condition that is associated with the activation of sialyltransferase may be a cancer, an immune disease or an inflammatory disease.

The details of one or more embodiments of the invention are set forth in the accompanying description below. Other features and advantages of the invention will be apparent from the detail descriptions, and from claims.

BRIEF DESCRIPTION OF THE DRAWINGS

The present description will be better understood from the following detailed description read in light of the accompanying drawings, where.

DESCRIPTION

Figure 1:
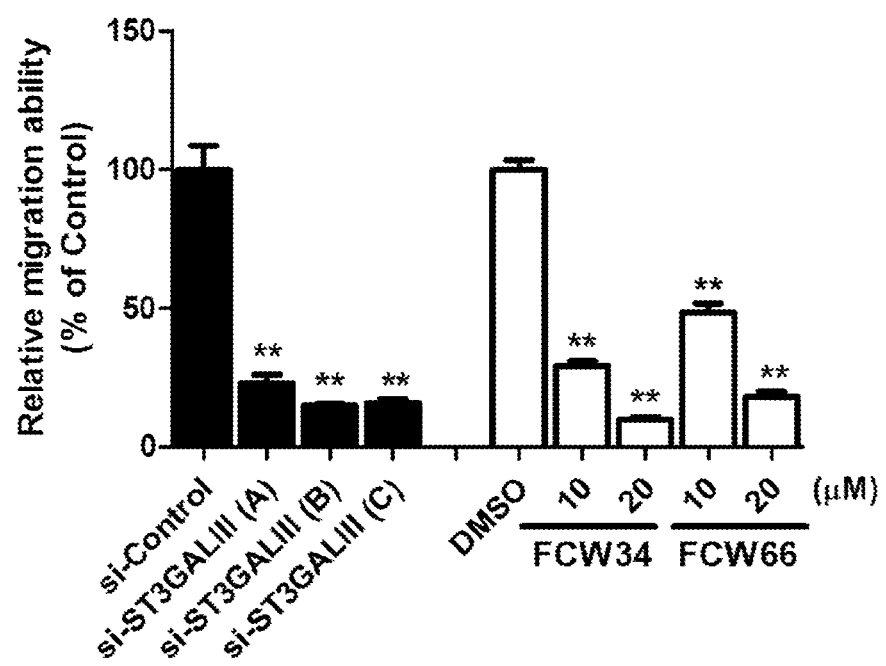
FIG. 1 are bar graphs illustrating the effects of FCW34 and FCW66 on migrating MDA-MB-231 cells in accordance with one embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

Unless otherwise indicated, the term "alkyl" means a straight chain, branched and/or cyclic ("cycloalkyl") hydrocarbon having from 1 to 20 (e.g., 1 to 10, 1 to 9, 1 to 8, 1 to 7, 1 to 6, 1 to 5, 1 to 4, 1 to 3, 1 to 2, or 1) carbon atoms. Examples of alkyl groups include methyl, ethyl, propyl, isopropyl, n-butyl, t-butyl, isobutyl, 2-isopropyl-3-methyl butyl, pentyl, pentan-2-yl, hexyl, isohexyl, heptyl, heptan-2-yl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, and cyclohexyl. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl; preferably, unsubstituted $C_{1-6}$ alkyl. In one preferred example, the alkyl group is n-hexyl.

Unless otherwise indicated, the term "substituted," when used to describe a chemical structure or moiety, refers to a derivative of that structure or moiety wherein one or more of its hydrogen atoms is substituted with one or more of: alkoxy, alkyl, aryl, halo, haloalkyl, or hydroxyl. Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

The term "subject" or "patient" refers to an animal including the human species that is treatable with the method of the present invention. The term "subject" or "patient" intended to refer to both the male and female gender unless one gender is specifically indicated. Accordingly, the term "subject" or "patient" comprises any mammal which may benefit from the treatment method of the present disclosure.

The term "administered", "administering" or "administration" are used interchangeably herein to refer a mode of delivery, including, without limitation, intraveneously, intramuscularly, intraperitoneally, intraarterially, subcutaneously, or transdermally administering an agent (e.g., a compound or a composition) of the present invention.

The term "an effective amount" as used herein refers to an amount effective, at dosages, and for periods of time necessary, to achieve the desired result with respect to the treatment of a disease. For example, in the treatment of an infection, an agent (i.e., a compound or a composition) which decrease, prevents, delays or suppresses or arrests any symptoms of the infection would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

The term "treatment" as used herein are intended to mean obtaining a desired pharmacological and/or physiologic effect, e.g., inhibiting the growth of gram-positive bacteria. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition from occurring in an individual who may be pre-disposed to the disease but has not yet been diagnosed as having it; (2) inhibiting a disease (e.g., by arresting its development); or (3) relieving a disease (e.g., reducing symptoms associated with the disease). According to specific embodiments of the present disclosure, an effective amount of a the present compound is administered to a subject suffering from a disease and/or disorder associated with the activation of sialyltransferase, as compared with that of the un-treated subject, and thereby alleviate or ameliorate one or more symptoms associated with the disease, the severity of one or more symptoms associated with the disease and/or the progression of the disease. In preferred embodiments, an effective amount of the compound of the present disclosure is administered to a subject suffering from a disease assocated with the activation of sialyltransferase, so as to alleviate or ameliorate one or more symptoms associated with the disease, and thereby achieving the purpose of treating the disease.

The singular forms "a", "and", and "the" are used herein to include plural referents unless the context clearly dictates otherwise.

2. The Present Sialyltransferase Inhibitors

The present disclosure is based, at least in part, unexpected discovery that some lithocholic acid derivatives, particularly the compound of formula (I), is capable of preventing the sialyltransferas from being activated, and thus the lithocholic acid derivatives of the present disclosure may be used as a lead compound for the development of a medicament for treating diseases and/or conditions associated with the activation of sialyltransferas, such as cancer, immune disease or inflammatory diseases.

The lithocholic acid derivatives of the present disclosure are those of formula (I),

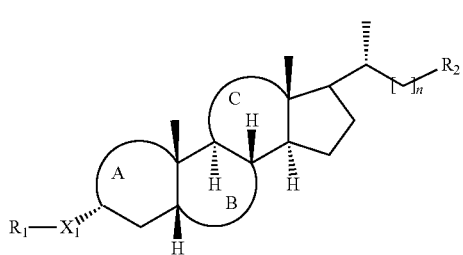

(1)

and pharmaceutically acceptable salts and solvates thereof, wherein, n is an integral from 1 to 4;

A, B, and C are independently a 6- or 7-membered saturated or unsaturated carbon cyclic ring, a homolactone or a homolactam, in which the carbon cyclic ring, the homolactone or the homolactam is optionally substituted with one or more fluoro or hydroxy;

$X_1$ is O or NH; or $X_1$ is fluoro, provided that $R_1$ is null;

$R_1$ is selected from the group consisting of null, H,

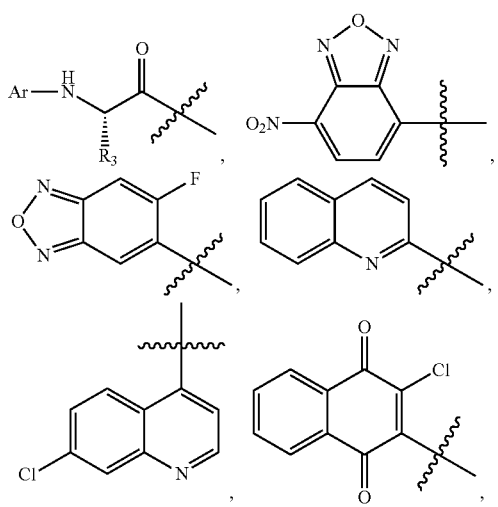

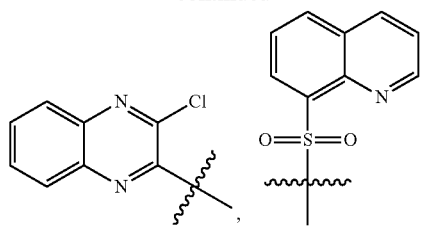

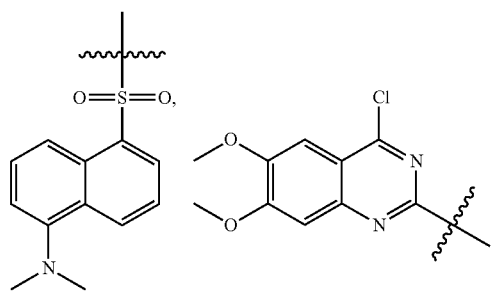

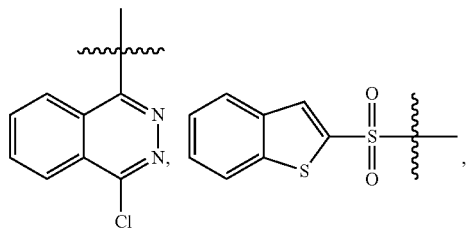

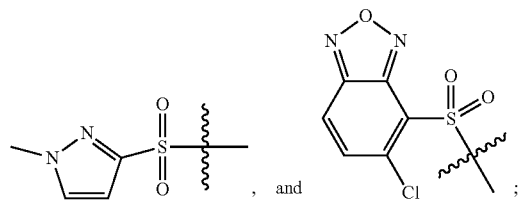

$R_3$ is selected from the group consisting of $CH_3$, $CH_2OH$, $R_aCOOH$, $R_aNH_2$, $R_aNHC(NH_2)=NH$, $R_aSR_b$,

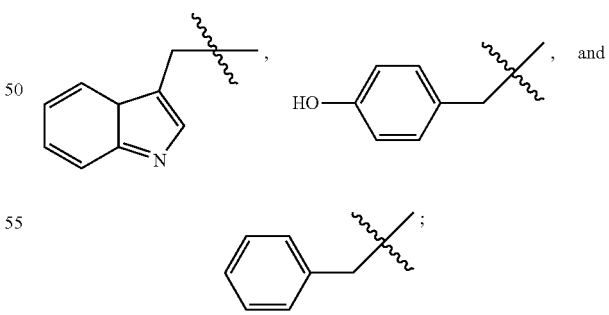

or $R_3$ and the neighboring carbon and nitrogen atoms are taken together to form a 5-membered heterocyclic ring;

$R_a$ and $R_b$ are independently H or $C_{1-6}$ alkyl;

$R_2$ is COOH, CH(COOH)COOH, or $COX_2(CH_2CH_2O)_mCH_2CH_2N_3$, $X_2$ is O or NH,
m is an integral from 1 to 4; and
Ar is selected from the group consisting of, H,
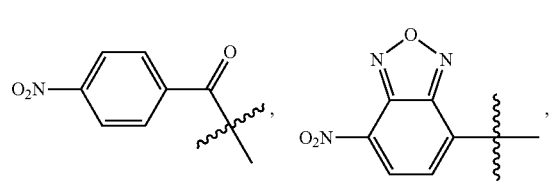
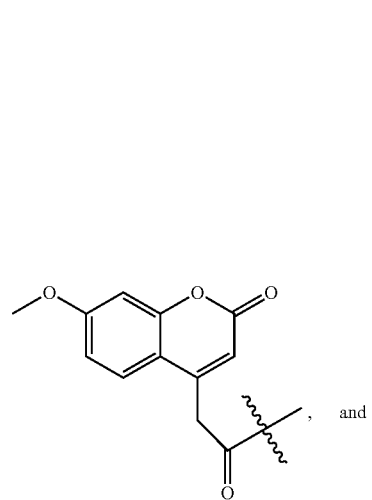
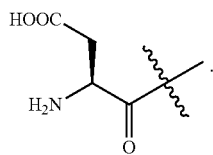
In some embodiments, particular compounds are of formula (1-1),
wherein p is an integral from 1 to 4; and Ar is selected from the group consisting of,
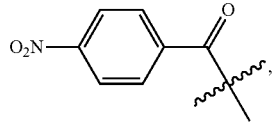
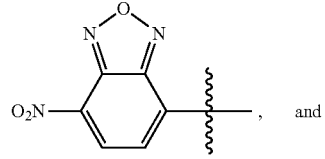
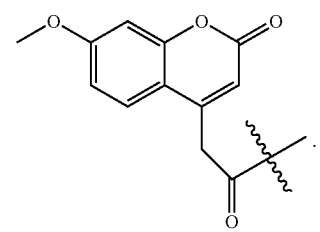
In one embodiment, in formula (1-1), p is 2, and Ar is
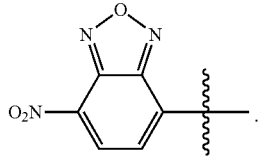
In another embodiment, in formula (1-1), p is 3, and Ar is
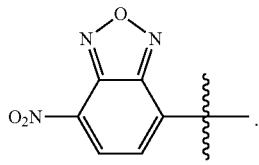
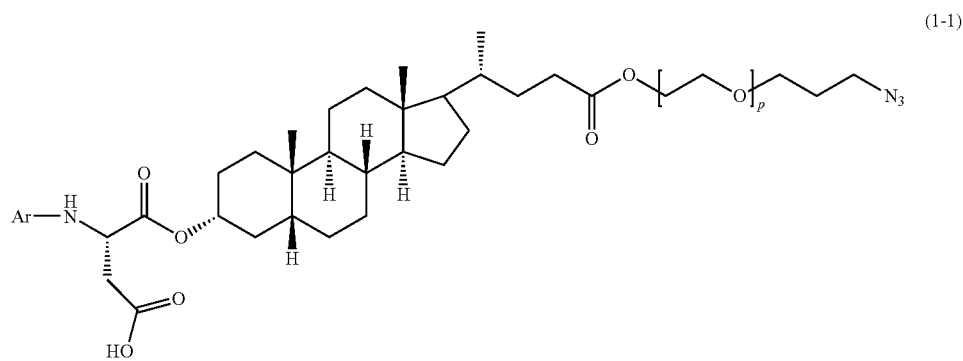
(1-1)

In some embodiments, particular compounds are of formula (1-2),

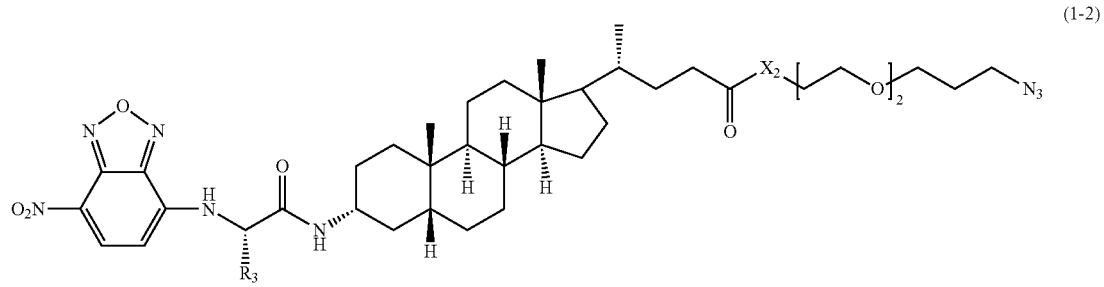

(1-2)

wherein, $X_2$ is O or N; $R_3$ is selected from the group consisting of $CH_3$, $R_aCOOH$, $R_aNH_2$, $R_aNHC(NH_2)\!=\!\!NH$, $R_aSR_b$,

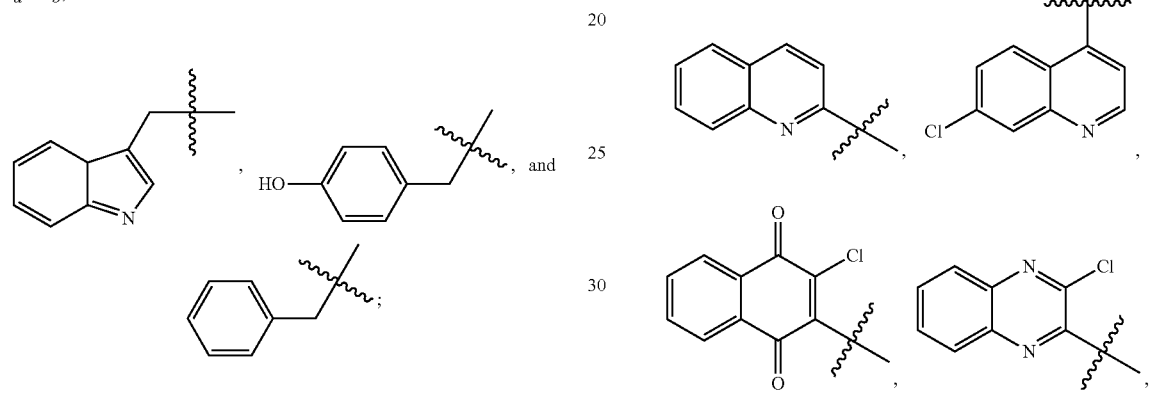

or $R_3$ and the neighboring carbon and nitrogen atoms are taken together to form a 5-membered heterocyclic ring; and $R_a$ and $R_b$ are independently H or $C_{1-6}$ alkyl.

According to one preferred embodiment, in formula (1-2), $X_2$ is N, $R_3$ is —$CH_2COOH$.

In some embodiments, particular compounds are of formula (1-3), (1-3)

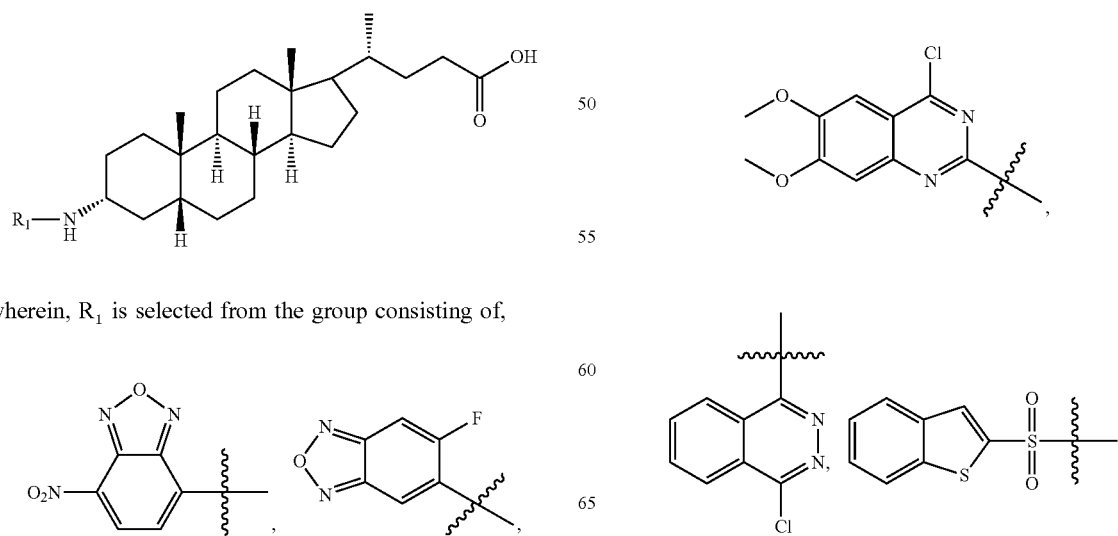

wherein, $R_1$ is selected from the group consisting of,

-continued

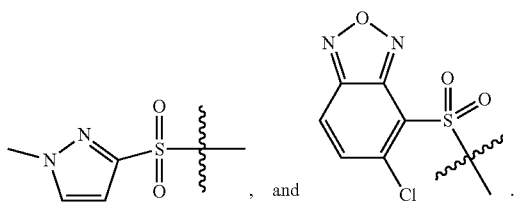, and

In further embodiments, particular compounds are of formula (1-4),

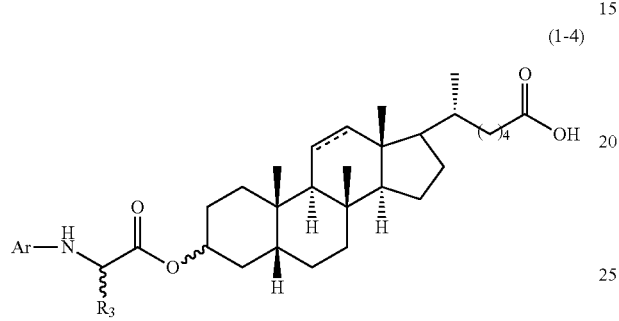

(1-4)

wherein, ===== is a single or a double bond; and $R_3$ is selected from the group consisting of, $CH_2OH$, $R_aCOOH$, $R_aNH_2$, $R_aNHC(NH_2)=NH$, $R_aSR_b$,

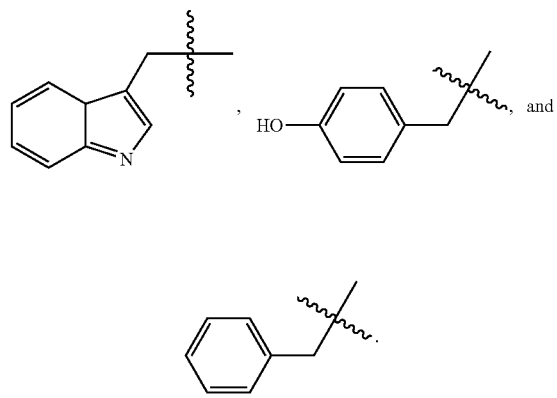

In some embodiments, particular compounds are of formula (1-5),

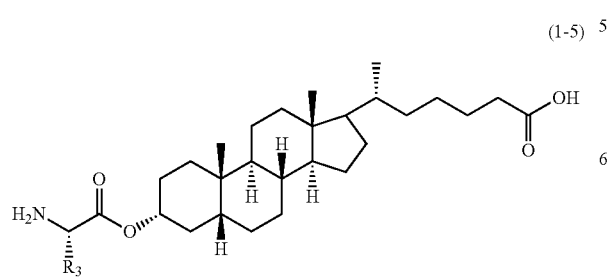

(1-5)

wherein, $R_3$ is $CH_2COOH$, or $CH_2CH_2COOH$.

In other embodiments, particular compounds are of formula (1-6),

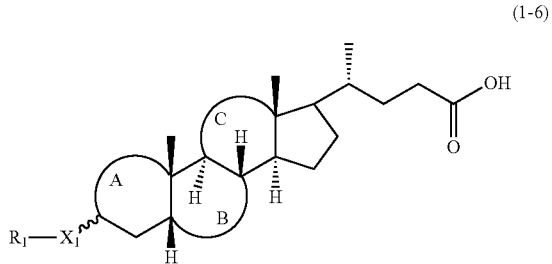

(1-6)

wherein, A, B, and C are independently a 6-membered saturated carbon cyclic ring substituted with at least one fluoro; $X_1$ is H, O or fluoro, and in the case when $X_1$ is fluoro, then $R_1$ is null, H, or

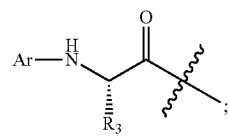

;

and $R_3$ is $CH_2COOH$ or

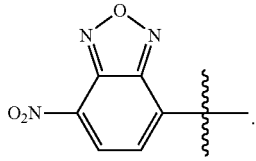 [SMILES: *c1ccc([N+](=O)[O-])c2nonc12]

.

In still further embodiments, particular compounds are of formula (1-7),

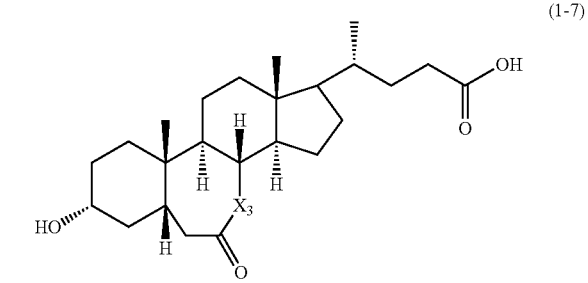

(1-7)

wherein, $X_3$ is O or N.

In some embodiments, particular compounds are of formula (1-8)

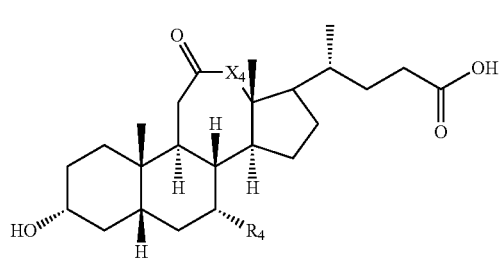

Wherein, $X_4$ is O or N; and $R_4$ is H or OH.

In still further embodiments, particular compound is of formula (1-9),

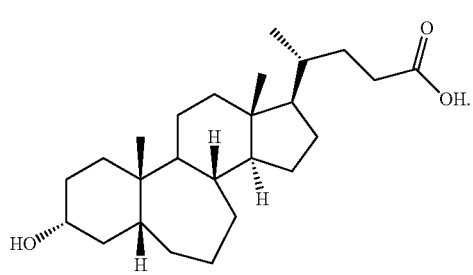

Compounds of the invention may contain one or more stereocenters, and can exist as racemic mixtures of enantiomers or mixtures of diastereomers. This invention therefore encompasses stereomerically pure forms of such compounds, such as the enantiomers, the diastereomers, as well as a racemic mixture thereof, and/or a combination thereof. The enantiomers of the compound of formula (I-1) to (1-9) may be prepared by chiral synthesis or enantioselective synthesis, in which a specific chiral compound is used as the starting material for the synthesis of a desired stereocompound. Alternatively, the stereoisomer of formula (I-1) to (1-9) may be obtained by routine isolating techniques, which include, and are not limited to, crystallization, chromatography, and the use of resolving agents. For example, each enantiomers may be isolated from the racemic mixture by use of HPLC. Alternatively, one enantiomer is separated from the other enantiomer by allowing its racemic mixture to react with a resolving agent, which allows one enantiomer to become solvable in the resolving agent while the other enantiomer remains precipitated. The present invention also encompasses the structural isoforms of the compound of formula (I-1) to (1-9), such as those in cis- and/or trans-conformations, either with or without the presence of double bond(s) in its structure. Accordingly, this invention further encompasses configurational isomers of compounds disclosed herein, either in admixture or in pure or substantially pure form, such as cis (Z) and trans (E) isomers.

Preferred compounds of the present invention are sialyltransferase inhibitors. Certain compounds of the present disclosure selectively inhibit α2,3(N)-sialyltransferase ST3GALIII and α2,6(N)-sialyltransferases ST6GALI, but not α2,3(O)-sialyltransferase ST3GALI.

Shown below are exemplary compounds, compounds 1-94, of this invention:

Compound 1

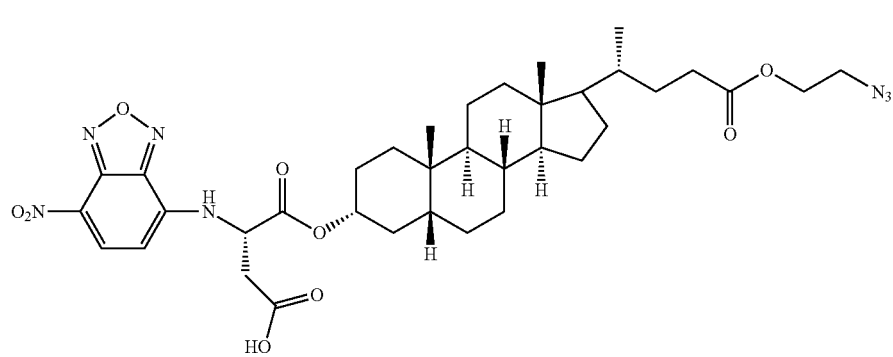

Compound 2

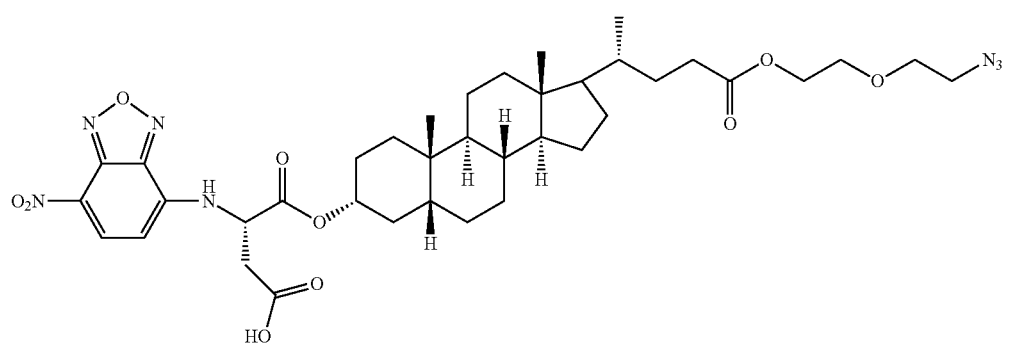

-continued
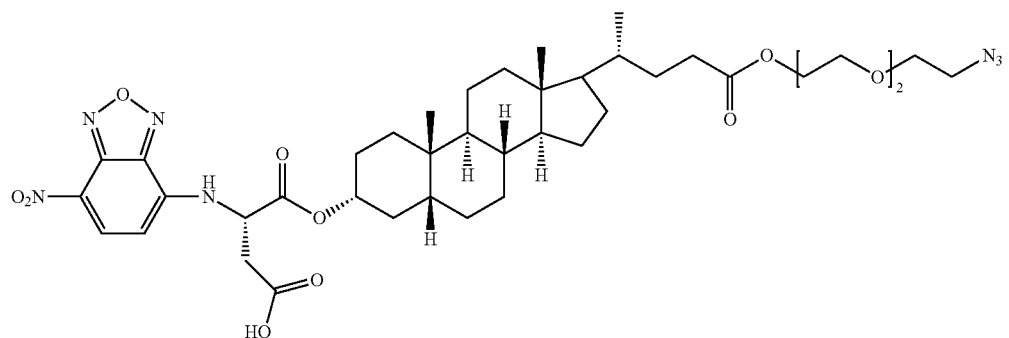
Compound 3
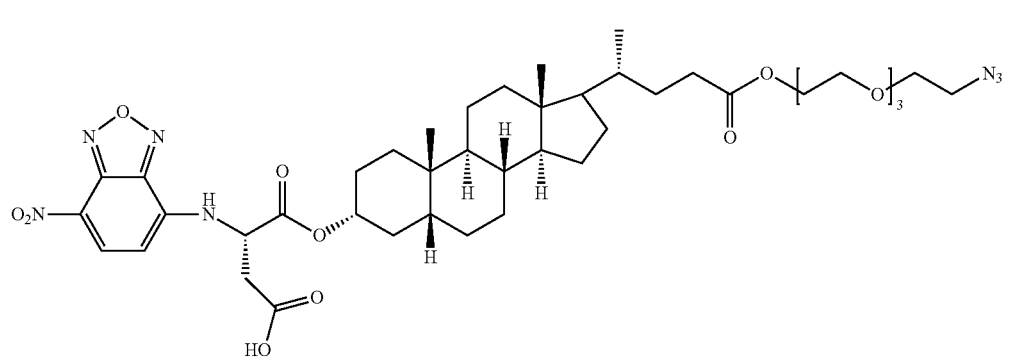
Compound 4
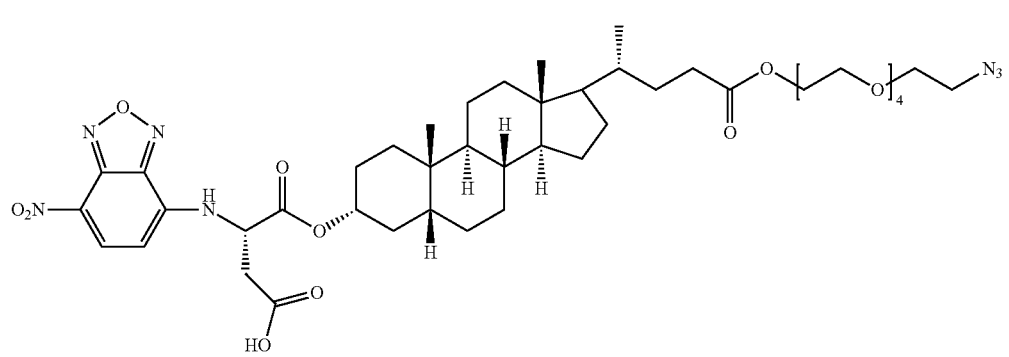
Compound 5
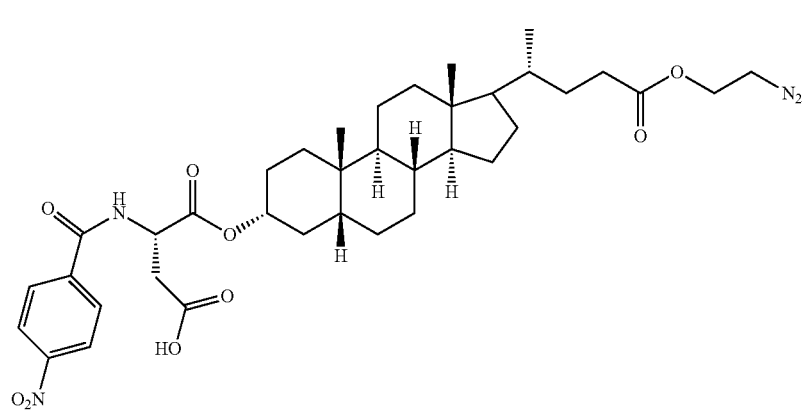
Compound 6

-continued
Compound 7
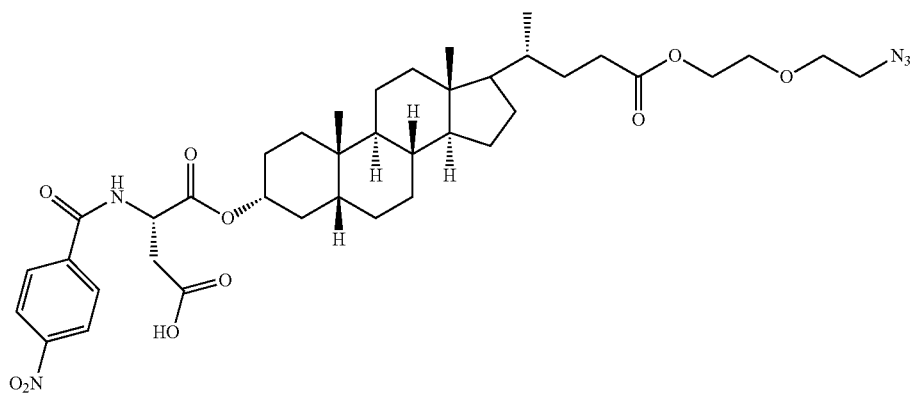
Compound 8
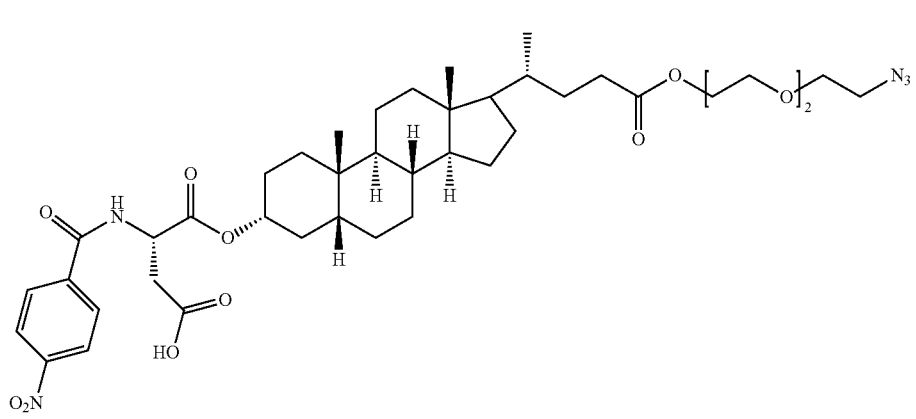
Compound 9
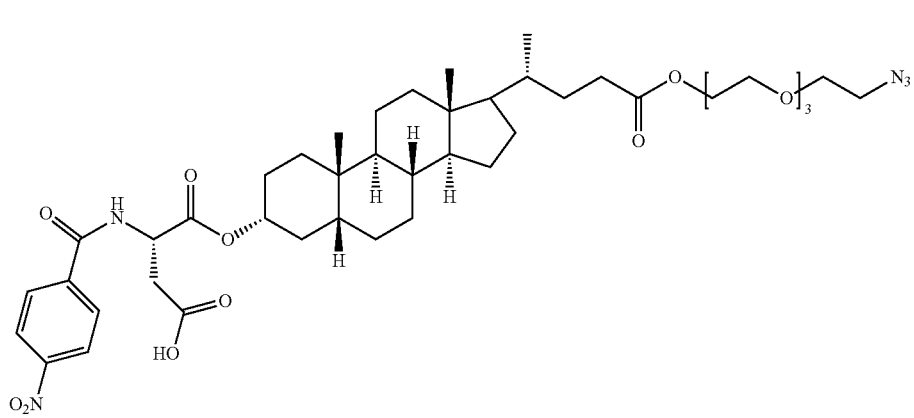
Compound 10
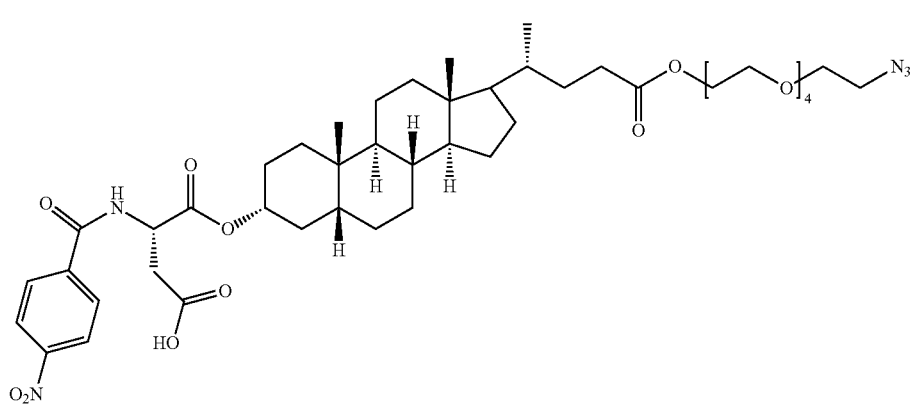

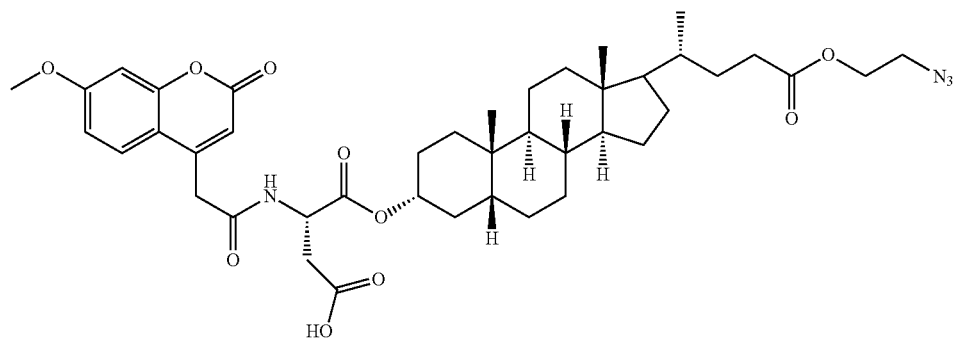
Compound 11
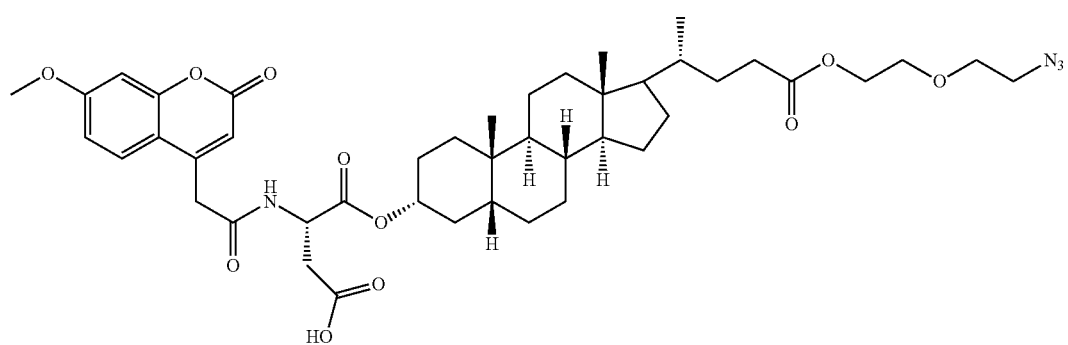
Compound 12
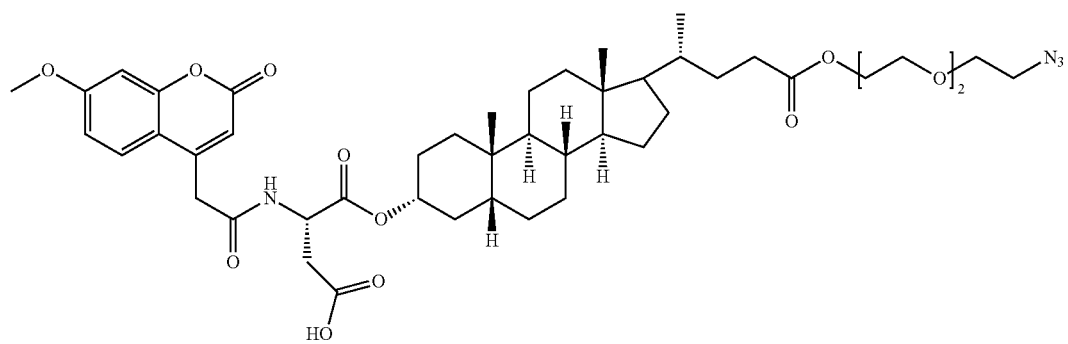
Compound 13
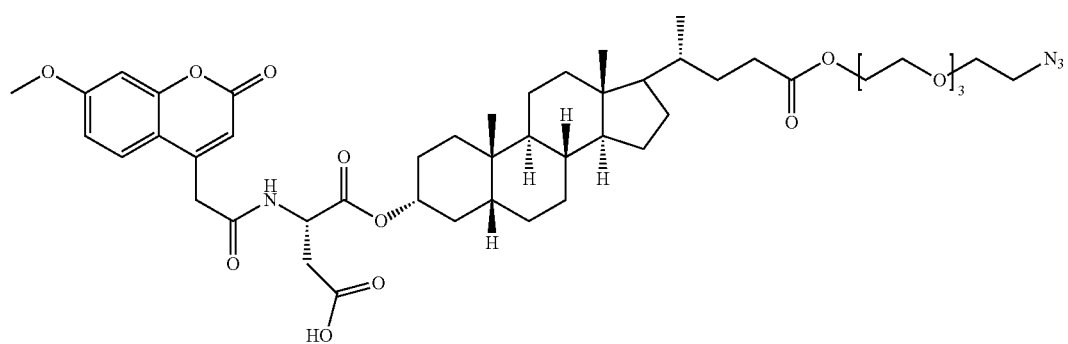
Compound 14

-continued
Compound 15
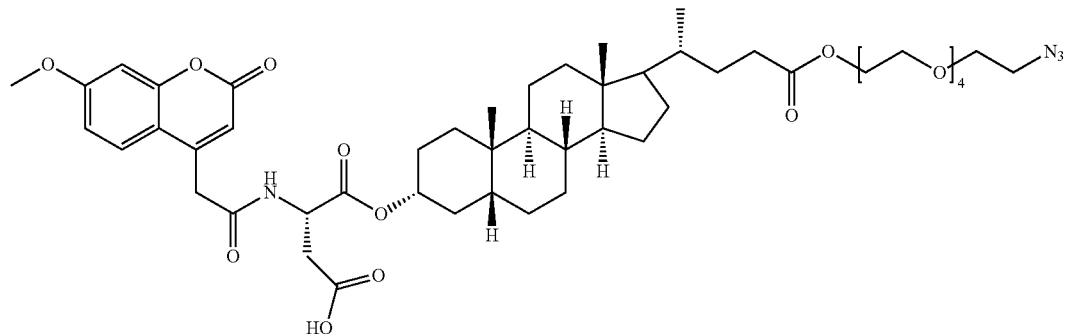
Compound 16
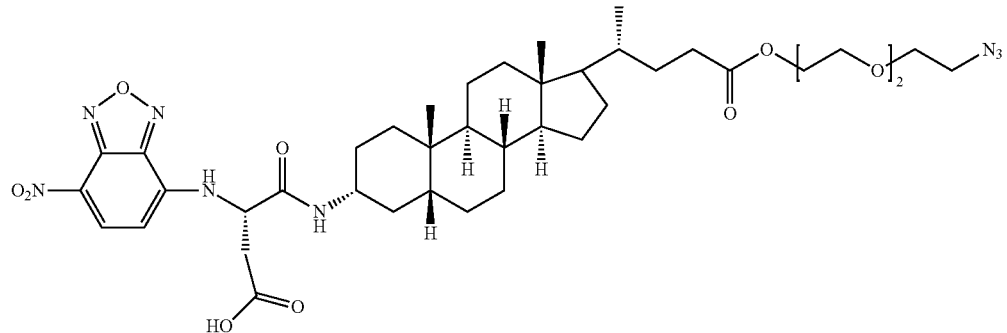
Compound 17
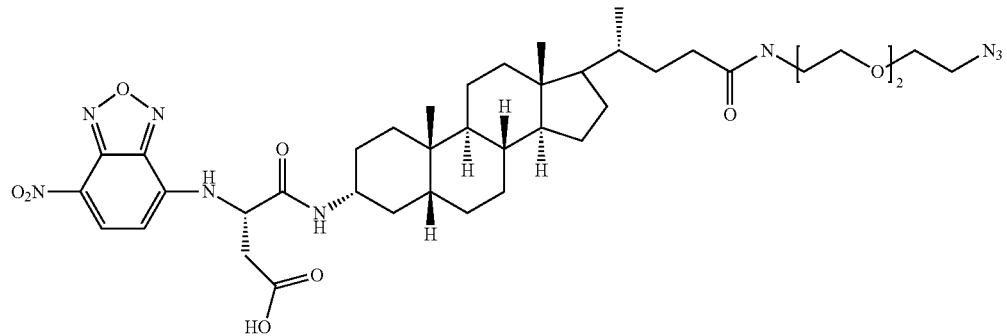
Compound 18
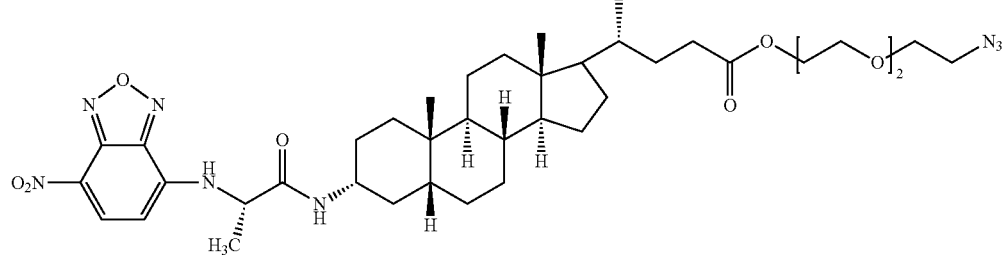
Compound 19
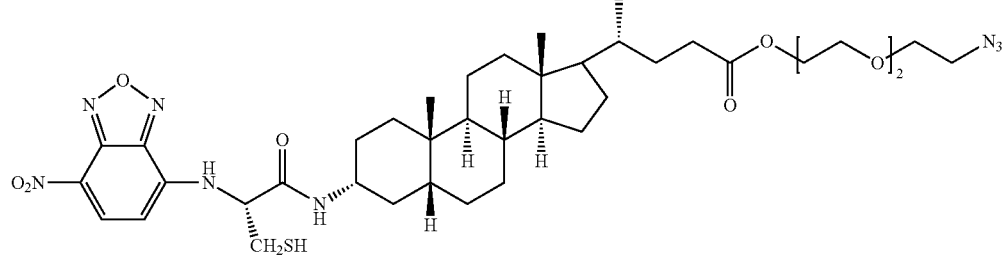

-continued
Compound 20
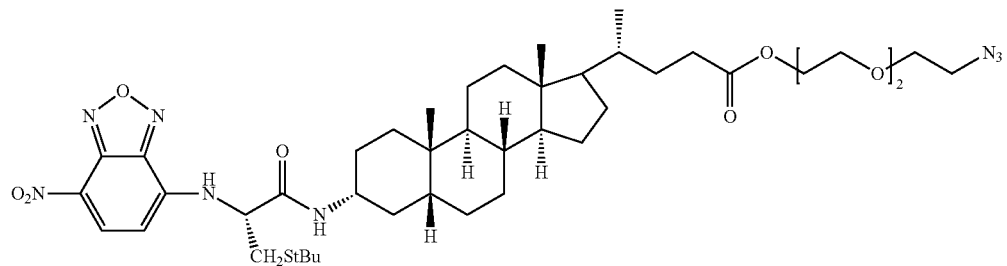
Compound 21
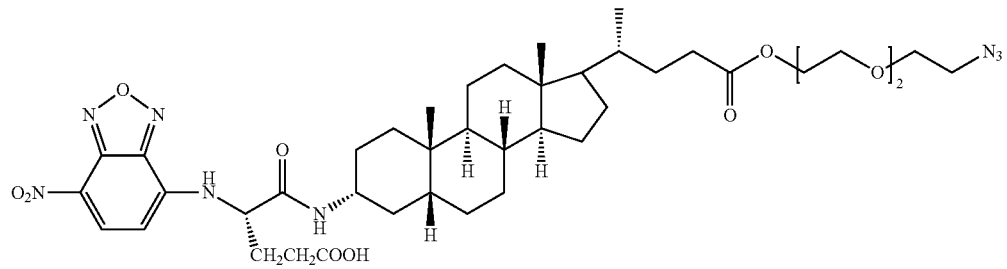
Compound 22
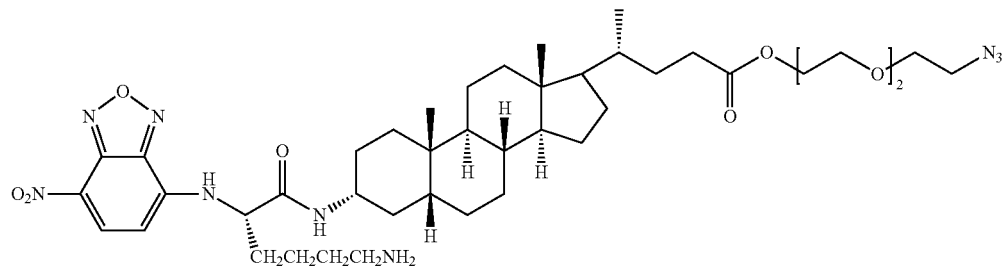
Compound 23
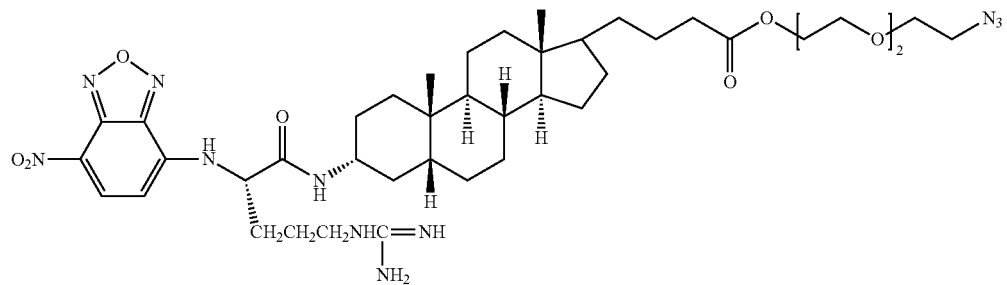
Compound 24
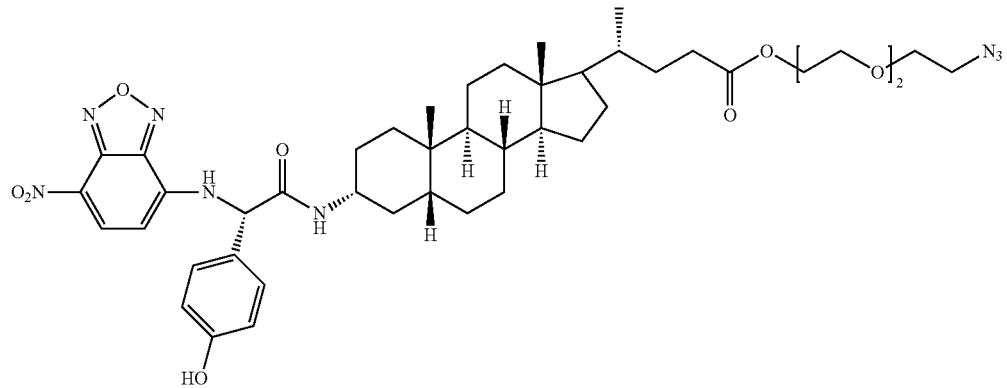

-continued
Compound 25
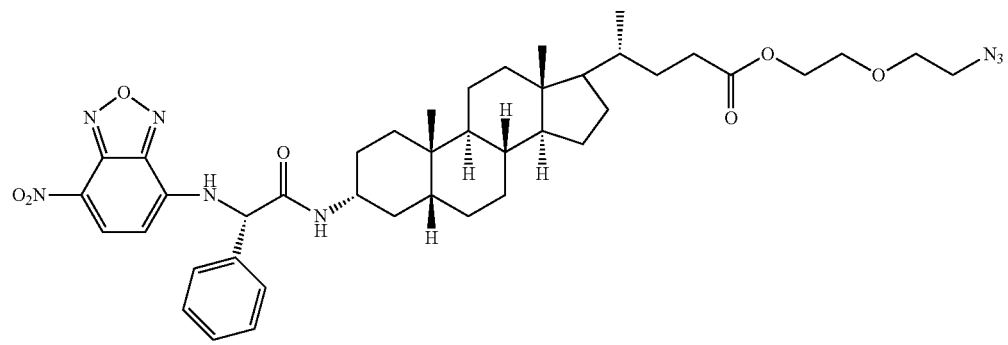
Compound 26
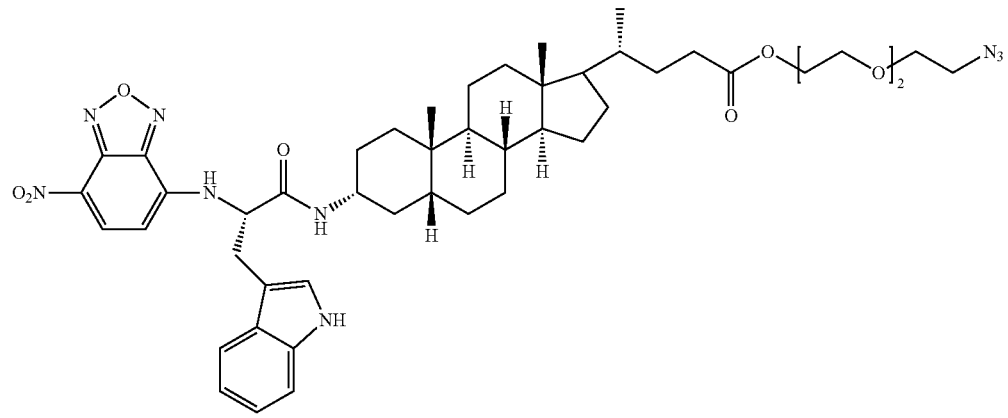
Compound 27
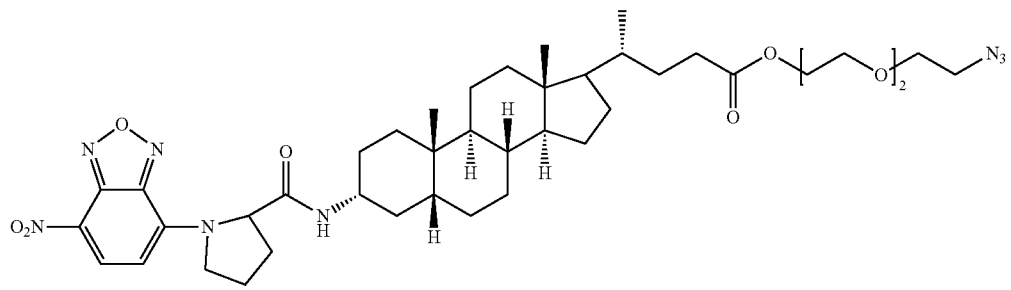
compound 28
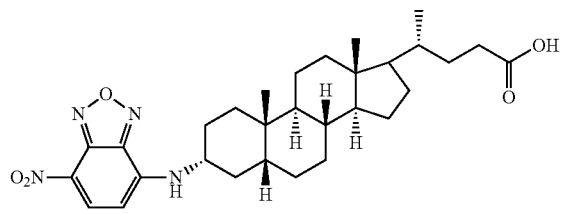
compound 29
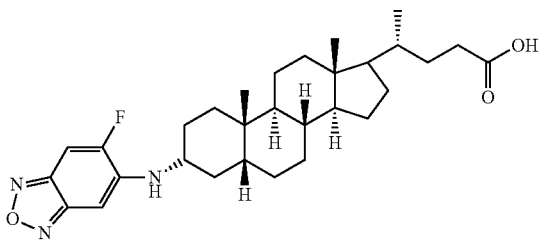
compound 30
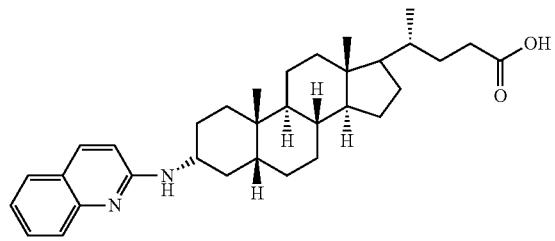
compound 31
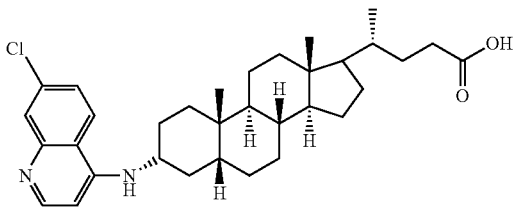

-continued
Compound 32
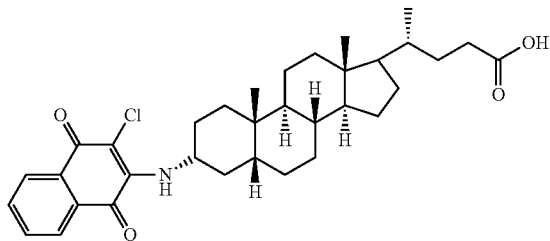
Compound 33
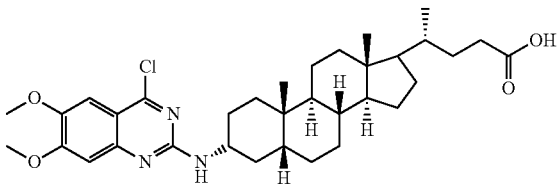
Compound 34
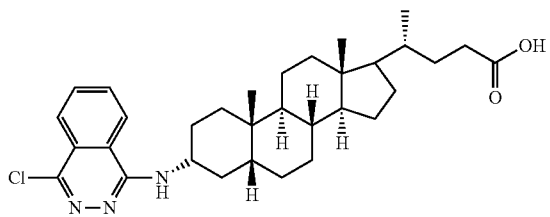
Compound 35
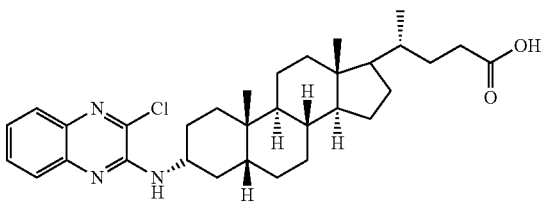
Compound 36
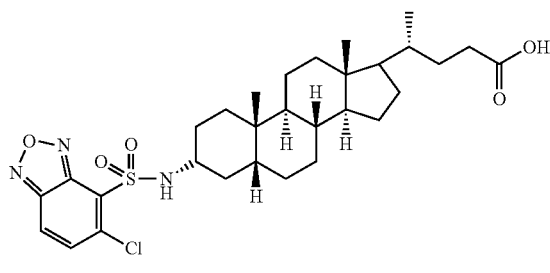
Compound 37
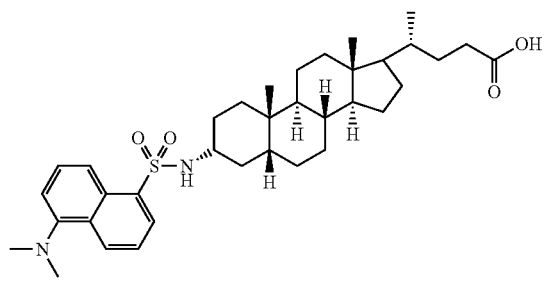
Compound 38
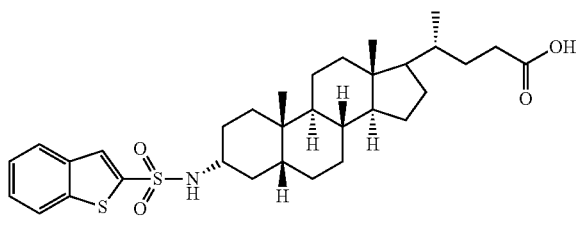
Compound 39
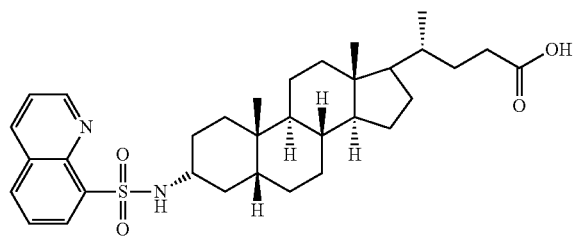
compound 40
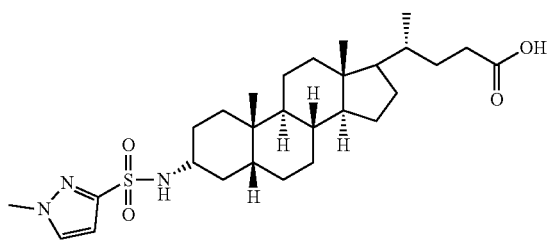
compound 41
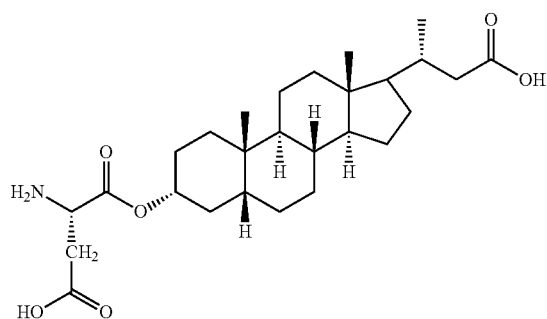

-continued
compound 42
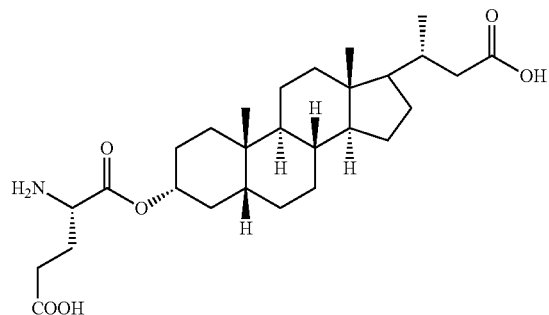
compound 43
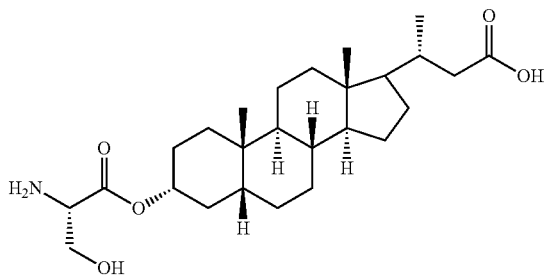
compound 44
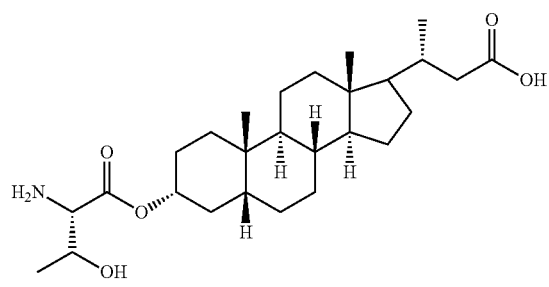
compound 45
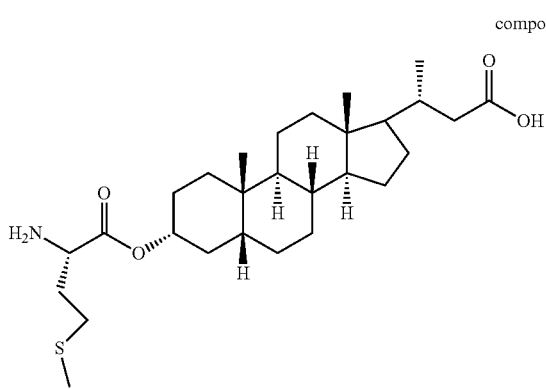
compound 46
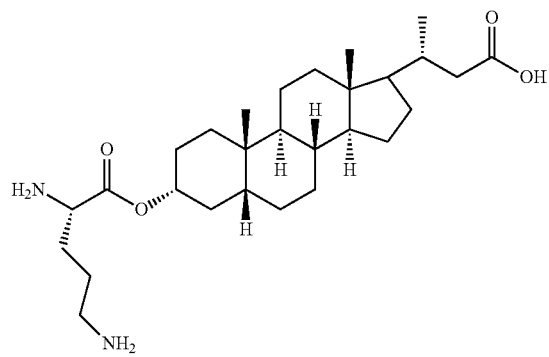
compound 47
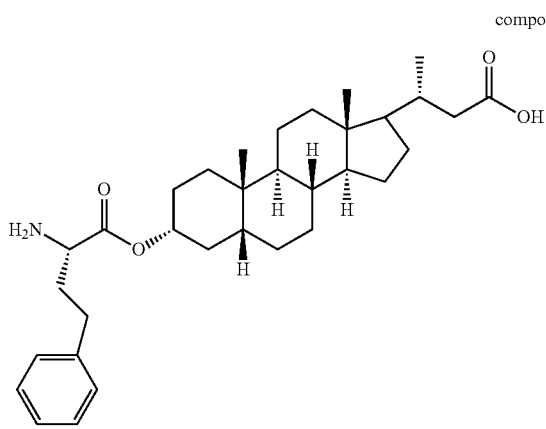
compound 48
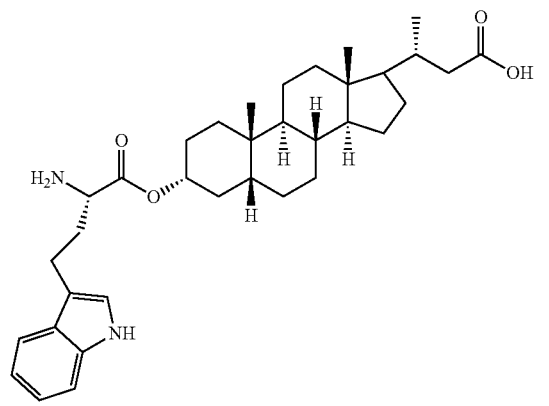
Compound 49
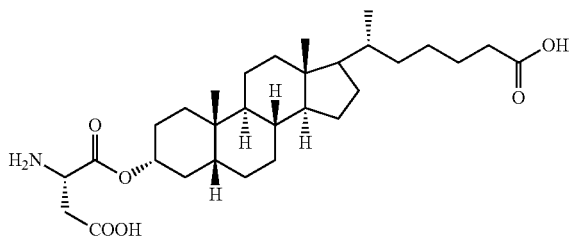

-continued
Compound 50
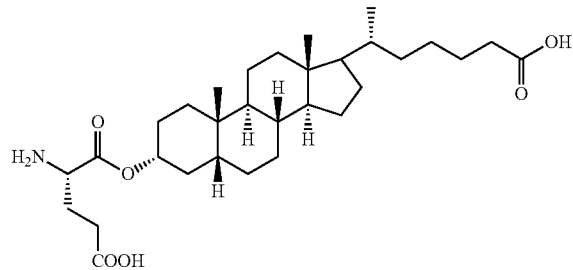
Compound 51
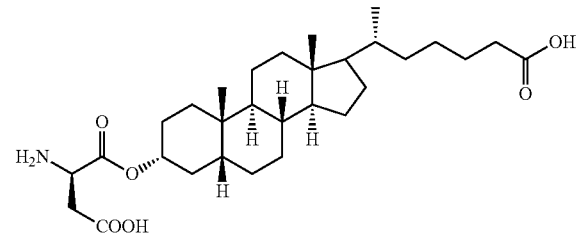
Compound 52
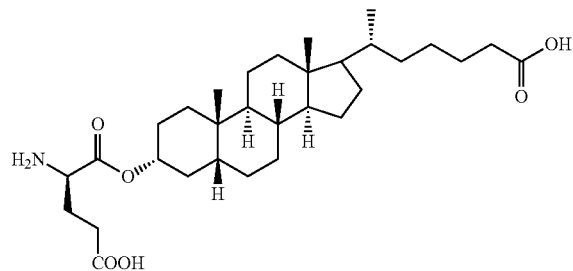
Compound 53
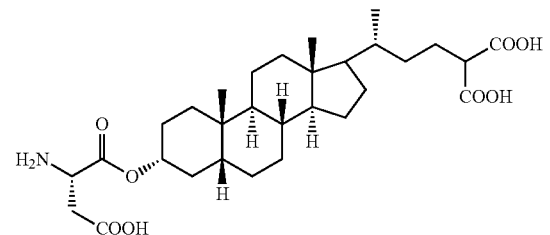
Compound 54
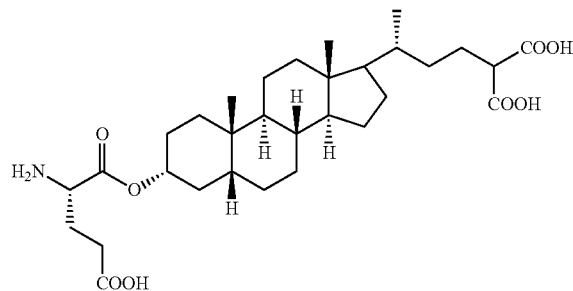
Compound 55
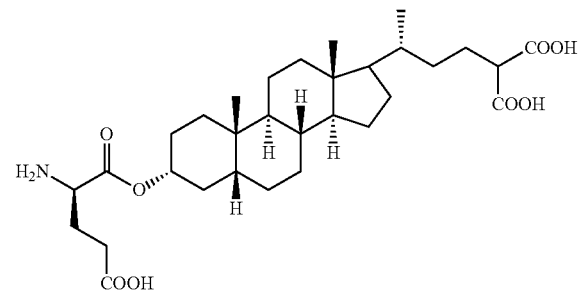
Compound 56
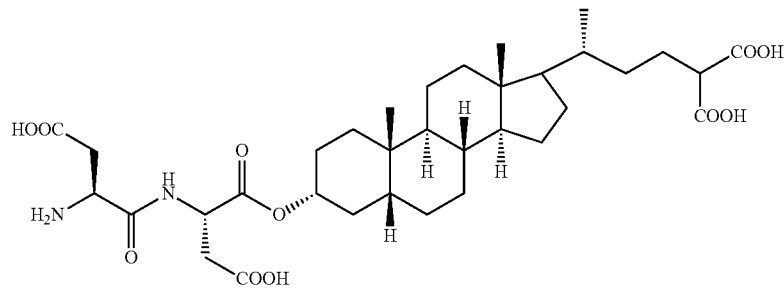
Compound 57
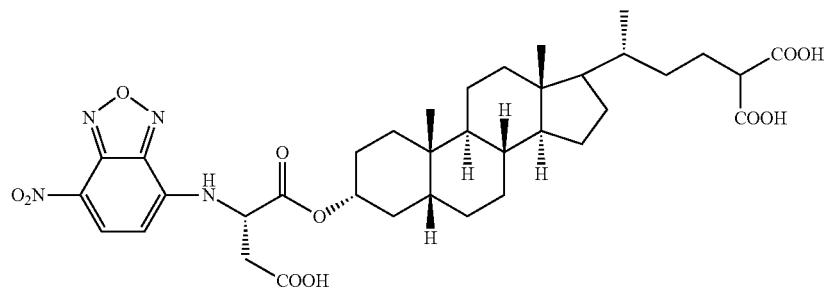

-continued
compound 58
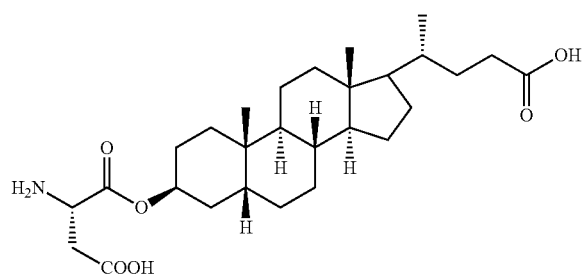
compound 59
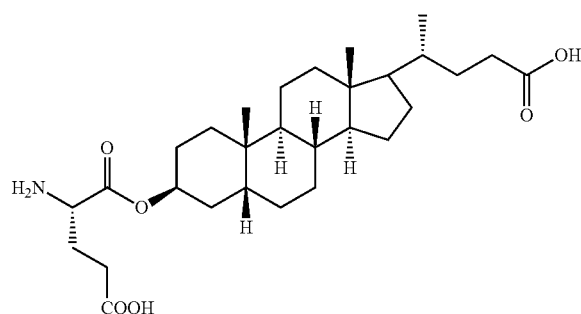
compound 60
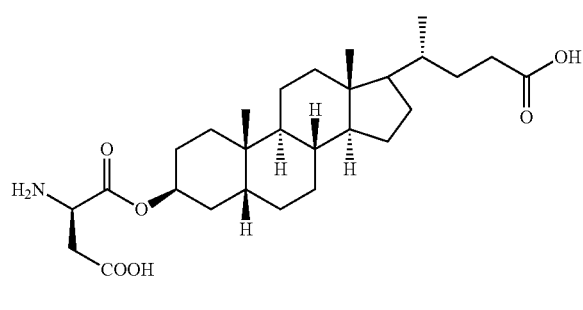
compound 61
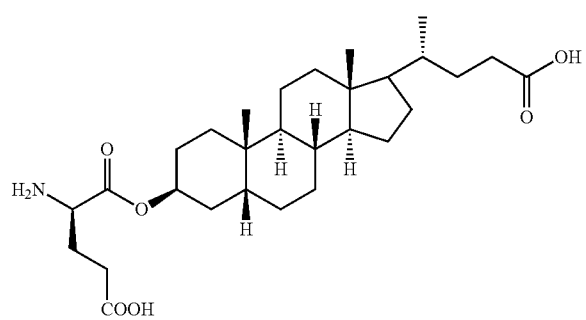
compound 62
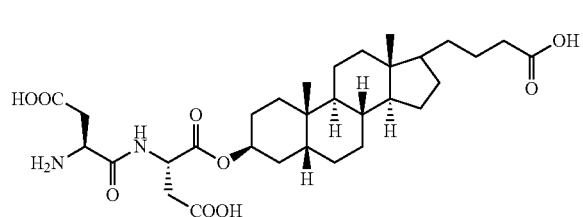
compound 63
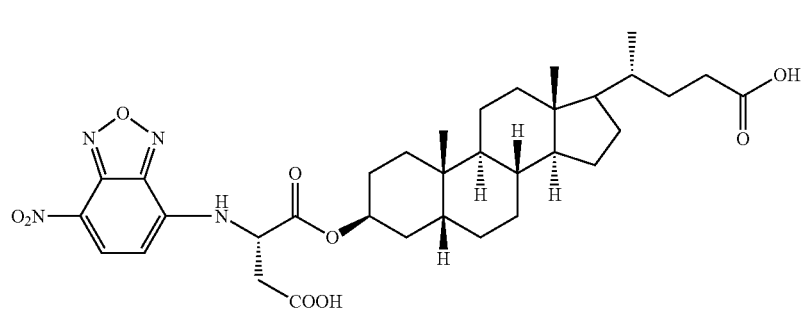
compound 64
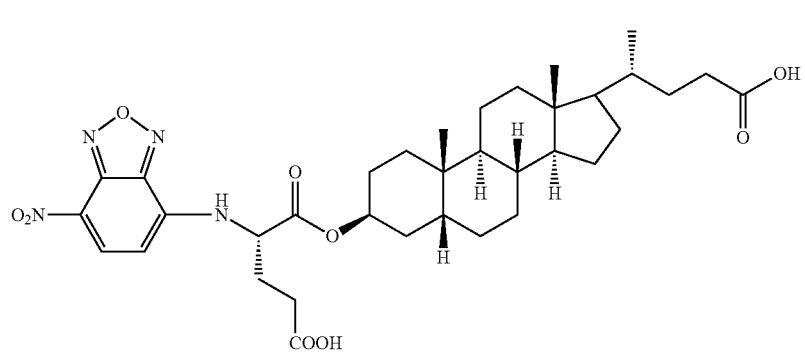

-continued
compound 65
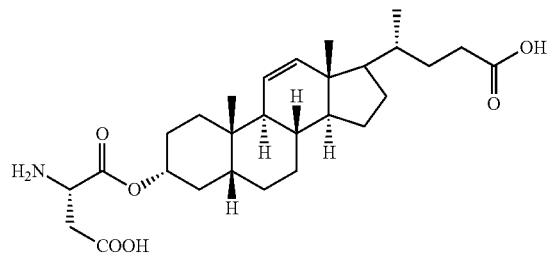
compound 66
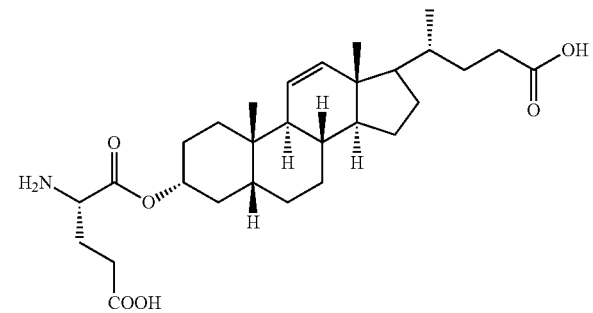
compound 67
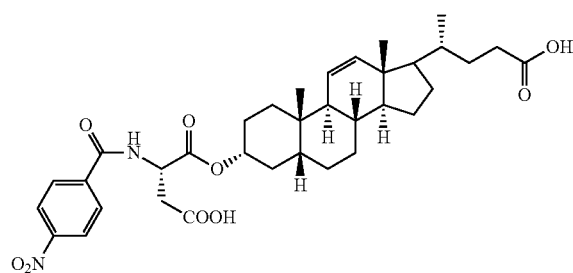
compound 68
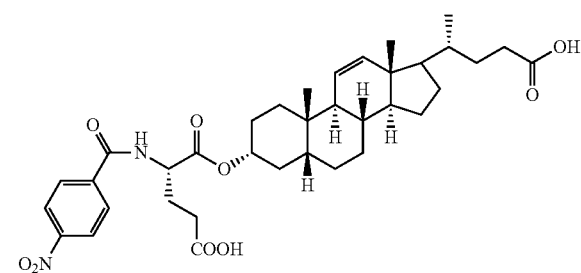
compound 69
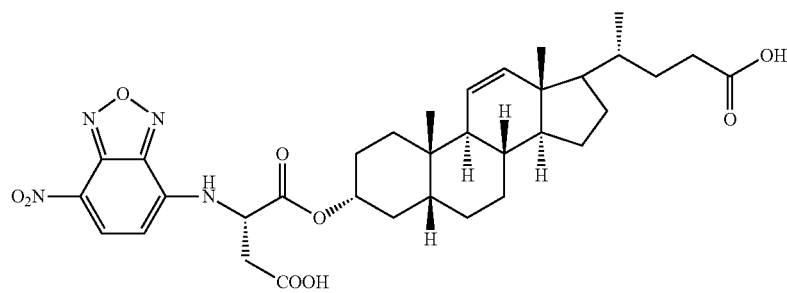
compound 70
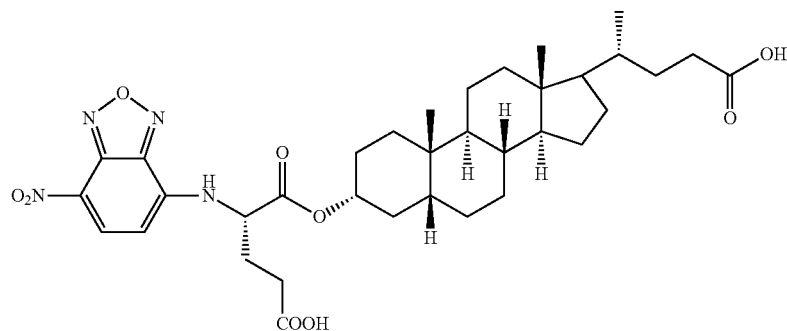
compound 71
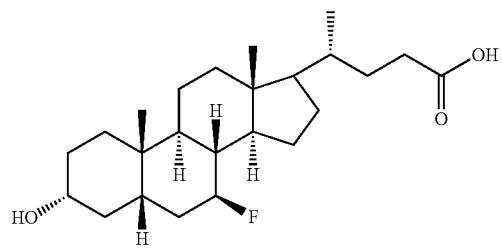
compound 72
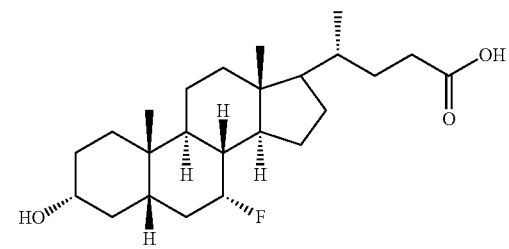

-continued
compound 73
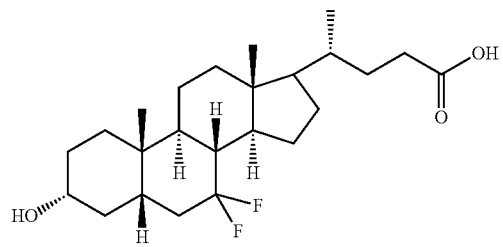
compound 74
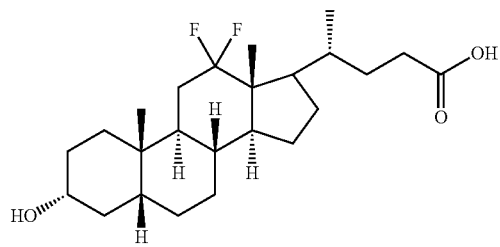
compound 75
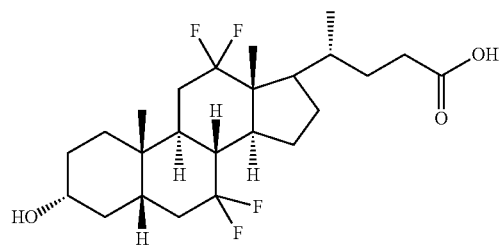
compound 76
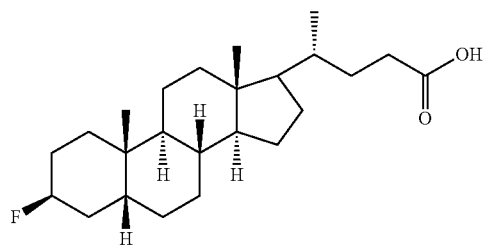
compound 77
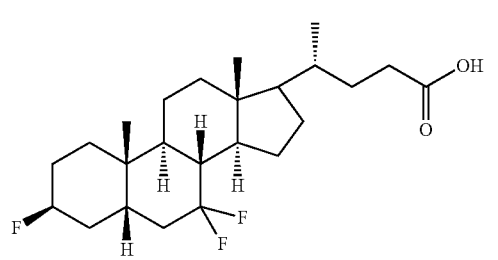
compound 78
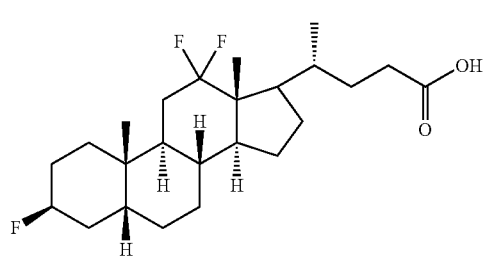
compound 79
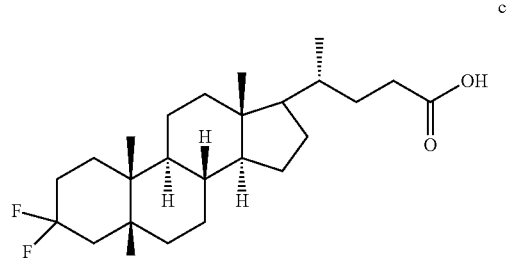
compound 80
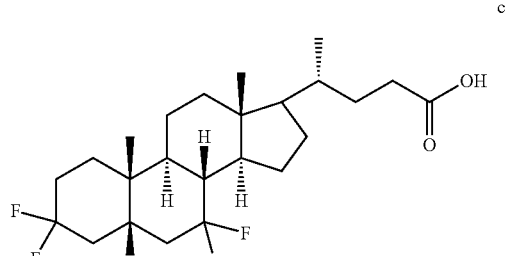
compound 81
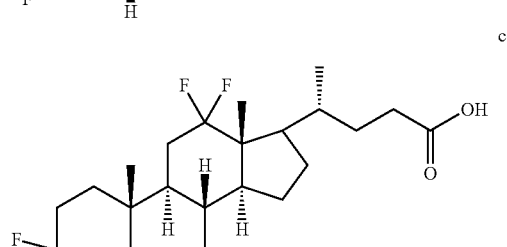
compound 82
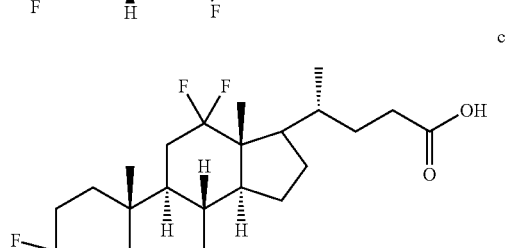
compound 83
compound 84
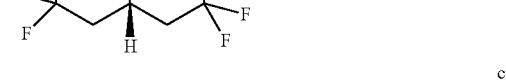
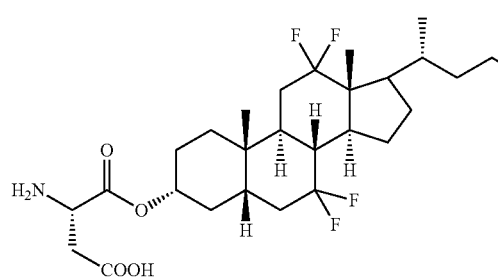
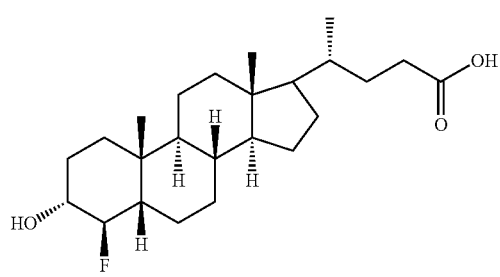

compound 85
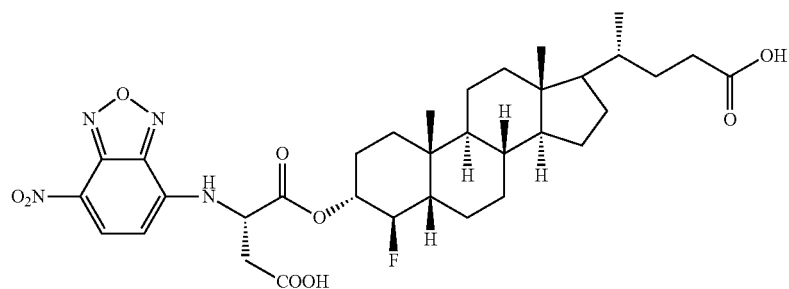
compound 86
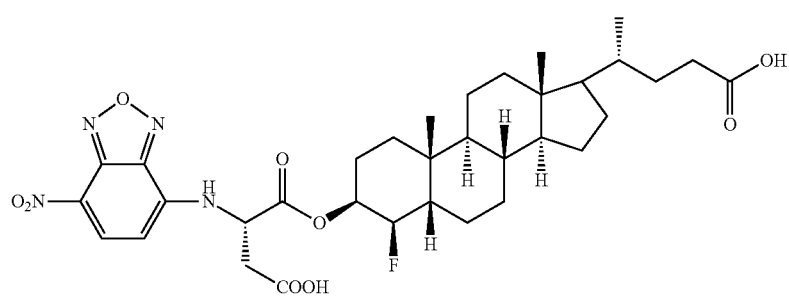
compound 87
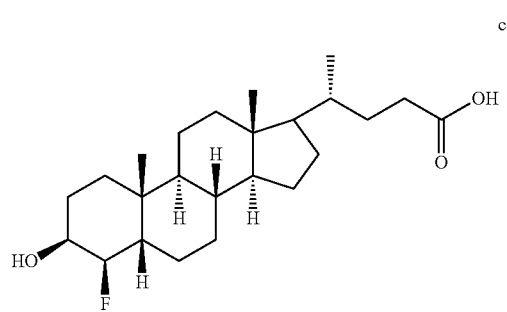
compound 88
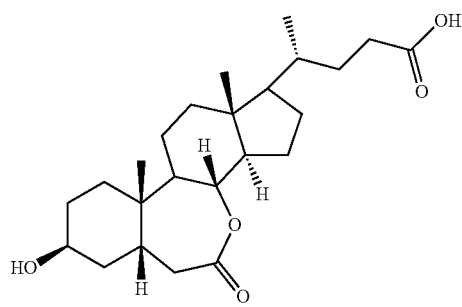
compound 89
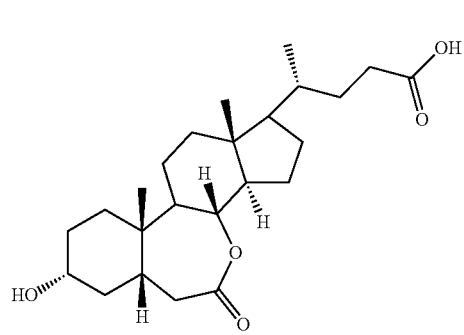
compound 90
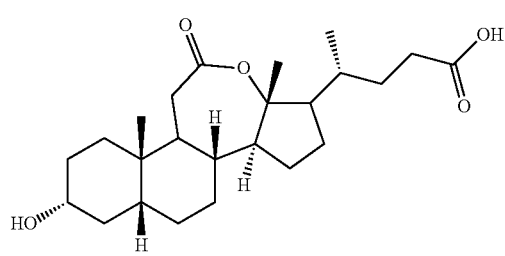
compound 91
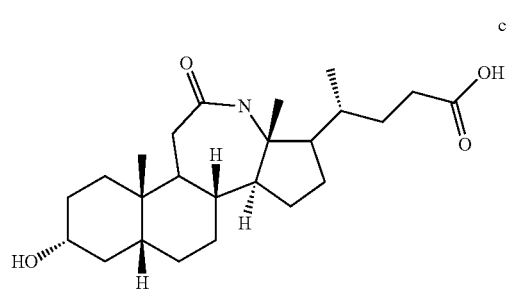
compound 92
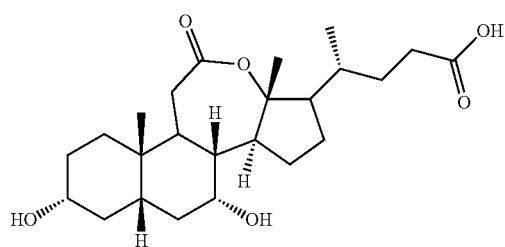

compound 93

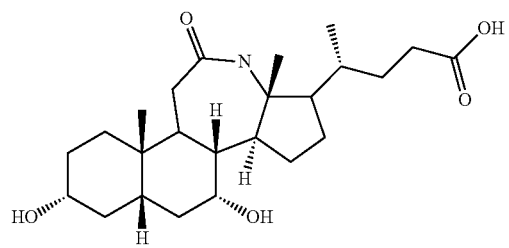

compound 94

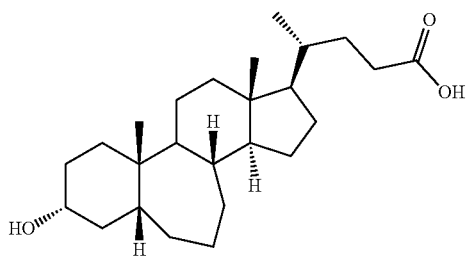

Each compounds of formula (I-1) to (1-9) is a derivative of lithocholic acid, and may be synthesized in accordance with methods set forth in the working examples of the present disclosure.

2. Uses of Lithocholic Acid Derivatives

Also within the scope of the present disclosure is a method for treating a subject suffering from a disease and/or a condition associated with the activation of sialyltransferase. The method includes steps of, administering an effective amount of the compound of formula (I), particularly the compounds of formula (1-1) to (1-9), to the subject, so as to alleviate or ameliorate one or more symptoms related to the disease and/or condition associated with the activation of sialyltransferase.

The disease and/or condition known to associate with the activation of sialyltransferase includes, but is not limited to, a cancer, an immune or inflammatory disease.

Cancer is a class of diseases in which a group of cells having the capacity for autonomous growth, i.e., an abnormal state or condition characterized by rapidly proliferating cell growth and sometimes tumor metastasis. Examples of cancers include, but are not limited to, carcinoma and sarcoma such as breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratocarcinoma, neuroblastoma, glioma, glioblastoma, keratoacanthomas, analplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL). The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma; whereas tumor of mesenchymal origin is fibrosarcomas or rhabdomyosarcomas.

The cancer may be metastatic or drug-resistant. According to one embodiment, the cancer is metastatic breast cancer. According to another embodiment, the cancer is metastatic pancreatic cancer.

An inflammatory disease is characterized by a local or systemic, acute or chronic inflammation. Examples include retinopathy (e.g., diabetic retinopathy and proliferative retinopathy), inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease (ILD), idiopathic pulmonary fibrosis, and ILD associated with rheumatoid arthritis), macular edema, asthma, and allergic rhinitis.

An immune disease is characterized by a hyper- or hypo-reaction of the immune system. Examples include, but are not limited to, autoimmune diseases (e.g., rheumatoid arthritis, psoriatic arthritis, systemic lupus erythematosus, myasthenia gravis, Type I diabetes mellitus, glomerulonephritis, autoimmune throiditis, ankylosing spondylitis, systemic sclerosis, and multiple sclerosis), acute and chronic inflammatory diseases (e.g., systemic anaphylaxia or hypersensitivity responses, drug allergies, insect sting allergies, graft rejection, including allograft rejection, and graft-versus-host disease), Sjogren's syndrome, and human immunodeficiency virus infection.

One embodiment encompasses a method of treating a subject having or suffering from a cancer, which comprises administering to the subject an effective amount of a compound of the present disclosure, particularly, a compound of formula (1-1) to (1-9), so as to alleviate or ameliorate one or more symptoms related to the cancer.

Another embodiment encompasses a method of treating an immune or inflammatory disease in a subject, which comprises administering to the subject an effective amount of a compound of the present disclosure, particularly, a compound of formula (1-1) to (1-9), so as to alleviate or ameliorate one or more symptoms related to the immune or inflammatory disease.

The amount, route of administration and dosing schedule of a compound will depend upon factors such as the specific indication to be treated, prevented, or managed, and the age, sex and condition of the patient. The roles played by such factors are well known in the art, and may be accommodated by routine experimentation. In general, the compound of formula (I-1) to (1-9) is administered to the subject in need thereof in an amount of about 1-100 mg/Kg body weight, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/Kg body weight; preferably about 20-80 mg/Kg body weight, such as 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80 mg/Kg body weight; more preferably about 40-60 mg/Kg body weight, such as 40, 41, 42, 43, 44, 45, 46, 47, 48, 49, 50, 51, 52, 53, 54, 55, 56, 57, 58, 59, and 60 mg/Kg body weight. The amount may be administered in a single dosage or in multiple dosages in a day, such as in 2, 3, or 4 dosages per day. The actual amount of the compound of formula (I-1) to (1-9) will depend on the specific symptoms of the subject, and the physical conditions of the subject such as age, sex, medical history and etc.; and may be readily determined by the attending physician in accordance with his/her experience.

In some embodiments, the method further includes administering another chemotherapeutic agent, an anti-inflammatory agent or an immunosuppressive agent, before, concurrently with, or after the administration of the compound of formula (I-1) to (1-9).

Examples of the chemotherapeutic agent include, but are not limited to, Bleomycin, Buserelin, Busulfan, Capecitabine, carboplatin, Carmustine, chlorambucil, cisplatin, Cladribine, Clodronate, cyclophosphamide, cyproterone, Cytarabine, Dacarbazine, Dactinomycin, Daunorubicin, diethylstilbestrol, Docetaxel, Doxorubicin, Epirubicin, Estramustine, etoposide, Exemestane, Filgrastim, Fludarabine, Fludrocortisone, fluorouracil, Fluoxymesterone, Flutamide, Gemcitabine, Goserelin, hydroxyurea, Idarubicin, Ifosfamide, Imatinib, Interferon Alfa, Mnotecan, Letrozole, Leucovorin, Leuprolide, Levamisole, Lomustine, Mechlorethamine, Medroxyprogesterone, Megestrol, Melphalan, mercaptopurine, Mesna, methotrexate, mitomycin, Mitotane, Mitoxantrone, Nilutamide, Octreotide, Oxaliplatin, Paclitaxel, Pamidronate, Pentostatin, Plicamycin, Porfimer, procarbazine, Raltitrexed, Rituximab, streptozocin, Tamoxifen, Temozolomide, Teniposide, testosterone, thioguanine, Thiotepa, Topotecan, Trastuzumab, Tretinoin, Vinblastine, Vincristine, Vindesine, Vinorelbine and the like.

Examples of the anti-inflammatory agent include, but are not limited to, anthranilic acids, aspirin (5-acetylsalicylic acid), aclofenac, aloxiprin, aproxen, aspirin, acemetacin, amtolmetin, azapropazone, benorilate, benoxaprofen, benzydamine hydrochloride, bromfenac, bufexamac, butibufen, carprofen, celecoxib, choline salicylate, clonixin, desoxysulindac, diflunisal, dipyrone, droxicam, etodolac, etofenamate, etoricoxib, fenbufen, felbinac, fentiazac, fenoprofen, flufenamic acid, floctafenine, indomethacin, indoprofen, isoxicam, ketoralac, lomoxicam, loxoprofen, licofelone, fepradinol, mefenamic acid, magnesium salicylate, meclofenamic acid, meloxicam, morniflumate, niflumic acid, nimesulide, oxaprozen, phenylbutazone, piroxicam, piketoprofen, priazolac, pirprofen, propyphenazone, proquazone, rofecoxib, salalate, salicylamide, salicylic acid, sodium salicylate, sodium thiosalicylate, sulindac, suprofen, tolmetin, tenoxicam, tramadol, tenidap, tiaprofenic acid, trolamine salicylate, zomepirac, and the like.

Examples of the immunosuppressive agent include, but are not limited to, azathioprine, anthracyclines, bleomycin, cyclosporin, cyclophosphamide, cyclosporine A, fluorouracil, mercaptopurine, mitomycin C, methotrexate, Tacrolimus, Sirolimus and the like.

4. Pharmaceutical Composition

The present disclosure also encompasses a pharmaceutical composition for treating a disease and/or a condition associated with the activation of sialyltransferase. The pharmaceutical composition comprises a therapeutically or prophylactically effective amount of the compound of formula (I); and a pharmaceutically acceptable excipient.

The compound of formula (I) of this invention is present at a level of about 0.1% to 99% by weight, based on the total weight of the pharmaceutical composition. In some embodiments, the compound of formula (I) of this invention is present at a level of at least 1% by weight, based on the total weight of the pharmaceutical composition. In certain embodiments, the compound of formula (I) of this invention is present at a level of at least 5% by weight, based on the total weight of the pharmaceutical composition. In still other embodiments, the compound of formula (I) of this invention is present at a level of at least 10% by weight, based on the total weight of the pharmaceutical composition. In still yet other embodiments, the compound of formula (I) of this invention is present at a level of at least 25% by weight, based on the total weight of the pharmaceutical composition.

The pharmaceutical composition is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

According to some optional embodiments, the pharmaceutical composition further includes, a chemotherapeutic agent, an anti-inflammatory agent or an immunosuppressive agent.

Examples of the chemotherapeutic agent include, but are not limited to, Bleomycin, Buserelin, Busulfan, Capecitabine, carboplatin, Carmustine, chlorambucil, cisplatin, Cladribine, Clodronate, cyclophosphamide, cyproterone, Cytarabine, Dacarbazine, Dactinomycin, Daunorubicin, diethylstilbestrol, Docetaxel, Doxorubicin, Epirubicin, Estramustine, etoposide, Exemestane, Filgrastim, Fludarabine, Fludrocortisone, fluorouracil, Fluoxymesterone, Flutamide, Gemcitabine, Goserelin, hydroxyurea, Idarubicin, Ifosfamide, Imatinib, Interferon Alfa, Mnotecan, Letrozole, Leucovorin, Leuprolide, Levamisole, Lomustine, Mechlorethamine, Medroxyprogesterone, Megestrol, Melphalan, mercaptopurine, Mesna, methotrexate, mitomycin, Mitotane, Mitoxantrone, Nilutamide, Octreotide, Oxaliplatin, Paclitaxel, Pamidronate, Pentostatin, Plicamycin, Porfimer, procarbazine, Raltitrexed, Rituximab, streptozocin, Tamoxifen, Temozolomide, Teniposide, testosterone, thioguanine, Thiotepa, Topotecan, Trastuzumab, Tretinoin, Vinblastine, Vincristine, Vindesine, Vinorelbine and the like.

Examples of the anti-inflammatory agent include, but are not limited to, anthranilic acids, aspirin (5-acetylsalicylic acid), aclofenac, aloxiprin, aproxen, aspirin, acemetacin, amtolmetin, azapropazone, benorilate, benoxaprofen, benzydamine hydrochloride, benzydamine hydrochloride, bromfenal, bufexamac, butibufen, carprofen, celecoxib, choline salicylate, clonixin, desoxysulindac, diflunisal, dipyrone, droxicam, etodolac, etofenamate, etoricoxib, fenbufen, felbinac, fentiazac, fenoprofen, flufenamic acid, floctafenine, indomethacin, indoprofen, isoxicam, ketoralac, lomoxicam, loxoprofen, licofelone, fepradinol, mefenamic acid, magnesium salicylate, meclofenamic acid meclofenamic acid, meloxicam, morniflumate, niflumic acid, nimesulide, oxaprozen, phenylbutazone, piroxicam piketoprofen, priazolac, pirprofen, propyphenazone, proquazone, rofecoxib, salalate, salicylamide, salicylic acid, sodium salicylate, sodium thiosalicylate, sulindac, suprofen, tolmetin, tenoxicam, tramadol, tenidap, tiaprofenic acid, trolamine salicylate, zomepirac, and the like.

Examples of the immunosuppressive agent include, but are not limited to, azathioprine, anthracyclines, bleomycin, ciclosporin, cyclophosphamide, cyclosporine A, fluorouracil, mercaptopurine, mitomycin C, methotrexate, Tacrolimus, Sirolimus and the like.

The compound of formula (I) of the present invention may be formulated into a single dosage suitable for oral, transmembrane (such as intranasal, sublingual, intravaginal, buccal, and/or endorectal), and/or parenteral administration (e.g., subcutaneous, intravenous, intramuscular, intraperitoneal or bolus injection) Examples of the dosage include, but are not limited to, tablets, caplets, capsules (e.g., soft elastic gelatin capsules), cachets, troches, lozengesm dispersions, suppositories, ointments, cataplasms (or poultices) creams, plasters, solutions, patches, aerosols, or gels. The compound of formula (I) of the present invention may be formulated into a liquid pharmaceutical compositions, which are sterile solutions, suspensions (e.g., water solvable or insolvable liquid suspension, oil-in-water emulsion or water-in-oil emulsion) or elixirs that can be administered by, for example, oral ingestion, or intravenous, intramuscular, subcutaneous or intraperitoneal injection.

The compound of the present invention is formulated in accordance with the intended routes for its administration. For example, if the compound of the present invention is intended to be administered by oral ingestion, an enteric coating may be applied on the formulation so as to prevent the compound of the present invention from being degraded in the acidic environment or until it reaches the intestines of the subject. The formulation may further include additional components that help deliver the compound of the present invention to its intended target site. In some examples, the compound of the present invention is enclosed in a liposome to prevent it from enzymatic degradation, and to help transporting the compound of the present disclosure through the circulation system of the subject, and/or across cell membrane to its intended cellular target site.

Further, the least soluble compound of the present invention may be formulated with additional agents, such as a solvating agent, an emulsifying agent and/or a surfactant, into a liquid formulation. Examples of the additional agent include, but are not limited to, cyclodextrin, and non-aqueous solvents, which include but are not limited to, ethanol, isopropanol, ethyl carbonate, ethyl acetate, benzyl alcohol, benzyl benzoate, propyl glycol, 1,3-butyl glycol, dimethyl formamide, dimethyl sulfoxide, biocompatible oils (e.g., cottonseed oil, peanut oil, corn oil, wheat germ oil, castor oil, olive oil, sesame oil, glycerol, tetrahydrogen furan, polyethyl glycol, fatty acid esters of sorbitan, and a combination thereof).

The amount of the compound of the present disclosure in the formulation varies with the route of administration. For example, formulations for acute treatment will contain larger amounts of one or more of the active compounds, as compared to formulations that are for chronic treatment. Similarly, parental formulations will comprise less amounts of one or more of the active compounds, as compared to formulations that are for oral ingestion. Also within the scope of the present disclosure are formulations suitable for other administration routes.

4.1 Formulation for Oral Ingestion

The compound of present disclosure may be formulation into compositions suitable for oral ingestion. Examples of such formulations include, but are not limited to, chewable tablets, tablets, capsules, and syrups, which may be prepared in accordance with procedures described in Remington's Pharmaceutical Sciences (18$^{th}$ ed., Mack Publishing, Easton, Pa. (1990)). The oral formulation is prepared by mixing a pre-determined amount of the active compound and one or more pharmaceutically acceptable excipients in accordance with procedures well known in the related art.

Tablets and capsules are two most common forms of oral formulation, which may be either liquid or solid composition form. In general, the tablets and capsules are manufactured by mixing the active components with liquid or milled solid excipients, then press into pre-determined forms. The solid formulation may further include disintegrants, which increase solubility; and lubricants.

4.2 Formulation for Parental Administration

Parental formulations are those suitable for subcutaneous, intravenous (which includes bolus injection), intramuscular, and intraperitoneal injection. To this purpose, sterile injectable or suspension are required so as to prevent the recipients from microorganism infections. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

4.3 Transmembrane Formulation

Transmembrane formulations are those suitable for topical and transmucosal uses, which include but are not limited to, ophthalmic solutions, sprays, aerosols, creams, lotions, ointments, gels, solutions, suspensions, skin patches and the like. The patches include reservoir type and matrix type skin patches, and may adhere onto the skin for a certain period of time to allow the active component to be adsorbed into the subject's body.

For topical administration, a wide variety of dermatologically acceptable inert excipients well known to the art may be employed. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

For transmucosal administration, the pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

The present invention will now be described more specifically with reference to the following embodiments, which are provided for the purpose of demonstration rather than limitation.

EXAMPLES

Materials and Methods
Cell Lines and Culture

Cell lines used in the present disclosure include metastatic human breast cancer cell line MDA-MB-231; human pancreatic epithelial-like cell line PANC-1; and lymphatic-tropic cell line LN. Each cell lines were cultured and maintained in Dulbecco's modified Eagle media (DMEM) supplemented with 10% fetal calf serum, 100 IU/ml penicillin, 100 μg/ml streptomycin, and 2 mM glutamine in 5% $CO_2$ at 37° C., unless indicated otherwise.

Established LN Cell Line

The LN cell line was established by orthotopically injected $5\times10^5$ PANC-1 cells to the pancreas of SCID mice. After one month, mestastasis was found in lymph nodes, cancerous cells were then isolated from lymph nodes. The genomic DNA of the isolated cancer cells from lymph nodes were extracted and sent for genotyping analysis, which confirmed that LN cells were indeed derived from PANC-1 cells (data not shown). Cell surface expression analysis conducted by real-time PCR and western blot also confirmed that α-2,3 sialic acid and α-2,6 sialic acid were significantly overexpressed in LN cells (data not shown).

Experimental Animals

Athymic nude mice (BALB/cAnN.Cg-Foxn1nu/CrlNarl, 4-5 weeks old) were supplied from the Laboratory Animal Core Facility (BioLASCO Taiwan Co., Ltd) and given a standard laboratory diet and distilled $H_2O$ ad libitum and kept on a 12 h light/dark cycle at 22±2° C. All experimental protocols were approved by the Institutional Animal Care and Utilization Committee (IACUC), Academia Sinica, Taiwan, R.O.C.

Sialyltransferases Activity Assay

The enzymes analyzed in the present study included rat ST3Gal(I), rat ST3Gal(III), and human ST6Gal(I). Rat ST3Gal(I) and rat ST3Gal(Ill), were purchased from Calbiochem®, while human ST6Gal(I) was purchased from RnDSystems.com.

Sialyltransferase inhibition assay (α2,6-N-ST) was performed as follows: Sialyltransferase activity was determined by measuring the level of the end product of sialylated saccharides with reverse-phase HPLC. The assay mixtures contained the following components: 200 mM MES buffer; 100 mM NaCl; 0.5 mM EDTA; 0.01% Triton X-100; 1.4 mU ST3GALI; 2.5 mM T-antigen; 1 mM CMP-Neu5Ac and different concentration of Sialyltransferase inhibitors to a total volume of 50 μl. The assay mixture was incubated at 37° C. for 15 mins and then quenched by heating up to 101'C for 10 mins. The sialylated product was resolved by reversed-phase HPLC. Kinetic data were obtained by fitting the initial rate data to the nonlinear regression equation.

Sialyltransferase inhibition assay (α2,6-N-ST) was performed as follows: Sialyltransferase activity was determined by measuring the level of the end product of sialylated saccharides with reverse-phase HPLC. The assay mixtures contained the following components: 200 mM MES buffer; 100 mM NaCl; 0.5 mM EDTA; 0.01% Triton X-100; 1.4 mU ST6GALI; 25 μM Galβ1-4GlcNAc; 1 mM CMP-Neu5Ac and different concentration of Sialyltransferase inhibitors to a total volume of 50 μl. The assay mixture was incubated at 37° C. for 15 mins and then quenched by heating up to 101° C. for 10 mins. The sialylated product is resolved with reversed-phase HPLC. Kinetic data were obtained by fitting the initial rate data to the nonlinear regression equation.

Lith-O-Asp and AL-10, which were reported to have low inhibitory effects toward sialyltransferase (ST) were employed here as a comparative control.

Knockdown the Expression of ST3GAL(III)

Human breast cancer cells were seeded onto the 6-well plates to 40-60% confluent. The siRNAs against Human ST3GALIII (Invitrogen, as indicated in the following Table) were dissolved with DEPC water to form 20 μM solutions.

| Name of the Primer | Sequence | SEQ ID NO: |
|---|---|---|
| ST3GALIII (HSS143938) | 5'-GGACGCACAAUAUCCAGCGAGAGAA-3' | 1 |
| | 5'-UUCUCUCGCUGGAUAUUGUGCGUCC-3' | 2 |
| ST3GALIII (HSS143939) | 5'-GGAAGCUGGUGAAAGCUCGCGUCAU-3' | 3 |
| | 5'-AUGACGCGAGCUUUCACCAGCUUCC-3' | 4 |
| ST3GALIII (HSS143940) | 5'-GGGACUCUUGGUAUUUGUGCGCAAU-3' | 5 |
| | 5'-AUUGCGCACAAAUACCAAGAGUCCC-3' | 6 |

Lipofectamine RNAiMAX transfection reagent was diluted in Opti-MEM medium and siRNA was also diluted in Opti-MEM medium and mix with Lipofectamine RNAiMAX reagent in a 1:1 ratio and then added to cells. After 72 h, cells were harvested for further analysis.

Transwell Migration Assay

Migration assays were done using a transwell, in which a polycarbonate filter pre-coated with Matrigel (8-μm pores, Millicell; Millipore, Billerica, Mass.) was inserted therein. Cells were serum-starved for 24 h and then seeded ($5\times10^5$ cells per upper chamber) and treated with or without the present compound(s) (concentrations as indicated), and the assays were run for 6 h. Cells that had migrated to the underside of the inserted filter were stained with hematoxylin solution. The cells in the upper side of the inserted membrane were rubbed with a cotton swab. The migrated cells on the underside were pictured in a 200× magnification field and quantified.

MTT Assay

MTT assay is a colorimetric assay that measures the activity of enzymes (i.e., reductase) that reduce (3-(4,5-dimethylthiazol-2yl)-2,5-diphenyltetrazoliumbromide (MTT), a yellow tetrazole, to purple formazan, in living cells. This reduction only takes place when cells are alive; hence MTT assay is generally used to assess the viability and proliferation of cells. Briefly, cells were challenged with 10 or 20 μM of the tested compound for 48 or 72 hours. Then, MTT dye (500 μg/ml) was added and the reaction was allowed to proceed for 4 hours before being terminated by the addition of 500 μl of isopropanol. The absorbance of the solution at 570 nm was measured by spectrophotometer.

Inhibition of Tumor Genesis of MDA-MB-231 Cells in BALB/c Mice

BALB/c mice (4-5 weeks old) were subcutaneously injected with $1\times10^6$ MDA-MB-231 cells to the mammary fat pad on day 0. Tumors were allowed to grow in the mice until the size of the tumor reached 100 mm$^3$, and then the animals were randomly assigned to 3 groups (n=6-8 per group): tumor (vehicle) control, 10 mg/kg the present compound (e.g., FCW34 or FCW66) treatment group. The present compound was intraperitoneally (i.p.) injected to test animals every three days. The growth and metastasis of the tumors were observed by IVIS imaging system, and the metastasized tumor tissues were collected on day 60, and measured for the volume (V) using calipers and calculated by the formula $V=(L\times W^2)/2$, where L is the length and W is the width of tumor.

Inhibition of Pancreatic Tumor Growth in SCID Mice

SCID mice (6 weeks old) were orthotopically injected with $1\times10^5$ human pancreatic cells PANC-1 grown in glucose-containing or fructose-containing medium with or without the presence of the present compound (e.g., FCW34, 5 µM) on day 0. The progression of the tumor was followed by bioluminescence IVIS image analysis, and the test animals were then sacrificed by cervical dislocation after 14 weeks, and respective tumors and the liver sections were collected, and analyzed by histochemical staining with SNA lectin to measure 2,6-sialylation levels utilizing FACS analysis.

Inhibition of Melanoma Tumor Growth in C57BL Mice

Six C57BL mice (3-6 weeks old) were subcutaneously or intravenously injected with $5\times10^5$ primary melanoma cells (i.e., B16-F10/Luc cells) on day 0 and allowed the tumor to grow for 7 days to create primary or metastatic melanoma model. Then, the test compound (e.g., FCW393, 10 mg/Kg, i.p.) was administered by intraperitoneal injection at the interval of 3 times per week, until day 26 in each animal model. Tumor sizes were measured using calipers at designated days, and tumor volume was calculated using the formula: volume=width$^2$×length×0.52. The average body weight (BW) of the animals was measured daily, and the concentration of the test compound(s) (i.e., FCW393) in i.p. injection was adjusted proportionally to the BW respectively at the indicated dosage and time. After treatment, mice were sacrificed and their white blood cells (WBC), red blood cells (RBC), platelets (PLT), hemoglobin (HGB), hematocrit (HCT), mean corpuscular volume (MCV), mean corpuscular hemoglobin (MCH), and mean corpuscular hemoglobin concentration (MCHC) were respectively determined; their weights of lymph nodes, thymus, and spleen were measured; as well as the levels of aspartate aminotransferase (AST), analine aminotransferase (ALT), albumin, triglyceride, blood urea nitrogen (BUN), creatinine, and uric acid were measured.

Statistical Analysis

All data are presented as mean±standard deviation unless otherwise indicated. For multiple comparisons, analysis of variance (ANOVA) with Bonferroni adjustment was performed. A probability value of P<0.05 was considered to represent statistical significance.

Example 1 Synthesis of the Compound of Formula (1)

The compound of formula (I) were synthesized in accordance with schemes set forth in the following examples, the structures of the thus produced compounds were respectively confirmed by NMR spectra.

1.1 Synthesis of Compounds 1 to 15

In general, compounds 1 to 15 (i.e., compounds of formula (1-1)) were prepared by adding N$_3$ linker to the carboxy group of lithocholic acid, in which compound 1-1-9 was reacted with a N$_3$ linker (i.e., compounds 1a to 1e) in according to steps set forth in scheme 2. The N$_3$ linkers were synthesized in according to steps set forth in scheme 1.

Scheme 1:

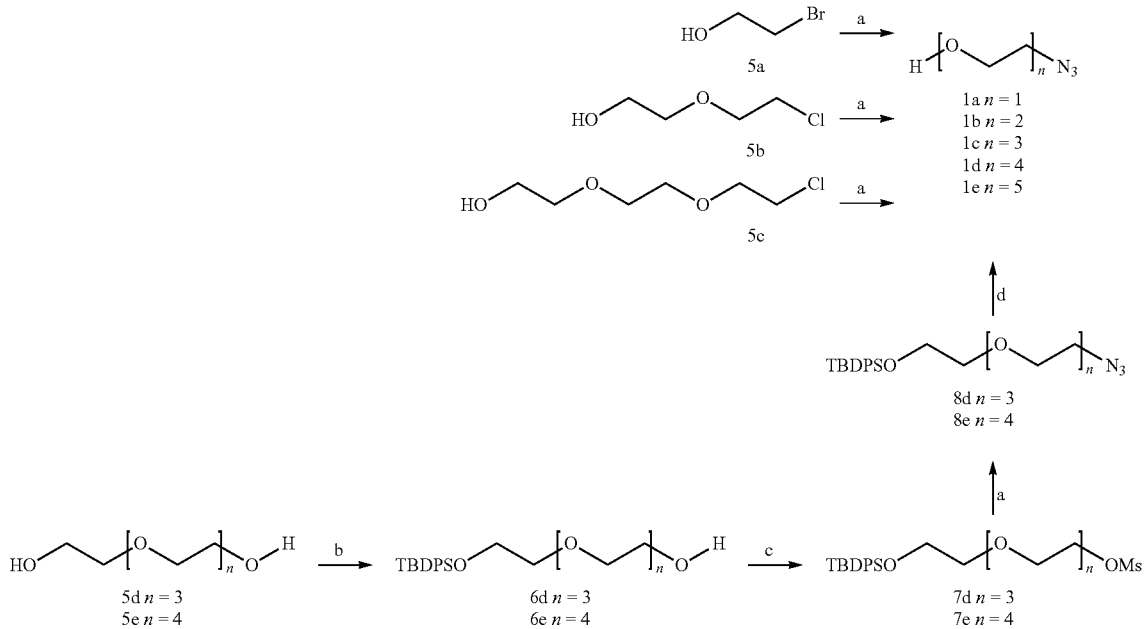

Reagents and conditions: (a) NaN$_3$, EtOH, reflux, 16 h (1a 90%, 1b 85%, 1c 90%, 8d 96%, 8e 92%), (b) TBDPSCl, imidazole, DMF, 0° C. to rt, 12 h (6d 45%, 6e 33%), (c) MsCl, N-methyl morpholine, THF, 0° C. to rt, 3 h (7d 95%, 7e 92%), (d) TBAF (1M in THF), THF, 0° C. to rt, 12 h (1d 90%, 1e 85%).

Synthesis of Compounds 1a to 1e

Compounds 1a to 1e were respectively synthesized in accordance with the general procedures I or II, as described below.

General Procedure I. NaN$_3$ (24.0 mmol) was added to a stirred solution of halogen substituted ethanol (8.0 mmol) in 10 mL EtOH. The reaction was heated to reflux for 16 h. The reaction mixture was treated with water. After extraction with ethyl acetate (EA) (3×), the combined organic layers were washed with H$_2$O (2×) and brine (2×) and dried over MgSO$_4$ prior to filtration, and concentration under reduced pressure yielded the crude product. The residue was purified by flash column chromatography to produce the product as oil.

General Procedure 11. Imidazole (2.57 mmol) was added to a stirred 0° C. solution of diol compound (5.15 mmol) in 5 mL dimethylformamide (DMF). The reaction was stirred at 0° C. for 1 h, then added tert-butyl(chloro)diphenylsilane (TBDPSCl) (2.57 mmol) dropwisely. The reaction was stirred at room temperature for 12 h. The reaction mixture was quenched with H$_2$O. After extraction with EA (3×), the combined organic layers were washed with H$_2$O (2×) and brine (2×) and dried over MgSO$_4$ prior to filtration, and concentration under reduced pressure yielded the crude product. The residue was purified by flash column chromatography to afford the TBDPS protected alcohol as oil.

To a stirred 0° C. solution of TBDPS protected alcohol (1.68 mmol) in 10 mL dry tetrahydrofuran (THF), N-methyl morpholine (2.51 mmol) was added dropwisely. The reaction was stirred at 0° C. for 30 min, then methanesulfonyl chloride (3.35 mmol) was added dropwisely. The reaction was stirred at room temperature for 3 h. The reaction mixture was quenched with H$_2$O. After extracting with EA (3×), the combined organic layers were washed with H$_2$O (2×) and brine (2×) and dried over MgSO$_4$ prior to filtration, and concentration under reduced pressure yielded the crude product. The residue was purified by flash column chromatography to afford the TBDPS protected alcohol with mesylate OMs leaving group compound as oil.

Synthesis of Compound 1a

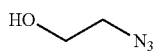

As described in general procedure I. Yield 90% (oil), 1H NMR (400 MHz, CDCl$_3$): δ 3.75 (t, J=4.8 Hz, 2H), 3.41 (t, J=4.8 Hz, 2H), 2.02 (s, 1H). 13C NMR (100 MHz, CDCl$_3$): δ 61.4, 53.5.

Synthesis of Compound 1b

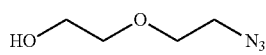

As described in general procedure I. Yield 85% (oil), 1H NMR (400 MHz, CDCl$_3$): δ 3.63-3.62 (m, 2H), 3.58 (t, J=4.8 Hz, 2H), 3.49 (t, J=4.8 Hz, 2H), 3.31 (t, J=4.8 Hz, 2H), 2.86 (s, 1H). 13C NMR (100 MHz, CDCl3): δ 72.2, 69.6, 61.3, 50.4. HRMS calcd for C$_4$H$_{10}$O$_2$N$_3$ (M+H)+, 132.0773; found, 132.0774.

Synthesis of Compound 1c

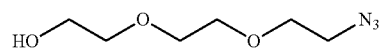 [SMILES: [N-]=[N+]=NCCOCCOCCO]

As described in general procedure I. Yield 90% (oil), 1H NMR (400 MHz, CDCl$_3$): δ 3.71-3.66 (m, 4H), 3.63-3.61 (m, 4H), 3.59-3.54 (m, 3H), 3.34 (t, J=4.8 Hz, 1H), 2.66-2.64 (m, 1H). 13C NMR (100 MHz, CDCl$_3$): δ 72.5, 71.2, 70.5, 70.2, 61.4, 50.6. HRMS calcd for C$_6$H$_{14}$O$_3$N$_3$ (M+H)+, 176.1035; found, 176.1034.

Synthesis of Compound Id

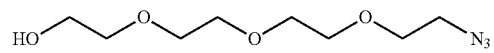

As described in general procedure II. Yield 40% over four steps (oil), 1H NMR (400 MHz, CDCl$_3$): δ 3.65 (t, J=4.8 Hz, 2H), 3.61-3.59 (m, 10H), 3.54-3.52 (m, 2H), 3.32 (t, J=4.8 Hz, 2H), 2.77 (brs, 1H). 13C NMR (100 MHz, CDCl$_3$): δ 72.4, 70.6, 70.5, 70.4, 70.2, 69.9, 61.6, 50.5. HRMS calcd for C$_8$H$_{18}$O$_4$N$_3$ (M+H)+, 220.1297; found, 220.1300.

Synthesis of Compound 1e

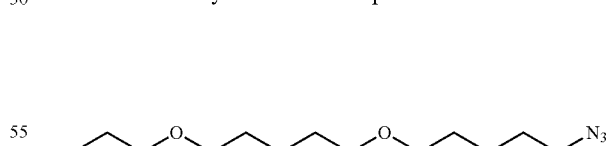

As described in general procedure II. Yield 24% over four steps (oil), 1H NMR (400 MHz, CDCl$_3$): δ 3.72 (t, J=4.4 Hz, 2H), 3.68-3.66 (m, 14H), 3.61-3.59 (m, 2H), 3.40 (t, J=5.2 Hz 2H), 2.42 (s, brs, 1H). 13C NMR (100 MHz, CDCl$_3$): δ 72.6, 70.6, 70.5, 70.1, 69.9, 61.6, 50.6. HRMS calcd for C$_{10}$H$_{22}$O$_5$N$_3$ (M+H)+, 264.1559; found, 264.1555.

Scheme 2:
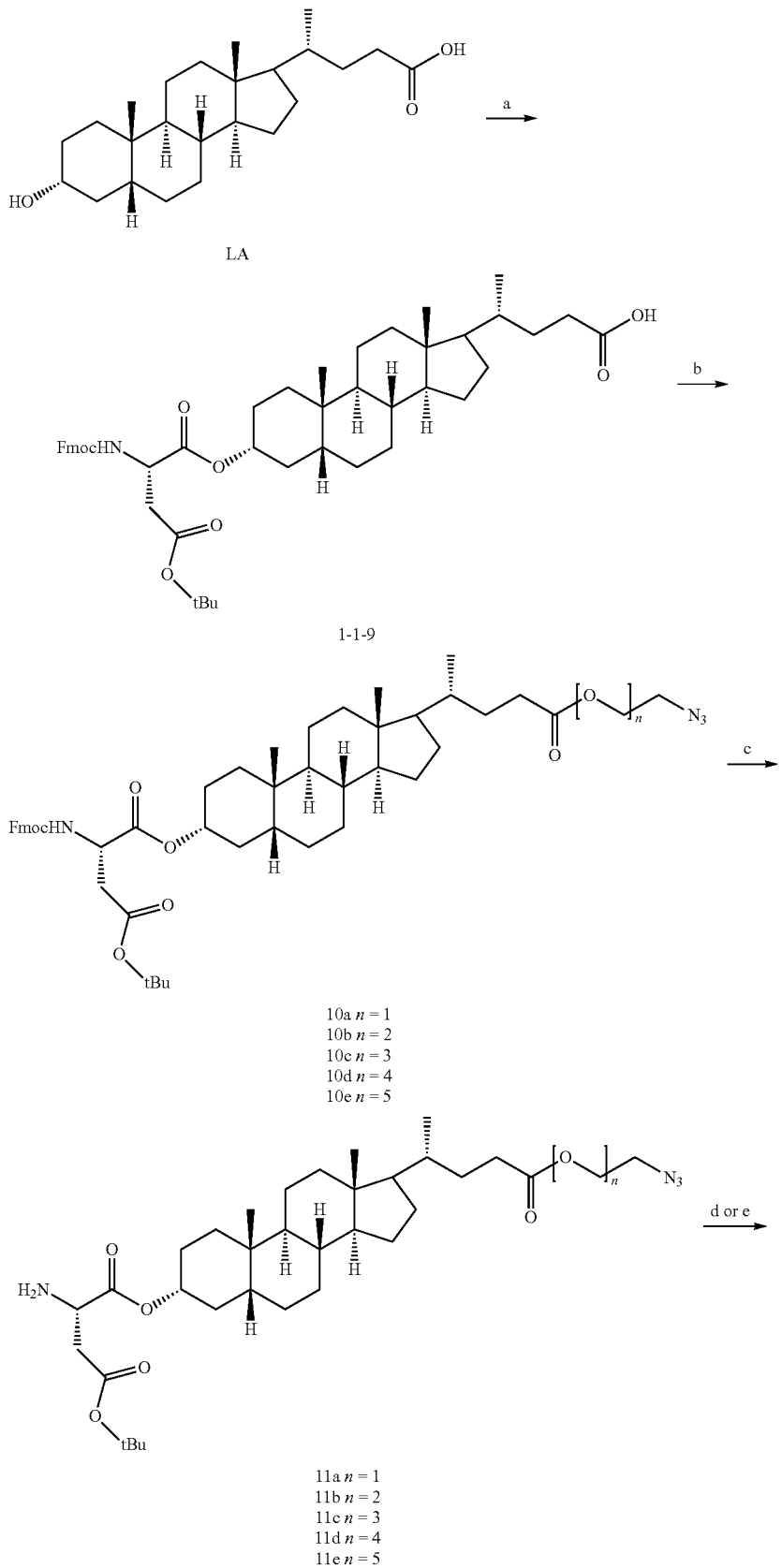

-continued

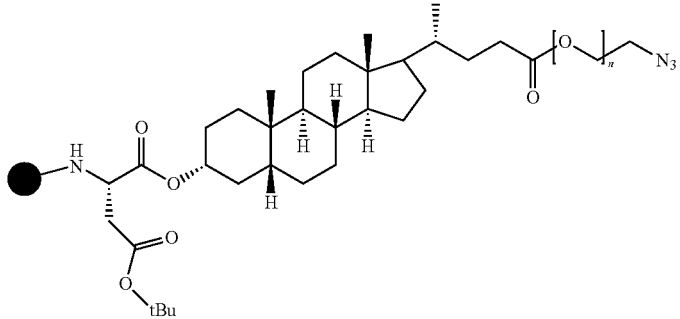

| | |
|---|---|
| 12aA n = 1 | 12aB n = 1 |
| 12bA n = 2 | 12bB n = 2 |
| 12cA n = 3 | 12cB n = 3 |
| 12dA n = 4 | 12dB n = 4 |
| 12eA n = 5 | 12eB n = 5 |

12aC n = 1
12bC n = 2
12cC n = 3
12dC n = 4
12eC n = 5

↓ f

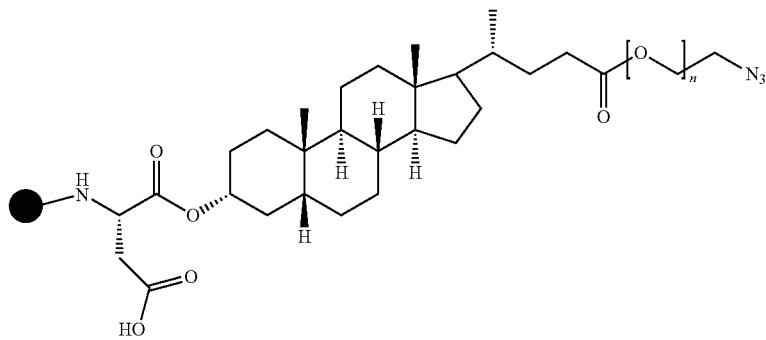

| | |
|---|---|
| 1, n = 1 | 6, n = 1 |
| 2, n = 2 | 7, n = 2 |
| 3, n = 3 | 8, n = 3 |
| 4, n = 4 | 9, n = 4 |
| 5, n = 5 | 10, n = 5 |

11, n = 1
12, n = 2
13, n = 3
14, n = 4
15, n = 5

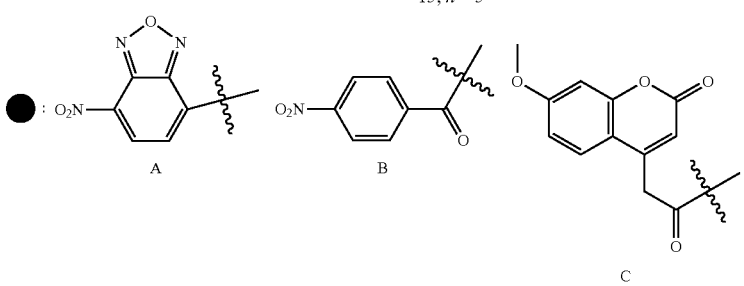

Reagents and conditions: (a) Fmoc—L-Asp(OtBu)—OH, DCC, DMAP, CH$_2$Cl$_2$, rt, 8 h (50%); (b) 1a or 1b or 1c or 1d or 1e, DCC, DMAP, CH$_2$Cl$_2$, rt, 3 h (10a 88%, 10b 86%, 10c 80%, 10d 71%, 10e 75%); (c) DBU, CH$_2$Cl$_2$, rt, 2 h (11a 93%, 11b 92%, 11c 85%, 11d 81%, 11e 80%); (d) NBD—Cl, THF—EtOH, rt, 2 days (12aA 48%, 12bA 35%, 12cA 40%, 12dA 38%, 12eA 40%); (e) p-nitrobenzoic acid or 2-(7-methoxy-2-oxo-2H-chromen-4-yl)acetic acid, HBTU, DIPEA, CH$_2$Cl$_2$, rt. 3 h (12aB 98%, 12bB 95%, 12cB 85%, 12dB 90%, 12eB 88%, 12aC 95%, 12bC 90%, 12cC 88%, 12dC 93%, 12eC 85%); (f) TFA, H$_2$O, CH$_2$Cl$_2$, rt, 2 h (1 85%, 2 82%, 3(FCW34) 91%, 4(FCW66) 88%, 5 85%, 6 80%, 7 82%, 8 90%, 9 82%, 10 84%, 11 90%, 12 82%, 13 85%, 14 80%, 15 82%).

Synthesis of Compound 1-1-9

To a stirred solution of lithocholic acid (LA) (13.3 mmol) and Fmoc-L-Asp(O-tBu)-OH (15.9 mmol) in 150 mL CH$_2$Cl$_2$, N,N'-dicyclohexylcarbodiimide (DCC) (15.9 mmol) and 4-dimethylaminopyridine (DMAP) (4.0 mmol) were added. The reaction was stirred at room temperature for 8 h. After reaction, removed solid by filtration, and the filtrate was extracted with CH$_2$Cl$_2$ (3×), the combined organic layers were washed with H$_2$O (2×) and brine (2×) and dried over MgSO$_4$ prior to filtration, reduced pressure concentration resulted in the crude product. The residue was purified by flash column chromatography to afford the target product as powder.

Synthesis of Compounds 10a to 10e

In a flask, mixed compound 1-1-9 (1.30 mmol) and a N$_3$ linker (i.e., any compounds 1a to 1e) (1.69 mmol) in 30 mL CH$_2$Cl$_2$, then DCC (1.69 mmol) and DMAP (0.39 mmol) were added to the mixed solution. The reaction was stirred at room temperature for 3 h. After reaction, removed solid by filtration, and the filtrate was extracted with CH$_2$Cl$_2$ (3×), the combined organic layers were washed with H$_2$O (2×) and brine (2×) and dried over MgSO$_4$ prior to filtration, and concentration under reduced pressure yielded the crude products compounds. The residue was purified by flash column chromatography to afford the target products, compounds 10a to 10e, as powder.

Synthesis of Compounds 11a to 11e

To a stirred solution of the Fmoc-protected compounds 10a to 10d (0.84 mmol) in 10 mL CH$_2$Cl$_2$, 1,8-diazabicyclo[5.4.0]undec-7-ene (DBU) (1.00 mmol) was added and the mixture was stirred at room temperature for 2 h. Reaction mass was concentrated and product was purified by flash column chromatography to yield the desired compounds 11a to 11e.

Synthesis of Compounds 12aA to 12eA

To a stirred solution of any free amine compounds 11a to 11e (0.67 mmol) and nitrobenzoxadiazole chloride (NBD-Cl) (0.81 mmol) in 10 mL THF and 10 mL EtOH, NaHCO$_3$ (1.35 mmol) was added. The reaction was stirred in the dark at room temperature for 2 days. The reaction mixture was treated with H$_2$O. After extraction with EA (3×), the combined organic layers were washed with H$_2$O (2×) and brine (2×) and dried over MgSO$_4$ prior to filtration, and concentration under reduced pressure yielded the crude product. The residue was purified by flash column chromatography to produce the target product, compounds 12aA to 12eA.

Synthesis of Compounds 12aB to 12eB

To a stirred solution of any free amine compounds 11a to 11e (0.31 mmol) and nitrobenzoic acid (NB) (0.37 mmol) in 10 mL CH$_2$Cl$_2$, O-(benzotriazol-1-yl)-N,N,N',N'-tetramethyluronium hexafluorophosphate (HBTU) (0.46 mmol) and N,N-diisopropylethylamine (DIPEA) (0.92 mmol) were added dropwisely. The reaction was stirred at room temperature for 3 h. The reaction mixture was treated with H$_2$O. After extraction with CH$_2$Cl$_2$ (3×), the combined organic layers were washed with H$_2$O (2×) and brine (2×) and dried over MgSO$_4$ prior to filtration, concentration under reduced pressure yielded the crude product. The residue was purified by flash column chromatography to produce the target products, i.e., compounds 12aB to 12eB.

Synthesis of Compounds 12aC to 12eC

Synthetic procedures for compounds 12aC to 12eC were similar to those of compounds 12aB to 12eB except the reactant nitrobenzoic acid (NB) with replaced by 7-methoxycoumarin-4-acetic acid.

Synthesis of Compounds 1-15

Compounds 1-5, 6-10, and 11-15 were prepared by removing the protective tBu group from the compounds 12aA to 12eA, 12aB to 12eB, 12aC to 12eC, respectively. In general, the tBu protected compound (0.1 mmol) was dissolved in 5 mL trifluoroacetic acid (TFA) with ddH$_2$O (100 μL) and the reaction mixture was stirred at room temperature for 2 h. The TFA solution was then removed on rotary evaporator. The crude product was purified by reverse phase HPLC (RP-HPLC) (solvent A: water+0.1% TFA; solvent B: acetonitrile+0.05% TFA). The final product was obtained as oil or solid upon lyophilization.

(3S)-4-(((3R,5R,8R,9S,10S,13R,14S)-17-((R)-5-(2-azidoethoxy)-5-oxo pentan-2-yl)-10,13-dimethyl-hexadecahydro-1H-cyclopenta[a]phenanthren-3-yl)oxy)-3-((7-nitrobenzo[c][1,2,5]oxadiazol-4-yl)amino)-4-oxobutanoic acid (Compound 1)

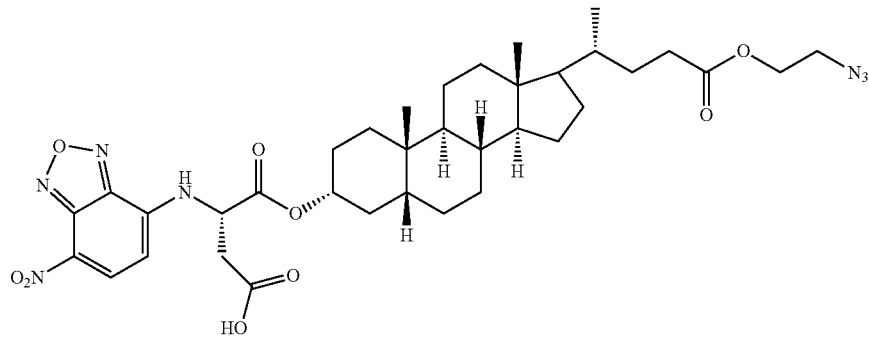

Yield 17% over five steps (powder), mp 78-79° C., 1H NMR (400 MHz, CDCl$_3$): δ 8.46 (d, J=8.4 Hz, 1H), 6.97 (d, J=8.4 Hz, 1H), 6.26 (d, J=8.4 Hz, 1H), 4.87-4.80 (m, 2H), 4.23 (t, J=4.8 Hz, 2H), 3.46 (t, J=4.8 Hz, 2H), 3.21-3.06 (m, 2H), 2.42-2.34 (m, 1H), 2.29-2.21 (m, 1H), 1.95-1.89 (m, 1H), 1.86-1.75 (m, 5H), 1.67-1.64 (m, 1H), 1.55-1.52 (m, 2H), 1.50-1.29 (m, 8H), 1.28-1.20 (m, 3H), 1.16-0.97 (m, 6H), 0.91-0.88 (sd, J=6.4 Hz, 6H), 0.62 (s, 3H). 13C NMR (100 MHz, CDCl$_3$): δ 174.2, 173.3, 168.6, 144.3, 143.8, 142.3, 135.7, 125.5, 100.0, 77.8, 62.9, 56.4, 55.9, 52.6, 49.8, 42.7, 41.9, 40.5, 40.1, 35.7, 35.3, 34.8, 34.6, 32.0, 31.1, 30.9, 28.1, 26.9, 26.4, 26.3, 24.2, 23.3, 20.8, 18.2, 12.0. HRMS calcd for C$_{36}$H$_{48}$N$_7$O$_9$ (M−H)−, 722.3514; found, 722.3510.

(3S)-4-(((3R,5R,8R,9S,10S,13R,14S)-17-((R)-5-(2-(2-azidoethoxy)ethoxy)-5-oxopentan-2-yl)-10,13-dimethylhexadecahydro-1H-cyclopenta[a]phenanthren-3-yl)oxy)-3-((7-nitrobenzo[c][1,2,5]oxadiazol-4-yl)amino)-4-oxobutanoic acid (Compound 2)

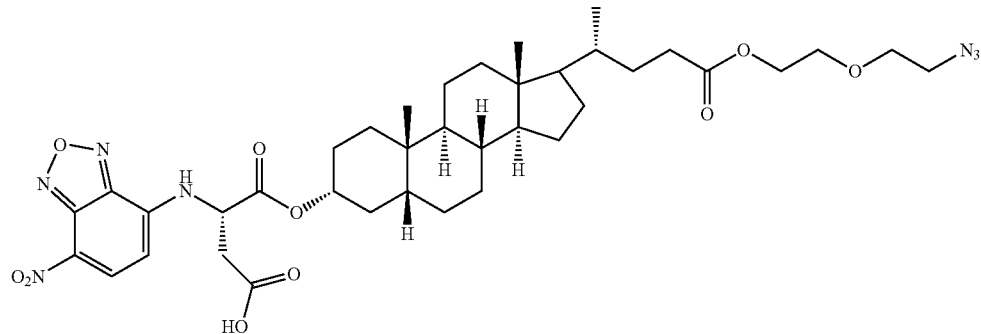

Yield 11% over five steps (powder), mp 75-76° C., 1H NMR (400 MHz, CDCl$_3$): δ 8.45 (d, J=8.4 Hz, 1H), 7.02 (d, J=7.6 Hz, 1H), 6.27 (d, J=8.4 Hz, 1H), 44.86-4.81 (m, 2H), 4.22 (t, J=4.8 Hz, 2H), 3.70-3.65 (m, 4H), 3.37 (t, J=4.8 Hz, 2H), 3.20-3.05 (m, 2H), 2.40-2.33 (m, 1H), 2.27-2.19 (m, 1H), 1.94-1.91 (m, 1H), 1.86-1.73 (m, 5H), 1.67-1.64 (m, 1H), 1.54-1.52 (m, 2H), 1.44-1.29 (m, 8H), 1.27-1.19 (m, 3H), 1.15-0.97 (m, 6H), 0.90-0.86 (sd, J=6.4 Hz, 6H), 0.61 (s, 3H). 13C NMR (100 MHz, CDCl$_3$): δ 174.5, 173.5, 168.7, 144.3, 143.8, 142.3, 135.8, 125.3, 100.0, 77.7, 70.0, 69.2, 63.3, 56.4, 56.0, 52.6, 50.6, 42.7, 41.9, 40.5, 40.0, 35.7, 35.3, 34.8, 34.5, 32.0, 31.1, 30.9, 28.1, 26.9, 26.4, 26.3, 24.1, 23.2, 20.8, 18.2, 12.0. HRMS calcd for $C_{38}H_{52}N_7O_{10}$ (M−H)−, 766.3776; found, 766.3767.

(3S)-4-(((3R,5R,8R,9S,10S,13R,14S)-17-((R)-5-(2-(2-(2-azidoethoxy)ethoxy)ethoxy)-5-oxopentan-2-yl)-10,13-dimethylhexadecahydro-1H-cyclopenta[a]phenanthren-3-yl)oxy)-3-((7-nitrobenzo[c][1,2,5]oxadiazol-4-yl)amino)-4-oxobutanoic acid (Compound 3)—FCW34

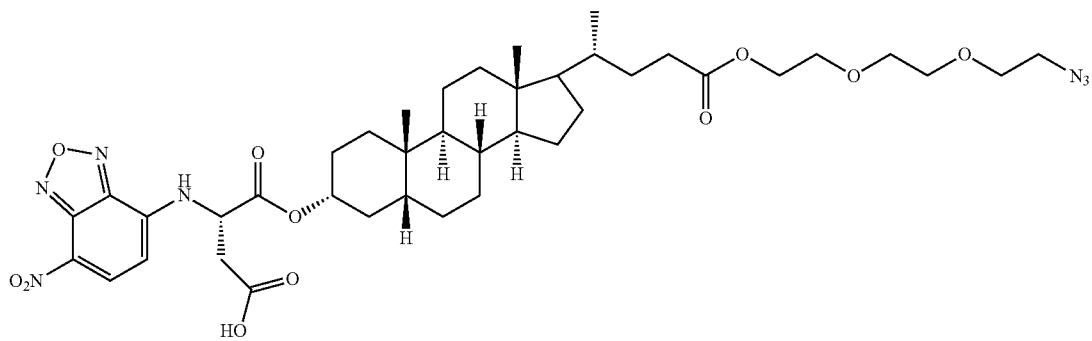

Yield 12% over five steps (powder), mp 71-73° C., 1H NMR (400 MHz, CDCl$_3$): δ 8.46 (d, J=8.8 Hz, 1H), 6.98 (d, J=6.0 Hz, 1H), 6.27 (d, J=8.8 Hz, 1H), 4.87-4.81 (m, 2H), 4.21 (t, J=5.2 Hz, 2H), 3.71-3.66 (m, 8H), 3.38 (t, J=5.2 Hz, 2H), 3.19-3.05 (m, 2H), 2.40-2.32 (m, 1H), 2.26-2.18 (m, 1H), 1.95-1.92 (m, 1H), 1.86-1.72 (m, 5H), 1.67-1.63 (m, 1H), 1.55-1.52 (m, 2H), 1.45-1.29 (m, 8H), 1.27-1.19 (m, 3H), 1.15-0.97 (m, 6H), 0.91-0.87 (sd, J=6.4 Hz, 6H), 0.61 (s, 3H). 13C NMR (100 MHz, CDCl$_3$): δ 174.5, 172.9, 168.6, 144.3, 143.8, 142.3, 135.7, 125.4, 100.0, 77.7, 70.7, 70.6, 70.1, 69.3, 63.4, 56.4, 55.9, 52.6, 50.7, 42.7, 41.9, 40.5, 40.1, 35.7, 35.3, 34.8, 34.6, 32.0, 31.9, 31.1, 30.9, 28.2, 26.9, 26.5, 26.4, 26.3, 24.2, 23.3, 20.8, 18.3, 12.0. HRMS calcd for $C_{40}H_{57}N_7O_{11}Na$ (M+Na)+, 834.4014; found, 834.4014.

(3S)-4-(((3R,5R,8R,9S,10S,13R,14S)-17-((R)-1-azido-13-oxo-3,6,9,12-tetraoxaheptadecan-6-yl)-10,13-dimethylhexadecahydro-1H-cyclopenta[a]phenanthren-3-yl)oxy)-3-((7-nitrobenzo[c][1,2,5]oxadiazol-4-yl)amino)-4-oxobutanoic acid
(Compound 4)-FCW66

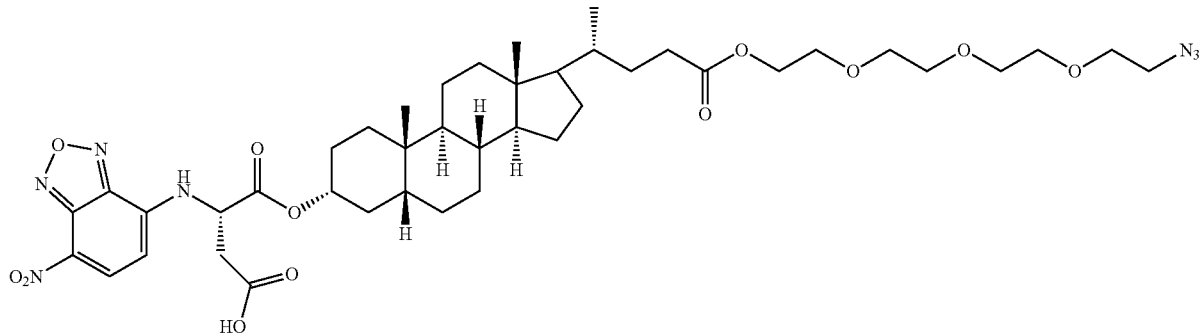

Yield 10% over five steps (oil), 1H NMR (500 MHz, CDCl$_3$): δ 8.44 (d, J=8.5 Hz, 1H), 7.16 (brs, 1H), 6.26 (d, J=8.0 Hz, 1H), 4.81 (brs, 2H), 4.19 (t, J=4.5 Hz, 2H), 3.68-3.64 (m, 12H) 3.70 (t, J=5.0 Hz, 2H), 3.14-3.07 (m, 2H), 2.37-2.31 (m, 1H), 2.24-2.18 (m, 1H), 1.92-1.90 (m, 1H), 1.85-1.72 (m, 5H), 1.64 (brs, 1H), 1.53-1.52 (m, 2H), 1.43-1.27 (m, 8H), 1.25-1.19 (m, 3H), 1.13-0.96 (m, 6H), 0.89-0.85 (sd, J=6.0 Hz, 6H), 0.60 (s, 3H). 13C NMR (125 MHz, CDCl$_3$): δ 174.4, 172.8, 168.8, 144.3, 143.8, 142.6, 135.8, 125.2, 100.1, 77.6, 70.7, 70.6, 70.5, 70.0, 69.2, 63.4, 56.4, 55.9, 52.9, 50.7, 42.7, 41.9, 40.5, 40.1, 35.7, 35.3, 34.8, 34.6, 32.0, 31.1, 30.9, 28.1, 26.9, 26.4, 26.3, 24.1, 23.3, 20.8, 18.3, 12.0. HRMS calcd for $C_{42}H_{60}N_7O_{12}$ (M–H)–, 854.4300; found, 854.4293.

(3S)-4-(((3R,5R,8R,9S,10S,13R,14S)-17-((R)-1-azido-16-oxo-3,6,9,12,15-pentaoxaicosan-19-yl)-10,13-dimethylhexadecahydro-1H-cyclopenta[a]phenanthren-3-yl)oxy)-3-((7-nitrobenzo[c][1,2,5]oxadiazol-4-yl)amino)-4-oxobutanoic acid
(Compound 5)

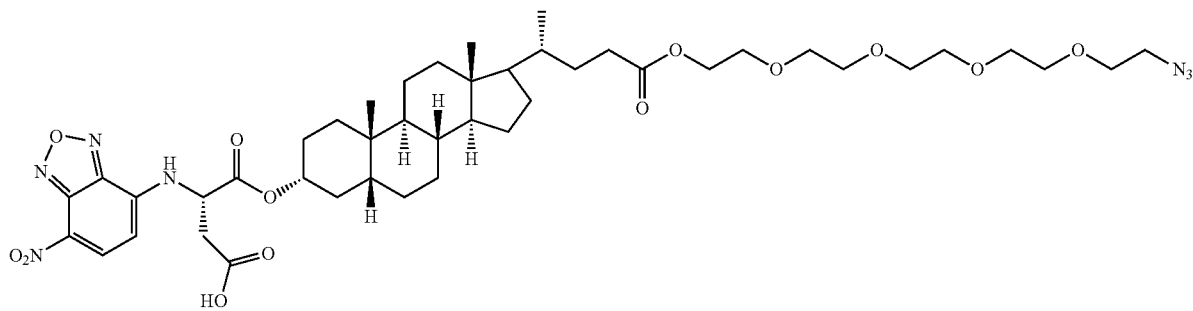

Yield 10% over five steps (oil), 1H NMR (500 MHz, CDCl$_3$): δ 8.44 (d, J=8.5 Hz, 1H), 6.26 (d, J=7.5 Hz, 1H), 4.81 (brs, 2H), 4.20 (t, J=4.5 Hz, 2H), 3.68-3.63 (m, 16H) 3.37 (t, J=4.5 Hz, 2H), 3.14-3.06 (m, 2H), 2.37-2.31 (m, 1H), 2.24-2.18 (m, 1H), 1.92-1.90 (m, 1H), 1.85-1.75 (m, 5H), 1.65 (brs, 1H), 1.52-1.51 (m, 2H), 1.40-1.31 (m, 8H), 1.22-1.19 (m, 3H), 1.13-0.96 (m, 6H), 0.89-0.86 (sd, J=6.0 Hz, 6H), 0.60 (s, 3H). 13C NMR (125 MHz, CDCl$_3$): δ 174.4, 168.8, 144.3, 143.8, 142.6, 135.8, 125.1, 100.1, 77.5, 70.6, 70.5, 70.0, 69.2, 63.4, 56.5, 55.9, 53.0, 50.7, 42.7, 41.9, 40.5, 40.1, 35.7, 35.3, 34.8, 34.6, 32.0, 31.0, 30.9, 28.1, 26.9, 26.4, 26.3, 24.1, 23.2, 20.8, 18.3, 12.0. HRMS calcd for $C_{44}H_{64}N_7O_{13}$ (M–H)–, 898.4562; found, 898.4556.

(3S)-4-(((3R,5R,8R,9S,10S,13R,14S)-17-((R)-5-(2-azidoethoxy)-5-oxopentan-2-yl)-10,13-dimethyl-hexadecahydro-1H-cyclopenta[a]phenanthren-3-yl)oxy)-3-(4-nitrobenzamido)-4-oxobutanoic acid
(Compound 6)

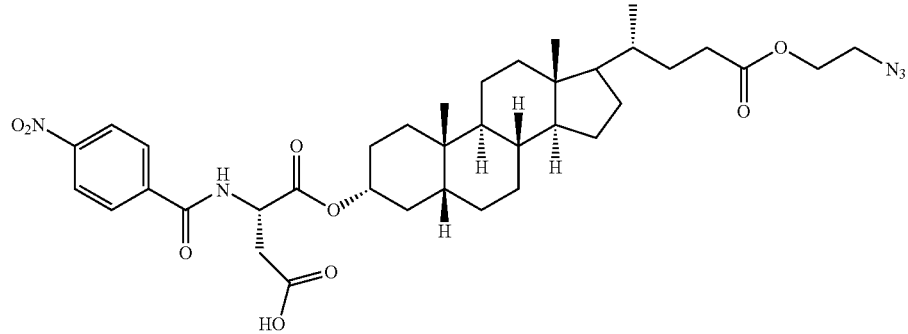

Yield 32% over five steps (powder), mp 61-62° C., 1H NMR (400 MHz, CDCl$_3$): δ 8.29 (d, J=8.4 Hz, 2H), 7.97 (d, J=8.4 Hz, 2H), 7.37 (d, J=7.6 Hz, 1H), 5.00-4.97 (m, 1H), 4.86-4.80 (m, 1H), 4.24 (t, J=5.2 Hz, 2H), 3.47 (t, J=5.2 Hz, 2H), 3.17 (dd, J=17.4 Hz, 4.0 Hz, 1H), 3.06 (dd, J=17.2 Hz, 4.0 Hz, 1H), 2.43-2.36 (m, 1H), 2.31-2.23 (m, 1H), 1.98-1.95 (m, 1H), 1.91-1.80 (m, 5H), 1.68-1.66 (m, 1H), 1.57-1.54 (m, 2H), 1.43-1.37 (m, 8H), 1.30-1.23 (m, 3H), 1.19-0.98 (m, 6H), 0.93-0.91 (sd, J=7.6 Hz, 6H), 0.65 (s, 3H). 13C NMR (100 MHz, CDCl$_3$): δ 174.0, 169.8, 165.2, 149.9, 139.1, 128.4, 123.8, 62.8, 56.4, 55.9, 49.8, 49.3, 42.7, 41.9, 40.4, 40.0, 35.7, 35.3, 34.8, 34.5, 32.0, 31.0, 30.8, 28.1, 26.9, 26.4, 26.2, 24.1, 23.2, 20.8, 18.2, 12.0. HRMS calcd for C$_{37}$H$_{51}$N$_5$O$_9$Na (M+Na)+, 732.3584; found, 732.3593.

(3S)-4-(((3R,5R,8R,9S,10S,13R,14S)-17-((R)-5-(2-(2-azidoethoxy)ethoxy)-5-oxopentan-2-yl)-10,13-dimethylhexadecahydro-1H-cyclopenta[a]phenanthren-3-yl)oxy)-3-(4-nitrobenzamido)-4-oxobutanoic acid (Compound 7)

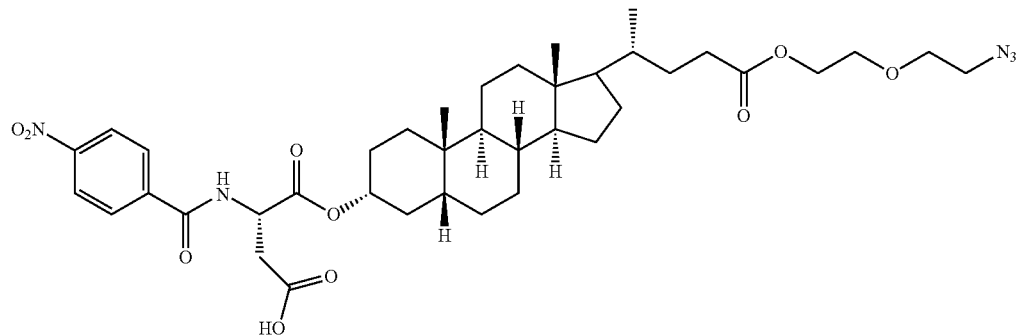

Yield 30% over five steps (powder), mp 57-58° C., 1H NMR (400 MHz, CDCl$_3$): δ 8.26 (d, J=8.8 Hz, 2H), 7.95 (d, J=8.4 Hz, 2H), 7.34 (d, J=6.8 Hz, 1H), 4.97-4.95 (m, 1H), 4.83-4.77 (m, 1H), 4.21 (t, J=4.6 Hz, 2H), 3.70-3.64 (m, 4H), 3.37 (t, J=5.2 Hz, 2H), 3.16-3.02 (m, 2H), 2.40-2.33 (m, 1H), 2.27-2.19 (m, 1H), 1.95-1.92 (m, 1H), 1.89-1.74 (m, 5H), 1.65-1.63 (m, 1H), 1.55-1.52 (m, 2H), 1.40-1.27 (m, 8H), 1.24-1.20 (m, 3H), 1.16-1.00 (m, 6H), 0.90-0.87 (sd, J=6.4 Hz, 6H), 0.62 (s, 3H). 13C NMR (100 MHz, CDCl$_3$): δ 174.4, 169.8, 165.3, 149.9, 139.1, 128.4, 123.8, 70.0, 69.2, 63.2, 56.4, 56.0, 50.6, 49.3, 42.7, 41.9, 40.4, 40.1, 35.7, 35.3, 34.9, 34.6, 32.0, 31.1, 30.9, 28.1, 26.9, 26.4, 26.3, 24.1, 23.3, 20.8, 18.3, 12.0. HRMS calcd for C$_{39}$H$_{55}$N$_5$O$_{10}$Na (M+Na)+, 776.3847; found, 776.3840.

(3S)-4-(((3R,5R,8R,9S,10S,13R,14S)-17-((R)-5-(2-(2-(2-azidoethoxy)ethoxy) ethoxy)-5-oxopentan-2-yl)-10,13-dimethylhexadecahydro-1H-cyclopenta[a]phenanthren-3-yl)oxy)-3-(4-nitrobenzamido)-4-oxobutanoic acid (Compound 8)

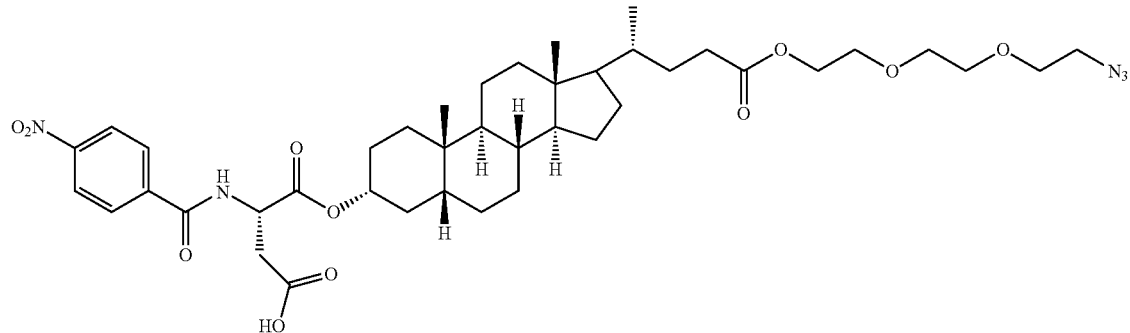

Yield 24% over five steps (powder), mp 52-53° C., 1H NMR (400 MHz, CDCl$_3$): δ 8.27 (d, J=8.8 Hz, 2H), 7.95 (d, J=8.4 Hz, 2H), 7.36 (d, J=7.2 Hz, 1H), 4.98-4.95 (m, 1H), 4.83-4.77 (m, 1H), 4.20 (t, J=4.8 Hz, 2H), 3.70-3.65 (m, 8H), 3.37 (t, J=4.8 Hz, 2H), 3.16-3.00 (m, 2H), 2.39-2.32 (m, 1H), 2.26-2.18 (m, 1H), 1.95-1.92 (m, 1H), 1.89-1.73 (m, 5H), 1.66-1.64 (m, 1H), 1.55-1.52 (m, 2H), 1.40-1.26 (m, 8H), 1.23-1.16 (m, 3H), 1.14-0.96 (m, 6H), 0.90-0.87 (sd, J=6.4 Hz, 6H), 0.62 (s, 3H). 13C NMR (100 MHz, CDCl$_3$): δ 174.4, 169.8, 165.2, 149.8, 139.1, 128.4, 123.8, 70.7, 70.6, 70.1, 69.3, 63.4, 56.4, 56.0, 50.7, 49.3, 42.7, 41.9, 40.4, 40.1, 35.7, 35.3, 34.9, 34.6, 32.0, 31.1, 30.9, 28.1, 27.0, 26.4, 26.3, 24.1, 23.3, 20.8, 18.3, 12.0. HRMS calcd for $C_{41}H_{59}N_5O_{11}Na$ (M+Na)+, 820.4109; found, 820.4103.

(3S)-4-(((3R,5R,8R,9S,10S,13R,14S)-17-((R)-1-azido-13-oxo-3,6,9,12-tetraoxaheptadecan-16-yl)-10,13-dimethylhexadecahydro-1H-cyclopenta[a]phenanthren-3-yl)oxy)-3-(4-nitrobenzamido)-4-oxobutanoic acid (Compound 9)

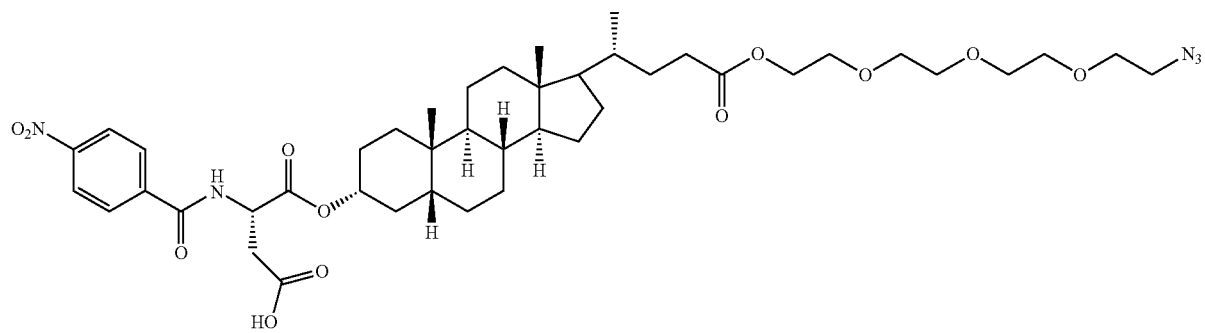

Yield 21% over five steps (oil), 1H NMR (400 MHz, CDCl$_3$): δ 8.27 (d, J=8.8 Hz, 2H), 7.96 (d, J=8.4 Hz, 2H), 7.36 (d, J=7.6 Hz, 1H), 4.7-4.96 (m, 1H), 4.80-4.79 (m, 1H), 3.72-3.58 (m, 14H), 3.38 (t, J=4.8 Hz, 2H), 3.18-2.98 (m, 2H), 2.36-2.33 (m, 1H), 2.27-2.20 (m, 1H), 1.95-1.92 (m, 1H), 1.89-1.78 (m, 5H), 1.67-1.66 (m, 1H), 1.55-1.52 (m, 2H), 1.40-1.34 (m, 8H), 1.23-1.17 (m, 3H), 1.15-0.97 (m, 6H), 0.91-0.87 (sd, J=4.0 Hz, 6H), 0.62 (s, 3H). 13C NMR (100 MHz, CDCl3): δ 175.3, 174.4, 169.9, 165.3, 149.8, 139.1, 128.5, 123.8, 72.4, 70.6, 70.5, 70.2, 70.0, 69.2, 63.4, 61.6, 56.4, 55.9, 50.6, 49.3, 42.7, 41.9, 40.4, 40.1, 36.1, 35.7, 35.4, 34.9, 34.6, 32.0, 30.9, 30.7, 28.2, 27.0, 26.3, 24.1, 23.3, 20.9, 18.3, 12.0. HRMS calcd for $C_{43}H_{63}N_5O_{12}Na$ (M+Na)+, 864.4371; found, 864.4362.

(3S)-4-(((3R,5R,8R,9S,10S,13R,14S)-17-((R)-1-azido-16-oxo-3,6,9,12,15-pentaoxaicosan-19-yl)-10,13-dimethylhexadecahydro-1H-cyclopenta[a]phenanthren-3-yl)oxy)-3-(4-nitrobenzamido)-4-oxobutanoic acid (Compound 10)

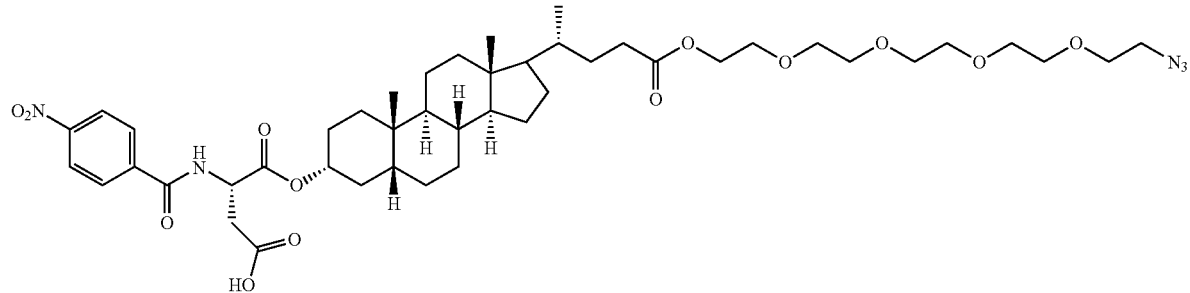

Yield 22% over five steps (oil), 1H NMR (400 MHz, CDCl$_3$): δ 8.25 (d, J=8.4 Hz, 2H), 7.96 (d, J=8.4 Hz, 2H), 7.44 (d, J=6.4 Hz, 1H), 4.95 (brs, 1H), 4.78 (brs, 1H), 4.18 (t, J=4.0 Hz, 2H), 3.63-3.62 (m, 16H), 3.35 (t, J=4.4 Hz, 2H), 3.14-2.97 (m, 2H), 2.37-2.30 (m, 1H), 2.24-2.16 (m, 1H), 1.93-1.90 (m, 1H), 1.84-1.76 (m, 5H), 1.64-1.62 (m, 1H), 1.53-1.51 (m, 2H), 1.39-1.33 (m, 8H), 1.25-1.19 (m, 3H), 1.15-0.94 (m, 6H), 0.89-0.86 (sd, J=6.4 Hz, 6H), 0.60 (s, 3H). 13C NMR (100 MHz, CDCl$_3$): δ 174.4, 169.9, 165.2, 149.8, 139.1, 128.5, 123.8, 70.6, 70.5, 70.4, 69.9, 69.1, 63.4, 56.4, 55.9, 50.6, 49.4, 42.7, 41.9, 40.4, 40.0, 35.7, 35.3, 34.8, 34.5, 32.0, 31.1, 30.8, 28.1, 26.9, 26.4, 26.2, 24.1, 23.2, 20.8, 18.2, 12.0. HRMS calcd for $C_{45}H_{67}N_5O_{13}Na$ (M+Na)+, 908.4633; found, 908.4630.

(3S)-4-(((3R,5R,8R,9S,10S,13R,14S)-17-((R)-5-(2-azidoethoxy)-5-oxopentan-2-yl)-10,13-dimethyl-hexadecahydro-1H-cyclopenta[a]phenanthren-3-yl)oxy)-3-(2-(7-methoxy-2-oxo-2H-chromen-4-yl)acetamido)-4-oxobutanoic acid (Compound 11)

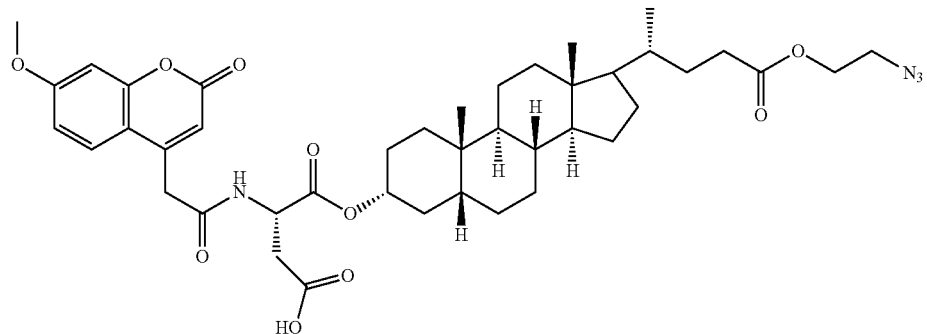

Yield 35% over five steps (powder), mp 151-152° C., 1H NMR (400 MHz, CDCl$_3$): δ 7.58 (d, J=8.8 Hz, 1H), 7.31 (d, J=7.6 Hz, 1H), 6.83 (dd, J=8.8 Hz, 2.4 Hz, 1H), 6.73 (d, J=2.4 Hz, 1H), 6.28 (s, 1H), 4.78-4.70 (m, 2H), 4.21 (t, J=5.0 Hz, 2H), 3.82 (s, 3H), 3.74 (s, 2H), 3.45 (t, J=5.0 Hz, 2H), 3.03-2.87 (m, 2H), 2.41-2.33 (m, 1H), 2.28-2.20 (m, 1H), 1.93-1.91 (m, 1H), 1.84-1.74 (m, 5H), 1.61-1.53 (m, 2H), 1.49-1.46 (m, 1H), 1.39-1.27 (m, 8H), 1.23-1.14 (m, 4H), 1.10-0.93 (m, 5H), 0.89-0.88 (sd, J=4.4 Hz, 6H), 0.61 (s, 3H). 13C NMR (100 MHz, CDCl$_3$): δ 174.3, 174.0, 169.8, 167.9, 163.0, 161.5, 155.4, 149.9, 126.0, 112.9, 112.8, 112.5, 101.0, 62.8, 56.3, 55.9, 55.8, 49.8, 49.2, 42.7, 41.9, 40.4, 40.0, 39.7, 35.8, 35.3, 34.9, 34.5, 32.0, 31.1, 30.9, 28.1, 27.0, 26.4, 26.3, 24.1, 23.3, 20.8, 18.2, 12.0. HRMS calcd for $C_{42}H_{56}N_4O_{10}Na$ (M+Na)+, 799.3894; found, 799.3890.

(3S)-4-(((3R,5R,8R,9S,10S,13R,14S)-17-((R)-5-(2-(2-azidoethoxy)ethoxy)-5-oxopentan-2-yl)-10,13-dimethylhexadecahydro-1H-cyclopenta[a]phenanthren-3-yl)oxy)-3-(2-(7-methoxy-2-oxo-2H-chromen-4-yl)acetamido)-4-oxobutanoic acid
(Compound 12)

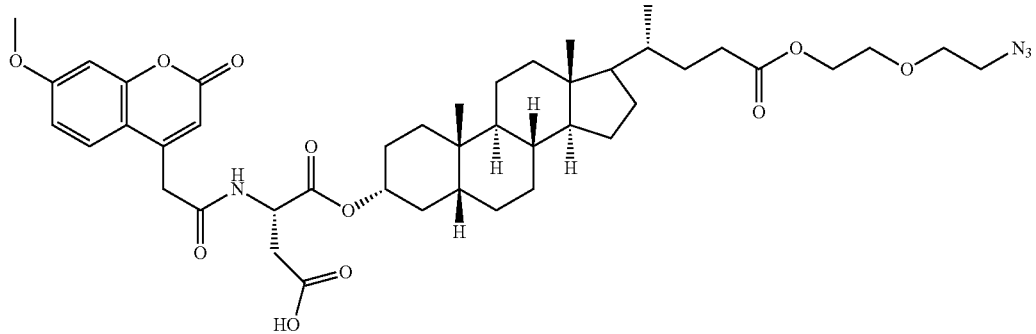

Yield 29% over five steps (powder), mp 142-143° C., 1H NMR (400 MHz, CDCl$_3$): δ 7.58 (d, J=9.2 Hz, 1H), 7.30 (d, J=7.6 Hz, 1H), 6.83 (dd, J=8.8 Hz, 2.4 Hz, 1H), 6.73 (d, J=2.4 Hz, 1H), 6.28 (s, 1H), 4.77-4.70 (m, 2H), 4.21 (t, J=4.8 Hz, 2H), 3.82 (s, 3H), 3.74 (s, 2H), 3.69-3.64 (m, 4H), 3.36 (t, J=4.8 Hz, 2H), 3.02-2.87 (m, 2H), 2.40-2.32 (m, 1H), 2.26-2.18 (m, 1H), 1.93-1.91 (m, 1H), 1.83-1.74 (m, 5H), 1.61-1.46 (m, 3H), 1.39-1.26 (m, 8H), 1.23-1.10 (m, 4H), 1.08-0.94 (m, 5H), 0.88-0.86 (sd, J=6.0 Hz, 6H), 0.60 (s, 3H). 13C NMR (100 MHz, CDCl$_3$): δ 174.3, 169.8, 167.9, 162.9, 161.5, 155.4, 149.9, 126.0, 112.9, 112.7, 112.5, 101.0, 70.0, 69.2, 63.2, 56.3, 56.0, 55.8, 50.6, 49.1, 42.7, 41.9, 40.4, 40.0, 39.7, 35.7, 35.3, 34.8, 34.5, 32.0, 31.1, 30.9, 28.1, 26.9, 26.4, 26.2, 24.1, 23.3, 20.8, 18.2, 12.0. HRMS calcd for C$_{44}$H$_{60}$N$_4$O$_{11}$Na (M+Na)+, 843.4156; found, 843.4147.

(3S)-4-(((3R,5R,8R,9S,10S,10S,3R,14S)-17-((R)-5-(2-(2-(2-azidoethoxy)ethoxy) ethoxy)-5-oxopentan-2-yl)-10,13-dimethylhexadecahydro-1H-cyclopenta[a]phenanthren-3-yl)oxy)-3-(2-(7-methoxy-2-oxo-2H-chromen-4-yl)acetamido)-4-oxo butanoic acid
(Compound 13)

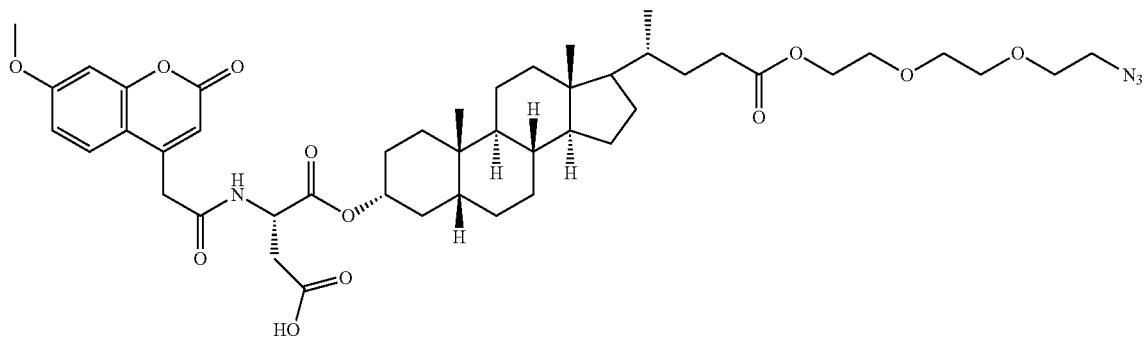

Yield 25% over five steps (powder), mp 134-135° C., 1H NMR (400 MHz, CDCl$_3$): δ 7.57 (d, J=8.8 Hz, 1H), 7.36 (d, J=7.2 Hz, 1H), 6.82 (dd, J=8.8 Hz, 2.0 Hz, 1H), 6.72 (d, J=2.0 Hz, 1H), 6.27 (s, 1H), 4.77-4.69 (m, 2H), 4.20 (t, J=4.8 Hz, 2H), 3.81 (s, 3H), 3.74 (s, 2H), 3.70-3.64 (m, 8H), 3.36 (t, J=5.2 Hz, 2H), 3.02-2.85 (m, 2H), 2.38-2.31 (m, 1H), 2.25-2.17 (m, 1H), 1.92-1.90 (m, 1H), 1.82-1.73 (m, 5H), 1.57-1.44 (m, 3H), 1.38-1.25 (m, 8H), 1.22-1.13 (m, 4H), 1.08-0.93 (m, 5H), 0.87-0.86 (sd, J=5.2 Hz, 6H), 0.60 (s, 3H). 13C NMR (100 MHz, CDCl$_3$): δ 174.4, 174.3, 169.8, 168.0, 162.9, 161.5, 155.3, 149.9, 126.0, 113.0, 112.7, 112.5, 100.9, 70.6, 70.5, 70.0, 69.2, 63.3, 56.3, 56.0, 55.7, 50.6, 49.1, 42.7, 41.9, 40.3, 40.0, 39.6, 35.7, 35.3, 34.8, 34.5, 32.0, 31.2, 30.9, 28.1, 26.9, 26.3, 26.2, 24.1, 23.2, 20.8, 18.2, 12.0. HRMS calcd for C$_{46}$H$_{64}$N$_4$O$_{12}$Na (M+Na)+, 887.4418; found, 887.4417.

(3S)-4-(((3R,5R,8R,9S,10S,13R,14S)-17-((R)-1-azido-13-oxo-3,6,9,12-tetraoxaheptadecan-16-yl)-10,13-dimethylhexadecahydro-1H-cyclopenta[a]phenanthren-3-yl)oxy)-3-(2-(7-methoxy-2-oxo-2H-chromen-4-yl)acetamido)-4-oxobutanoic acid
(Compound 14)

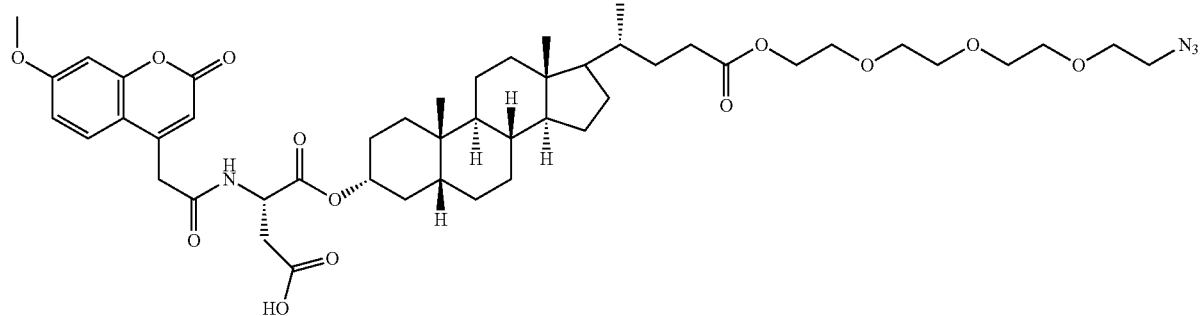

Yield 21% over five steps (powder), mp 126-127° C., 1H NMR (500 MHz, CDCl$_3$): δ 7.57 (d, J=9.0 Hz, 1H), 7.34 (d, J=7.5 Hz, 1H), 6.83 (dd, J=9.0 Hz, 2.0 Hz, 1H), 6.72 (d, J=2.0 Hz, 1H), 6.27 (s, 1H), 4.77-4.69 (m, 2H), 4.19 (t, J=4.5 Hz, 2H), 3.82 (s, 3H), 3.74 (s, 2H), 3.68-3.64 (m, 12H), 3.36 (t, J=4.5 Hz, 2H), 3.02-2.85 (m, 2H), 2.37-2.31 (m, 1H), 2.24-2.17 (m, 1H), 1.92-1.90 (m, 1H), 1.82-1.74 (m, 5H), 1.60-1.45 (m, 3H), 1.37-1.26 (m, 8H), 1.25-1.10 (m, 4H), 1.07-0.93 (m, 5H), 0.87-0.86 (sd, J=6.5 Hz, 6H), 0.60 (s, 3H). 13C NMR (125 MHz, CDCl$_3$): δ 174.3, 174.0, 169.8, 167.9, 163.0, 161.4, 155.4, 149.8, 126.0, 113.0, 112.7, 112.5, 101.0, 70.7, 70.6, 70.5, 70.0, 69.2, 63.4, 56.4, 56.0, 55.8, 50.7, 49.2, 42.7, 41.9, 40.4, 40.0, 39.7, 35.8, 35.3, 34.9, 34.6, 32.0, 31.2, 30.9, 28.1, 27.0, 26.4, 26.3, 24.1, 23.3, 20.8, 18.3, 12.0. HRMS calcd for $C_{48}H_{68}N_4O_{13}Na$ (M+Na)+, 931.4681; found, 931.4681.

(3S)-4-(((3R,5R,8R,9S,10S,13R,14S)-17-((R)-1-azido-16-oxo-3,6,9,12,15-pentaoxaicosan-19-yl)-10,13-dimethylhexadecahydro-1H-cyclopenta[a]phenanthren-3-yl)oxy)-3-(2-(7-methoxy-2-oxo-2H-chromen-4-yl)acetamido)-4-oxobutanoic acid
(Compound 15)

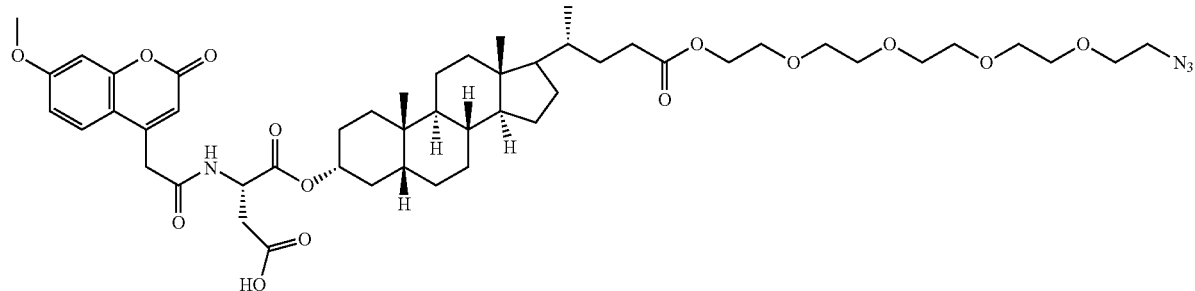

Yield 21% over five steps (powder), mp 113-114° C., 1H NMR (500 MHz, CDCl$_3$): δ 7.57 (d, J=8.5 Hz, 1H), 7.34 (d, J=7.0 Hz, 1H), 6.82 (dd, J=9.0 Hz, 2.0 Hz, 1H), 6.73 (d, J=2.0 Hz, 1H), 6.27 (s, 1H), 4.75-4.71 (m, 2H), 4.18 (t, J=5.0 Hz, 2H), 3.81 (s, 3H), 3.73 (s, 2H), 3.67-3.62 (m, 16H), 3.35 (t, J=5.0 Hz, 2H), 3.01-2.85 (m, 2H), 2.37-2.31 (m, 1H), 2.23-2.17 (m, 1H), 1.92-1.90 (m, 1H), 1.79-1.73 (m, 5H), 1.59-1.44 (m, 3H), 1.35-1.26 (m, 8H), 1.25-1.10 (m, 4H), 1.07-0.92 (m, 5H), 0.87-0.85 (sd, J=6.5 Hz, 6H), 0.59 (s, 3H). 13C NMR (125 MHz, CDCl$_3$): δ 174.2, 169.8, 167.9, 162.9, 161.3, 155.4, 149.7, 126.0, 113.1, 112.7, 112.5, 101.0, 76.6, 70.7, 70.6, 70.6, 70.5, 70.0, 69.2, 63.4, 56.3, 56.0, 55.7, 50.7, 49.2, 42.7, 41.9, 40.4, 40.0, 39.7, 35.8, 35.3, 34.9, 34.5, 32.0, 31.2, 30.9, 28.1, 26.9, 26.4, 26.3, 24.1, 23.2, 20.8, 18.3, 12.0. HRMS calcd for $C_{50}H_{72}N_4O_{14}Na$ (M+Na)+, 975.4943; found, 975.4945.

1.2 Synthesis of Compounds 16 to 27

The compounds 16 to 27 (i.e., compounds of formula (1-2)) were synthesized in accordance with procedures set forth in Schemes 3 to 8, in which Schemes 3 to 6 were for the synthesis of compounds with modification at α-3-NH$_2$; whereas Schemes 7 and 8 were for the synthesis of compounds having amino acid side chain modification at α-3-NH$_2$ of lithocholic acid (LA).

Scheme 3:
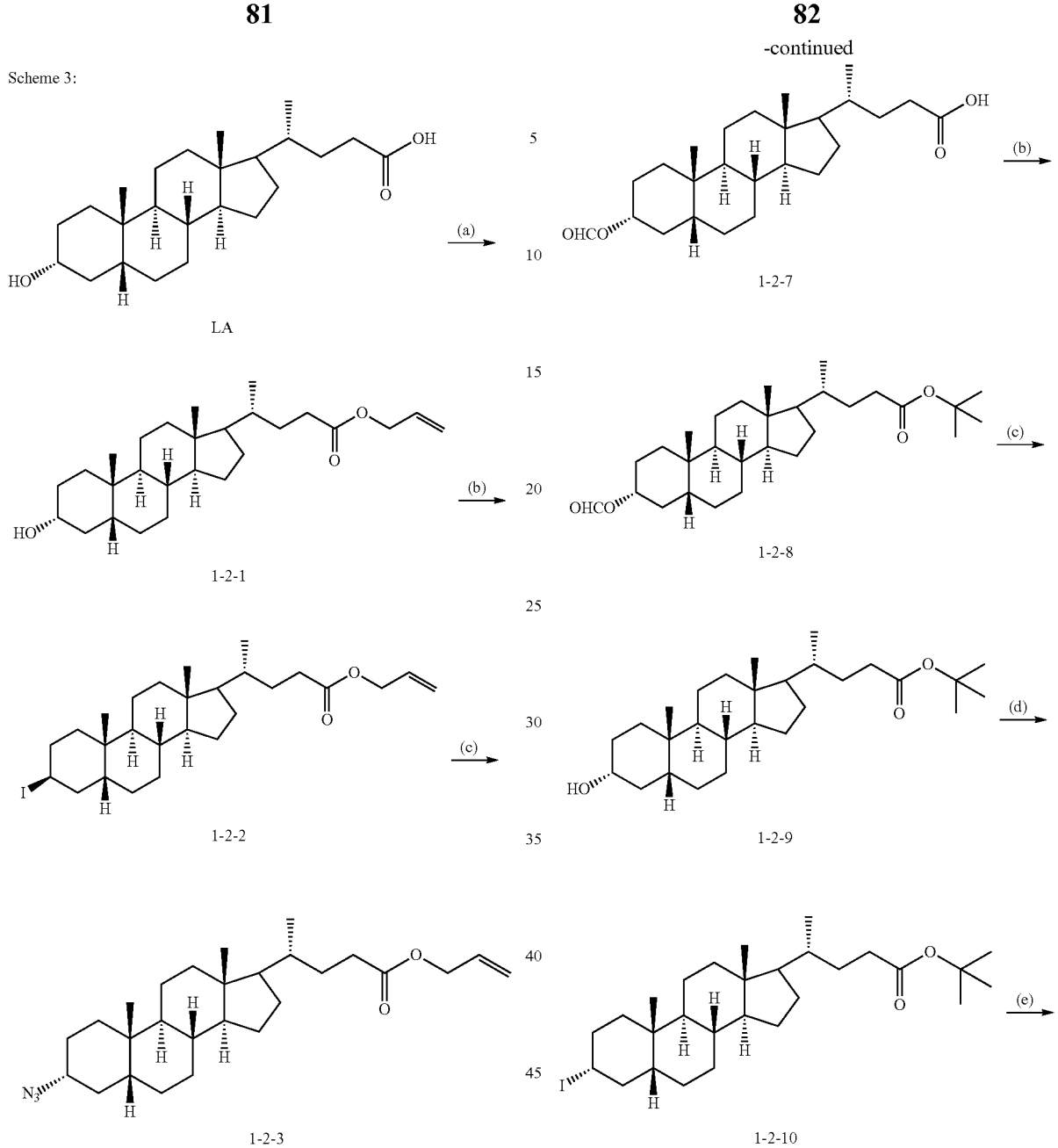
Reagents and conditions: (a) allyl bromide, K₂CO₃, DMF, 100° C., 12 h, 99%, (b) I₂, PPh₃, imidazole, CH₂Cl₂, 0° C. to rt, 3 h, 74%, (c) NaN₃, DMF, 120° C., 12 h, 99%.
Scheme 4:
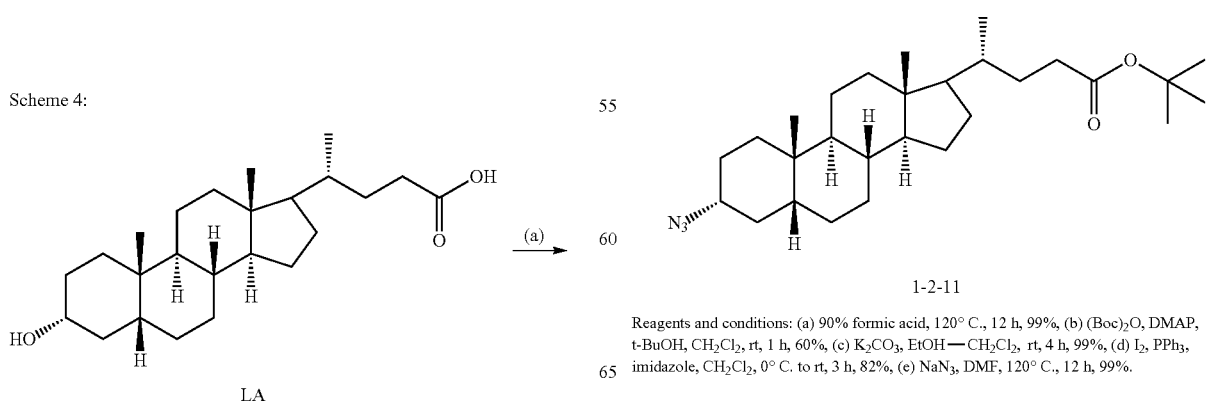
Reagents and conditions: (a) 90% formic acid, 120° C., 12 h, 99%, (b) (Boc)₂O, DMAP, t-BuOH, CH₂Cl₂, rt, 1 h, 60%, (c) K₂CO₃, EtOH—CH₂Cl₂, rt, 4 h, 99%, (d) I₂, PPh₃, imidazole, CH₂Cl₂, 0° C. to rt, 3 h, 82%, (e) NaN₃, DMF, 120° C., 12 h, 99%.

Scheme 5:
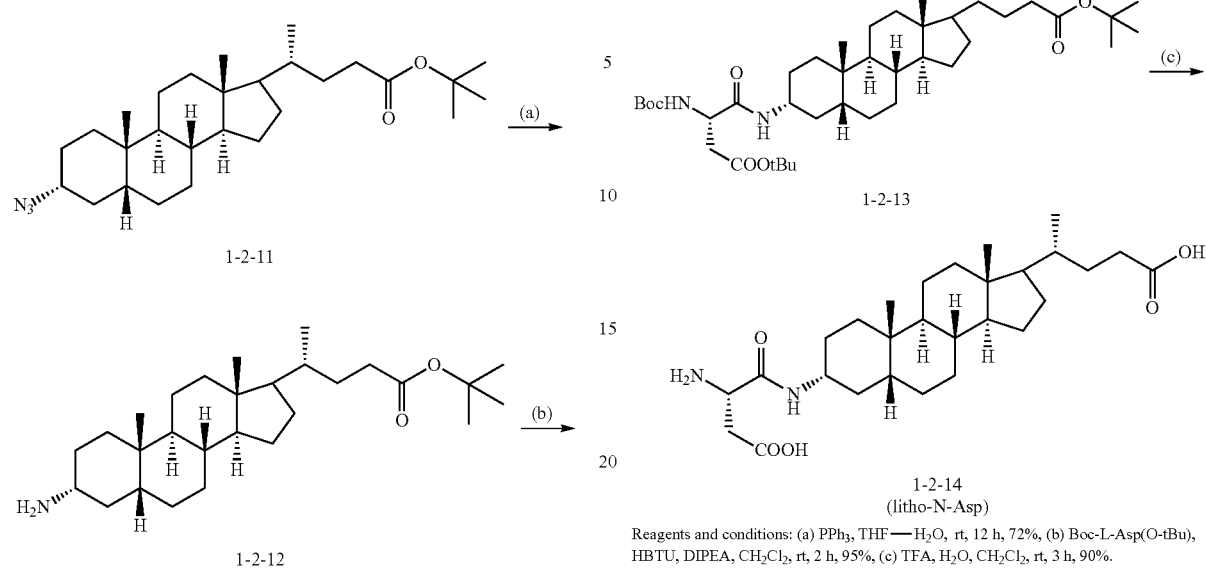
Reagents and conditions: (a) PPh₃, THF—H₂O, rt, 12 h, 72%, (b) Boc-L-Asp(O-tBu), HBTU, DIPEA, CH₂Cl₂, rt, 2 h, 95%, (c) TFA, H₂O, CH₂Cl₂, rt, 3 h, 90%.
Scheme 6:
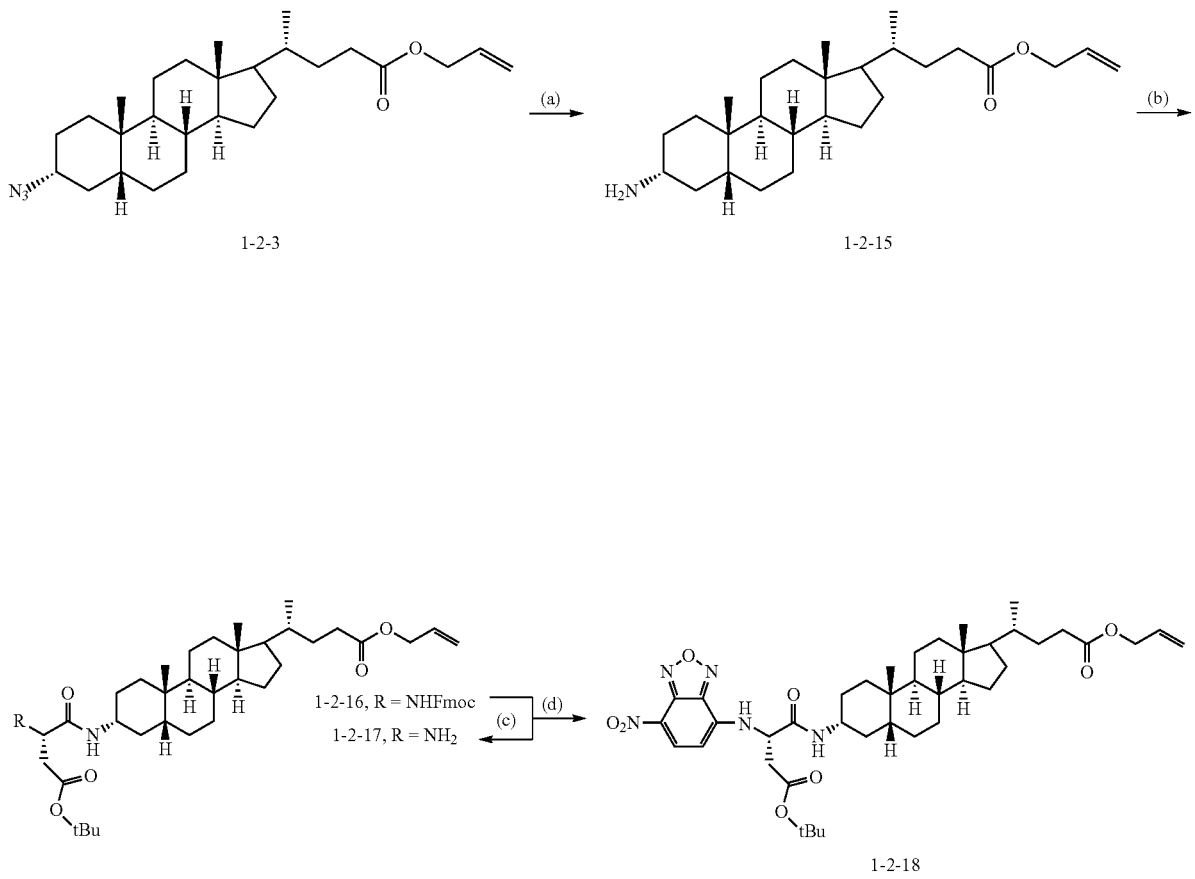

-continued

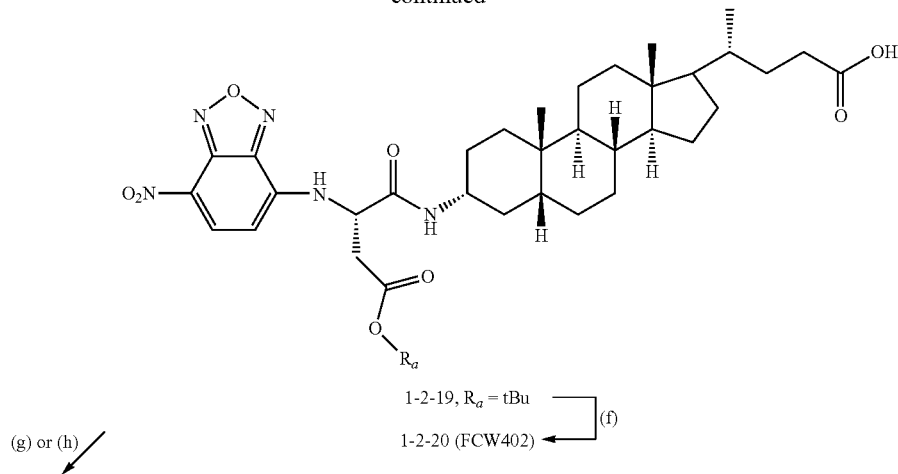

1-2-19, $R_a$ = tBu
1-2-20 (FCW402) ← (f)

(g) or (h)

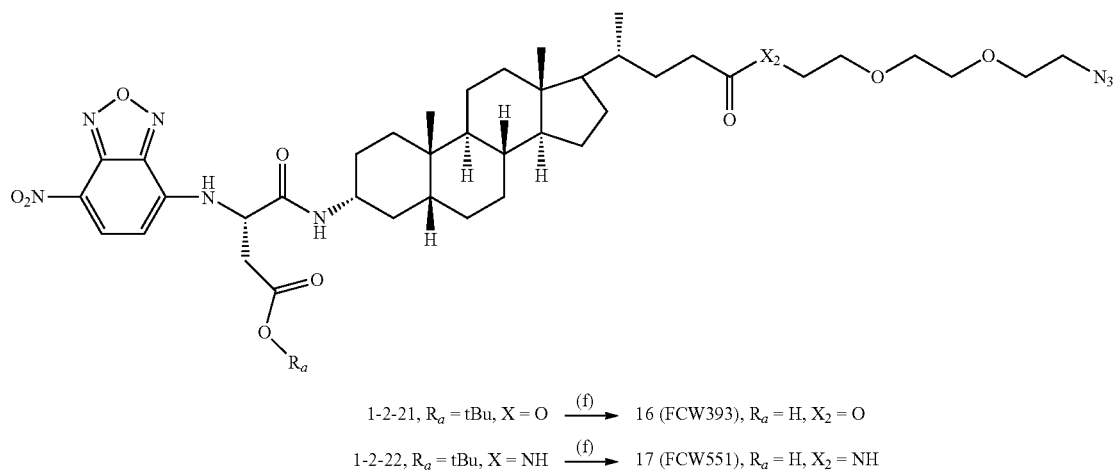

1-2-21, $R_a$ = tBu, X = O  →(f)  16 (FCW393), $R_a$ = H, $X_2$ = O
1-2-22, $R_a$ = tBu, X = NH →(f) 17 (FCW551), $R_a$ = H, $X_2$ = NH

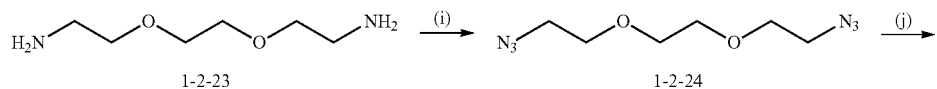

1-2-23 → 1-2-24

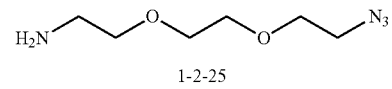

1-2-25

Reagents and conditions: (a) PPh$_3$, THF—H$_2$O, rt, 12 h, 72%, (b) Fmoc-L-Asp(O-tBu), HBTU, DIPEA, CH$_2$Cl$_2$, rt, 3 h, 93%, (c) DBU, CH$_2$Cl$_2$, rt, 0.5 h, 92%, (d) NBD—Cl, NaHCO$_3$, THF, EtOH, rt, 2 days, 42%, (e) Pd(PPh$_3$)$_4$, PhSiH$_3$, CH$_2$Cl$_2$, rt, 2 h, 95%, (f) TFA, H$_2$O, CH$_2$Cl$_2$, rt, 3 h, 1-2-20, 90%; 16, 88%; 17, 85%, (g) 1C, DCC, DMAP, CH$_2$Cl$_2$, rt, 6 h, 72%, (h) 1-2-26, HBTU, DIPEA, CH$_2$Cl$_2$, rt, 2 h, 95%, (i) T$_f$N$_3$ in CH$_2$Cl$_2$, CuSO$_4$·5H$_2$O, K$_2$CO$_3$, MeOH, H$_2$O, 0° C. to rt, 16 h, 92%, (j) PPh$_3$, Et$_2$O—THF—1M HCl$_{(aq)}$, rt, 12 h, 88%.

General Procedures for Allyl Protection $K_2CO_3$ (45.53 mmol) and allyl bromide (16.70 mmol) were added dropwise to a stirred solution of LA (15.18 mmol) in 20 mL DMF. The reaction was stirred at 100° C. for 12 h. After reaction remove solid by filtration, and filtrate was concentrated then extracted with $CH_2Cl_2$ (3×), the combined organic layers were washed with $H_2O$ (2×) and brine (2×) and dried over $MgSO_4$ prior to filtration and concentration under reduced pressure to yield the crude product. The residue was purified by flash column chromatography to afford the target product as powder.

General Procedures for Iodination $I_2$ (60.71 mmol) and imidazole (124.46 mmol) were added to a stirred 0° C. solution of $PPh_3$ (54.64 mmol) in 125 mL $CH_2Cl_2$. The reaction was stirred at 0° C. for 30 min, then added compound 1-2-1 (15.18 mmol) in 125 ml $CH_2Cl_2$ dropwisely. The reaction was stirred at room temperature for 3 h. The reaction mixture was quenched with $Na_2S_2O_3$ $_{(aq)}$. After extraction with $CH_2Cl_2$ (3×), the combined organic layers were washed with $H_2O$ (2×) and brine (2×) and dried over $MgSO_4$ prior to filtration and concentration under reduced pressure to yield the crude product. The residue was purified by flash column chromatography to afford the compound 1-2-2.

General Procedures for Azide Formation $NaN_3$ (33.73 mmol) was added to a stirred solution of compound 1-2-2 (11.24 mmol) in 30 mL DMF. The reaction was stirred at 120° C. for 12 h. After reaction remove solid by filtration, and filtrate was concentrated then extracted with $CH_2Cl_2$ (3×), the combined organic layers were washed with $H_2O$ (2×) and brine (2×) and dried over $MgSO_4$ prior to filtration and concentration under reduced pressure to yield the crude product. The residue was purified by flash column chromatography to afford compound 1-2-3 as oil.

General Procedures for CHO Protection

In a flask, mixed LA (13.28 mmol) in 30 mL 90% formic acid, then the reaction was stirred at 120° C. for 12 h. Collected solid by filtration, then solid was washed with water. The solid was dried by reduced pressure to afford the compound 1-2-7.

General Procedures for t-Bu Protection $(Boc)_2O$ (13.62 mmol) and DMAP (2.04 mmol) were added to a stirred solution of compound 1-2-7 (6.81 mmol) in 30 mL $CH_2Cl_2$ and 30 mL t-butanol. The reaction was stirred at room temp for 1 h, then reaction mass was concentrated and the product was purified by flash column chromatography to give compound 1-2-8.

Synthesis of Compound 1-2-9

$K_2CO_3$ (34.56 mmol) was added to a stirred solution of compound 1-2-8 (4.32 mmol) in 20 mL $CH_2Cl_2$ and 40 mL EtOH. The reaction was stirred at room temp for 4 h. After reaction, removed solid by filtration, and the filtrate was concentrated, then extracted with $CH_2Cl_2$ (3×), the combined organic layers were washed with $H_2O$ (2×) and brine (2×) and dried over $MgSO_4$ prior to filtration and concentration under reduced pressure to yield the crude product. The residue was purified by flash column chromatography to afford compound 1-2-9 as oil.

General Procedures for De-protecting CHO Group

To a stirred solution of compound 1-2-8 (4.32 mmol) in 20 mL $CH_2Cl_2$ and 40 mL EtOH was added $K_2CO_3$ (34.56 mmol). The reaction was stirred at rt for 4 h. After reaction remove solid by filtration, and filtrate was concentrated then extracted with $CH_2Cl_2$ (3×), the combined organic layers were washed with $H_2O$ (2×) and brine (2×) and dried over $MgSO_4$ prior to filtration and concentration under reduced pressure to yield the crude product. The residue was purified by flash column chromatography to afford compound 1-2-9 as oil.

General Procedures for Reducing Azide to Amine

To a stirred solution of compound 1-2-3 (40.09 mmol) in 60 mL $H_2O$ and 180 mL THF was added $PPh_3$ (80.18 mmol). The reaction was stirred at rt for 12 h then reaction mass was concentrated and crude product was extracted with $CH_2Cl_2$ (3×), the combined organic layers were washed with $H_2O$ (2×) and brine (2×) and dried over $MgSO_4$ prior to filtration and concentration under reduced pressure to yield the crude product. The residue was purified by flash column chromatography to afford compound 1-2-15 as oil.

General Procedures for De-protecting Allyl Group

To a stirred solution of compound 1-2-18 (4.60 mmol) in 60 mL $CH_2Cl_2$ was added $Pd(Ph_3)_4$ (0.46 mmol) and phenyl silane (9.20 mmol) dropwise. The reaction was stirred at rt for 2 h, then reaction mass was concentrated and product was purified by flash column chromatography to get compound 1-2-19.

General Procedures for De-Protecting Boc Group

The Boc protected compound (0.1 mmol) was dissolved in 5 mL TFA with dd$H_2O$ (100 μL) and the reaction mixture was stirred at room temperature for 3 h, then reaction mass was concentrated and product was purified by flash column chromatography to get target compound.

General Procedures for Converting Amine to Azide $TfN_3$ was prepared fresh prior to the reaction as follows. Six molar equivalents per substrate of $NaN_3$ (222.67 mmol) were dissolved in a minimum volume of water (40 mL) and cooled to 0° C. An equal volume of $CH_2Cl_2$ (40 mL) was added, followed by slow addition of $Tf_2O$ (111.34 mmol) to the vigorously stirred solution. The reaction was stopped and stirring was continued at 0° C. for 2 h. Saturated $NaHCO_3$ was added carefully while stirring continued and subsequently the mixture was transferred to a separatory funnel after $CO_2$ evolution had ceased. The aqueous phase was washed twice with $CH_2Cl_2$ and combined organic layers were washed with saturated $NaHCO_3$. The $TfN_3$ in $CH_2Cl_2$ solution was used without further purification. Diamine compound 1-2-23 (37.11 mmol), $K_2CO_3$ (44.53 mmol) and $CuSO_4.5H_2O$ (0.37 mmol) were dissolved in water (30 mL). The freshly prepared $TfN_3$ solution was added at once under vigorous stirring. Methanol (100 mL) was added slowly, then the reaction was stirred at rt for 16 h then reaction mass was concentrated in vacuo. The aqueous solution was acidified with 1N HCl to pH2 and was extracted with ethyl acetate (EA) (3×). The combined organic layers were dried over MgSO$_4$ prior to filtration and concentration under reduced pressure to yield the crude product. The residue was purified by flash column chromatography to afford compound 1-2-25 as oil.

General Procedures for Reducing Azide to Amine

To a stirred solution of compound 1-2-25 (20.97 mmol) in 33 mL Et$_2$O, 6.6 mL THF and 26.4 mL 1N HCl$_{(aq)}$ was added PPh$_3$ (20.97 mmol) in 33 mL Et$_2$O dropwise. The reaction was stirred at rt for 12 h then reaction mass was concentrated and crude product was extracted with CH$_2$Cl$_2$ (3×), the combined organic layers were washed with H$_2$O (2×) and brine (2×) and dried over MgSO$_4$ prior to filtration and concentration under reduced pressure to yield the crude product. The residue was purified by flash column chromatography to afford compound 1-2-26 as oil.

(4R)-4-((3R,5R,10S,13R)-3-((S)-2-amino-3-carboxypropanamido)-10,13-dimethylhexadecahydro-1H-cyclopenta[a]phenanthren-17-yl)pentanoic acid. 1-2-14 (litho-N-Asp)

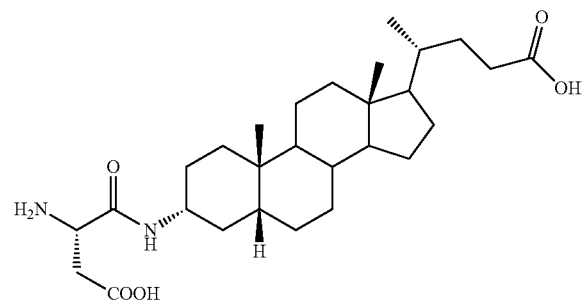 [SMILES: C[C@H](CCC(=O)O)C1CCC2C3CC[C@@H]4C[C@H](NC(=O)[C@@H](N)CC(=O)O)CC[C@]4(C)C3CC[C@@]21C]

(4R)-4-((3R,5R,10S,13R)-3-((S)-3-carboxy-2-((7-nitrobenzo[c][1,2,5]oxa diazol-4-yl)amino)propanamido)-10,13-dimethylhexadecahydro-1H-cyclopenta[a]phenanthren-17-yl)pentanoic acid. 1-2-20 (FCW402)

mp 134-136° C., 1H NMR (400 MHz, MeOD): δ 8.53 (d, J=8.4 Hz, 1H), 8.15 (d, J=8.4 Hz, 1H), 6.42 (d, J=8.8 Hz, 1H), 3.76-3.65 (m, 1H), 3.08-2.96 (m, 2H), 2.35-2.27 (m, 1H), 2.22-2.14 (m, 1H), 2.00-1.94 (m, 1H), 1.93-1.73 (m, 5H), 1.61-1.53 (m, 2H), 1.43-1.35 (m, 7H), 1.33-1.22 (m, 5H), 1.15-0.99 (m, 6H), 0.95 (s, 3H), 0.92 (d, J=6.8 Hz, 3H), 0.67 (s, 3H). 13C NMR (100 MHz, MeOD): δ 178.2, 170.8, 146.1, 145.8, 145.5, 125.0, 102.2, 58.1, 57.7, 56.1, 51.5, 44.1, 44.0, 41.9, 41.6, 37.3, 37.2, 36.8, 35.8, 34.1, 32.5, 32.2, 29.3, 28.3, 27.7, 25.3, 24.1, 22.0, 18.9, 12.6. HRMS calcd for C$_{34}$H$_{46}$N$_5$O$_8$ (M−H)−, 652.3346; found, 652.3339.

(3S)-4-(((3R,5R,10S,13R)-17-((R)-5-(2-(2-(2-azidoethoxy)ethoxy)ethoxy)-5-oxopentan-2-yl)-10,13-dimethylhexadecahydro-1H-cyclopenta[a]phenanthren-3-yl)amino)-3-((7-nitrobenzo[c][1,2,5]oxadiazol-4-yl)amino)-4-oxobutanoic acid. Compound 16 (FCW393)

mp 158-160° C., 1H NMR (400 MHz, MeOD): δ 4.07-4.01 (m, 1H), 3.72-3.65 (m, 1H), 2.82-2.68 (m, 2H), 2.35-2.29 (m, 1H), 2.24-2.16 (m, 1H), 2.04-2.01 (m, 1H), 1.95-1.78 (m, 5H), 1.62-1.59 (m, 2H), 1.48-1.42 (m, 6H), 1.34-1.22 (m, 6H), 1.18-1.04 (m, 6H), 0.98 (s, 3H), 0.95 (d, J=6.4 Hz, 3H), 0.70 (s, 3H). 13C NMR (100 MHz, MeOD): δ 178.3, 174.5, 168.7, 58.1, 57.7, 51.9, 51.4, 44.0, 42.0, 41.6, 37.4, 37.3, 37.1, 36.8, 35.8, 34.2, 32.4, 32.1, 29.3, 28.3, 27.7, 25.4, 24.1, 22.1, 18.9, 12.6. HRMS calcd for C$_{28}$H$_{47}$N$_2$O$_5$ (M+H)+, 491.3485; found, 491.3480.

mp 80-81° C., 1H NMR (400 MHz, CDCl$_3$): δ 8.37 (s, 1H), 7.77 (s, 1H), 7.01 (s, 1H), 6.35 (s, 1H), 4.87-4.76 (m, 1H) 4.21 (s, 2H), 3.80-3.66 (m, 9H), 3.38 (s, 2H), 3.14-3.06 (m, 2H), 2.35-2.30 (m, 1H), 2.23-2.16 (m, 1H), 1.79-1.72 (m, 7H), 1.46-1.09 (m, 13H), 1.02-0.98 (m, 3H), 0.86 (s, 3H), 0.79 (d, J=4.0 Hz, 3H), 0.74-0.67 (m, 3H) 0.53 (s, 3H). 13C NMR (100 MHz, CDCl$_3$): δ 174.8, 173.2, 168.2, 144.3, 143.7, 142.8, 136.4, 124.5, 100.8, 70.6, 70.5, 70.0, 69.2, 63.5, 56.5, 56.1, 54.1, 50.7, 50.4, 42.6, 42.3, 40.4, 40.1, 35.7, 35.6, 35.3, 34.4, 32.9, 31.2, 30.9, 28.1, 27.3, 26.9, 26.2, 24.0, 23.4, 20.7, 18.2, 11.9. HRMS calcd for C$_{40}$H$_{58}$NO$_{10}$Na (M+Na)+, 833.4174; found, 833.4181.

(3S)-4-(((3R,5R,10S,13R)-17-((R)-5-((2-(2-(2-azidoethoxy)ethoxy)ethyl) amino)-5-oxopentan-2-yl)-10,13-dimethylhexadecahydro-1H-cyclopenta[a]phenanthren-3-yl)amino)-3-((7-nitrobenzo[c][1,2,5]oxadiazol-4-yl)amino)-4-oxobutanoic acid.
Compound 17 (FCW551)

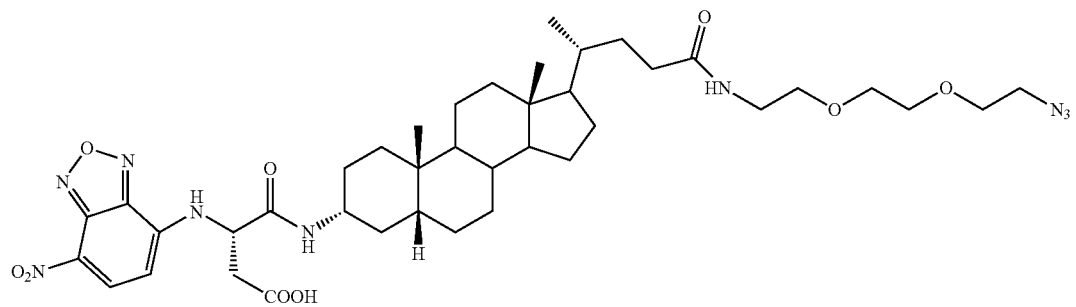 [SMILES: C[C@H](CCC(=O)NCCOCCOCCN=[N+]=[N-])C1CCC2C3CC[C@@H]4C[C@H](NC(=O)[C@H](CC(=O)O)Nc5ccc([N+](=O)[O-])c6nonc56)CC[C@]4(C)C3CC[C@@]21C]

mp 90-91° C., 1H NMR (400 MHz, CDCl$_3$): δ 8.33 (d, J=8.8 Hz, 1H), 7.89 (d, J=7.6 Hz, 1H), 7.18 (d, J=8.0 Hz, 1H), 6.51 (t, J=4.8 Hz, 1H), 6.35 (d, J=8.8 Hz, 1H), 4.85-4.76 (m, 1H), 3.85-3.76 (m, 1H), 3.67-3.61 (m, 6H), 3.54 (t, J=5.2 Hz, 2H), 3.44-3.42 (m, 2H), 3.38 (t, J=5.2 Hz, 2H), 3.10 (d, J=5.2 Hz, 2H), 2.28-2.21 (m, 1H), 2.06-1.96 (m, 1H), 1.84-1.55 (m, 6H), 1.49-1.42 (m, 2H), 1.39-1.30 (m, 2H), 1.24-1.12 (m, 8H), 1.04-0.86 (m, 5H), 0.82 (s, 3H), 0.71 (d, J=5.6 Hz, 3H), 0.67-0.51 (m, 3H), 0.46 (s, 3H). 13C NMR (100 MHz, CDCl$_3$): δ 175.4, 173.0, 167.9, 144.3, 143.5, 142.9, 136.6, 124.0, 100.5, 70.4, 70.1, 70.0, 69.6, 56.5, 56.2, 54.3, 50.6, 50.2, 42.4, 42.2, 40.2, 40.1, 39.5, 36.2, 35.7, 35.6, 35.4, 34.3, 33.6, 32.6, 31.8, 28.1, 27.0, 26.8, 26.1, 23.9, 23.3, 20.6, 18.1, 11.8. HRMS calcd for C$_{40}$H$_{58}$N$_9$O$_9$ (M−H)−, 808.4358; found, 808.4358.

Scheme 7:

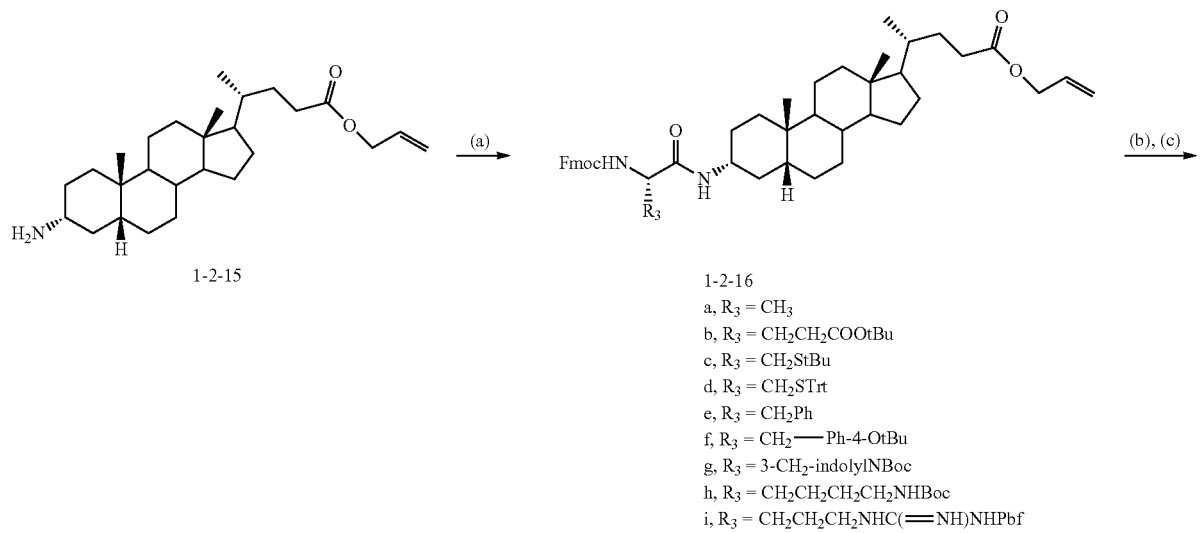

1-2-15

1-2-16
a, R$_3$ = CH$_3$
b, R$_3$ = CH$_2$CH$_2$COOtBu
c, R$_3$ = CH$_2$StBu
d, R$_3$ = CH$_2$STrt
e, R$_3$ = CH$_2$Ph
f, R$_3$ = CH$_2$—Ph-4-OtBu
g, R$_3$ = 3-CH$_2$-indolylNBoc
h, R$_3$ = CH$_2$CH$_2$CH$_2$CH$_2$NHBoc
i, R$_3$ = CH$_2$CH$_2$CH$_2$NHC(═NH)NHPbf -continued
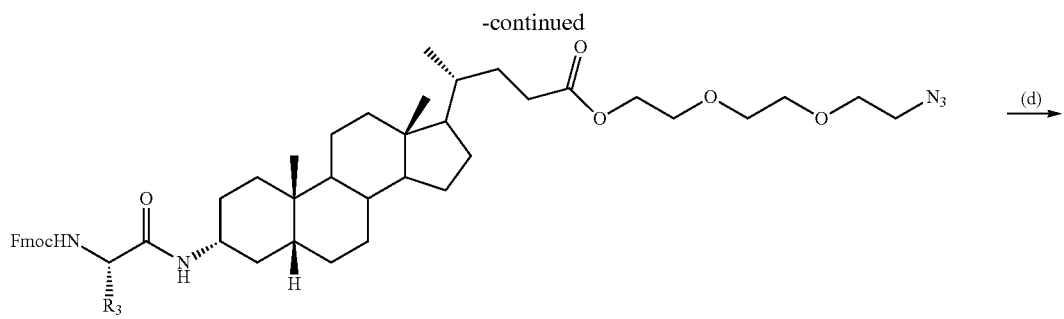
1-2-17
a, R₃ = CH₃
b, R₃ = CH₂CH₂COOtBu
c, R₃ = CH₂StBu
d, R₃ = CH₂STrt
e, R₃ = CH₂Ph
f, R₃ = CH₂—Ph-4-OtBu
g, R₃ = 3-CH₂-indolylNBoc
h, R₃ = CH₂CH₂CH₂CH₂NHBoc
i, R₃ = CH₂CH₂CH₂NHC(=NH)NHPbf
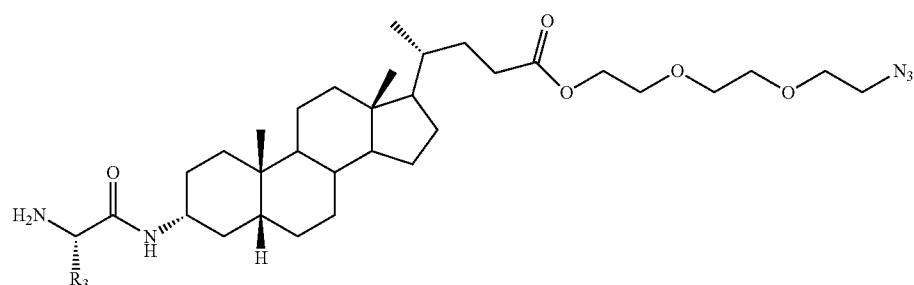
1-2-18
a, R₃ = CH₃
b, R₃ = CH₂CH₂COOtBu
c, R₃ = CH₂StBu
d, R₃ = CH₂STrt
e, R₃ = CH₂Ph
f, R₃ = CH₂—Ph-4-OtBu
g, R₃ = 3-CH₂-indolylNBoc
h, R₃ = CH₂CH₂CH₂CH₂NHBoc
i, R₃ = CH₂CH₂CH₂NHC(=NH)NHPbf

95

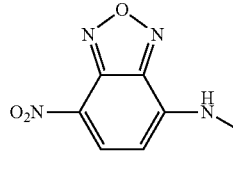

1-2-19
a, R₃ = CH₃
b, R₃ = CH₂CH₂COOtBu
c, R₃ = CH₂StBu
d, R₃ = CH₂STrt
e, R₃ = CH₂Ph
f, R₃ = CH₂—Ph-4-OtBu
g, R₃ = 3-CH₂-indolylNBoc
h, R₃ = CH₂CH₂CH₂CH₂NHBoc
i, R₃ = CH₂CH₂CH₂NHC(=NH)NHPbf (f) →
(g) →
(f) →
(f) →
↓ (g)

1-2-20
i, R₃ = CH₂CH₂CH₂NHC(=NH)NH₂

96

-continued

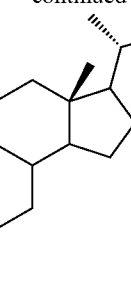

1-2-20
b, R₃ = CH₂CH₂COOH
d, R₃ = CH₂SH
f, R₃ = CH₂—Ph-4-OH
g, R₃ = 3-CH₂-indolylNH
h, R₃ = CH₂CH₂CH₂CH₂NH₂

Reagents and conditions: (a) Different amino acids, HBTU, DIPEA, CH₂Cl₂, rt, 3 h, 1-2-16: a, 99%, b, 95% c, 90%, d, 75% , e, 96%, f, 98%, g, 82%, h, 91%, i, 62% , (b) Pd(Ph₃)₄, PhSiH₃, CH₂Cl₂, rt, 2 h, (c) 1C, DCC, DMAP, CH₂Cl₂, rt, 12 h, 1-2-17: a, 74%, b, 65%, c, 73%, d, 72%, e, 60%, f, 68%, g, 70%, h, 60%, i, 55% (two steps), (d) DBU, CH₂Cl₂, rt, 1 h, 1-2-18: a, 98%, b, 88%, c, 90% d, 92%, e, 85%, f, 88%, g, 91%, h, 85%, i, 90% (e) NBD-Cl, NaHCO₃, THF, EtOH, rt, 2 days, 1-2-19: a, 33%, b, 35%, c, 42%, d, 38%, e, 35%, f, 38%, g, 40%, h, 31%, i, 30%, (f) TFA, H₂O, CH₂Cl₂, rt, 3 h, 1-2-21: b, 92% , f, 95%, g, 85%, h, 80%, (g) TFA, TIPS, H₂O, CH₂Cl₂, rt, 4 h, 1-2-21: d, 88%, 41i, 85%.

Scheme 8:

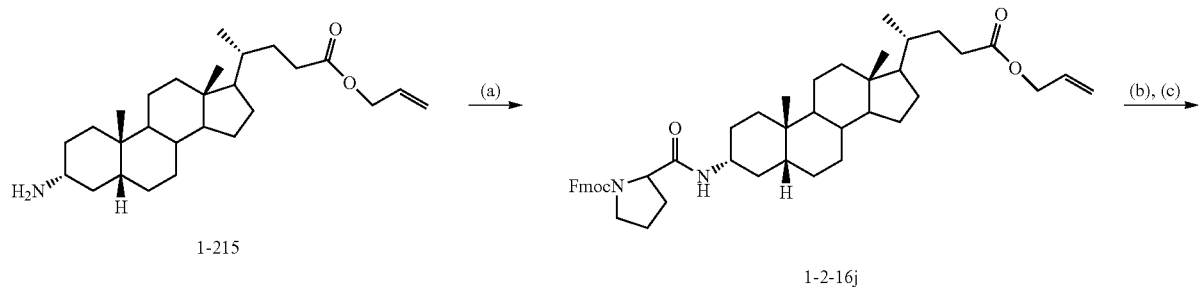

-continued
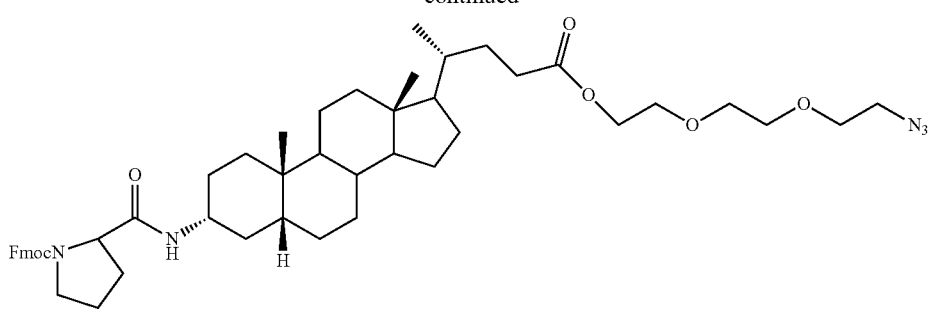
1-2-17j
↓ (d)
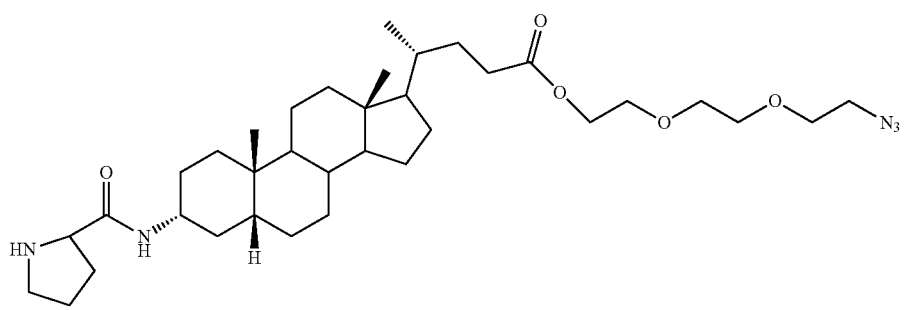
1-2-18j
↓ (e)
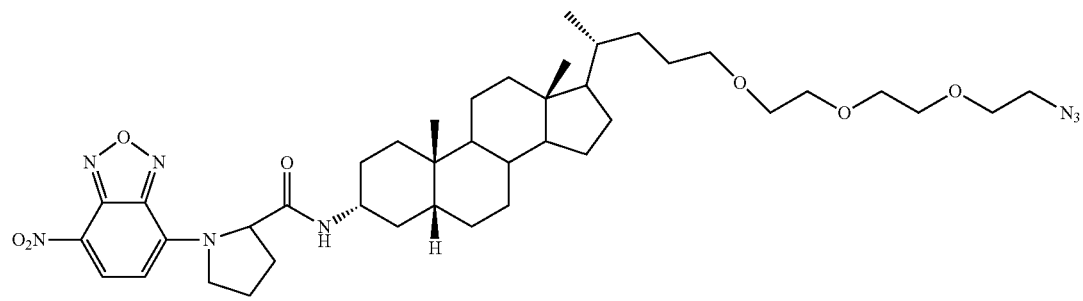
27
Reagents and conditons: (a) Fmoc-Pro-OH, HBTU, DIPEA, CH$_2$Cl$_2$, rt, 3 h, 1-2-16j, 98%, (b) Pd(Ph$_3$)$_4$, PhSiH$_3$, CH$_2$Cl$_2$, rt, 2 h, (c) 1C, DCC, DMAP, CH$_2$Cl$_2$, rt, 12 h, 1-2-17 j, 78% (two steps), (d) DBU, CH$_2$Cl$_2$, rt, 1 h, 1-2-18j, 98%, (e) NBD-Cl, NaHCO$_3$, THF, EtOH, rt, 2 h, 27 88%.

General Procedures for De-Protecting Trt Group

The compound 1-2-19d (i.e., the Trt protected compound) (0.1 mmol) was dissolved in 10 mL TFA and 10 mL $CH_2Cl_2$ was added $ddH_2O$ (500 μL) and TIPS (0.2 mmol) and the reaction mixture was stirred at room temperature for 4 h, then reaction mass was concentrated and product was purified by flash column chromatography to get target compound 1-2-20d (or compound 19).

General Procedures for De-Protecting Pbf Group

The compound 1-2-19i (i.e., the Pbf protected compound) (0.05 mmol) was dissolved in 5 mL TFA and 5 mL $CH_2Cl_2$ was added $ddH_2O$ (250 μL) and TIPS (0.1 mmol) and the reaction mixture was stirred at room temperature for 4 h, then reaction mass was concentrated and product was purified by flash column chromatography to get target compound 1-2-20i (or compound 23).

(4R)-2-(2-(2-azidoethoxy)ethoxy)ethyl-4-((3R,5R,10S,13R)-10,13-dimethyl-3-((S)-2-((7-nitrobenzo[c][1,2,5]oxadiazol-4-yl)amino)propanamido)hexadecahydro-1H-cyclopenta[a]phenanthren-17-yl)pentanoate. 1-2-19a (Compound 18)

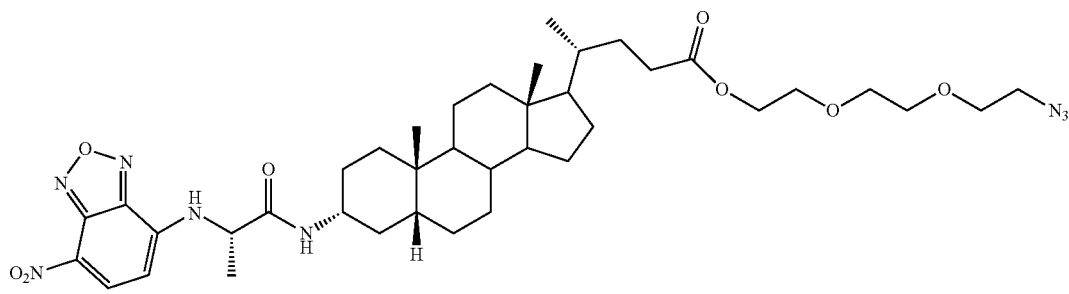 [SMILES: C[C@H](Nc1ccc([N+](=O)[O-])c2nonc12)C(=O)N[C@@H]1CC[C@]2(C)C3CC[C@@]4(C)C(CCC4[C@H](C)CCC(=O)OCCOCCOCCN=[N+]=[N-])C3CC[C@@H]2C1]

mp 69-70° C., 1H NMR (400 MHz, $CDCl_3$): δ 8.44 (d, J=8.4 Hz, 1H), 6.91 (d, J=6.4 Hz, 1H), 6.15 (d, J=8.4 Hz, 1H), 5.95 (d, J=8.0 Hz, 1H), 4.30 (brs, 1H), 4.21 (t, J=4.8 Hz, 2H), 3.86-3.77 (m, 1H), 3.70-3.65 (m, 8H), 3.37 (t, J=4.8 Hz, 2H), 2.38-2.31 (m, 1H), 2.25-2.17 (m, 1H), 1.92-1.89 (m, 1H), 1.86-1.71 (m, 6H), 1.64 (d, J=6.8 Hz, 3H), 1.50-1.45 (m, 2H), 1.42-1.25 (m, 6H), 1.23-1.12 (m, 6H), 1.07-0.94 (m, 5H), 0.90 (s, 3H), 0.86 (d, J=6.4 Hz, 3H), 0.60 (s, 3H). 13C NMR (100 MHz, $CDCl_3$): δ 174.4, 169.4, 144.3, 143.9, 142.3, 135.9, 125.0, 100.1, 70.7, 70.6, 70.1, 69.3, 63.4, 56.7, 56.1, 53.7, 50.7, 50.1, 42.7, 42.3, 40.6, 40.2, 35.7, 35.6, 35.3, 34.5, 33.4, 31.1, 30.9, 28.2, 27.8, 26.9, 26.3, 24.1, 23.5, 20.8, 19.1, 18.3, 12.0. HRMS calcd for $C_{39}H_{58}N_8O_8Na$ (M+Na)+, 789.4275; found, 789.4280.

2-((7-nitrobenzo[c][1,2,5]oxadiazol-4-yl)amino)propanamido)-10,13-dimethyl hexadecahydro-1H-cyclopenta[a]phenanthren-17-yl)pentanoate. 1-2-19c (Compound 20)

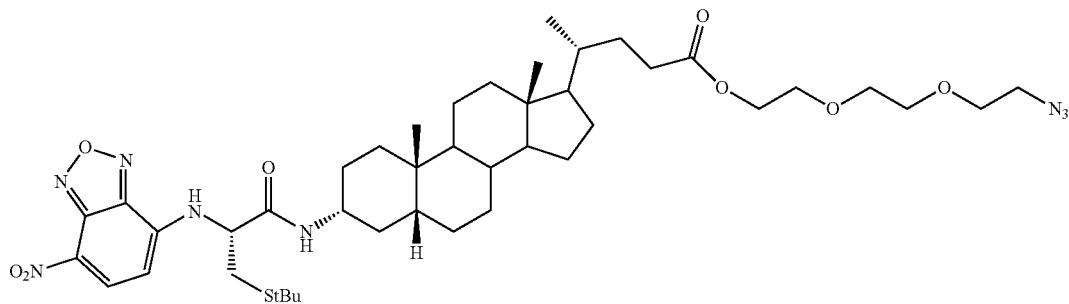

mp 64-65° C., 1H NMR (400 MHz, CDCl₃): δ 8.43 (d, J=8.4 Hz, 1H), 7.13 (brs, 1H), 6.28 (d, J=8.0 Hz, 1H), 6.17 (d, J=8.4 Hz, 1H), 4.30-4.27 (m, 1H), 4.19 (t, J=4.8 Hz, 2H), 3.84-3.78 (m, 1H), 3.69-3.64 (m, 8H), 3.36 (t, J=4.8 Hz, 2H), 3.12 (dd, J=6.4, 12.8 Hz, 1H), 3.04 (dd, J=6.4, 12.8 Hz, 1H), 2.36-2.29 (m, 1H), 2.24-2.14 (m, 1H), 1.90-1.87 (m, 1H), 1.84-1.73 (m, 5H), 1.68-1.59 (m, 2H), 1.50-1.39 (m, 3H), 1.34 (s, 9H), 1.30-1.13 (m, 9H), 0.89 (s, 5H), 0.84 (d, J=6.4 Hz, 3H), 0.58 (s, 3H). 13C NMR (100 MHz, CDCl₃): δ 174.2, 167.3, 144.3, 143.7, 142.2, 135.8, 125.4, 100.4, 70.7, 70.6, 70.0, 69.2, 63.4, 57.2, 56.5, 56.0, 50.7, 50.3, 43.7, 42.7, 42.3, 40.5, 40.1, 35.7, 35.2, 34.5, 33.3, 31.1, 30.9, 30.8, 28.1, 27.7, 26.9, 26.3, 24.1, 23.4, 20.7, 18.2, 12.0. HRMS calcd for C₄₂H₆₆N₈O₈SNa (M+Na)+, 877.4617; found, 877.4654.

(4R)-2-(2-(2-azidoethoxy)ethoxy)ethyl-4-((3R,5R,10S,13R)-10,13-dimethyl-3-((S)-2-((7-nitrobenzo[c][1,2,5]oxadiazol-4-yl)amino)-3-phenylpropanamido)hexadecahydro-1H-cyclopenta[a]phenanthren-17-yl)pentanoate. 1-2-19e (Compound 25)

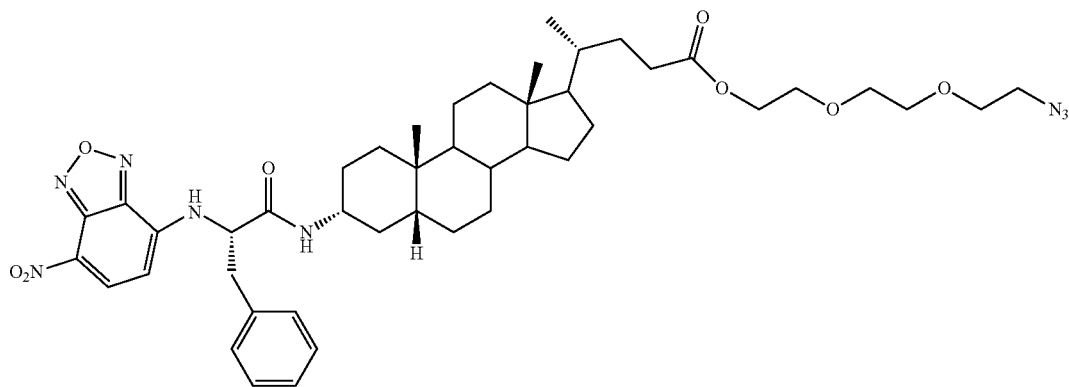 [SMILES: C[C@H](CCC(=O)OCCOCCOCCN=[N+]=[N-])C1CCC2C3CC[C@@H]4C[C@H](NC(=O)[C@H](Cc5ccccc5)Nc5ccc([N+](=O)[O-])c6nonc56)CC[C@]4(C)C3CC[C@@]21C]

mp 65-66° C., 1H NMR (400 MHz, CDCl₃): δ 8.40 (d, J=8.4 Hz, 1H), 7.36-7.25 (m, 5H), 6.91 (d, J=6.8 Hz, 1H), 6.14 (d, J=8.4 Hz, 1H), 5.55 (d, J=8.0 Hz, 1H), 4.49-4.46 (m, 1H), 4.20 (t, J=4.8 Hz, 2H), 3.72-3.65 (m, 9H), 3.37 (t, J=4.8 Hz, 2H), 3.30 (dd, J=6.0, 13.6 Hz, 1H), 3.18 (dd, J=6.0, 13.6 Hz, 1H), 2.38-2.31 (m, 1H), 2.25-2.15 (m, 1H), 1.92-1.89 (m, 1H), 1.83-1.72 (m, 6H), 1.50-1.47 (m, 1H), 1.44-1.41 (m, 3H), 1.40-1.36 (m, 1H), 1.33-1.21 (m, 5H), 1.19-1.15 (m, 3H), 1.03-0.91 (m, 6H), 0.87 (d, J=6.0 Hz, 3H), 0.85 (s, 3H), 0.59 (s, 3H). 13C NMR (100 MHz, CDCl₃): δ 174.3, 167.8, 144.2, 143.9, 142.4, 135.8, 135.2, 129.3, 129.2, 127.8, 100.3, 70.7, 70.6, 70.1, 69.3, 63.4, 59.3, 56.6, 56.0, 50.7, 50.0, 42.7, 42.2, 40.5, 40.2, 39.2, 35.7, 35.3, 34.5, 33.3, 31.1, 30.9, 28.2, 27.4, 26.9, 26.3, 24.1, 23.4, 20.7, 18.2, 12.0. HRMS calcd for C₄₅H₆₂N₈O₈Na (M+Na)+, 865.4588; found, 865.4579.

(4R)-2-(2-(2-azidoethoxy)ethoxy)ethyl-4-((3R,5R,10S,13R)-10,13-dimethyl-3-(1-(7-nitrobenzo[c][1,2,5]oxadiazol-4-yl)pyrrolidine-2-carboxamido)hexadecahydro-1H-cyclopenta[a]phenanthren-17-yl)pentanoate. 1-2-19j (Compound 27)

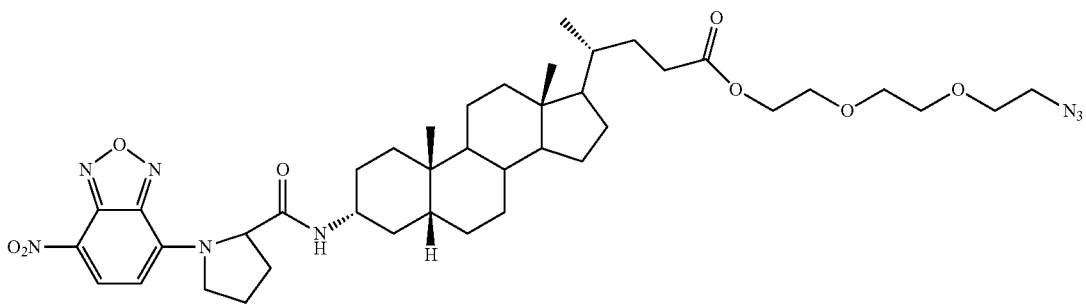 [SMILES: C[C@H](CCC(=O)OCCOCCOCCN=[N+]=[N-])C1CCC2C3CC[C@@H]4C[C@H](NC(=O)C5CCCN5c5ccc([N+](=O)[O-])c6nonc56)CC[C@]4(C)C3CC[C@@]21C]

mp 62-64° C., 1H NMR (400 MHz, CDCl₃): δ 8.37 (d, J=9.2 Hz, 1H), 6.08 (d, J=9.2 Hz, 1H), 6.02 (s, 1H), 4.20 (t, J=4.8 Hz, 2H), 3.86-3.65 (m, 10H), 3.37 (t, J=4.8 Hz, 2H), 2.52-2.14 (m, 8H), 1.90-1.87 (m, 1H), 1.81-1.68 (m, 4H), 1.64-1.61 (m, 1H), 1.58-1.54 (m, 1H), 1.48-1.46 (m, 1H), 1.37-1.10 (m, 13H), 1.04-0.90 (m, 5H), 0.86 (d, J=4.0 Hz, 3H), 0.84 (s, 3H), 0.58 (s, 3H). 13C NMR (125 MHz, CDCl₃): δ 174.3, 169.6, 144.8, 144.4, 143.5, 135.4, 123.0, 102.3, 70.7, 70.6, 70.1, 69.3, 65.7, 63.4, 56.6, 56.1, 50.7, 50.0, 42.7, 42.3, 40.6, 40.2, 35.7, 35.3, 34.5, 33.2, 31.7, 31.2, 31.0, 28.2, 27.6, 26.8, 26.3, 24.1, 23.4, 20.8, 18.2, 12.0. HRMS calcd for $C_{41}H_{60}N_8O_8Na$ (M+Na)+, 815.4426; found, 815.4429.

(4S)-5-(((3R,5R,10S,13R)-17-((R)-5-(2-(2-(2-azido-ethoxy)ethoxy)ethoxy)-5-oxopentan-2-yl)-10,13-dimethylhexadecahydro-1H-cyclopenta[a]phenanthren-3-yl)amino)-4-((7-nitrobenzo[c][1,2,5]oxadiazol-4-yl)amino)-5-oxopentanoic acid. 1-2-20b (Compound 21)

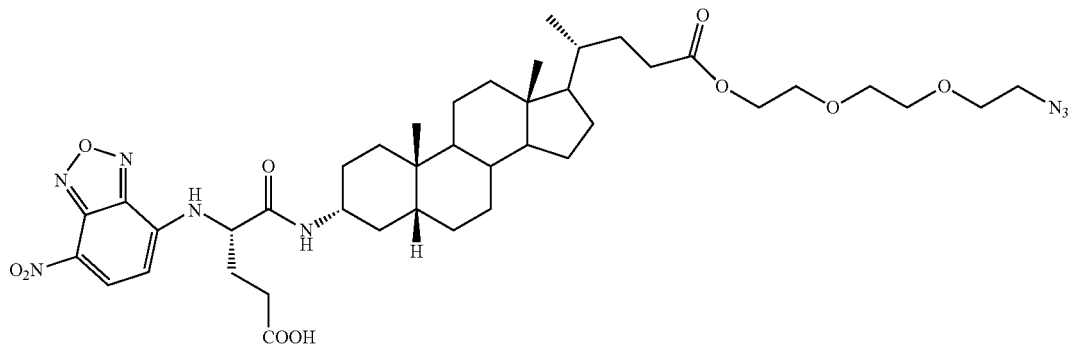 [SMILES: C[C@H](CCC(=O)OCCOCCOCCN=[N+]=[N-])C1CCC2C3CC[C@@H]4C[C@H](NC(=O)[C@H](CCC(=O)O)Nc5ccc([N+](=O)[O-])c6nonc56)CC[C@]4(C)C3CC[C@@]21C]

mp 77-78° C., 1H NMR (500 MHz, CDCl₃): δ 8.38 (d, J=8.0 Hz, 1H), 8.05 (brs, 1H), 6.98 (brs, 1H), 6.27 (d, J=8.0 Hz, 1H), 4.48-4.46 (m, 1H), 4.22 (t, J=4.5 Hz, 2H), 3.87-3.81 (m, 1H), 3.71-3.66 (m, 8H), 3.38 (t, J=4.5 Hz, 2H), 2.68-2.63 (m, 2H), 2.36-2.32 (m, 3H), 2.22-2.20 (m, 1H), 1.84-1.52 (m, 7H), 1.45-1.15 (m, 14H), 1.01-0.90 (m, 4H), 0.86 (s, 3H), 0.81 (d, J=5.5 Hz, 3H), 0.70-0.69 (m, 1H), 0.54 (s, 3H). 13C NMR (125 MHz, CDCl₃): δ 176.9, 174.7, 169.1, 144.4, 143.7, 143.3, 136.6, 124.3, 100.4, 70.7, 70.6, 70.1, 69.2, 63.5, 58.0, 56.6, 56.1, 50.7, 50.2, 42.6, 42.3, 40.5, 40.1, 35.7, 35.6, 35.3, 34.4, 33.0, 31.2, 31.0, 30.1, 28.2, 27.5, 27.3, 26.9, 26.2, 24.1, 23.4, 20.7, 18.2, 11.9. HRMS calcd for $C_{41}H_{60}N_8O_{10}Na$ (M+Na)+, 847.4324; found, 847.4342.

(4R)-2-(2-(2-azidoethoxy)ethoxy)ethyl-4-((3R,5R,10S,13R)-3-((R)-3-mercapto-2-((7-nitrobenzo[c][1,2,5]oxadiazol-4-yl)amino)propanamido)-10,13-dimethylhexadecahydro-1H-cyclopenta[a]phenanthren-17-yl)pentanoate. 1-2-20d (Compound 19)

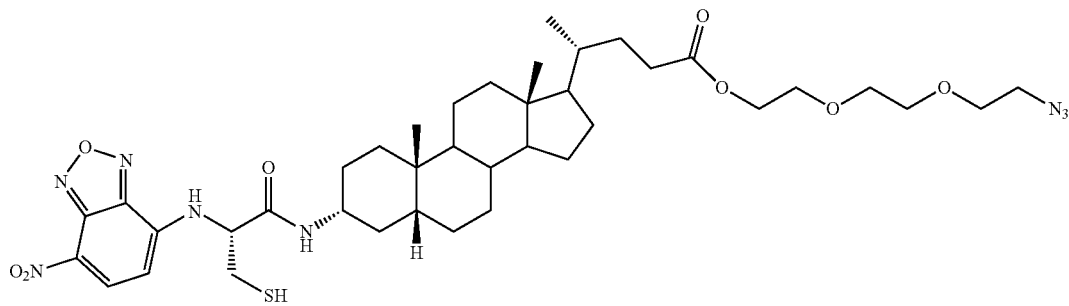 [SMILES: C[C@H](CCC(=O)OCCOCCOCCN=[N+]=[N-])C1CCC2C3CC[C@@H]4C[C@H](NC(=O)[C@H](CS)Nc5ccc([N+](=O)[O-])c6nonc56)CC[C@]4(C)C3CC[C@@]21C]

mp 68-69° C., 1H NMR (500 MHz, CDCl₃): δ 8.43 (d, J=8.0 Hz, 1H), 7.20 (d, J=4.5 Hz, 1H), 6.40 (d, J=7.0 Hz, 1H), 6.24 (d, J=8.0 Hz, 1H), 4.50-4.41 (m, 1H), 4.20 (t, J=4.0 Hz, 2H), 3.83-3.65 (m, 10H), 3.37 (t, J=4.0 Hz, 2H), 3.22-3.19 (m, 1H), 3.05-2.98 (m, 1H), 2.35-2.31 (m, 1H), 2.23-2.20 (m, 1H), 1.88-1.86 (m, 1H), 1.78-1.62 (m, 6H), 1.49-1.43 (m, 3H), 1.32-1.18 (m, 10H), 1.04-0.95 (m, 6H), 0.88 (s, 3H), 0.83 (d, J=6.0 Hz, 3H), 0.57 (s, 3H). 13C NMR (125 MHz, CDCl₃): δ 174.6, 166.9, 144.3, 143.9, 142.4, 136.0, 125.2, 100.9, 70.7, 70.6, 70.2, 69.3, 63.6, 59.3, 56.7, 56.0, 50.7, 50.4, 42.7, 42.4, 40.6, 40.2, 35.7, 35.4, 34.6, 33.4, 31.1, 30.9, 28.2, 27.9, 27.3, 26.9, 26.3, 24.2, 23.5, 20.8, 18.3, 12.1. HRMS calcd for $C_{39}H_{58}N_8O_8SNa$ (M+Na)+, 821.3996; found, 821.3990.

(4R)-2-(2-(2-azidoethoxy)ethoxy)ethyl-4-((3R,5R,10S,13R)-3-((S)-3-(4-hydroxyphenyl)-2-((7-nitrobenzo[c][1,2,5]oxadiazol-4-yl)amino)propanamido)-10,13-dimethylhexadecahydro-1H-cyclopenta[a]phenanthren-17-yl)pentanoate. 1-2-20f (Compound 24)

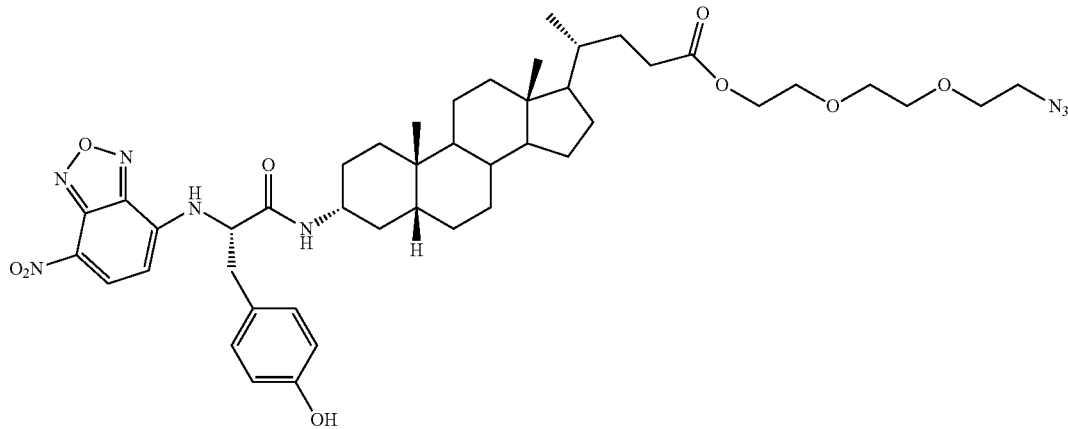 [SMILES: C[C@H](CCC(=O)OCCOCCOCCN=[N+]=[N-])C1CCC2C3CC[C@@H]4C[C@H](NC(=O)[C@H](Cc5ccc(O)cc5)Nc5ccc([N+](=O)[O-])c6nonc56)CC[C@]4(C)C3CC[C@@]21C]

mp 72-73° C., 1H NMR (400 MHz, CDCl₃): δ 8.34 (d, J=8.4 Hz, 1H), 7.19 (d, J=4.4 Hz, 1H), 7.04 (d, J=8.4 Hz, 2H), 6.71 (d, J=8.4 Hz, 2H), 6.43 (d, J=4.4 Hz, 1H), 6.15 (d, J=8.4 Hz, 1H), 4.56-4.41 (m, 1H), 4.17 (t, J=5.2 Hz, 2H), 3.84-3.73 (m, 1H), 3.70-3.63 (m, 8H), 3.36 (t, J=5.2 Hz, 2H), 3.18 (d, J=5.2 Hz, 2H), 2.36-2.28 (m, 1H), 2.24-2.16 (m, 1H), 1.86-1.80 (m, 1H), 1.73-1.58 (m, 5H), 1.55-1.48 (m, 1H), 1.42-1.34 (m, 4H), 1.25-1.20 (m, 5H), 1.15-1.10 (m, 5H), 0.99-0.87 (m, 3H), 0.84-0.81 (m, 9H), 0.55 (s, 3H). 13C NMR (100 MHz, CDCl₃): δ 174.7, 168.7, 155.8, 144.2, 143.8, 143.1, 136.4, 130.4, 126.5, 124.1, 116.0, 100.4, 70.6, 70.5, 70.0, 69.2, 63.5, 59.5, 56.5, 56.0, 50.6, 50.1, 42.6, 42.2, 40.4, 40.1, 38.4, 35.6, 35.3, 34.4, 33.1, 31.1, 30.9, 28.2, 27.3, 26.9, 26.2, 24.0, 23.4, 20.7, 18.2, 11.9. HRMS calcd for $C_{45}H_{62}N_8O_9Na$ (M+Na)+, 881.4532; found, 881.4567.

(4R)-2-(2-(2-azidoethoxy)ethoxy)ethyl-4-((3R,5R,10S,13R)-3-((S)-3-(1H-indol-3-yl)-2-((7-nitrobenzo[c][1,2,5]oxadiazol-4-yl)amino)propanamido)-10,13-di methylhexadecahydro-1H-cyclopenta[a]phenanthren-17-yl)pentanoate. 1-2-20g (Compound 26)

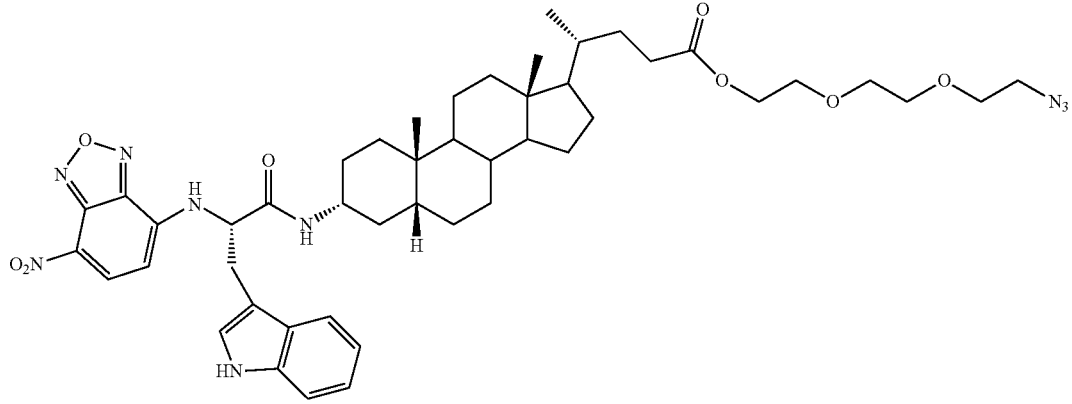 [SMILES: C[C@H](CCC(=O)OCCOCCOCCN=[N+]=[N-])C1CCC2C3CC[C@@H]4C[C@H](NC(=O)[C@H](Cc5c[nH]c6ccccc56)Nc5ccc([N+](=O)[O-])c6nonc56)CC[C@]4(C)C3CC[C@@]21C]

mp 86-87° C., 1H NMR (500 MHz, CDCl₃): δ 8.63 (s, 1H), 8.30 (d, J=8.5 Hz, 1H), 7.59 (d, J=8.0 Hz, 1H), 7.34 (d, J=8.0 Hz, 1H), 7.19 (d, J=2.0 Hz, 1H), 7.15 (t, J=7.5 Hz, 1H), 7.06 (t, J=7.5 Hz, 1H), 7.04 (d, J=2.0 Hz, 1H), 6.13 (d, J=8.5 Hz, 2H), 4.63-4.50 (m, 1H), 4.19 (t, J=5.0 Hz, 2H), 3.74-3.59 (m, 9H), 3.50 (dd, J=6.0, 14.5 Hz, 1H), 3.43 (dd, J=6.0, 14.5 Hz, 1H), 3.36 (t, J=5.0 Hz, 2H), 2.32-2.27 (m, 1H), 2.21-2.14 (m, 1H), 1.84-1.81 (m, 1H), 1.76-1.60 (m, 4H), 1.43-1.29 (m, 5H), 1.25-1.02 (m, 10H), 0.95-0.86 (m, 4H), 0.83 (s, 3H), 0.80 (d, J=6.5 Hz, 3H), 0.76-0.70 (m, 2H), 0.53 (s, 3H). 13C NMR (125 MHz, CDCl₃): δ 174.5, 169.2, 144.1, 143.6, 142.8, 136.3, 136.2, 127.0, 124.4, 123.6, 122.6, 120.0, 118.3, 111.6, 108.9, 100.5, 70.5, 70.4, 70.0, 69.2, 63.4, 58.4, 56.5, 55.9, 50.6, 50.2, 42.7, 42.5, 42.1, 40.3, 40.0, 35.5, 35.2, 34.3, 32.7, 31.1, 30.8, 29.0, 28.1, 27.1, 26.8, 26.1, 24.0, 23.3, 20.6, 18.1, 11.9. HRMS calcd for $C_{47}H_{63}N_9O_8Na$ (M+Na)+, 904.4692; found, 904.4696.

(4R)-2-(2-(2-azidoethoxy)ethoxy)ethyl-4-((3R,5R,10S,13R)-3-((S)-6-amino-2-((7-nitrobenzo[c][1,2,5]oxadiazol-4-yl)amino)hexanamido)-10,13-dimethylhexadecahydro-1H-cyclopenta[a]phenanthren-17-yl)pentanoate. 1-2-20 h (Compound 22)

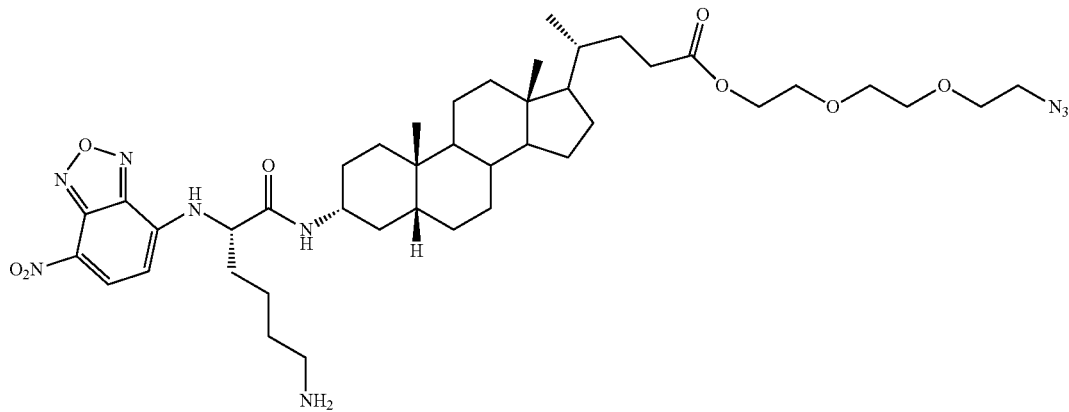 [SMILES: C[C@H](CCC(=O)OCCOCCOCCN=[N+]=[N-])C1CCC2C3CC[C@@H]4C[C@H](NC(=O)[C@H](CCCCN)Nc5ccc([N+](=O)[O-])c6nonc56)CC[C@]4(C)C3CC[C@@]21C]

mp 84-85, 1H NMR (400 MHz, CDCl₃): δ 8.26 (d, J=6.0 Hz, 1H), 8.12 (d, J=2.4 Hz, 1H), 7.91 (brs, 2H), 7.27 (brs, 1H), 6.29-6.22 (m, 1H), 4.21 (t, J=4.8 Hz, 2H), 3.71-3.65 (m, 9H), 3.37 (t, J=4.8 Hz, 2H), 3.03-2.99 (m, 1H), 2.70-2.65 (m, 3H), 2.35-2.33 (m, 1H), 2.25-2.18 (m, 1H), 2.04-2.02 (m, 2H), 1.84-1.54 (m, 10H), 1.42-1.16 (m, 13H), 0.94-0.83 (m, 12H), 0.57 (s, 3H). 13C NMR (100 MHz, CDCl₃): δ 174.5, 169.7, 144.2, 143.8, 137.1, 123.1, 115.2, 100.3, 70.7, 70.6, 70.1, 69.2, 63.5, 58.2, 56.4, 56.2, 50.7, 50.4, 42.6, 42.5, 40.4, 40.0, 39.5, 35.7, 35.4, 34.5, 32.9, 31.9, 31.4, 31.0, 28.2, 27.3, 27.0, 26.7, 26.3, 24.1, 23.5, 22.3, 20.8, 18.2, 12.0. HRMS calcd for $C_{42}H_{66}N_9O_8$ (M+H)+, 824.5028; found, 824.5016.

(4R)-2-(2-(2-azidoethoxy)ethoxy)ethyl-4-((3R,5R,10S,13R)-3-((S)-5-guanidino-2-((7-nitrobenzo[c][1,2,5]oxadiazol-4-yl)amino)pentanamido)-10,13-dimethylhexadecahydro-1H-cyclopenta[a]phenanthren-17-yl)pentanoate. 1-2-19j (Compound 23)

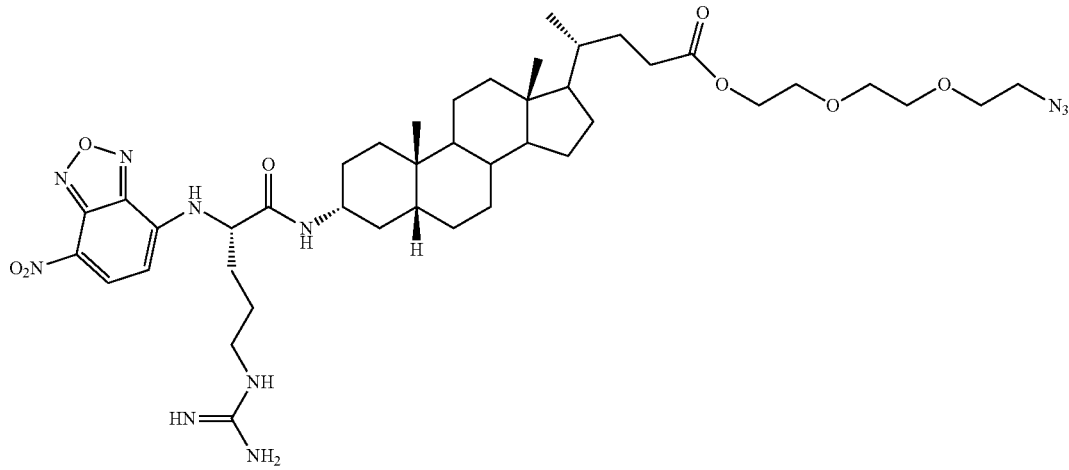 [SMILES: C[C@H](CCC(=O)OCCOCCOCCN=[N+]=[N-])C1CCC2C3CC[C@@H]4C[C@H](NC(=O)[C@H](CCCNC(=N)N)Nc5ccc([N+](=O)[O-])c6nonc56)CC[C@]4(C)C3CC[C@@]21C]

mp 78-79° C., 1H NMR (500 MHz, d6-DMSO): δ 9.26 (s, 1H), 8.58 (d, J=6.5 Hz, 1H), 8.22 (s, 1H), 7.70 (s, 1H), 7.38-6.95 (m, 3H), 6.27 (d, J=6.5 Hz, 1H), 4.30-4.20 (m, 1H), 4.10 (t, J=6.0 Hz, 2H), 3.71-3.64 (m, 2H), 3.60-3.54 (m, 8H), 3.11 (t, J=6.0 Hz, 2H), 2.35-2.29 (m, 1H), 2.23-2.17 (m, 1H), 1.92-1.90 (m, 3H), 1.80-1.78 (m, 2H), 1.72-1.68 (m, 3H), 1.58-1.52 (m, 3H), 1.43-1.42 (m, 1H), 1.39-1.27 (m, 7H), 1.21-1.18 (m, 6H), 0.88 (s, 3H), 0.85 (d, J=5.5 Hz, 3H), 0.59 (s, 3H). 13C NMR (125 MHz, d6-DMSO): δ 173.4, 168.6, 158.5, 156.7, 144.5, 144.1, 137.9, 121.9, 99.9, 70.6, 69.8, 69.7, 69.4, 68.4, 63.1, 57.4, 56.2, 55.7, 50.0, 49.0, 43.6, 42.3, 41.9, 40.4, 35.6, 35.4, 34.8, 34.3, 32.8, 30.6, 28.7, 27.8, 27.2, 26.7, 26.2, 25.4, 23.9, 23.3, 20.4, 18.1, 11.9. HRMS calcd for $C_{42}H_{64}N_{11}O_8$(M–H)–, 850.4939; found, 850.4932.
1.3 Synthesis of Compounds 28 to 40
The compounds 28 to 40 (i.e., compounds of formula (1-3)) were synthesized in accordance with procedures set forth in Scheme 9.
Scheme 9:
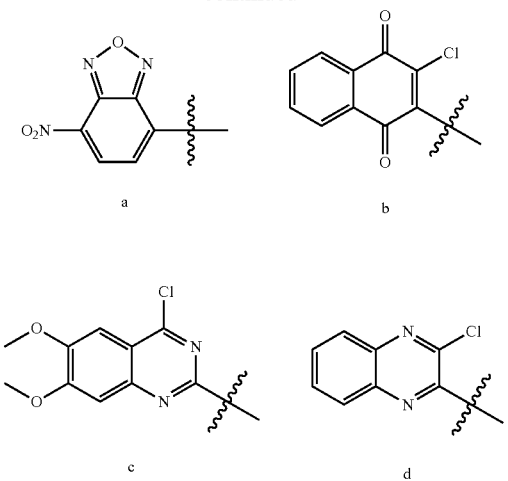
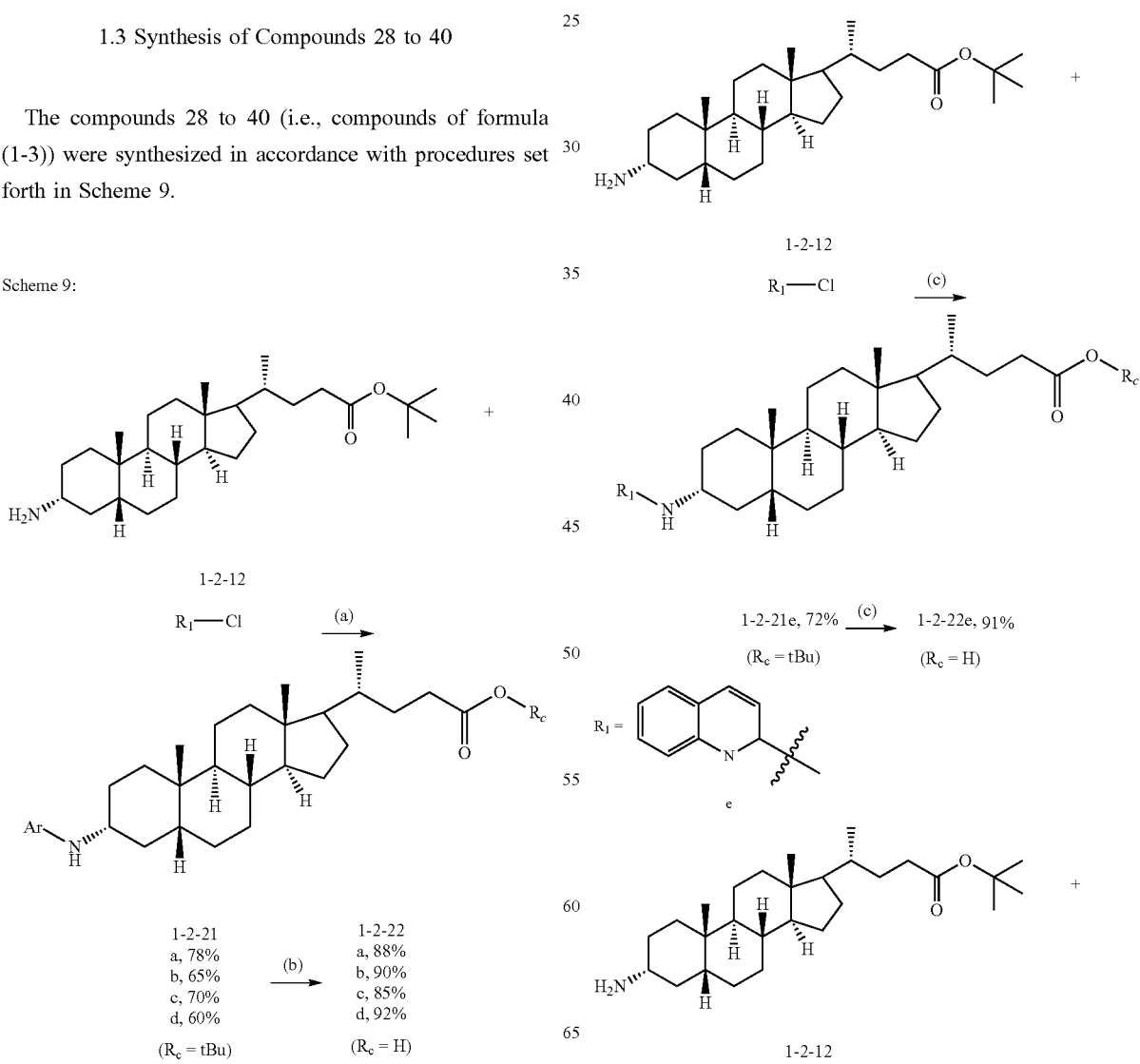

-continued

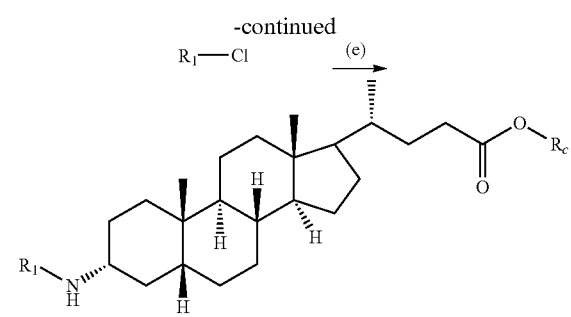

1-2-21
f, 58%
g, 62%
h, 66%
i, 62%

(f) →

1-2-22
f, 91%
g, 93%
h, 88%
i, 90%
(R_c = H)

R_1 =

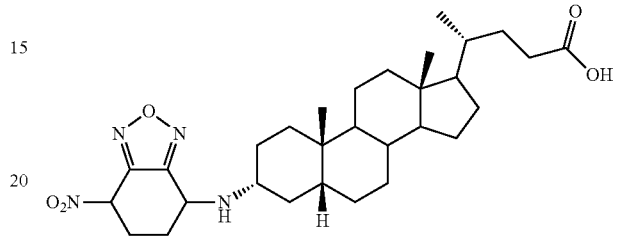

f g h i

Reagents and conditions: (a) Different R_1—Cl (a-d), NEt_3, 1-BuOH, 120° C., 12 h, (b) TFA, H_2O, CH_2Cl_2, rt, 3 h, (c)R_1—Cl (e), Pd_2(dba)_3, P(tBu)_3HBF_4, Cs_2CO_3, 1,4-dioxane, 120° C., 4 h, (d) TFA, H_2O, CH_2Cl_2, rt, 3 h, (e) Different R_1—Cl (f-i), DIPEA, CH_2Cl_2, rt, 6 h, (f) TFA, H_2O, CH_2Cl_2, rt, 3 h.

General Procedures for SN—R_1 Reaction

The compound 1-2-12 (1.02 mmol), R_1—Cl (1.02 mmol) and NEt_3 (2.04 mmol) were dissolved in 10 mL 1-butanol and the reaction mixture was stirred at 120° C. for 12 h. The reaction mass was concentrated and product was purified by flash column chromatography to get target compound.

General Procedures for Amination

To a stirred solution of 1-2-12 (1.02 mmol) and R_1—Cl (1.02 mmol) in 10 mL 1,4-dioxane was added Pd_2(dba)_3 (0.10 mmol), P(tBu)_3HBF_4 (0.20 mmol) and Cs_2CO_3 (2.04 mmol). The reaction mixture was stirred at 120° C. for 4 h. The reaction mass was concentrated and product was purified by flash column chromatography to get target compound.

General Procedure for Sulforamide Formation

To a stirred solution of 1-2-12 (1.11 mmol) and R_1—Cl (1.33 mmol) in 10 mL CH_2Cl_2 was added DIPEA (1.67 mmol) dropwise. The reaction mixture was stirred at rt for 6 h. The reaction mass was concentrated and product was purified by flash column chromatography to get target compound.

(4R)-4-((3R,5R,10S,13R)-10,13-dimethyl-3-((7-nitrobenzo[c][1,2,5]oxadiazol-4-yl)amino)hexadecahydro-1H-cyclopenta[a]phenanthren-17-yl)pentanoic acid. 1-2-22a (Compound 28)

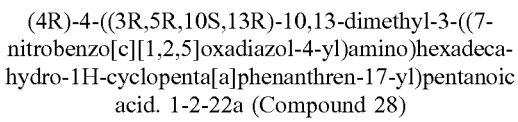

mp 137-139° C., 1H NMR (400 MHz, CDCl_3): δ 8.45 (d, J=8.8 Hz, 1H), 6.22 (d, J=8.0 Hz, 1H), 6.16 (d, J=8.8 Hz, 1H), 3.72-3.66 (m, 1H), 2.42-2.34 (m, 1H), 2.28-2.20 (m, 1H), 2.02-1.73 (m, 7H), 1.62-1.52 (m, 2H), 1.50-1.36 (m, 5H), 1.35-1.22 (m, 5H), 1.21-1.01 (m, 7H), 0.99 (s, 3H), 0.90 (d, J=6.4 Hz, 3H), 0.64 (s, 3H). 13C NMR (100 MHz, CDCl_3): δ 179.1, 144.4, 144.0, 142.9, 136.6, 123.5, 98.6, 56.5, 56.0, 54.1, 42.7, 42.5, 40.7, 40.1, 35.8, 35.6, 35.3, 34.8, 33.0, 30.8, 30.7, 28.1, 27.2, 27.0, 26.3, 24.1, 23.5, 20.9, 18.2, 12.0. HRMS calcd for $C_{30}H_{41}N_4O_5$ (M–H)$^-$, 537.3077; found, 537.3085.

(4R)-4-((3R,5R,10S,13R)-3-((3-chloro-1,4-dioxo-1,4-dihydronaphthalen-2-yl)amino)-10,13-dimethyl hexadecahydro-1H-cyclopenta[a]phenanthren-17-yl) pentanoic acid. 1-2-22b (Compound 32)

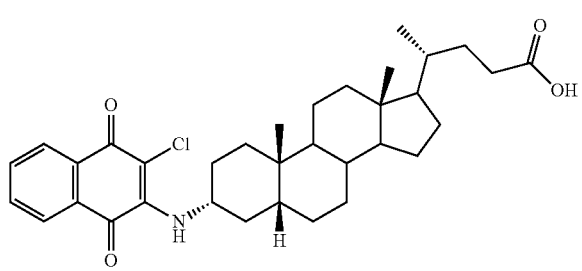 [SMILES: C[C@H](CCC(=O)O)C1CCC2C3CC[C@@H]4C[C@H](NC5=C(Cl)C(=O)c6ccccc6C5=O)CC[C@]4(C)C3CC[C@@]21C]

mp 120-122° C., 1H NMR (400 MHz, CDCl_3): δ 8.12 (d, J=7.2 Hz, 1H), 8.00 (d, J=7.2 Hz, 1H), 7.69 (t, J=7.2 Hz, 1H), 7.59 (t, J=7.2 Hz, 1H), 6.01 (brs, 1H), 4.45-4.35 (m, 1H), 2.42-2.34 (m, 1H), 2.28-2.20 (m, 1H), 2.02-1.94 (m, 1H), 1.89-1.72 (m, 6H), 1.69-1.61 (m, 1H), 1.59-1.47 (m, 2H), 1.43-1.23 (m, 10H), 1.18-1.02 (m, 6H), 0.94 (s, 3H), 0.90 (d, J=6.4 Hz, 3H), 0.63 (s, 3H). 13C NMR (100 MHz, CDCl_3): δ 180.6, 179.5, 176.8, 143.5, 134.9, 132.9, 132.3, 129.7, 126.8, 56.5, 56.0, 53.8, 42.7, 42.3, 40.6, 40.1, 35.8, 35.5, 35.4, 35.3, 34.6, 30.9, 30.8, 29.6, 28.1, 27.1, 26.4, 24.2, 23.4, 20.8, 18.2, 12.0. HRMS calcd for $C_{34}H_{43}NO_4Cl$ (M–H)$^-$, 564.2881; found, 564.2872.

113

(4R)-4-((3R,5R,10S,13R)-3-((2-chloro-6,7-dimethoxyquinazolin-4-yl)amino)-10,13-dimethylhexadecahydro-1H-cyclopenta[a]phenanthren-17-yl)pentanoic acid. 1-2-22c (Compound 33)

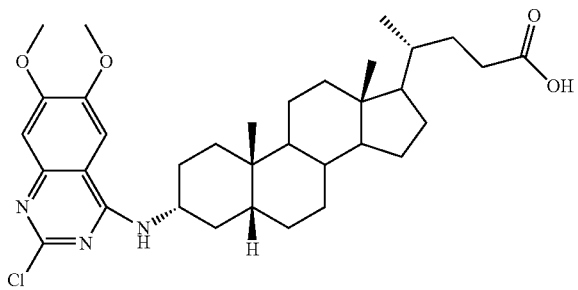 [SMILES: COc1cc2nc(Cl)nc(N[C@@H]3CC[C@]4(C)C5CC[C@@]6(C)C(CCC6[C@H](C)CCC(=O)O)C5CC[C@@H]4C3)c2cc1OC]

mp 178-180° C., 1H NMR (400 MHz, d6-DMSO): δ 8.00 (d, J=3.6 Hz, 1H), 7.63 (s, 1H), 7.04 (s, 1H), 4.21-4.10 (m, 1H), 3.90 (s, 3H), 3.87 (s, 3H), 2.27-2.20 (m, 1H), 2.14-2.06 (m, 1H), 1.99-1.73 (m, 6H), 1.66-1.64 (m, 2H), 1.50-1.48 (m, 5H), 1.41-1.35 (m, 4H), 1.26-1.15 (m, 4H), 1.12-1.04 (m, 5H), 0.94 (s, 3H), 0.87 (d, J=6.0 Hz, 3H), 0.62 (s, 3H). 13C NMR (100 MHz, d6-DMSO): δ 174.9, 159.1, 155.1, 154.4, 148.4, 147.1, 106.8, 106.4, 102.4, 56.2, 56.1, 55.8, 55.7, 50.4, 42.3, 42.0, 35.7, 35.3, 34.9, 34.3, 33.1, 32.5, 30.8, 30.6, 27.7, 26.7, 26.2, 23.8, 23.2, 20.4, 18.1, 11.8. HRMS calcd for $C_{34}H_{48}N_3O_4Cl$ (M+H)+, 598.3406; found, 598.3396.

(4R)-4-((3R,5R,10S,13R)-3-((3-chloroquinoxalin-2-yl)amino)-10,13-dimethylhexadecahydro-1H-cyclopenta[a]phenanthren-17-yl)pentanoic acid. 1-2-22d (Compound 34)

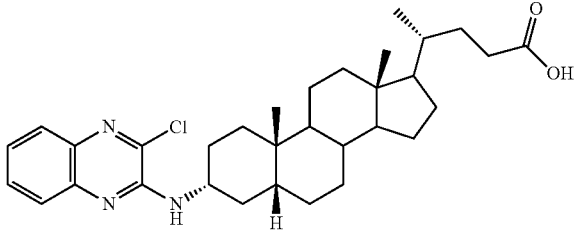 [SMILES: C[C@H](CCC(=O)O)C1CCC2C3CC[C@@H]4C[C@H](Nc5nc6ccccc6nc5Cl)CC[C@]4(C)C3CC[C@@]21C]

mp 118-120° C., 1H NMR (400 MHz, CDCl$_3$): δ 7.79-7.73 (m, 2H), 7.59 (t, J=8.4 Hz, 1H), 7.40 (t, J=8.4 Hz, 1H), 5.69-5.67 (m, 1H), 4.15-4.09 (m, 1H), 2.43-2.35 (m, 1H), 2.29-2.21 (m, 1H), 1.98-1.95 (m, 1H), 1.92-1.73 (m, 6H), 1.58-1.55 (m, 2H), 1.40-1.36 (m, 6H), 1.35-1.00 (m, 11H), 0.97 (s, 3H), 0.91 (d, J=6.4 Hz, 3H), 0.64 (s, 3H). 13C NMR (125 MHz, CDCl$_3$): δ 179.3, 146.5, 139.0, 138.0, 135.7, 130.9, 128.0, 125.5, 124.4, 56.6, 56.0, 51.8, 42.8, 42.3, 40.7, 40.2, 35.9, 35.6, 35.3, 34.7, 33.4, 30.8, 28.2, 27.6, 27.1, 26.4, 24.2, 23.5, 20.9, 18.3, 12.1. HRMS calcd for $C_{32}H_{45}N_3O_2Cl$ (M+H)+, 538.3194; found, 538.3205.

114

(4R)-4-((3R,5R,10S,13R)-10,13-dimethyl-3-(quinolin-2-ylamino)hexadecahydro-1H-cyclopenta[a]phenanthren-17-yl)pentanoic acid. 1-2-22e (Compound 30)

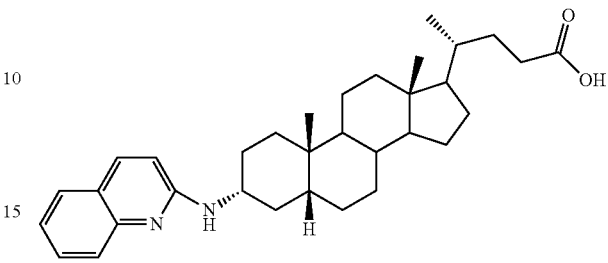

mp 140-142° C., 1H NMR (400 MHz, CDCl$_3$): δ 10.43 (d, J=5.2 Hz, 1H), 8.05 (d, J=9.2 Hz, 1H), 7.82 (d, J=9.2 Hz, 1H), 7.67-7.62 (m, 2H), 7.35 (t, J=8.0 Hz, 1H), 6.85 (d, J=9.6 Hz, 1H), 3.46-3.44 (m, 1H), 2.42-2.34 (m, 1H), 2.31-2.19 (m, 1H), 2.03-1.92 (m, 3H), 1.89-1.76 (m, 4H), 1.70-1.52 (m, 3H), 1.48-1.21 (m, 11H), 1.18-1.00 (m, 5H), 0.96 (s, 3H), 0.90 (d, J=6.4 Hz, 3H), 0.63 (s, 3H). 13C NMR (100 MHz, CDCl$_3$): δ 179.3, 152.8, 143.2, 137.7, 133.0, 128.0, 124.8, 120.5, 118.1, 109.5, 55.9, 55.8, 54.0, 42.8, 42.7, 40.4, 39.8, 35.9, 35.8, 35.3, 34.8, 33.2, 31.0, 30.8, 28.1, 27.3, 27.2, 26.3, 24.1, 23.6, 20.9, 18.2, 12.0. HRMS calcd for $C_{33}H_{47}N_2O_2$ (M+H)+, 503.3638; found, 503.3638.

(4R)-4-((3R,5R,10S,13R)-3-(5-chlorobenzo[c][1,2,5]oxadiazole-4-sulfonamido)-10,13-dimethylhexadecahydro-1H-cyclopenta[a]phenanthren-17-yl)pentanoic acid. 1-2-22f (Compound 36)

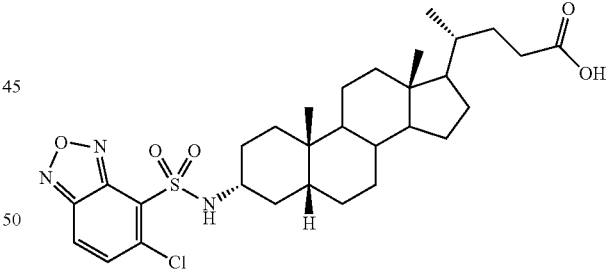

mp 128-130° C., 1H NMR (400 MHz, CDCl$_3$): δ 7.96 (d, J=9.2 Hz, 1H), 7.47 (d, J=9.2 Hz, 1H), 5.49 (d, J=7.6 Hz, 1H), 3.39-3.29 (m, 1H), 2.41-2.33 (m, 1H), 2.27-2.19 (m, 1H), 1.92-1.90 (m, 1H), 1.87-1.66 (m, 5H), 1.58-1.50 (m, 2H), 1.42-1.08 (m, 15H), 1.06-0.95 (m, 3H), 0.89 (d, J=6.4 Hz, 3H), 0.86 (s, 3H), 0.60 (s, 3H). 13C NMR (100 MHz, CDCl$_3$): δ 179.3, 148.0, 146.5, 138.3, 135.7, 128.2, 120.6, 56.4, 55.9, 54.9, 45.7, 42.7, 42.4, 40.4, 40.0, 35.7, 35.6, 35.3, 34.4, 34.3, 30.8, 30.7, 28.7, 28.1, 26.8, 26.2, 24.1, 23.3, 20.7, 18.2, 12.0. HRMS calcd for $C_{30}H_{42}N_3O_5ClNa$ (M+Na)+, 614.2456; found, 614.2422.

(4R)-4-((3R,5R,10S,13R)-3-(5-(dimethylamino)
naphthalene-1-sulfonamido)-10,13-dimethylhexa-
decahydro-1H-cyclopenta[a]phenanthren-17-yl)pen-
tanoic acid. 1-2-22g (Compound 37)

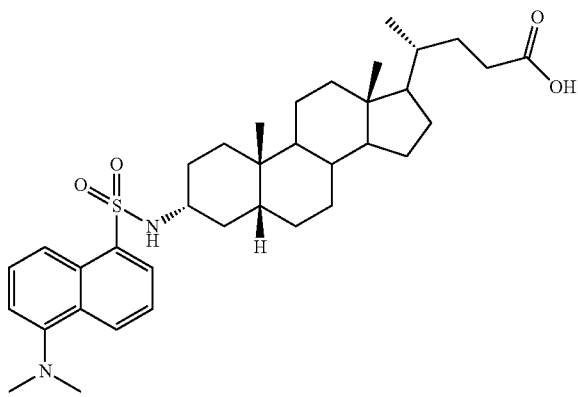 [SMILES: C[C@H](CCC(=O)O)C1CCC2C3CC[C@@H]4C[C@H](NS(=O)(=O)c5cccc6c(N(C)C)cccc56)CC[C@]4(C)C3CC[C@@]21C]

mp 136-138° C., 1H NMR (400 MHz, CDCl$_3$): δ 8.55 (d, J=8.8 Hz, 1H), 8.47 (d, J=8.8 Hz, 1H), 8.29 (dd, J=1.2, 7.6 Hz, 1H), 7.62-7.56 (m, 2H), 7.38 (d, J=7.6 Hz, 1H), 6.75 (s, 1H), 4.97 (d, J=6.4 Hz, 1H), 3.09 (s, 6H), 2.39-2.31 (m, 1H), 2.25-2.17 (m, 1H), 1.92-1.88 (m, 1H), 1.86-1.56 (m, 5H), 1.55-1.48 (m, 1H), 1.43-1.16 (m, 12H), 1.14-0.95 (m, 7H), 0.86 (d, J=6.0 Hz, 3H), 0.80 (s, 3H), 0.57 (s, 3H). 13C NMR (100 MHz, CDCl$_3$): δ 179.5, 147.0, 136.6, 129.6, 128.7, 128.5, 127.7, 124.7, 122.2, 116.3, 56.3, 55.9, 54.2, 45.9, 42.6, 42.5, 40.3, 40.0, 35.8, 35.6, 35.3, 34.6, 34.3, 30.9, 30.7, 28.8, 28.1, 26.8, 26.2, 24.1, 23.3, 20.7, 18.2, 11.9. HRMS calcd for C$_{36}$H$_{53}$N$_2$O$_4$S (M+H)+, 609.3726; found, 609.3718.

(4R)-4-((3R,5R,10S,13R)-3-(benzo[b]thiophene-2-
sulfonamido)-10,13-di methylhexadecahydro-1H-
cyclopenta[a]phenanthren-17-yl)pentanoic acid. 1-2-
22 h (Compound 38)

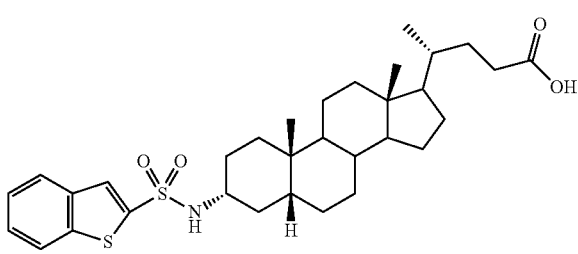 [SMILES: C[C@H](CCC(=O)O)C1CCC2C3CC[C@@H]4C[C@H](NS(=O)(=O)c5cc6ccccc6s5)CC[C@]4(C)C3CC[C@@]21C]

mp 132-134° C., 1H NMR (400 MHz, CDCl$_3$): δ 7.86-7.82 (m, 3H), 7.48-7.41 (m, 2H), 4.88 (d, J=7.6 Hz, 1H), 3.30-3.21 (m, 1H), 2.41-2.34 (m, 1H), 2.27-2.19 (m, 1H), 1.92-1.89 (m, 1H), 1.86-1.68 (m, 5H), 1.65-1.60 (m, 1H), 1.53-1.46 (m, 2H), 1.43-1.21 (m, 10H), 1.17-1.12 (m, 2H), 1.09-0.91 (m, 5H), 0.88 (d, J=6.4 Hz, 3H), 0.85 (s, 3H), 0.60 (s, 3H). 13C NMR (100 MHz, CDCl$_3$): δ 179.9, 142.5, 141.6, 137.6, 128.8, 127.0, 125.5, 125.3, 122.6, 56.3, 55.9, 54.5, 42.6, 42.5, 40.4, 40.0, 35.8, 35.7, 35.2, 34.5, 34.3, 30.9, 30.7, 28.8, 28.1, 26.8, 26.2, 24.1, 23.3, 20.7, 18.2, 11.9. HRMS calcd for C$_{32}$H$_{45}$NO$_4$S$_2$Na (M+Na)+, 594.2682; found, 594.2684.

(4R)-4-((3R,5R,10S,13R)-10,13-dimethyl-3-(quino-
line-8-sulfonamido)hexadecahydro-1H-cyclopenta
[a]phenanthren-17-yl)pentanoic acid. 1-2-22i (Com-
pound 39)

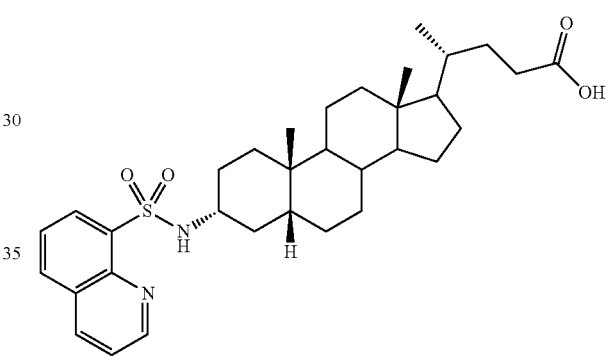

mp 138-140° C., 1H NMR (400 MHz, CDCl$_3$): δ 9.02 (dd, J=1.6, 4.4 Hz, 1H), 8.41 (dd, J=1.2, 7.6 Hz, 1H), 8.25 (dd, J=1.6, 8.4 Hz, 1H), 8.02 (dd, J=1.2, 8.4 Hz, 1H), 7.63 (t, J=7.6 Hz, 1H), 7.54 (dd, J=4.4, 8.0 Hz, 1H), 6.21 (brs, 1H), 3.11-3.06 (m, 1H), 2.41-2.33 (m, 1H), 2.27-2.19 (m, 1H), 1.89-1.87 (m, 1H), 1.85-1.74 (m, 2H), 1.73-1.49 (m, 4H), 1.47-1.14 (m, 12H), 1.10-0.95 (m, 7H), 0.88 (d, J=6.0 Hz, 3H), 0.78 (s, 3H), 0.58 (s, 3H). 13C NMR (100 MHz, CDCl$_3$): δ 178.9, 150.9, 143.3, 137.5, 137.0, 132.9, 130.5, 128.8, 125.7, 122.1, 56.4, 55.9, 54.6, 42.7, 42.4, 40.4, 40.1, 35.7, 35.3, 34.5, 34.4, 30.8, 28.6, 28.1, 26.9, 26.2, 24.1, 23.4, 20.7, 18.2, 12.0. HRMS calcd for C$_{33}$H$_{47}$N$_2$O$_4$S$_2$(M+H)+, 567.3251; found, 567.3267.

1.4 Synthesis of Compounds 41 to 48

The compounds 41 to 48 (i.e., compounds of formula (1-3)) were synthesized in accordance with procedures set forth in Schemes 10 to 19.

Scheme 10:

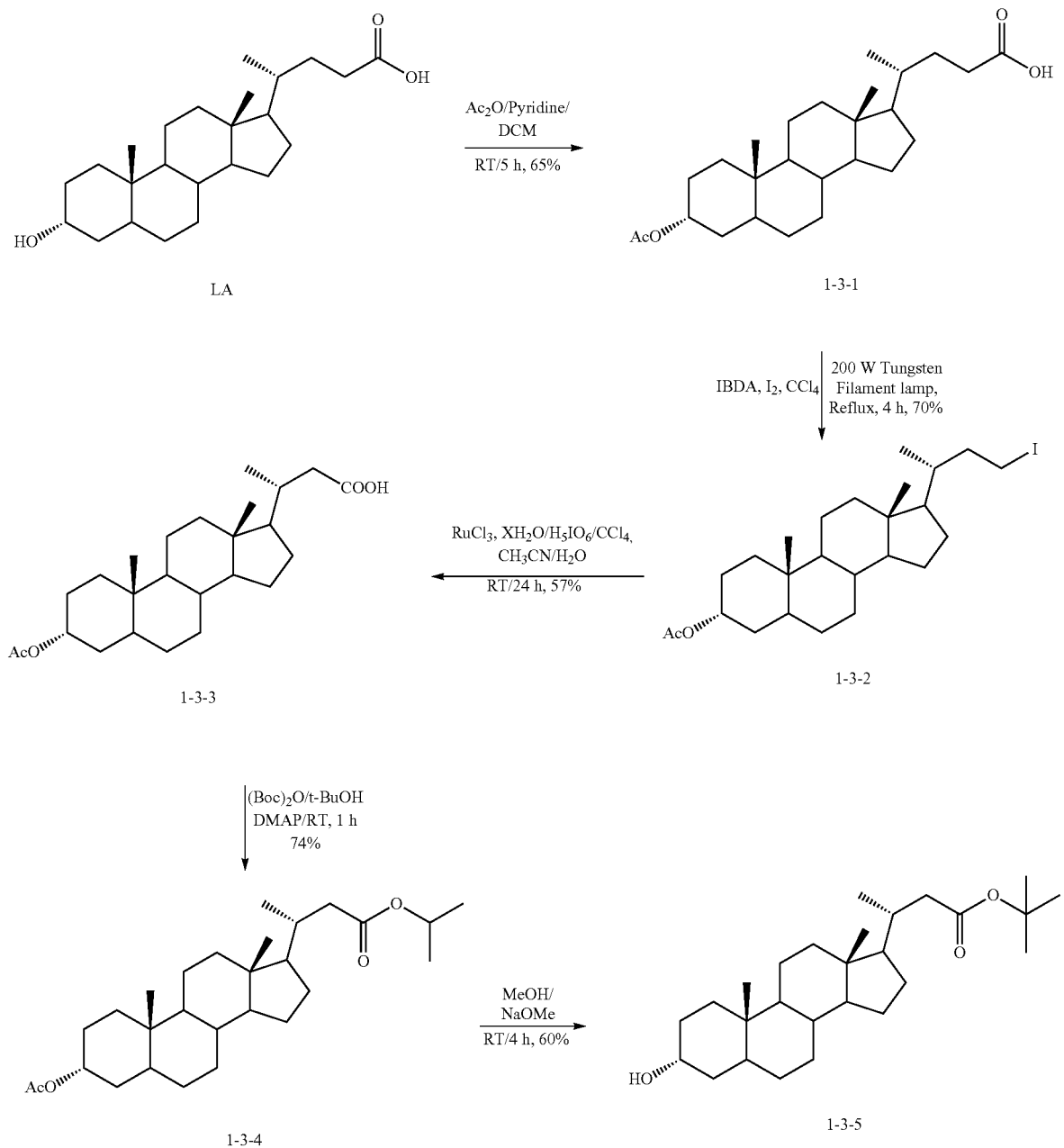

Synthesis of Compound 1-3-1

To a solution of lithocholic acid (LA) (8 mmole) in dichloromethane (20 ml) was added pyridine (23.90 mmole) followed by acetic anhydride (31.86 mmole) and resulting reaction mixture was stirred at room temperature for 24 hrs. Reaction mass was concentrated, the residue was dissolved in dicholomethane (DCM) (30 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 70:30) to give the target product 1-3-1 (65%).

Compound 1-3-1: $^1$H NMR (CDCl$_3$, 400 MHz): δ=4.72 (m, 1H), 2.39-2.23 (m, 2H), 2.00 (s, 3H), 1.95 (d, J=11.8 Hz, 1H), 1.85-1.75 (m, 5H), 1.72-1.69 (m, 1H), 1.65-1.55 (m, 2H), 1.43-1.31 (m, 8H), 1.23-1.20 (m, 2H), 1.08-0.99 (m, 6H), 0.92-0.88 (m, 6H), 0.63 (s, 3H); $^{13}$C NMR (100 MHz): δ=180.03, 170.66, 74.36, 56.43, 55.98, 55.92, 42.69, 41.83, 40.35, 40.08, 35.73, 35.24, 34.97, 34.52, 32.19, 30.91, 30.70, 28.10, 26.95, 26.57, 26.25, 24.11, 23.26, 21.41, 20.77, 18.18, 11.98.

Synthesis of Compound 1-3-2

A solution of 3α-acetoxy-5β-cholan-24-oic acid 1-3-1 (2.38 mmole) in CCl$_4$ (10 ml) containing IBDA (1.60 mmole) and iodine (1.45 mmole) was irradiated with 200-W tungsten-filament lamp for 45 min at reflux temperature. Another portion of iodosobenzene diacetate (IBDA) (1.50 mmole) and iodine (1.45 mmole) was then added and the irradiated at this temperature continue for 2 hrs. Reaction mixture was washed with sodium thiosulfate (2×30 ml) and water (2×30 ml). The organic layer was dried over sodium sulfate, filtered, and evaporated to dryness. The final residue was purified by column chromatography (hexane/ethyl acetate, 90:10) to give the target products 1-3-2 (70%).

Compound 1-3-2: $^1$H NMR (CDCl$_3$, 400 MHz): δ=4.73-4.67 (m, 1H) 3.28-3.26 (m, 1H), 3.08-3.06 (m, 1H), 2.00 (s, 3H), 1.85-1.95 (m, 1H), 1.82-1.77 (m, 4H), 1.75-1.67 (m, 1H), 1.53-1.50 (m, 4H), 1.40-1.35 (m, 7H), 1.24-1.20 (m, 3H), 1.14-1.10 (m, 2H), 1.04-1.00 (m, 4H), 0.90-0.88 (m, 6H), 0.64 (s, 3H); $^{13}$C NMR (100 MHz): δ=170.56, 74.33, 56.44, 55.85, 42.79, 41.83, 40.36, 40.30, 40.09, 37.15, 36.41, 35.73, 34.98, 34.53, 32.20, 28.14, 26.98, 26.58, 26.26, 24.09, 23.28, 21.42, 20.77, 17.79, 12.00, 5.09.

Synthesis of Compound 1-3-3

To a solution of 1-3-2 (6.00 mmole) in CCl$_4$ (15 ml), acetonitrile (15 ml) and water (26 ml) was added H$_5$IO$_6$ (6.38 mmole) and stirred for 15 minute. RuCl$_3$.H$_2$O (0.30 mmole) was added and resulting reaction mixture stirred at room temperature for 24 hrs. Reaction mass was cooled to 0° C. to it Et$_2$O was added with vigorous stirring and continue stirring for 10 min. The mixture was extracted with Et$_2$O (2×30 ml), organic layer washed with water (2×30 ml). The organic layer was dried over sodium sulfate, filtered, and evaporated to dryness. The final residue was purified by column chromatography (hexane/ethyl acetate, 70:30) to give the target products 1-3-3 (57%)

Compound 1-3-3: $^1$H NMR (CDCl$_3$, 400 MHz): δ=4.72-4.66 (m, 1H), 2.46 (d, J=12.2 Hz, 1H), 2.01 (s, 3H), 1.95-1.90 (m, 2H), 1.88-1.77 (m, 4H), 1.75-1.65 (m, 1H), 1.56-1.50 (m, 2H), 1.43-1.35 (m, 7H), 1.27-1.16 (m, 5H), 1.10-1.04 (m, 4H), 0.99-0.94 (m, 3H), 0.84 (s, 3H) 0.64 (s, 3H); $^{13}$C NMR (100 MHz): δ=179.12, 170.66, 74.38, 56.47, 55.97, 42.77, 41.82, 41.26, 40.34, 39.97, 35.74, 34.97, 34.53, 33.56, 32.19, 29.64, 28.25, 26.94, 26.57, 26.25, 24.10, 23.26, 21.41, 20.75, 19.45.

Synthesis of Compound 1-3-4

To a solution of 1-3-3 (6.67 mmole) in tert. butanol (30 ml) was added Boc-anhydride (13.34 mmole) followed by DMAP (2 mmole) and resulting reaction mixture was stirred at room temperature for 1 h. Reaction mass was concentrated, the residue was dissolved in DCM (40 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target products 1-3-4 (74%).

Compound 1-3-4: $^1$H NMR (CDCl$_3$, 400 MHz): δ=4.70-4.68 (m, 1H), 2.31 (d, J=10.7 Hz, 1H), 2.00 (s, 3H), 1.96-1.93 (m, 1H), 1.86-1.76 (m, 7H), 1.65-1.57 (m, 2H), 1.42 (s, 9H), 1.40-1.34 (m, 4H), 1.26-1.20 (m, 5H), 1.21-1.07 (m, 2H), 1.05-1.00 (m, 4H), 0.99 (d, J=5.9 Hz, 3H), 0.90 (s, 3H) 0.65 (s, 3H); $^{13}$C NMR (100 MHz): δ=173.07, 170.63, 79.91, 74.39, 56.52, 56.17, 42.82, 41.88, 40.39, 40.06, 35.78, 35.02, 34.57, 33.78, 32.24, 29.68, 28.21, 28.14, 27.00, 26.62, 26.29, 24.14, 21.45, 20.80, 19.37, 12.04.

Synthesis of Compound 1-3-5

Compound 1-3-4 (4.88 mmole) was dissolved in methanol (40 ml) to it sodium methoxide (14.65 mmole) was added and the resulting reaction mixture was stirred at room temperature for 12 h. Reaction mass was concentrated, the residue was dissolved in DCM (30 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target products 1-3-5 (60%)

Compound 1-3-5: $^1$H NMR (CDCl$_3$, 400 MHz): δ=3.62-3.57 (m, 1H), 2.31 (d, J=10.7 Hz, 1H), 1.92-1.86 (m, 1H), 1.84-1.74 (m, 7H), 1.65-1.57 (m, 2H), 1.42 (s, 9H), 1.40-1.34 (m, 4H), 1.26-1.20 (m, 5H), 1.21-1.07 (m, 2H), 1.05-1.00 (m, 4H), 0.99 (d, J=5.9 Hz, 3H), 0.90 (s, 3H) 0.65 (s, 3H); $^{13}$C NMR (100 MHz): δ=173.07, 79.90, 71.83, 56.51, 56.12, 42.80, 42.76, 42.06, 40.39, 40.07, 36.42, 35.81, 35.31, 34.54, 33.79, 30.52, 29.67, 28.21, 28.13, 27.15, 26.36, 24.14, 23.33, 20.77, 19.35, 12.02.

Synthesis of SVM-101

Scheme 11:

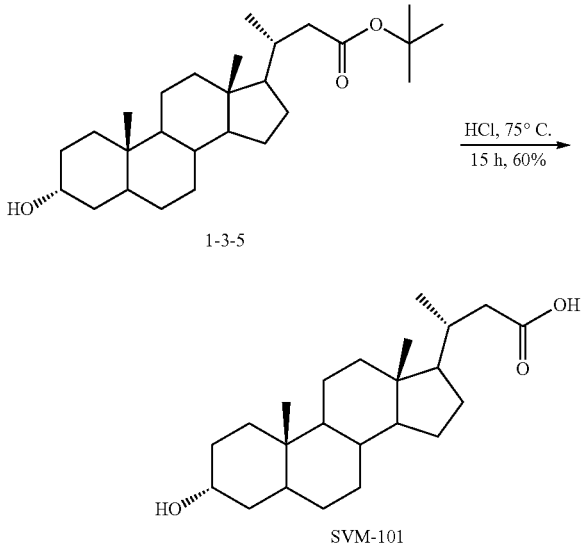

Compound 1-3-5 (0.477 mmole) was dissolved in HCl (5 ml), and the reaction mixture was stirred at 75° C. for 12 h. Reaction mass was neutralized with aq. NaOH solution and extracted with ethyl acetate. Organic layer washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 70:30) to give the target products SVM101 (60%).

Synthesis of Compounds 41 to 48

Scheme 12:

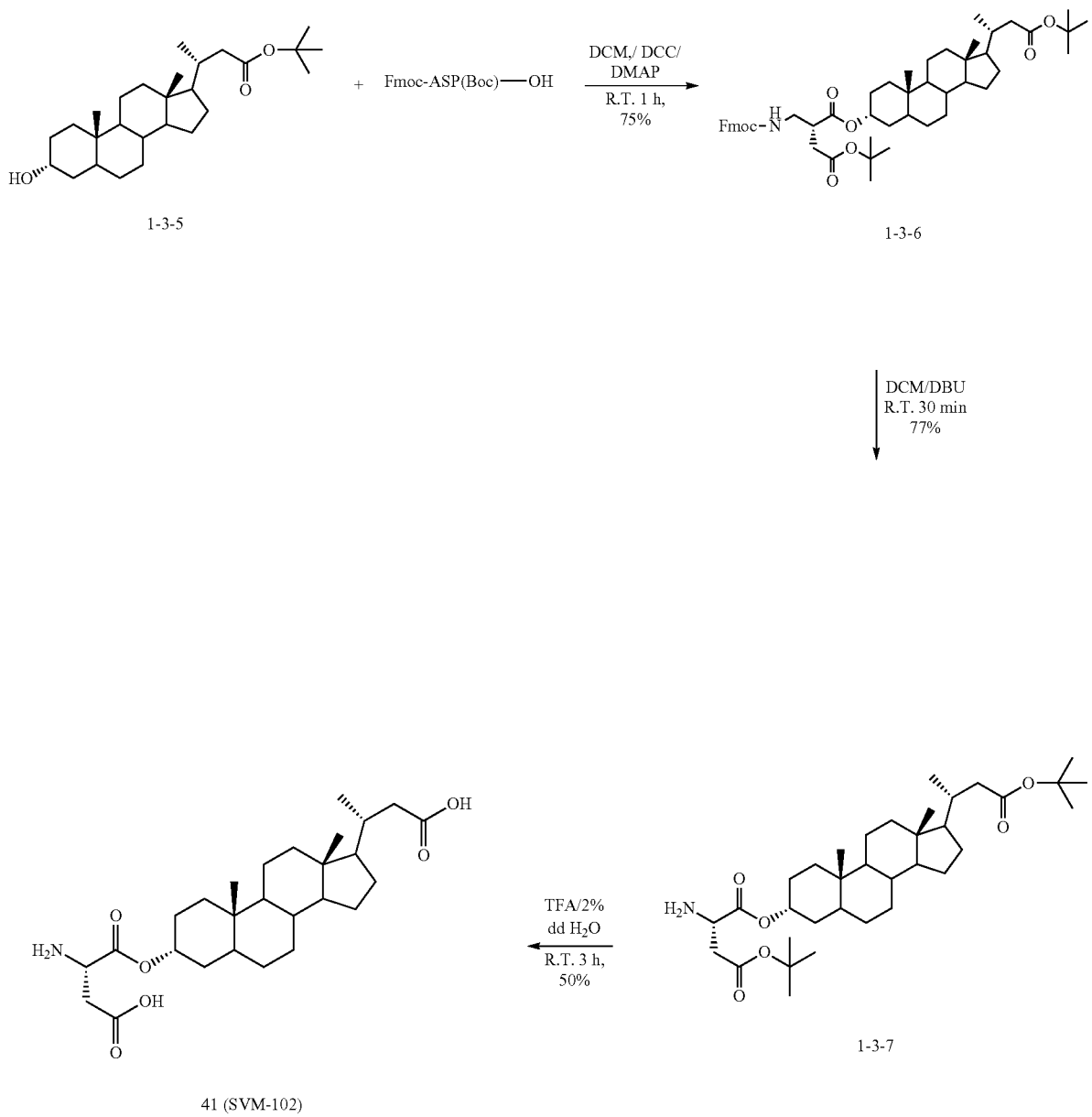

General Procedures for Synthesizing Compounds 1-3-6, 1-3-8, 1-3-10, 1-3-12, and 1-3-14

To a solution of corresponding Fmoc protected amino acid (0.286 mmole) in dichloromethane (5 ml) was added compound 1-3-5 (0.238 mmole), and stirred for 10 min. A solution of DCC (0.382 mmole) in DCM (5 ml) followed by DMAP (0.34 mmole) was added to above stirred solution and the resulting reaction mixture was stirred at room temperature for 1-2 hrs. Reaction mass was filtered and the filtrate was washed with water (2×20 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target products 1-3-6, 1-3-8, 1-3-10, 1-3-12, and 1-3-14 (75-90%).

General Procedures for Synthesizing Compounds 1-3-7, 1-3-9, 1-3-11, 1-3-13 and 1-3-15

To a solution of compound 1-3-6, 1-3-8, 1-3-10, 1-3-13 and 1-3-15 (0.218 mmole) in dichloromethane (10 ml) was added DBU (0.218 mmole) and stirred at room temperature for 1 h. Reaction mass was concentrated and product purified by flash column chromatography to get desired compound 1-3-7, 1-3-9, 1-3-11, 1-3-13, and 1-3-15 (80-91%).

Scheme 13:
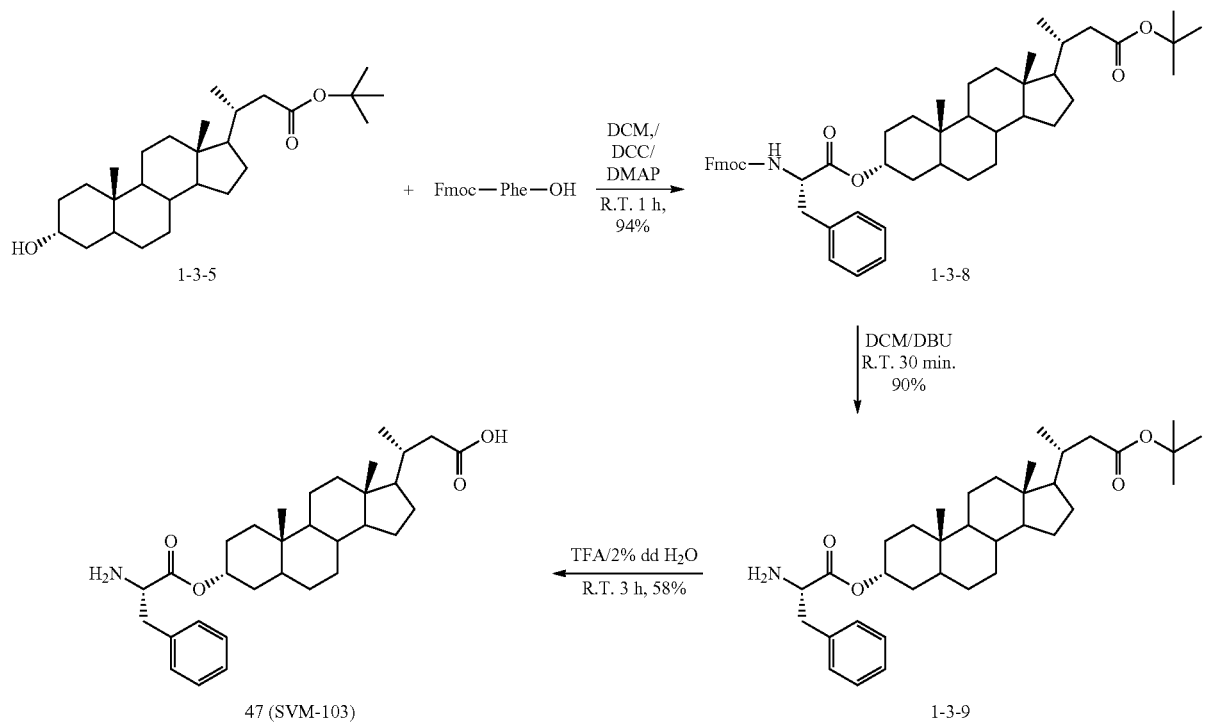
Scheme 14:
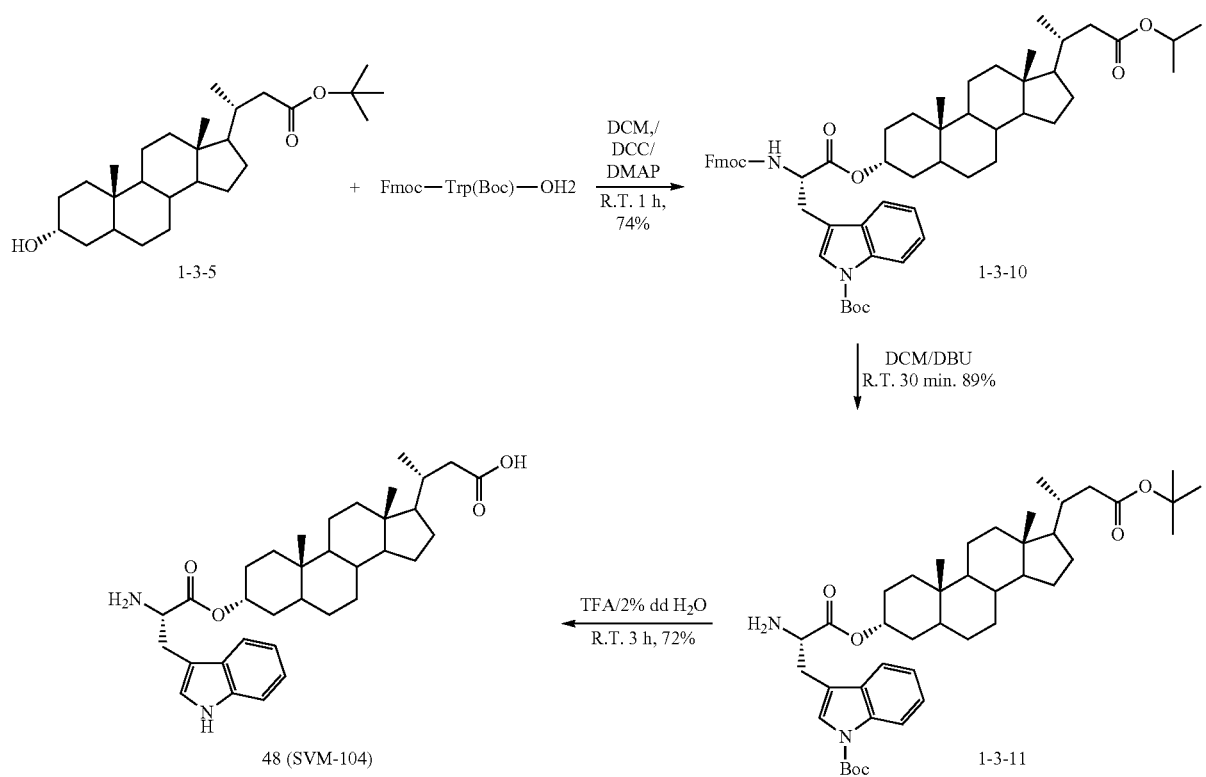

Scheme 15:
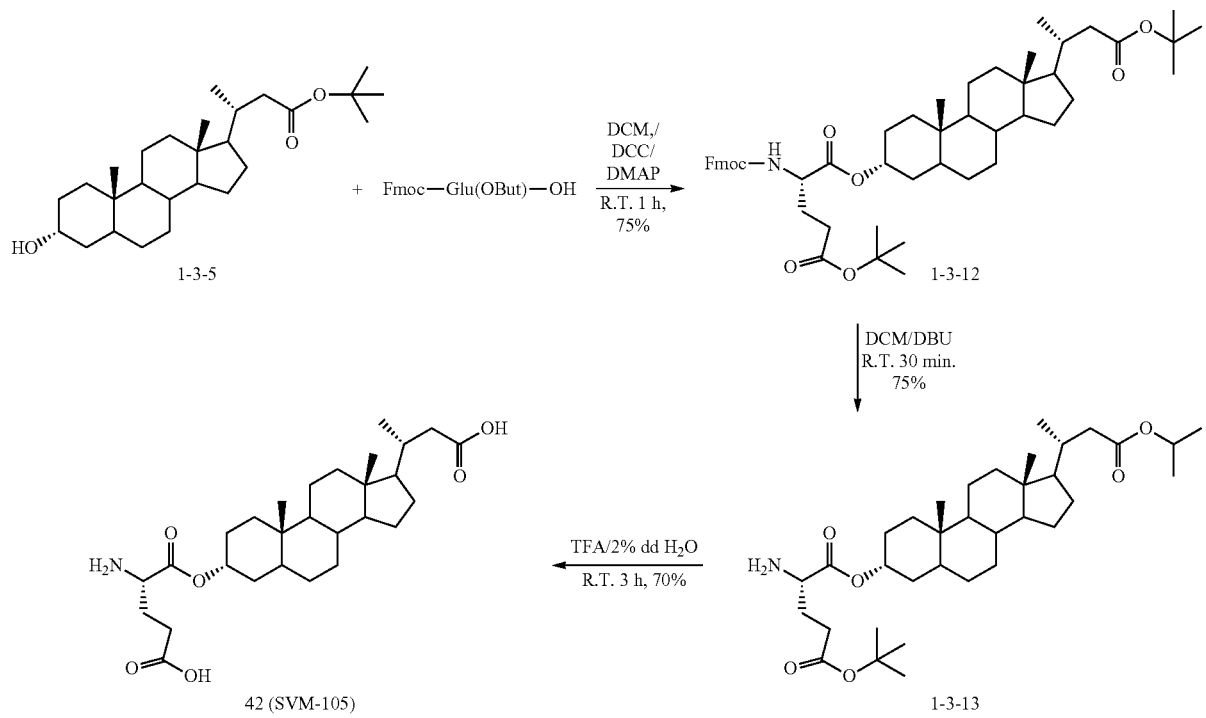
Scheme 16:
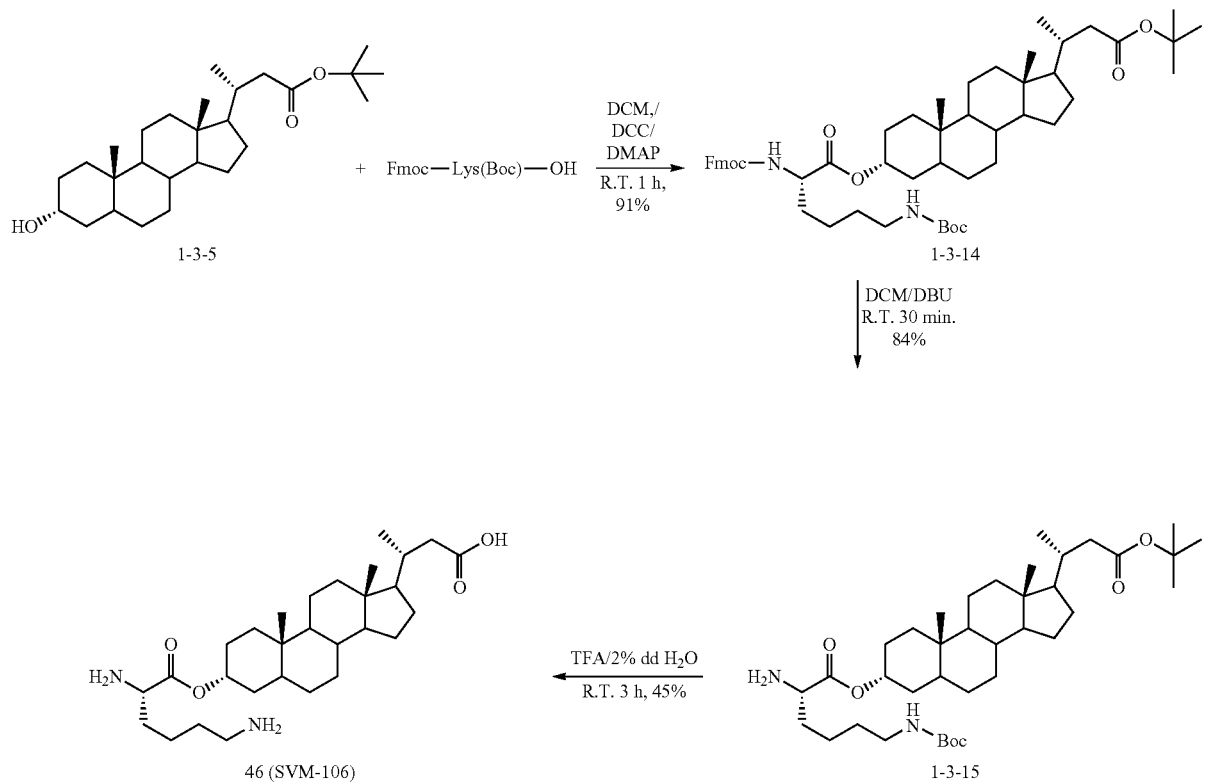

Synthesis of Compounds 1-3-17 and 1-3-22

To a solution of compound 1-3-16 or 1-3-23 (2.43 mmole) in DMF (10 ml) was added imidazole (6.33 mmole) and stirred for 10 min. TBDPS-Cl (6.091 mmole) was added slowly and resulting reaction mixture was stirred at room temperature for 16 hrs. Reaction mass was concentrated, the residue was dissolved in ethyl acetate (20 mL) and washed with water (2×20 ml) followed by saturated sodium chloride solution (2×20 ml). The organic layer was dried over sodium sulfate, filtered, and evaporated to dryness. Obtained slurry was dissolved in methanol: water (70:30) (10 ml) to it $K_2CO_3$ (6.090 mmole) was added and stirred at room temperature for 2 hrs. Methanol: water were removed, residue was dissolved in DCM (20 ml) and acidify with 10% aq. citric acid up to PH 2, extracted with DCM. Organic layer was dried over sodium sulfate, filtered, and evaporated, final residue was purified by column chromatography (methanol/DCM, 80:20) to give the target products 1-3-17 or 1-3-22 (60%).

Scheme 17:

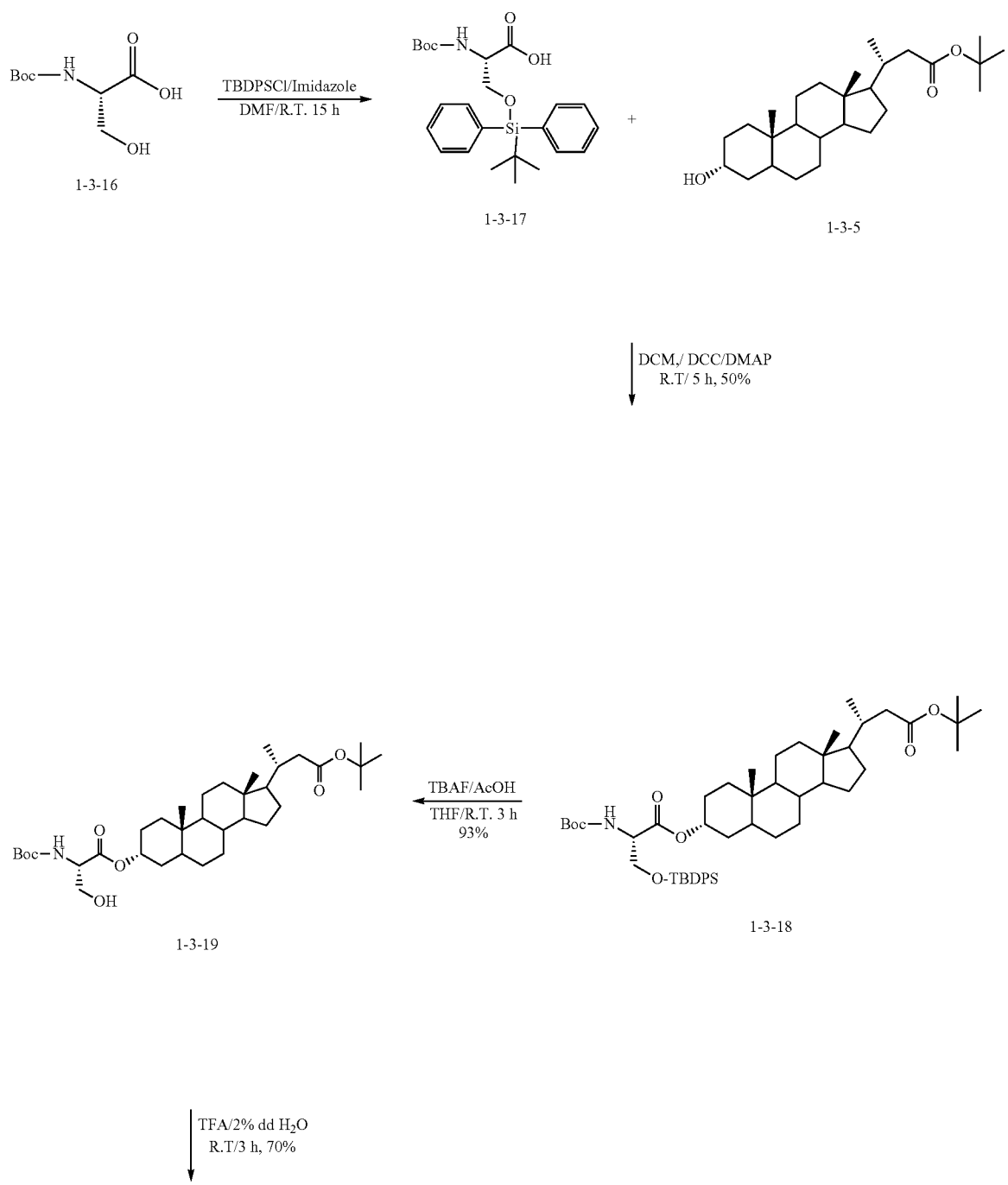

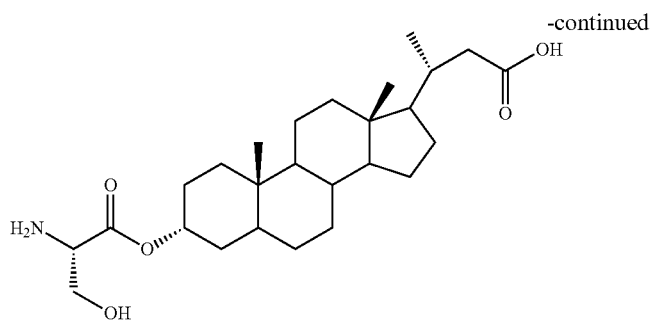

43 (SVM-107)

Scheme 18:

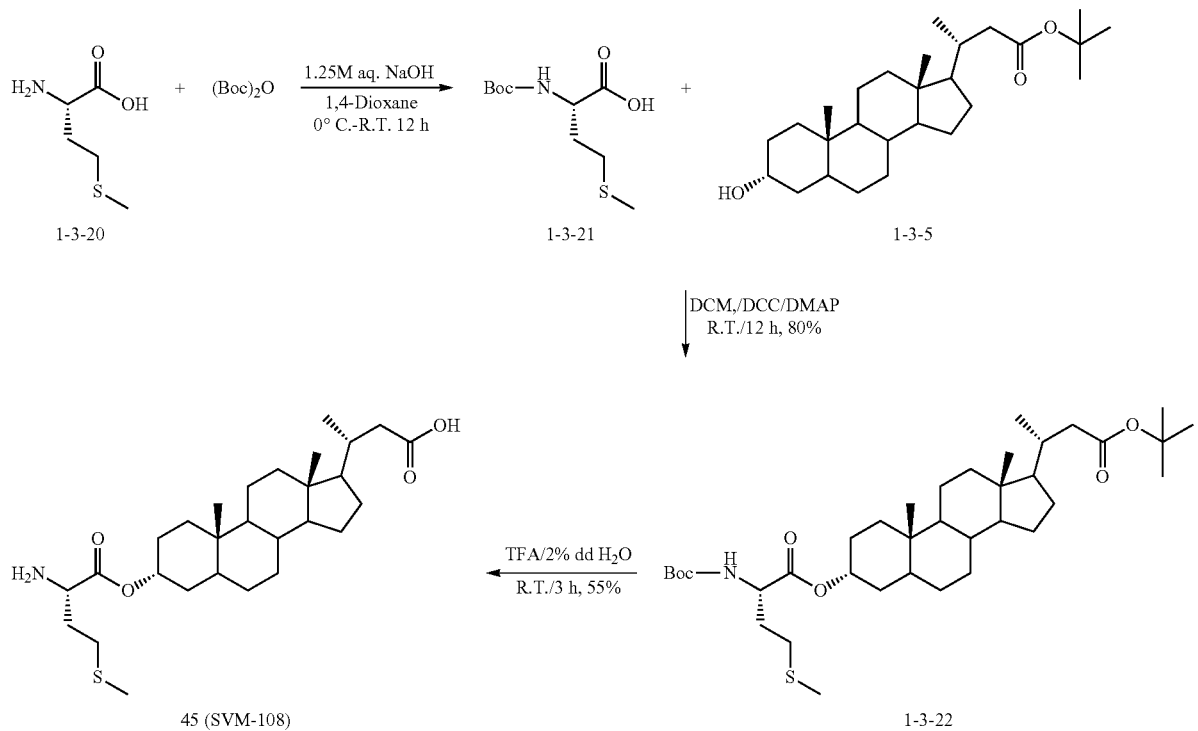

Synthesis of Compound 1-3-21

To a solution of compound 1-3-20 (3.35 mmole) in dioxane (10 ml) was added a solution of 1.25 M aq. NaOH (5 ml) at 0° C. and stirred for 10 min. A solution of Boc-anhydride (3.35 mmole, in dioxane 5 ml) slowly in 30 minutes at same temperature and resulting reaction mixture was stirred at room temperature for 12 h. Reaction mass was concentrated, obtained slurry dissolved in water (50 ml) and washed with hexane (3×20 ml). Water layer acidify with 10% aq. HCl up to PH 2 and extracted with DCM. Organic layer was dried over sodium sulfate, filtered, and evaporated, final residue was purified by column chromatography (methanol/DCM, 80:20) to give the target products 1-3-21 (70%).

General Procedures for the Synthesis of Compounds 1-3-18, 1-3-22, and 1-3-25

To a solution of corresponding Boc-protected amino acid (0.286 mmole) in dichloromethane (5 ml) was compound 1-3-5 (0.238 mmole) stirred for 10 min. A solution of DCC (0.382 mmole) in DCM (5 ml) followed by DMAP (0.34 mmole) was added to above stirred solution and resulting reaction mixture was stirred at room temperature for 1-2 hrs. Reaction mass was filtered and filtrate was washed with water (2×20 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target products 1-3-18, 1-3-22, and 1-3-25 (50-80%).

Scheme 19:

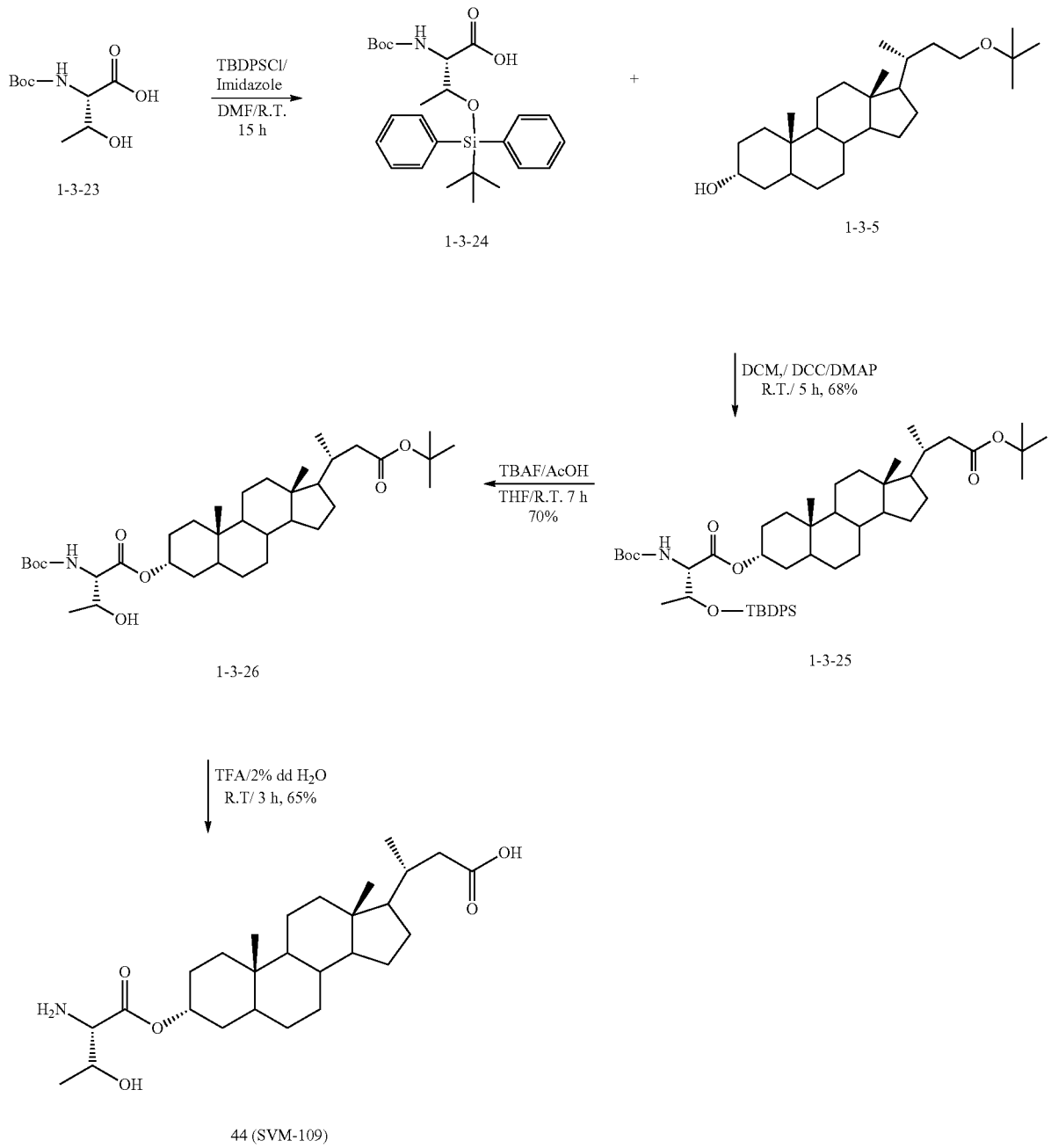

Treatment of Final Products

Compounds 1-3-7, 1-3-9, 1-3-11, 1-3-13, 1-3-15, 1-3-18, 1-3-22, and 1-3-25 (0.107 mmole) was dissolved in TFA (5 ml) at 0° C. water (50 μL) was added and the reaction mixture was stirred at room temperature for 3 h. The TFA solution was then removed on rotary evaporator and the residue was neutralized with saturated solution of aq. NaHCO$_3$, dialyzed using membrane and purified by perverse phase HPLC to get desired compounds as white solid.

Compound SVM-101: MP=137-138° C., $^1$H NMR (DMSO-D6, 400 MHz): δ=4.47-4.45 (m, 1H), 2.30 (dd, J=2.5 Hz, J=14.2 Hz, 2H), 1.92-1.90 (m, 1H), 1.80-1.74 (m, 4H), 1.65-1.60 (m, 2H), 1.58-1.51 (m, 2H), 1.35-1.30 (m, 6H), 1.21-1.15 (m, 7H), 1.04-1.02 (m, 3H), 0.92 (d, J=6.2 Hz, 3H), 0.86 (s, 3H), 0.63 (s, 3H); $^{13}$C NMR (100 MHz): δ=174.57, 70.28, 56.48, 55.88, 42.71, 41.93, 41.59, 36.68, 35.80, 35.55, 34.61, 33.44, 30.75, 28.15, 27.28, 26.53, 24.19, 23.65, 20.78, 19.77, 12.24, HPLC conditions: retention time=10.10 min. Solvents: A) 100% Water+0.1% TFA, B) 100% ACN+0.05% TFA, Column: Vydac C18.

Compound 41 (SVM-102): MP=158-159° C., $^1$H NMR (DMSO-D6, 500 MHz): δ=4.73 (m, 1H), 4.25 (m, 1H), 2.88 (dd, J=3.9 Hz, J=16.7 Hz, 2H), 2.30-2.27 (m, 1H), 1.84-1.75 (m, 6H), 1.61-1.49 (m, 4H), 1.44-1.35 (m, 5H), 1.21-1.08 (m, 10H), 0.92-0.90 (m, 6H), 0.63 (s, 3H); $^{13}$C NMR (125 MHz): δ=174.53, 171.17, 168.24, 76.39, 56.36, 55.90, 49.06, 42.69, 41.59, 41.45, 35.70, 34.71, 34.62, 34.53, 33.40, 31.92, 28.12, 26.94, 26.30, 24.12, 23.29, 20.78, 19.76, 12.20. HRMS m/z calcd for $C_{27}H_{44}NO_6$, 478.3169; found 478.3175 (M+H)+, HPLC conditions: retention time=10.70 min. Solvents: A) 100% Water+0.1% TFA, B) 100% ACN+0.05% TFA, Column: Vydac C18

Compound 47 (SVM-103): MP=204-205° C., $^1$H NMR (CD$_3$OD, 400 MHz): δ=7.39-7.34 (m, 3H), 7.28-7.26 (m, 2H), 4.80-4.76 (m, 1H), 4.26 (t, J=7.1 Hz, 1H), 3.20 (d, J=7.1 Hz, 2H), 2.41-2.40 (m, 1H), 2.05-2.02 (m, 1H), 1.98-1.83 (m, 6H), 1.62-1.52 (m, 3H), 1.47-1.21 (m, 11H), 1.12-1.07 (m, 4H), 1.06 (d, J=8 Hz, 3H), 1.03 (s, 3H), 0.73 (s, 3H); $^{13}$C NMR (125 MHz): δ=175.94, 168.07, 133.97, 129.08, 128.62, 127.45, 76.91, 56.49, 56.06, 42.51, 41.73, 40.97, 40.30, 39.93, 36.22, 35.69, 34.39, 34.17, 33.44, 31.61, 27.79, 26.59, 26.00, 25.81, 23.73, 22.18, 20.42, 18.51, 10.97; HRMS m/z calcd for $C_{32}H_{48}NO_4$. 510.3590; found 510.3600 (M+H)+, HPLC conditions: retention time=19.75 min. Solvents: A) 100% Water+0.1% TFA, B) 100% ACN+0.05% TFA, Column: Kromasil 300-5C4.

Compound 48 (SVM-104): MP=144-145° C., $^1$H NMR (CD$_3$OD, 500 MHz): δ=7.57 (d, J=10 Hz, 1H), 7.40 (d, J=10 Hz, 1H), 7.19 (s, 1H), 7.14 (t, J=5 Hz, 1H), 7.08 (t, J=7.5 Hz, 1H), 4.72-4.67 (m, 1H), 4.26 (t, J=5 Hz, 1H), 3.39-3.37 (m, 2H), 2.43-2.41 (m, 1H), 2.03-2.01 (m, 1H), 1.95-1.85 (m, 4H), 1.79-1.67 (m, 2H), 1.63-1.59 (m, 1H), 1.45-1.36 (m, 6H), 1.34-1.29 (m, 3H), 1.26-1.19 (m, 4H), 1.15-1.10 (m, 2H), 1.06-0.99 (m, 5H), 0.92 (s, 3H), 0.72 (s, 3H); $^{13}$C NMR (125 MHz): δ=177.58, 170.09, 138.42, 128.54, 122.57, 123.12, 120.42, 119.24, 112.79, 107.96, 78.51, 57.96, 57.66, 55.01, 44.09, 43.37, 42.60, 41.82, 41.46, 37.27, 36.02, 35.74, 35.06, 32.12, 29.40, 28.17, 27.96, 27.57, 27.17, 25.32, 22.01, 20.13, 12.57; HRMS m/z calcd for $C_{34}H_{49}N_2O_4$, 549.3692; found 549.3699 (M+H)+, HPLC conditions: retention time=20.45 min. Solvents: A) 100% Water+0.1% TFA, B) 100% ACN+0.05% TFA, Column: Kromasil 300-5C4.

Compound 42 (SVM-105): MP=149-150° C., $^1$H NMR (CD$_3$OD/DMSO-D6, 500 MHz): 4.75-4.71 (m, 1H), 3.96 (t, J=7 Hz, 1H), 2.43-2.36 (m, 2H), 2.29-2.27 (m, 1H), 2.06-2.01 (m, 2H), 1.91-1.89 (m, 1H), 1.85-1.74 (m, 6H), 1.52-1.49 (m, 2H), 1.42-1.33 (m, 6H), 1.18-1.04 (m, 5H), 1.01-0.94 (m, 4H), 0.89 (d, J=6 Hz, 1H), 0.86 (s, 3H), 0.60 (s, 3H); $^{13}$C NMR (125 MHz): δ=175.54, 173.81, 168.49, 77.06, 56.41, 56.01, 51.97, 42.56, 41.84, 41.07, 40.36, 39.91, 35.75, 34.53, 34.31, 33.48, 31.79, 28.95, 27.89, 26.73, 26.10, 25.36, 23.83, 22.44, 20.54, 18.75, 11.20; HRMS m/z calcd for $C_{28}H_{46}NO_6$, 492.3325; found 492.3320 (M+H), HPLC conditions: retention time=8.45 min. Solvents: A) 100% Water+0.1% TFA, B) 100% ACN+0.05% TFA, Column: Kromasil 300-5C4.

Compound 46 (SVM-106): MP=219-220° C., $^1$H NMR (CD$_3$OD, 500 MHz): δ=4.02 (t, J=6.4 Hz, 1H), 2.96 (t, J=7.9 Hz, 2H), 2.43 (d, J=11.4 Hz, 1H), 2.01-1.88 (m, 9H), 1.75-1.68 (m, 3H), 1.62-1.45 (m, 10H), 1.34-1.28 (m, 3H), 1.21-1.11 (m, 6H), 1.01 (d, J=6 Hz, 3H), 0.98 (s, 3H), 0.73 (s, 3H); $^{13}$C NMR (125 MHz): δ=177.57, 170.02, 78.60, 58.06, 57.67, 54.00, 44.11, 43.47, 42.60, 42.01, 41.52, 40.40, 37.34, 36.07, 35.85, 35.04, 33.34, 31.23, 29.39, 28.24, 28.17, 27.71, 27.64, 25.33, 23.85, 23.24, 22.07, 20.12, 12.59; HRMS m/z calcd for $C_{29}H_{51}N_2O_4$, 491.3849; found 491.3840 (M+H), HPLC conditions: retention time=19.80 min. Solvents: A) 100% Water+0.1% TFA, B) 100% ACN+0.05% TFA, Column: Kromasil 300-5C4.

Compound 43 (SVM-107): MP=165-166° C., $^1$H NMR (CD$_3$OD, 500 MHz): δ=4.07 (t, J=3.6 Hz, 1H), 3.98 (dd, J=3.5 Hz, J=11 Hz, 2H), 2.42 (d, J=11.3 Hz, 1H), 2.04-1.85 (m, 7H), 1.77-1.73 (m, 1H), 1.63-1.60 (m, 2H), 1.54-1.43 (m, 6H), 1.33-1.12 (m, 9H), 1.01 (d, J=6.1 Hz, 3H), 0.98 (s, 3H), 0.73 (s, 3H); $^{13}$C NMR (125 MHz): δ=177.57, 168.55, 78.59, 60.89, 58.04, 57.64, 56.35, 44.10, 43.46, 42.60, 41.97, 41.50, 37.33, 36.07, 35.83, 35.05, 33.31, 29.39, 28.25, 27.64, 27.57, 23.85, 22.06, 20.11, 12.59; HRMS m/z calcd for $C_{26}H_{44}NO_5$ 450.3219; found 450.3227 (M+H)$^+$, HPLC conditions: retention time=19.70 min. Solvents: A) 100% Water+0.1% TFA, B) 100% ACN+0.05% TFA, Column: Kromasil 300-5C4.

Compound 45 (SVM-108): MP=129-130° C., $^1$H NMR (CD$_3$OD, 500 MHz): δ=4167 (t, J=6.4 Hz, 1H), 2.66-2.63 (m, 2H), 2.43 (d, J=11.3 Hz, 1H), 2.23-2.14 (m, 2H), 2.13 (s, 3H), 2.04-1.86 (m, 7H), 1.76-1.74 (m, 1H), 1.63-1.61 (m, 2H), 1.54-1.48 (m, 6H), 1.35-1.28 (m, 3H), 1.24-1.09 (m, 6H), 1.01 (d, J=6.1 Hz, 3H), 0.98 (s, 3H), 0.73 (s, 3H); $^{13}$C NMR (125 MHz): δ=177.58, 170.00, 78.69, 58.01, 57.62, 53.10, 44.10, 43.45, 42.60, 41.98, 41.49, 37.33, 36.06, 35.84, 35.05, 33.32, 31.05, 30.26, 29.40, 28.24, 27.68, 27.63, 25.33, 23.85, 22.07, 20.11, 15.17, 12.59; HRMS m/z calcd for $C_{28}H_{48}NO_4S$, 494.3304; found 494.3295 (M+H)$^+$, HPLC conditions: retention time=19.25 min. Solvents: A) 100% Water+0.1% TFA, B) 100% ACN+0.05% TFA, Column: Kromasil 300-5C4.

Compound 44 (SVM-109): MP=181-182° C., $^1$H NMR (CD$_3$OD, 500 MHz): 56=4.26-4.22 (m, 1H), 3.84 (d, J=4.6 Hz, 1H), 2.42 (d, J=11.2 Hz, 1H), 2.04-1.88 (m, 8H), 1.77-1.75 (m, 1H), 1.63-1.60 (m, 2H), 1.51-1.45 (m, 6H), 1.33 (d, J=6.5 Hz, 3H), 1.32-1.30 (m, 3H), 1.26-1.08 (m, 6H), 1.01 (d, J=6.1 Hz, 3H), 0.98 (s, 3H), 0.73 (s, 3H); $^{13}$C NMR (125 MHz): δ=177.56, 168.84, 78.54, 66.60, 60.15, 58.03, 57.63, 44.10, 43.45, 42.58, 41.98, 41.50, 37.33, 36.07, 35.84, 35.05, 33.32, 29.40, 28.24, 27.63, 27.56, 25.33, 23.86, 22.06, 20.82, 20.11, 12.59; HRMS m/z calcd for $C_{27}H_{46}NO_5$, 464.3376; found 464.3372 (M+H)$^+$, HPLC conditions: retention time=18.25 min. Solvents: A) 100% Water+0.1% TFA, B) 100% ACN+0.05% TFA, Column: Kromasil 300-5C4.

1.5 Synthesis of Compounds 49 to 52

Compounds 49 to 52 were synthesized in accordance with procedures set forth in Schemes 20 to 23.

Scheme 20:

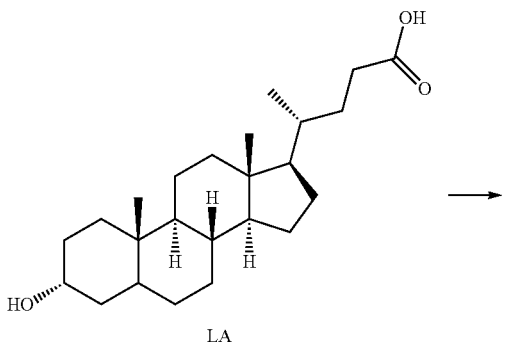

LA

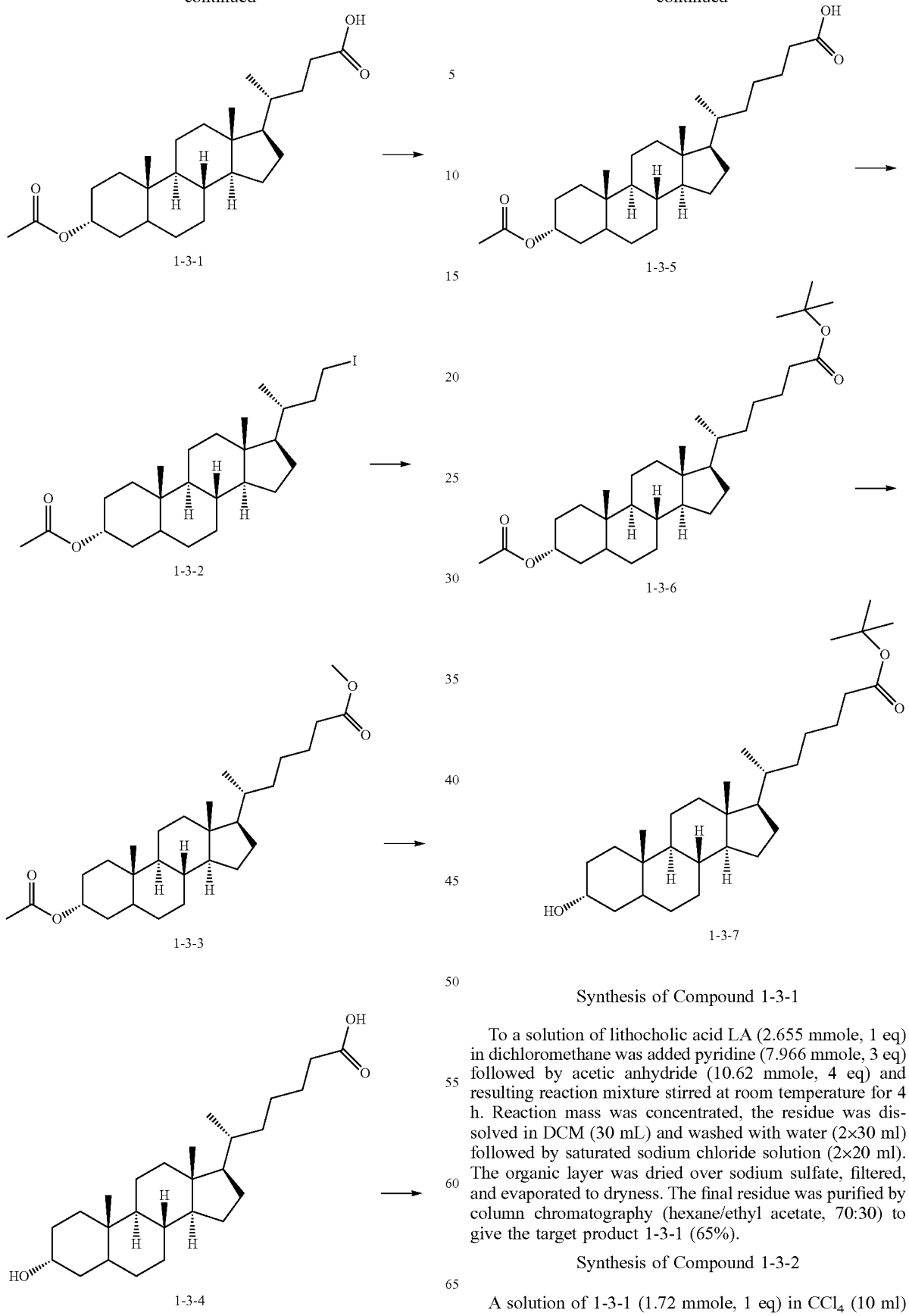

Synthesis of Compound 1-3-1

To a solution of lithocholic acid LA (2.655 mmole, 1 eq) in dichloromethane was added pyridine (7.966 mmole, 3 eq) followed by acetic anhydride (10.62 mmole, 4 eq) and resulting reaction mixture stirred at room temperature for 4 h. Reaction mass was concentrated, the residue was dissolved in DCM (30 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 70:30) to give the target product 1-3-1 (65%).

Synthesis of Compound 1-3-2

A solution of 1-3-1 (1.72 mmole, 1 eq) in $CCl_4$ (10 ml) containing IBDA (5.17 mmole, 0.65 eq) and iodine (1.72 mmole, 1 eq) was irradiated with 200-W tungsten-filament lamp for 45 min at reflux temperature. Another portion of IBDA (0.65 eq) and iodine (0.5 eq) was then added and the irradiated at this temperature continue for 2 hrs. Reaction mixture was washed with sodium thiosulfate (2×30 ml) and water (2×30 ml). The organic layer was dried over sodium sulfate, filtered, and evaporated to dryness. The final residue was purified by column chromatography (hexane/ethyl acetate, 90:10) to give the target product 1-3-2 (70%).

Synthesis of Compound 1-3-3

A solution of 1-3-2 (1.20 mmole, 1 eq) in toluene (10 ml) containing methyl acrylate (2.4 mmole, 1.2 eq), tris(trimethylsilyl)silane (TTMSS) (2.4 mmole, 1.2 eq) as a free radical mediator and AIBN (5 mol %) heated at 70° C. under nitrogen atmosphere. for 2 hr. Reaction mass was concentrated. The residue was dissolved in DCM (30 mL) and washed with water (2×30 ml). The organic layer was dried over sodium sulfate, filtered, and evaporated to dryness. The final residue was purified by column chromatography (hexane/ethyl acetate, 95:5) to give the target product 1-3-3 (64%).

Synthesis of Compound 1-3-4

Compound 1-3-3 (0.77 mmole, 1 eq) was dissolved in aqueous methanol (10 ml) to it 1N sodium hydroxide (2.31 mmole, 3 eq) was added and the resulting reaction mixture was reflux for 5 h. Reaction mass was concentrated, the residue was dissolved in water (30 mL) and washed with ether (2×30 ml). Aqueous layer was acidify with 6% HCl, and washed with ether (2×20 ml). The organic layer was dried over sodium sulfate, filtered, and evaporated to dryness to give the target product 1-3-4 (91%).

Synthesis of Compound 1-3-5

To a solution of bishomolithocholic acid 1-3-4 (0.69 mmole, 1 eq) in dichloromethane (DCM) was added pyridine (2.07 mmole, 3 eq) followed by acetic anhydride (2.76 mmole, 4 eq) and resulting reaction mixture stirred at room temperature for 4 h. Reaction mass was concentrated, the residue was dissolved in DCM (30 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 70:30) to give the target product 1-3-5 (65%).

Synthesis of Compound 1-3-6

To a solution of 1-3-5 (0.45 mmole, 1 eq) in tert. butanol (10 ml) was added Boc-anhydride (0.9 mmole, 2 eq) followed by DMAP (0.14 mmole, 0.3 eq) and resulting reaction mixture was stirred at room temperature for 1 h. Reaction mass was concentrated, the residue was dissolved in DCM (40 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target product 1-3-6 (74%).

Synthesis of Compound 1-3-7

Compound 1-3-6 (0.33 mmole, 1 eq) was dissolved in methanol (10 ml) to it sodium methoxide (1.98 mmole, 6 eq) was added and the resulting reaction mixture was stirred at room temperature for 5 h. Reaction mass was concentrated, the residue was dissolved in DCM (30 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target products 1-3-7 (60%).

Synthesis of Compound 49 (RS203)

Scheme 21

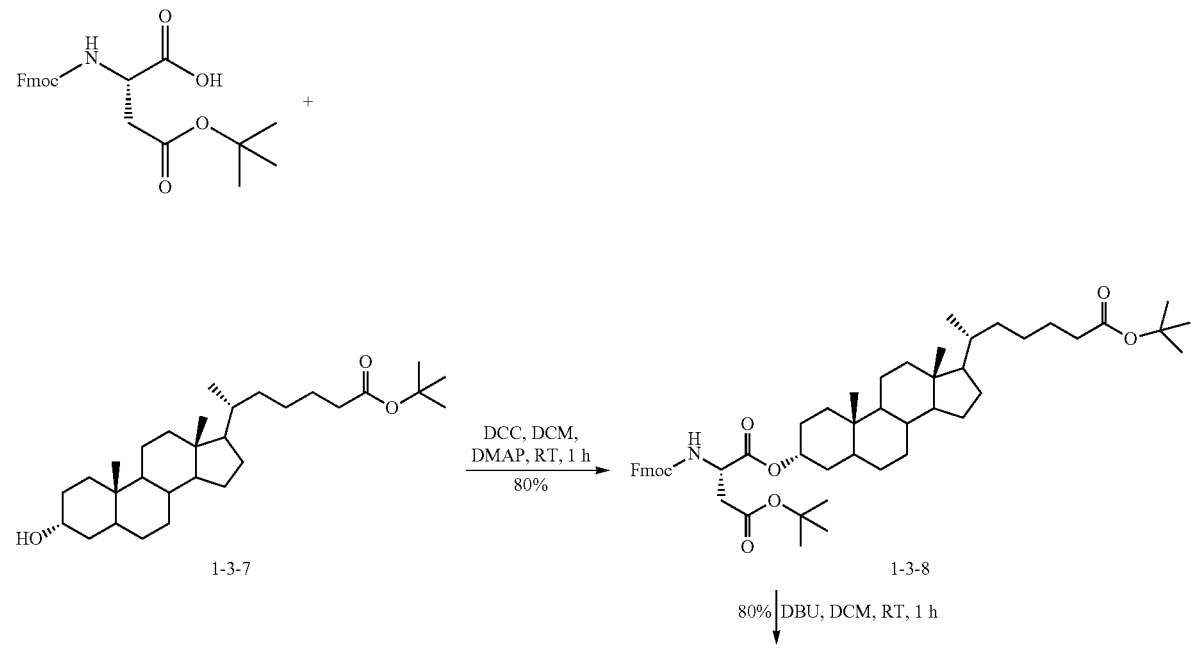

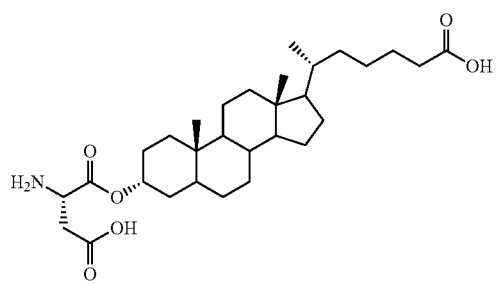

49 (RS 203)

TFA,
2% dd H₂O,
0° C.- RT, 3 h
45%

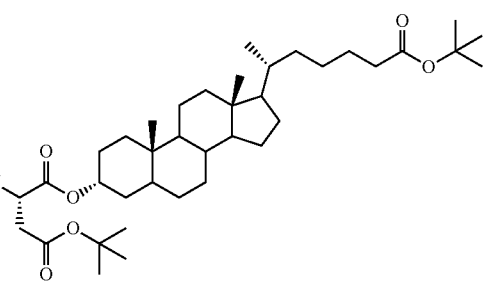

1-3-9

The solution of corresponding Fmoc protected amino acid (0.24 mmole, 1.2 eq) in dichloromethane (5 ml) was added to compound 1-3-7 (0.2 mmole, 1 eq), stirred for 10 min. A solution of N,N'-dicyclohexylcarbodiimide (DCC) (0.32 mmole, 1.6 eq) in DCM (5 ml) followed by DMAP (0.06 mmole, 0.3 eq) was added to above stirred solution and resulting reaction mixture was stirred at room temperature for 1-2 hrs. Reaction mass was filtered and filtrate was washed with water (2×20 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target product 1-3-8 (75-90%).

To a solution of compound 1-3-8 (0.16 mmole, 1 eq) in dichloromethane (10 ml) was added DBU (0.16 mmole, 1 eq) and stirred at room temperature for 1 h. Reaction mass was concentrated and product purified by flash column chromatography to get desired compound 1-3-9 (80-91%).

Compound 1-3-9 (0.13 mmole, 1 eq) was dissolved in TFA (5 ml) at 0° C., water (50 µL) was added and the reaction mixture was stirred at room temperature for 3 h. The TFA solution was then removed on rotary evaporator and the residue was neutralized with saturated solution of aq. NaHCO₃, dialyzed using membrane and purified by reverse phase HPLC to produce the desired compound 49 (RS203) as white solid.

Synthesis of RS201

Scheme 22

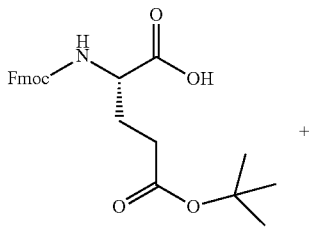

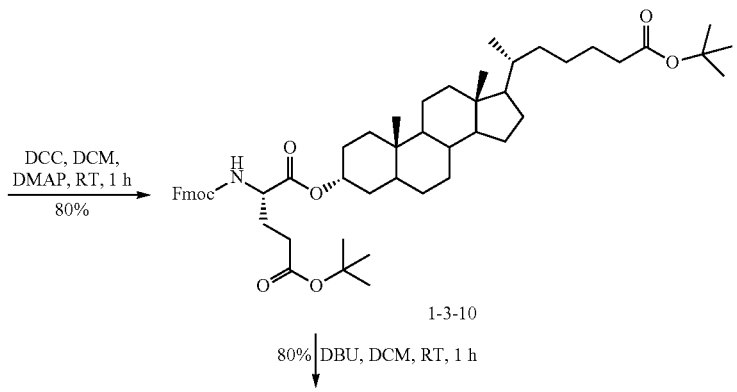

1-3-7

DCC, DCM,
DMAP, RT, 1 h
80%

1-3-10

80% DBU, DCM, RT, 1 h

141

-continued

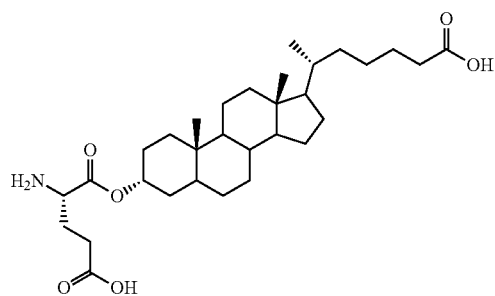

50 (RS 201)

TFA,
2% dd H₂O,
0° C.- RT, 3 h
45%

142

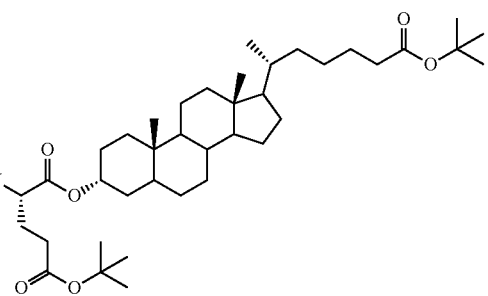

1-3-11

The solution of corresponding Fmoc protected amino acid (0.24 mmole, 1.2 eq) in dichloromethane (5 ml) was added to compound 1-3-7 (0.2 mmole, 1 eq), stirred for 10 min. A solution of DCC (0.32 mmole, 1.6 eq) in DCM (5 ml) followed by DMAP (0.06 mmole, 0.3 eq) was added to above stirred solution and resulting reaction mixture was stirred at room temperature for 1-2 hrs. Reaction mass was filtered and filtrate was washed with water (2×20 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target product 1-3-10 (75-90%).

To a solution of compound 1-3-10 (0.16 mmole, 1 eq) in dichloromethane (10 ml) was added DBU (0.16 mmole, 1 eq) and stirred at room temperature for 1 h. Reaction mass was concentrated and product purified by flash column chromatography to get desired compound 1-3-11 (80-91%).

Compound 1-3-11 (0.12 mmole, 1 eq) was dissolved in TFA (5 ml) at 0° C. water (50 µL) was added and the reaction mixture was stirred at room temperature for 3 h. The TFA solution was then removed on rotary evaporator and the residue was neutralized with saturated solution of aq. NaHCO₃, dialyzed using membrane and purified by reverse phase HPLC to get desired compounds 50 (RS201) as white solid.

Synthesis of Compound 52 (RS202)

Scheme 23

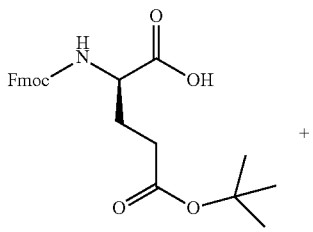

+

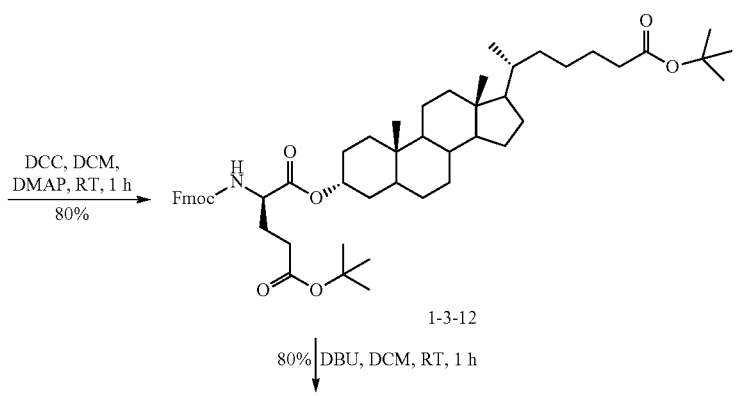

1-3-7

DCC, DCM,
DMAP, RT, 1 h
80%

1-3-12

80% DBU, DCM, RT, 1 h

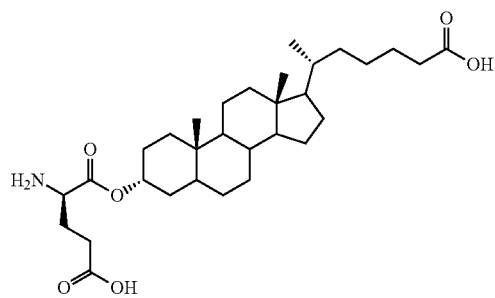

52 (RS 202)

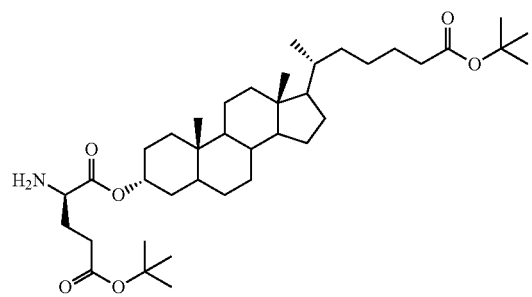

1-3-13

The solution of corresponding Fmoc protected amino acid (0.24 mmole, 1.2 eq) in dichloromethane (5 ml) was added to compound 1-3-7 (0.2 mmole, 1 eq), stirred for 10 min. A solution of DCC (0.32 mmole, 1.6 eq) in DCM (5 ml) followed by DMAP (0.06 mmole, 0.3 eq) was added to above stirred solution and resulting reaction mixture was stirred at room temperature for 1-2 hrs. Reaction mass was filtered and filtrate was washed with water (2×20 ml) followed by saturated sodium chloride solution (2×20 ml). The organic layer was dried over sodium sulfate, filtered, and evaporated to dryness. The final residue was purified by column chromatography (hexanefethyl acetate, 80:20) to give the target product 1-3-12 (75-90%).

To a solution of compound 1-3-12 (0.16 mmole, 1 eq) in dichloromethane (10 ml) was added DBU (0.16 mmole, 1 eq) and stirred at room temperature for 1 h. Reaction mass was concentrated and product purified by flash column chromatography to get desired compound 1-3-13 (80-91%).

Compound 1-3-13 (0.12 mmole, 1 eq) was dissolved in TFA (5 ml) at 0° C. water (50 µL) was added and the reaction mixture was stirred at room temperature for 3 h. The TFA solution was then removed on rotary evaporator and the residue was neutralized with saturated solution of aq. NaHCO$_3$, dialyzed using membrane and purified by reverse phase HPLC to get desired compounds 52 (RS202) as white solid.

1.6 Synthesis of Compounds 51 to 57

Compounds 51 to 57 (or compounds of formula (1-5)) were synthesized in accordance with procedures set forth in Schemes 24 to 28.

Scheme 24:

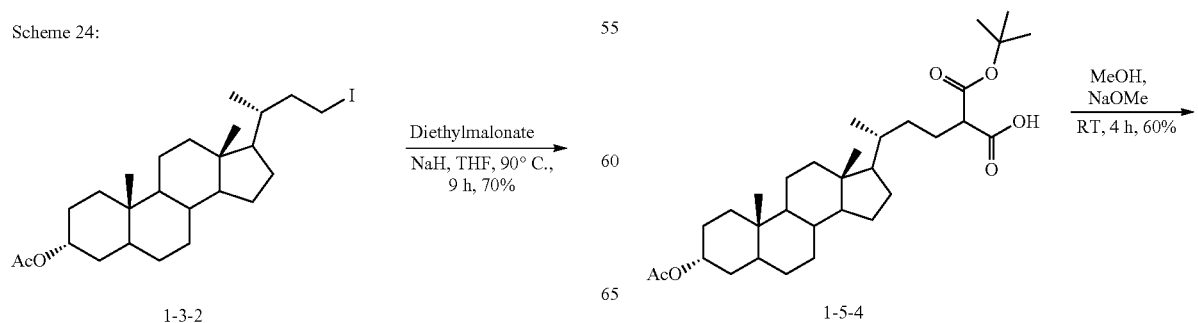

-continued

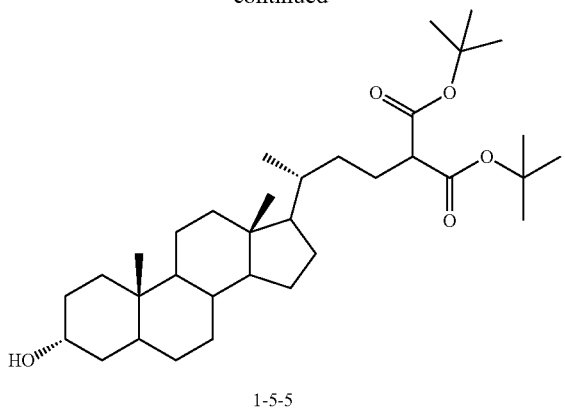

1-5-5

Synthesis of Compound 1-5-1

To a suspension of NaH (15 mmole) in dry THF (30 ml) was added diethylmalonate (17.5 mmole) and heated at 40° C. To it a solution of compound 1-3-2 (5 mmole) in THF was added slowly and resulting reaction mixture stirred at 90° C. for 6 hrs. Reaction mass was diluted with ethyl acetate and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target product 1-5-1 (70%).

Synthesis of Compound 1-5-2

Compound 1-5-1 (1 g) dissolved in methanol (10 ml), to it 40% NaOH (1 mL) was added and resulting reaction mixture reflux for 6 hrs under nitrogen. Reactions mass concentrated on rota, suspension acidify with 5% HCl solution, obtained solid filtered and washed with water. The white solid dried using high vacuum for several hours provides product 1-5-2 (75%). For biological study, compound purify by reverse phase HPLC.

Synthesis of Compound 1-5-3

To a solution of compound 1-5-2 (8 mmole) in dichloromethane (20 ml) was added pyridine (23.90 mmole) followed by acetic anhydride (31.86 mmole) and resulting reaction mixture stirred at room temperature for 24 hrs. Reaction mass was concentrated, the residue was dissolved in DCM (30 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 70:30) to give the target product 1-5-3 (65%).

Synthesis of Compound 1-5-4

To a solution of 1-5-3 (6.67 mmole) in tert. butanol (30 ml) was added Boc-anhydride (13.34 mmole) followed by DMAP (2 mmole) and resulting reaction mixture was stirred at room temperature for 1 h. Reaction mass was concentrated, the residue was dissolved in DCM (40 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target product 1-5-4 (74%).

Synthesis of Compound 1-5-5

Compound 1-5-4 (4.88 mmole) was dissolved in methanol (40 ml) to it sodium methoxide (14.65 mmole) was added and the resulting reaction mixture was stirred at room temperature for 12 h. Reaction mass was concentrated, the residue was dissolved in DCM (30 mL) and washed with water (2×30 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target products 1-5-5 (60%).

Scheme 25:

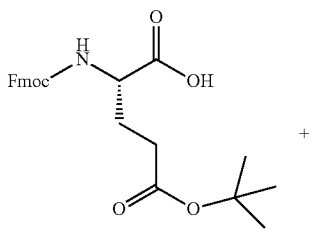

+

147 148
-continued
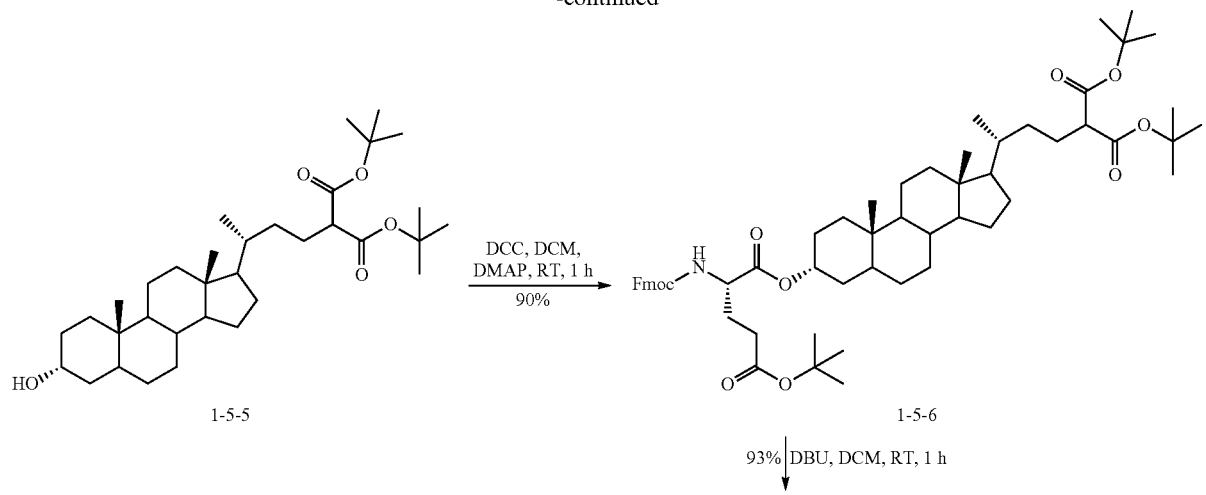
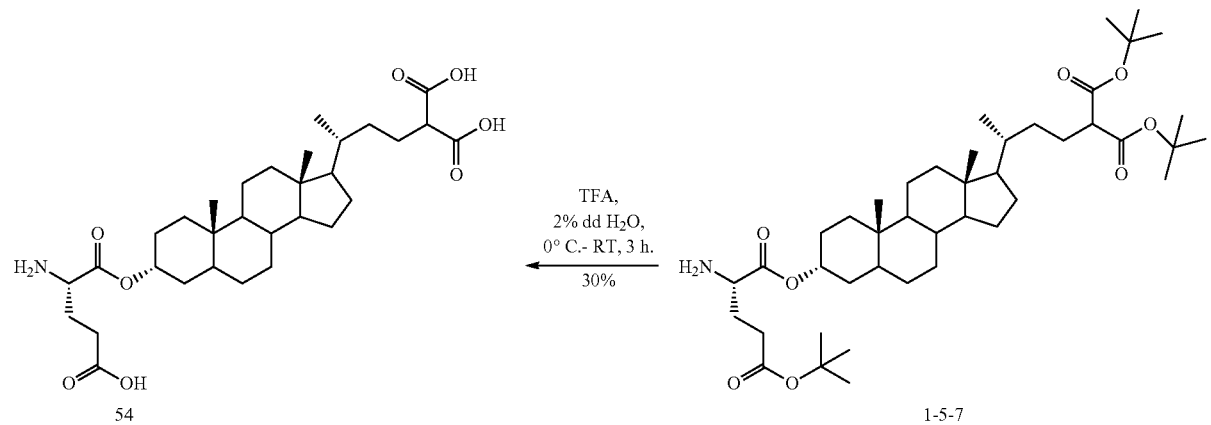
Scheme 26
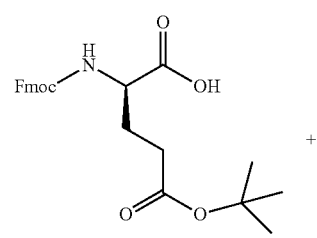
+

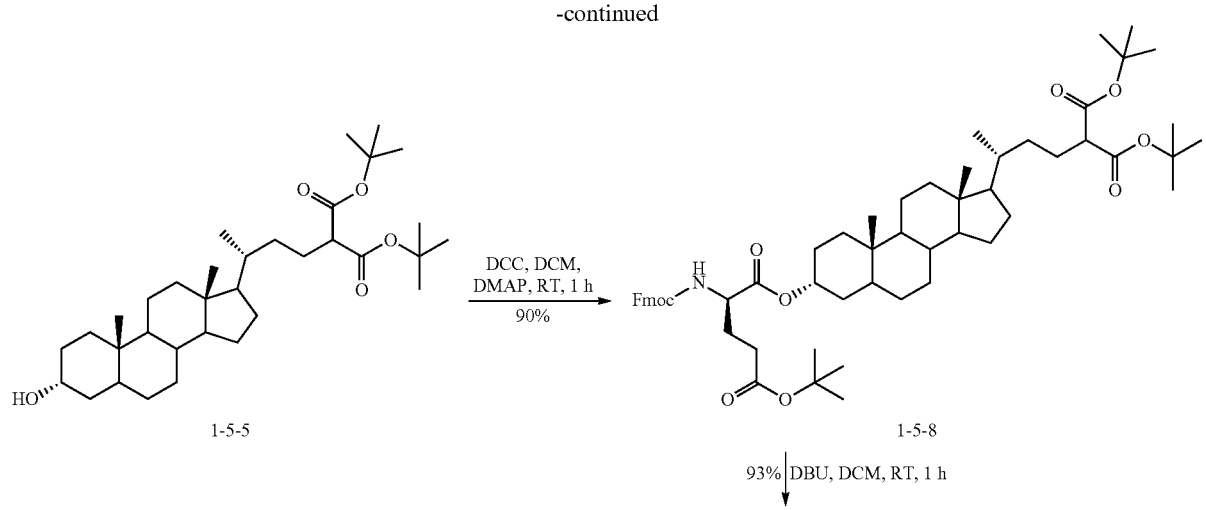
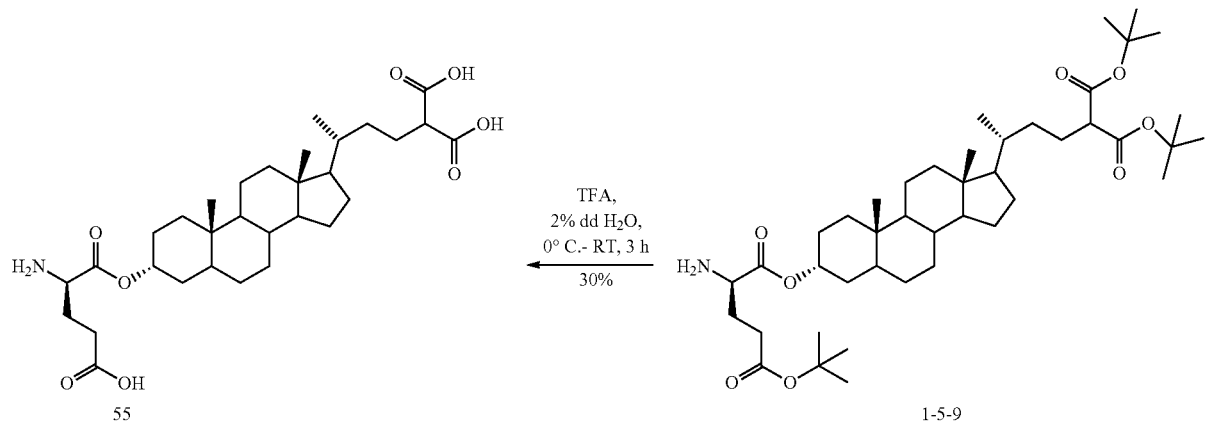
Scheme 27
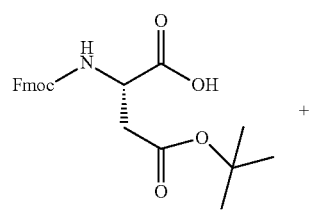

-continued
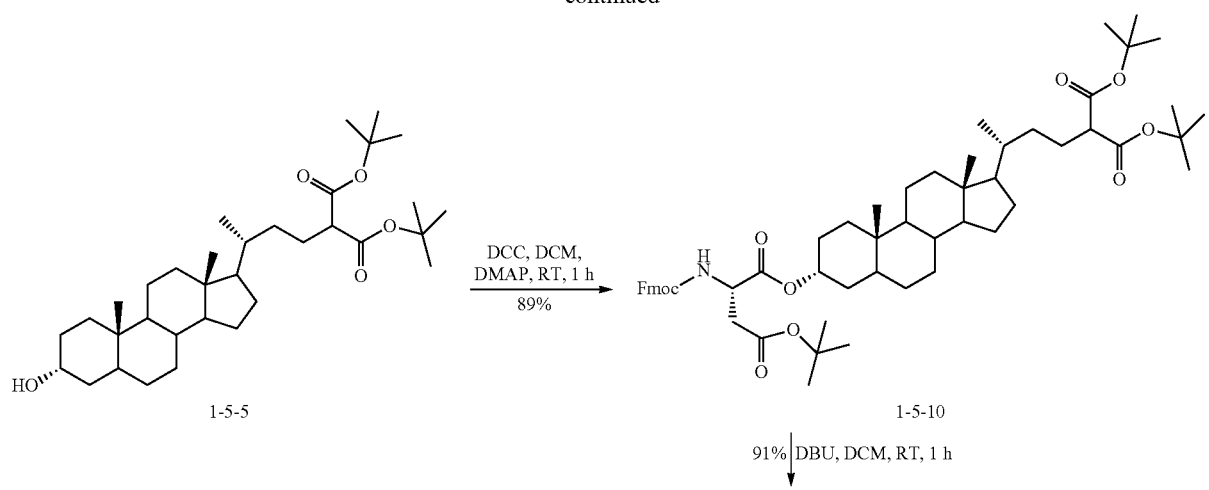
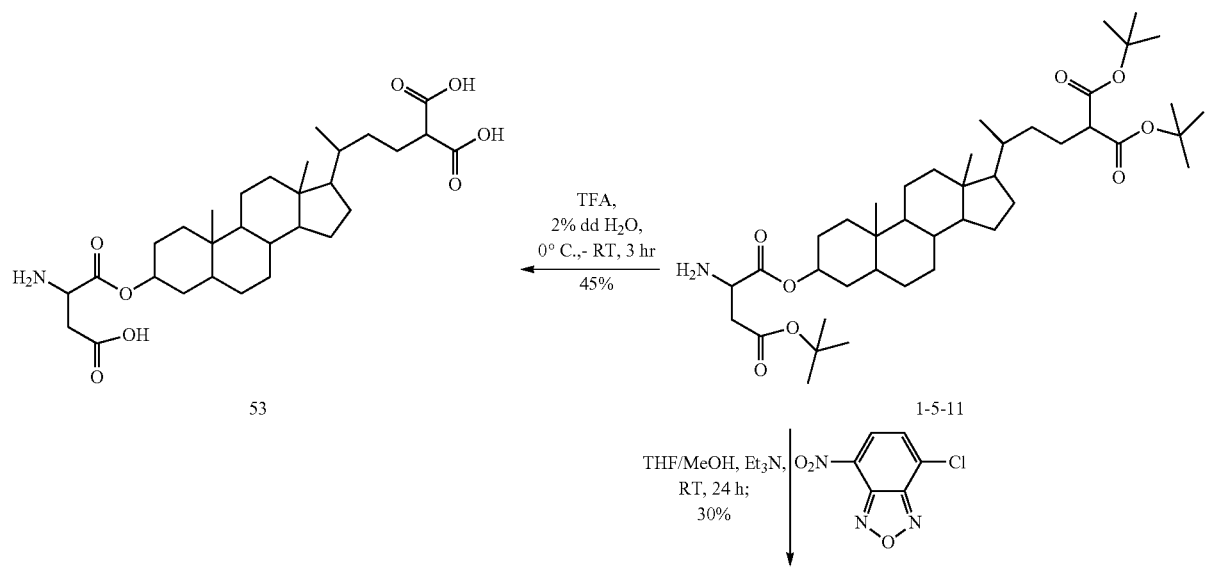
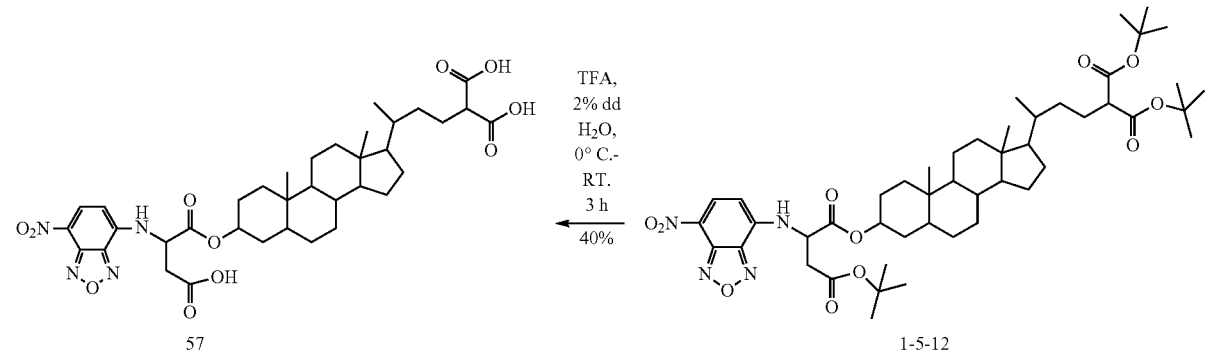

Scheme 28

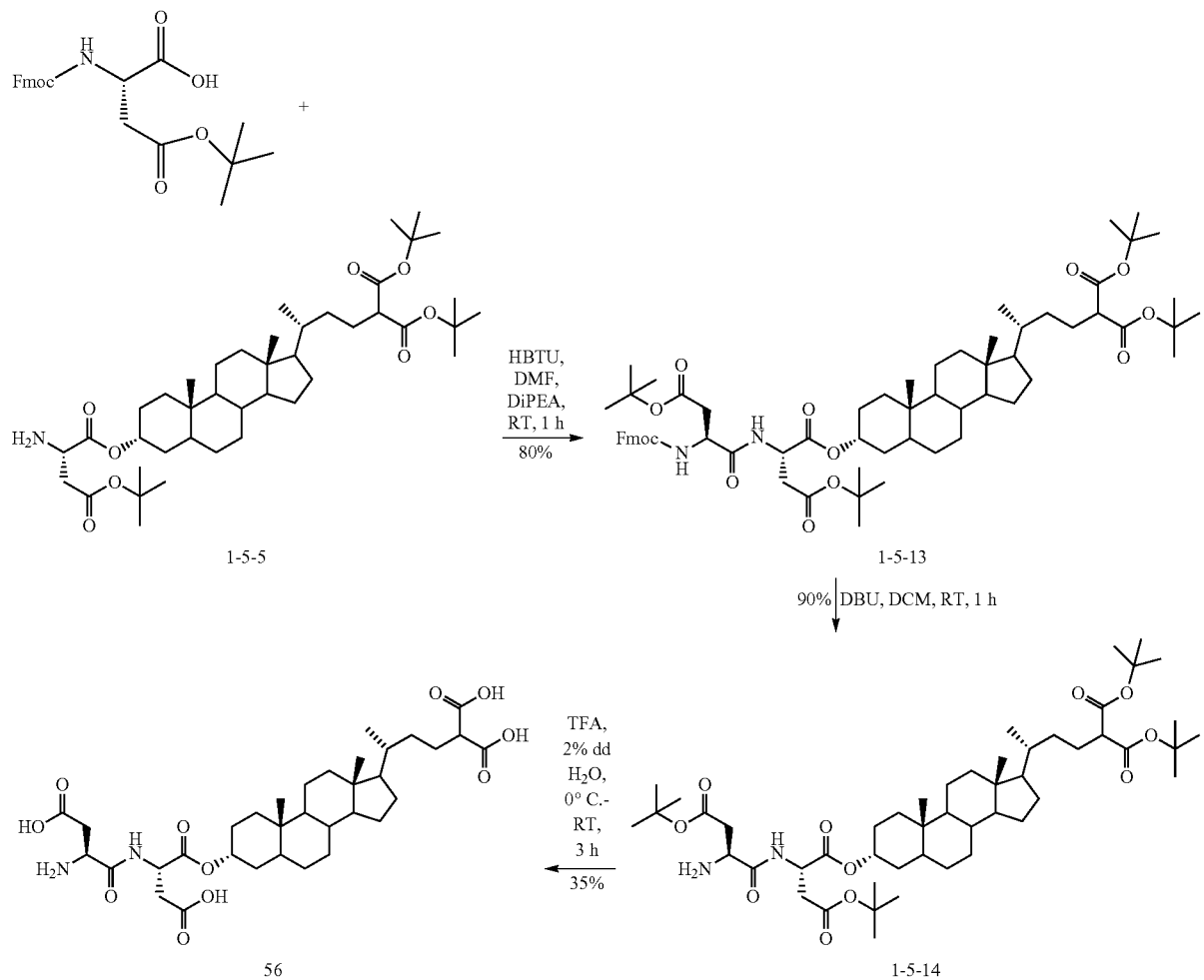

General Procedures for Synthesizing Compounds 1-5-6, 1-5-8, 1-5-10 and 1-5-13

To a solution of corresponding Fmoc protected amino acid (0.510 mmole) in dichloromethane (10 ml) was added compound 1-5-5, 1-5-11 (0.346 mmole) stirred for 10 min. A solution of DCC (0.553 mmole) in DCM (5 ml) followed by DMAP (0.102 mmole) was added to above stirred solution and resulting reaction mixture was stirred at room temperature for 1 h. Reaction mass was filtered and filtrate was washed with water (2×20 ml) followed by saturated sodium chloride solution (2×20 ml). The organic layer was dried over sodium sulfate, filtered, and evaporated to dryness. The final residue was purified by column chromatography (hexane/ethyl acetate, 80:20) to give the target products 1-5-6, 1-5-8, 1-5-10 and 1-5-13 (80-90%).

General Procedures for Synthesizing Compounds 1-5-7, 1-5-9, 1-5-11, and 1-5-14

To a solution of compound 1-5-6, 1-5-8, 1-5-10 or 1-5-13 (0.288 mmole) in dichloromethane (10 ml) was added DBU (0.288 mmole) and stirred at room temperature for 1 h. Reaction mass was concentrated and product purified by flash column chromatography to get desired compound 1-5-7, 1-5-9, 1-5-11, and 1-5-14 (90-93%).

General Procedures for Synthesizing Compound 1-5-12

Compound 1-5-11 (0.250 mmole) was dissolved in a mixture of THF:MeOH (1:1) (5 ml), then NaHCO$_3$ (0.375 mmole) was added, followed by NBD-Cl (0.275 mmole), and stirred at room temperature for 24 h (in dark). Reaction mass was concentrated and product purified by column chromatography to get desired compound 1-5-12 (30%).

General Procedures for Synthesizing Compounds 53, 54, 55, 56, and 57

Compound 1-5-7, 1-5-9, 1-5-11, 1-5-12 or 1-5-14 (0.107 mmole) was dissolved in TFA (5 ml) at 0° C., water (50 µL) was added and the reaction mixture was stirred at 0° C. to room temperature for 3 h. The TFA solution was then removed on rotary evaporator and the residue was neutralized with saturated solution of aq. NaHCO$_3$, dialyzed using membrane and purified by perverse phase HPLC to produce desired compounds as white solid.

Compound 1-5-1: $^1$H NMR (CDCl$_3$, 300 MHz): δ=4.71-4.67 (m, 1H), 4.22-4.13 (m, 4H), 3.25 (t, J=7.1 Hz, 1H), 1.95

(s, 3H), 1.92-1.86 (m, 2H), 1.82-1.72 (m, 4H), 1.68-1.53 (m, 2H), 1.49-1.36 (m, 8H), 1.28-1.19 (m, 10H), 1.14-1.04 (m, 6H), 0.92-0.88 (m, 6H), 0.63 (s, 3H).

Compound 1-5-5: $^1$H NMR (CDCl$_3$, 400 MHz): δ=3.62-3.56 (m, 1H), 3.04 (t, J=7.6 Hz, 1H), 1.94-1.92 (m, 1H), 1.82-1.78 (m, 4H), 1.75-1.68 (m, 7H), 1.43 (s, 18H), 1.37-1.35 (m, 7H), 1.23-1.21 (m, 5H), 1.10-1.01 (m, 6H), 0.92-0.88 (m, 6H), 0.63 (s, 3H); $^{13}$C NMR (100 MHz): δ=169.41, 169.30, 81.43, 72.21, 56.80, 56.20, 54.73, 43.01, 40.78, 40.46, 36.82, 36.19, 35.79, 35.68, 34.90, 33.60, 30.91, 27.53, 26.74, 25.56, 24.52, 23.68, 21.14, 18.87, 12.32.

Compound 54: $^1$H NMR (MeOD, 500 MHz): δ6=4.88-4.86 (m, 1H), 3.19 (m, 1H), 2.56-2.51 (m, 2H), 2.19-2.12 (m, 2H), 2.04-1.88 (m, 6H), 1.76-1.74 (m, 2H), 1.62-1.47 (m, 11H), 1.30-1.20 (m, 4H), 1.19-1.08 (m, 7H), 0.98-0.96 (m, 6H), 0.70 (s, 3H); $^{13}$C NMR (100 MHz): δ=175.68, 173.89, 173.84, 169.89, 78.72, 57.99, 57.46, 53.58, 44.01, 43.47, 41.98, 41.60, 37.33, 36.94, 36.07, 35.84, 34.68, 33.31, 30.55, 29.31, 28.27, 27.66, 27.62, 26.90, 26.86, 25.36, 23.86, 22.09, 19.92, 12.52, HRMS m/z calcd for C$_{31}$H$_{50}$NO$_8$, 564.3528; found 564.3536 (M+H)+, HPLC conditions: retention time=16.51 min. Solvents: A) 100% Water+0.1% TFA, B) 100% ACN+0.05% TFA, Column: Kromasil 300-5C4.

Compound 55: $^1$H NMR (MeOD, 500 MHz): δ=4.87-4.85 (m, 1H), 4.08-4.05 (m, 1H), 2.56-2.51 (m, 1H), 2.19-2.12 (m, 2H), 2.04-1.88 (m, 6H), 1.77-1.75 (m, 2H), 1.61-1.59 (m, 2H), 1.54-1.45 (m, 8H), 1.42-1.31 (m, 3H), 1.29-1.08 (m, 7H), 0.98-0.96 (m, 6H), 0.70 (s, 3H); $^{13}$C NMR (125 MHz): δ=175.64, 173.75, 173.72, 169.89, 78.73, 57.99, 57.46, 53.57, 44.02, 43.49, 41.99, 41.61, 37.34, 36.95, 36.08, 35.84, 34.71, 33.28, 30.55, 29.32, 28.24, 27.65, 26.92, 25.37, 23.87, 22.10, 19.18, 12.59, HRMS m/z calcd for C$_{31}$H$_{50}$NO$_8$, 564.3544; found 564.3536 (M+H)+, HPLC conditions: retention time=16.47 min. Solvents: A) 100% Water+0.1% TFA, B) 100% ACN+0.05% TFA, Column: Kromasil 300-5C4.

Compound 53: $^1$H NMR (MeOD, 500 MHz): δ=4.91-4.83 (m, 1H), 4.27-4.05 (t, J=4 Hz, 1H), 3.22-3.19 (m, 1H), 3.04-2.93 (m, 2H), 2.03-2.01 (m, 1H), 1.97-1.90 (m, 5H), 1.75-1.71 (m, 2H), 1.61-1.59 (m, 2H), 1.51-1.42 (m, 8H), 1.29-1.22 (m, 3H), 1.20-1.11 (m, 7H), 0.98-0.96 (m, 6H), 0.70 (s, 3H); $^{13}$C NMR (125 MHz): δ=173.72, 173.66, 173.00, 169.12, 78.79, 58.00, 57.49, 50.90, 44.02, 43.47, 41.98, 41.61, 37.33, 36.93, 36.05, 35.84, 35.11, 34.71, 33.21, 29.31, 28.27, 27.51, 26.81, 25.36, 23.86, 22.09, 19.18, 12.60, HRMS m/z calcd for C$_{30}$H$_{47}$NO$_8$, 550.3376; found 550.3380 (M+H)+, HPLC conditions: retention time=18.72 min. Solvents: A) 100% Water+0.1% TFA, B) 100% ACN+0.05% TFA, Column: Kromasil 300-5C4.

Compound 57: $^1$H NMR (MeOD, 500 MHz): δ=8.53 (d, J=8.5 Hz, 1H), 6.53 (d, J=9 Hz, 1H), 4.82-4.76 (m, 1H), 3.23 (t, J=7 Hz, 1H), 3.15-3.04 (m, 2H), 3.04-2.93 (m, 1H), 1.94-1.77 (m, 6H), 1.74-1.68 (m, 2H), 1.56-1.35 (m, 10H), 1.24-1.19 (m, 3H), 1.11-0.96 (m, 6H), 0.93-0.92 (m, 6H), 0.63 (s, 3H); $^{13}$C NMR (125 MHz): δ5=173.65, 173.45, 173.38, 171.02, 146.00, 145.54, 137.98, 124.95, 78.06, 57.85, 57.36, 53.58, 43.93, 43.45, 41.88, 41.53, 37.25, 36.93, 36.83, 36.11, 35.79, 34.79, 33.32, 29.28, 27.59, 26.84, 25.32, 23.88, 22.05, 19.18, 12.56, HRMS m/z calcd for C$_{36}$H$_{48}$N$_4$O$_{11}$, 713.3395; found 713.3398 (M+H), HPLC conditions: retention time=18.75 min. Solvents: A) 100% Water+0.1% TFA, B) 100% ACN+0.05% TFA, Column: Kromasil 300-5C4.

Compound 56: $^1$H NMR (MeOD, 500 MHz): δ=4.79-4.72 (m, 2H), 4.24-4.22 (m, 1H), 3.20 (t, J=7.5 Hz, 1H), 3.02-2.98 (m, 1H), 2.90-2.77 (m, 3H), 2.03-2.00 (m, 1H), 1.95-1.85 (m, 5H), 1.75-1.68 (m, 2H), 1.60-1.55 (m, 2H), 1.46-1.41 (m, 8H), 1.31-1.21 (m, 4H), 1.20-1.09 (m, 6H), 0.97-0.96 (m, 6H), 0.69 (s, 3H); $^{13}$C NMR (125 MHz): δ=174.04, 173.99, 173.79, 173.44, 171.42, 169.62, 77.59, 57.90, 57.43, 51.30, 50.30, 44.01, 43.51, 41.97, 41.60, 37.36, 36.95, 36.79, 36.70, 36.15, 35.85, 34.67, 33.39, 29.32, 28.30, 27.65, 26.93, 25.37, 23.91, 22.10, 19.18, 12.58, HRMS m/z calcd for C$_{34}$H$_{53}$N$_2$O$_{11}$, 665.3655; found 665.3649 (M+H)+, HPLC conditions: retention time=18.75 min. Solvents: A) 100% Water+0.1% TFA, B) 100% ACN+0.05% TFA, Column: Kromasil 300-5C4.

1.7 Synthesis of Compounds 58 to 70

Compounds 58 to 64 (or compounds of formula (1-4)) were synthesized in accordance with procedures set forth in Schemes 29 to 33, whereas compounds 65 to 70 were synthesized in accordance with procedures set forth in Schemes 34 to 40.

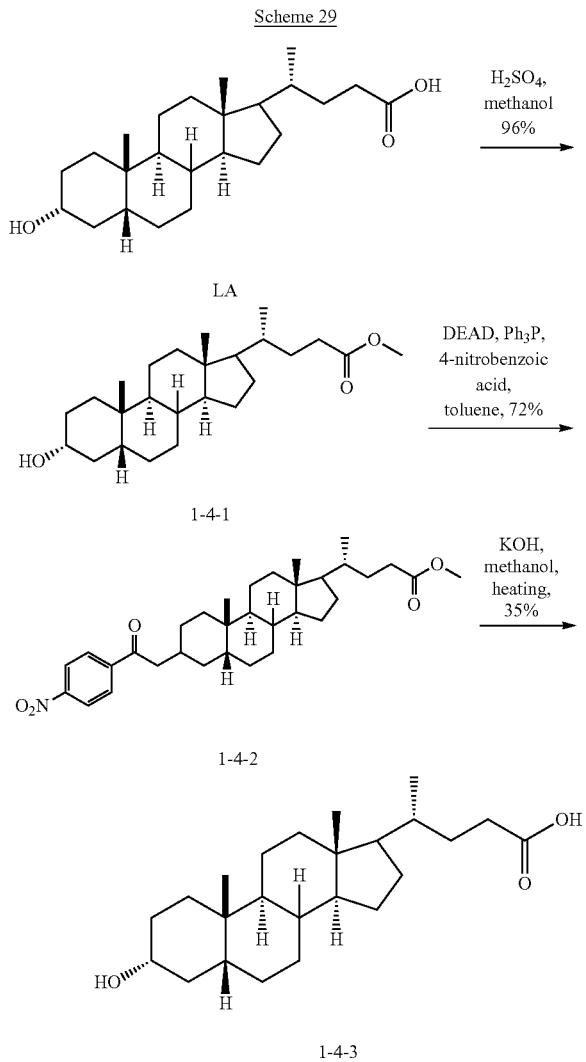

Scheme 29

Synthesis of Compound 1-4-1

Placed 5.0 g of lithocholic acid (13.28 mmol) in the bottom of a 100 mL round ended flask, added methanol and sulfuric acid (200 μL, 8M), allowed the mixture to react at room temperature for 3 hrs until the mixture turned into a clear solution. Reduced the volume of the clear solution by concentration, then added water to the concentrated solution to precipitate the product, washed with deionized water to give white solid compound 1-4-1 (5.00 g, 96%).

Compound 1-4-1: $^1$H NMR (400 MHz, CDCl$_3$): δ 3.63 (s, 3H), 3.58 (m, 1H), 2.32 (m, 1H), 2.18 (m, 1H), 1.92 (m, 1H), 1.84 (m, 2H), 1.78 (t, J=3.1 Hz, 1H), 1.75 (t, J=3.0 Hz, 1H), 1.70 (t, J=8.4 Hz, 1H), 1.63 (m, 1H), 1.50 (s, 4H), 1.38 (m, 5H), 1.3 (t, J=6.9 Hz, 2H), 1.25 (m, 2H), 1.20 (d, J=11.0 Hz, 2H), 1.13 (m, 1H), 1.08 (s, 1H), 1.03 (m, 2H), 0.96 (m, 1H), 0.90 (s, 4H), 0.86 (s, 2H), 0.61 (s, 3H).

Synthesis of Compound 1-4-2

In a 100 mL round ended flask, placed compound 1-4-1 (2.0 g, 5.12 mmol), Ph$_3$P (2.69 g, 10.24 mmol), and 4-nitrobenzoic acid (1.03 g, 6.13 mmol), 30 mL toluene was then added, and kept the mixture in an iced bath until the temperature of the reacting mixture reached 0° C., then diethyl azodicarboxylate was added, which turned the color of the mixture into orange, allowed the reaction to proceed for 24 hrs until its temperature returned to room temperature.

Concentrated the product to remove any un-reacted toluene, then dissolved the concentrated product in methylene dichloride, extracted it twice with brine. The organic layers were combined, dried with Na$_2$SO$_4$, then subjected to column chromatography, a white, non-crystallined solid or compound 1-4-2 was yield (2.0 g, 72%). TLC (Ethyl acetate/Hexane=2:8): R$_f$=0.40.

Compound 1-4-2: $^1$H NMR (400 MHz, CDCl$_3$): δ 8.26 (d, J=8.8 Hz, 2H), 8.17 (d, J=8.8 Hz, 2H), 5.34 (s, 1), 3.63 (s, 3H), 2.33 (m, 1H), 2.19 (m, 1H), 2.07 (m, 1H), 1.95 (t, J=6.2 Hz, 1H), 1.84 (m, 2H), 1.72 (m, 3H), 1.59 (m, 4H), 1.38 (t, J=6.5 Hz, 4H), 1.33 (d, J=3.1 Hz, 1H), 1.29 (m, 2H), 1.23 (t, J=5.9 Hz, 2H), 1.17 (m, 2H), 1.11 (d, J=9.5 Hz, 1H), 1.04 (m, 3H), 0.99 (s, 3H), 0.89 (d, J=6.4 Hz, 3H), 0.62 (s, 3H); $^{13}$C NMR (100 MHz, CDCl$_3$): δ 174.9, 164.1, 150.6, 136.7, 130.7, 123.6, 13.0, 56.7, 56.1, 42.9, 10.3, 10.1, 37.9, 35.8, 35.4, 35.1, 31.2, 31.2, 31.1, 30.8, 28.3, 26.6, 26.3, 25.3, 24.3, 24.2, 21.3, 18.4, 12.2.

Synthesis of Compound 1-4-3

Mixed compound 1-4-2 (2.0 mg, 3.71 mmol), methanol (40 mL), KOH (200 μL, 40%) in a flask, stirred and heated the mixture to 60° C., and allowed the mixture to react for 3 hrs.

Concentrated the product to remove any un-reacted methanol, then dissolved the concentrated product in methylene dichloride, extracted it twice with sodium bicarbonate. Collected the organic layer, extracted with brine, combined the collected organic layers, dried with Na$_2$SO$_4$, then subjected it to column chromatography (ethyl acetate/hexane=1:9), a white, non-crystallined solid or compound 1-4-3 was obtained (500 mg, 35%). TLC (Ethyl acetate/Hexane=3:7): R$_f$=0.20. m.p.=194-196° C.

Compound 1-4-3: $^1$H NMR (400 MHz, CDCl$_3$): δ 4.09 (m, 1H), 2.36 (m, 1H), 2.23 (m, 1H), 1.95 (m, 2H), 1.81 (m, 3H), 1.68 (t, J=4.8 Hz, 1H), 1.55 (m, 2H), 1.45 (s, 2H), 1.36 (m, 6H). 1.25 (m, 6H), 1.14 (m, 2H), 1.03 (m, 4H), 0.93 (s, 3H), 0.90 (d, J=6.4 Hz, 3H), 0.63 (s, 3H); 13C NMR (100 MHz, CDCl$_3$): δ 179.1, 67.4, 56.8, 56.2, 43.0, 40.4, 39.9, 36.8, 35.8, 35.5, 35.3, 33.7, 31.0, 30.1, 29.9, 28.4, 28.0, 26.8, 26.4, 24.4, 24.1, 21.3, 18.4, 12.3

HRMS (ESI) calculated for C$_{24}$H$_{39}$O$_3$(M−H)$^-$ 375.2899; found 375.2900.

Scheme 30

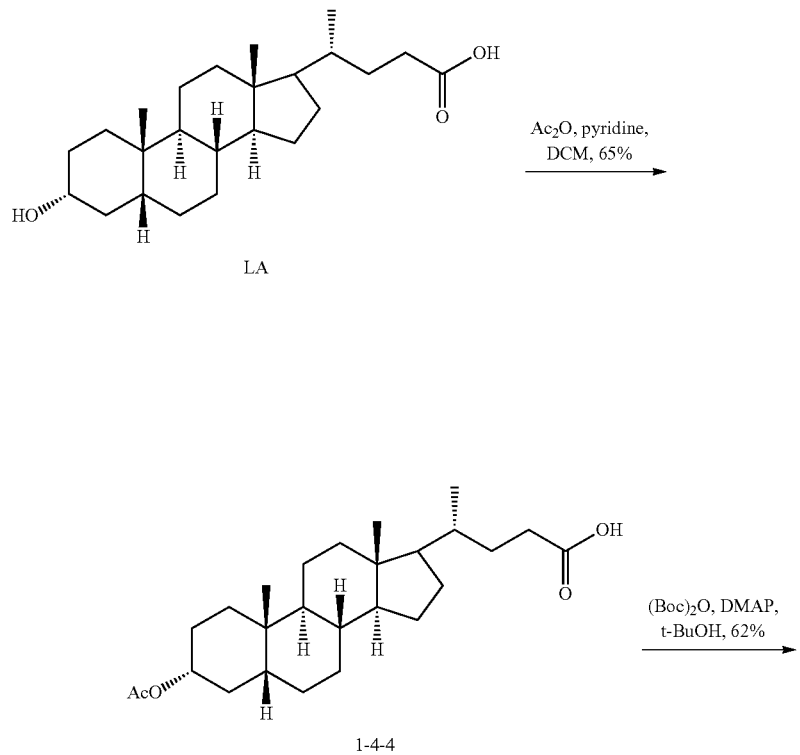

1-4-4

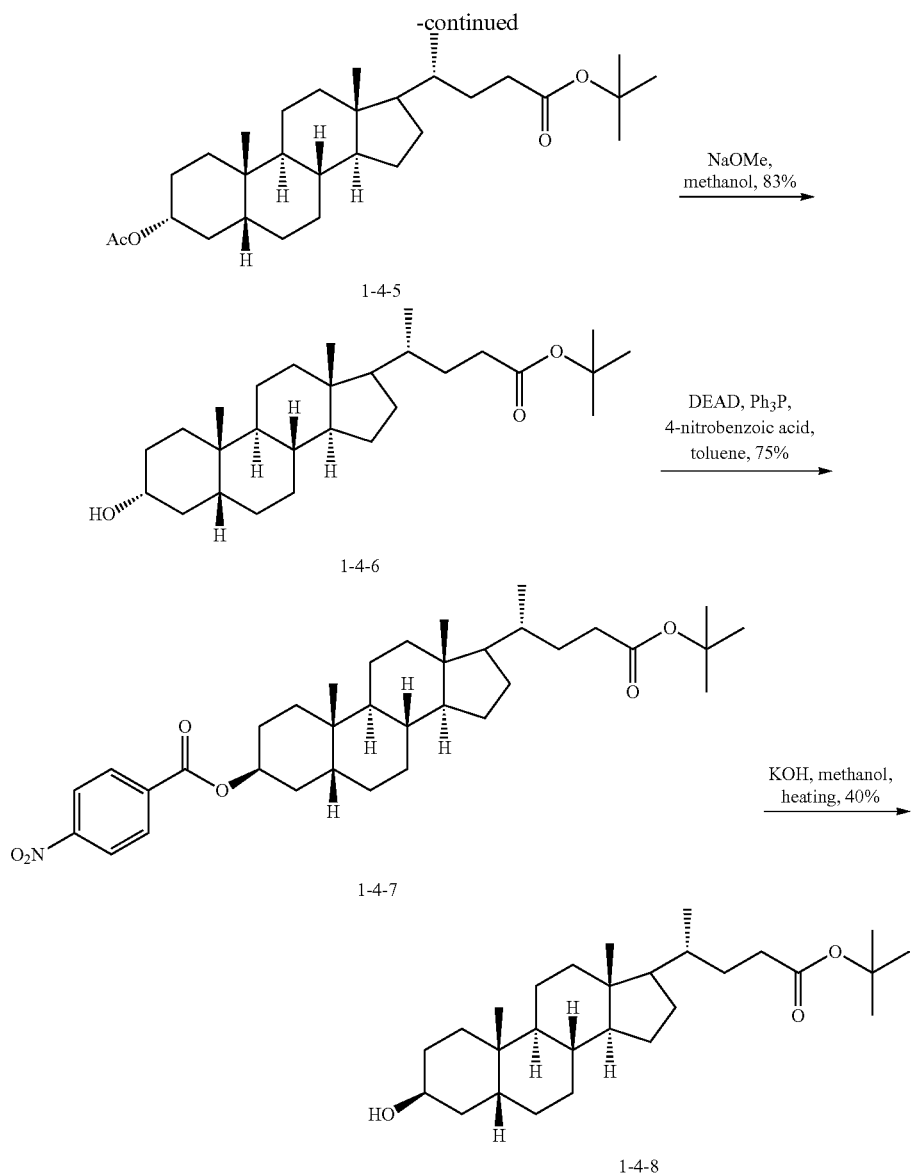

Synthesis of Compound 1-4-6

Dissolved lithocholic acid (4.00 mg, 10.6 mmol) in methylene dichloride (100 mL) in a 250 mL round ended flask, added pyridine (3.43 mL, 42.5 mmol), waited until all pyridine was dissolved, then added acetic anhydride (3.01 mL, 31.9 mmol), let the mixture to react at room temperature for 4 hrs.

Concentrated the product to remove any residual pyridine and acetic anhydride. Dissolved the concentrated product in methylene dichloride, extracted twice with 6% HCl, collected and combined the organic layers, extracted twice with sodium bicarbonate, dried with $Na_2SO_4$, then subjected it to column chromatography (ethyl acetate/hexane=1:9 to 3:7), vacuum dried to produce a white, non-crystallined solid or compound 1-4-4 (2.9 mg, 65%). TLC (Ethyl acetate/Hexane=3:7): $R_f$=0.45.

Synthesis of Compound 1-4-5

Mixed and dissolved compound 1-4-4 (4.0 g, 9.55 mmol) in t-butanol (200 mL) in a round ended flask, added $(Boc)_2O$ (4.09 mL, 19.11 mmol) and DMAP (350 mg, 2.87 mmol), and allowed the mixture to react at room temp for 3 hrs.

Concentrated the product to remove any residual t-butanol. Dissolved the concentrated product in methylene dichloride, extracted twice with water, collected and combined the organic layers, dried with $Na_2SO_4$, then subjected it to column chromatography (ethyl acetate/hexane=1:9), vacuum dried to produce a white, non-crystallined solid or compound 1-4-5 (2800 mg, 62%). TLC (Ethyl acetate/Hexane=2:8): $R_f$=0.80.

Synthesis of Compound 1-4-6

Mixed and dissolved compound 1-4-5 (5.0 g, 10.53 mmol) in methanol (200 mL) in a round ended flask, added $NaOCH_3$ (5.69 g, 105.3 mmol), and allowed the mixture to react at room temp for 2 hrs.

Concentrated the product to remove any residual methanol. Dissolved the concentrated product in methylene dichloride, extracted twice with water, collected and combined the organic layers, dried with Na₂SO₄, then subjected it to column chromatography (ethyl acetate/hexane=2:8), vacuum dried to produce a white, non-crystallined solid or compound 1-4-6 (3.8 g, 83%). TLC (Ethyl acetate/Hexane=3:7): R$_f$=0.55.

Compound 1-4-6: ¹H NMR (400 MHz, CDCl₃): δ 3.59 (m, 1H), 2.23 (m, 1H), 2.10 (m, 1H), 1.93 (m, 1H), 1.82 (m, 3H), 1.72 (m, 2H), 1.64 (s, 1H), 1.52 (s, 5H), 1.41 (s, 8H), 1.36 (t, J=4.3 Hz, 6H), 1.24 (m, 5H), 1.09 (m, 6H), 0.95 (s, 2H), 0.88 (d, J=7.6 Hz, 2H), 0.62 (s, 3H)

Synthesis of Compound 1-4-7

Mixed and dissolved compound 1-4-6 (2.0 g, 4.62 mmol), Ph3P (1.82 g, 6.93 mmol), and 4-nitrobenzoic acid (910 mg, 5.55 mmol) in a 250 mL round ended flask, 100 mL dry toluene was then added, and kept the mixture in an iced bath until the temperature of the reacting mixture reached 0° C., then diethyl azodicarboxylate was added, which turned the color of the mixture into orange, allowed the reaction to proceed for 24 hrs until its temperature returned to room temperature.

Concentrated the product to remove any un-reacted toluene, then dissolved the concentrated product in methylene dichloride, extracted it twice with brine. Collected and combined the organic layers, dried with Na₂SO₄, then subjected it to column chromatography (Ethyl acetate/Hexane=1:9), a white, non-crystallined solid of compound 1-4-7 was obtained (2.0 g, 75%). TLC (Ethyl acetate/Hexane=2:8): R$_f$=0.40.

Synthesis of Compound 1-4-8

Mixed compound 1-4-7 (2.0 mg, 3.43 mmol), methanol (40 mL), KOH (200 μL, 40%) in a flask, stirred and heated the mixture to 60° C., and allowed the mixture to react for 3 hrs.

Concentrated the product to remove any un-reacted methanol, then dissolved the concentrated product in methylene dichloride, extracted it twice with sodium bicarbonate. Collected the organic layer, extracted with brine, combined the collected organic layers, dried with Na₂SO₄, then subjected it to column chromatography (ethyl acetate/hexane=1:9), a white, non-crystallined solid or compound 1-4-8 was obtained (600 mg, 40%).

Compound 1-4-8: ¹H NMR (400 MHz, CDCl₃): δ 4.07 (s, 1H), 2.15 (m, 1H), 1.94 (m, 2H), 1.75 (m, 4H), 1.52 (m, 3H), 1.40 (s, 9H), 1.34 (m, 6H), 1.23 (m, 6H), 1.10 (m, 4H), 1.00 (m, 3H), 0.92 (s, 3H), 0.87 (d, J=6.4 Hz, 3H), 0.61 (s, 3H)
¹³C NMR (100 MHz, CDCl₃): δ 173.7, 79.8, 66.9, 56.6, 56.1, 42.7, 40.3, 39.8, 36.5, 35.6, 35.3, 35.1, 33.5, 32.5, 31.1, 29.9, 28.2, 27.8, 26.7, 26.3, 24.2, 23.9, 21.1, 19.3, 12.1.

Scheme 31

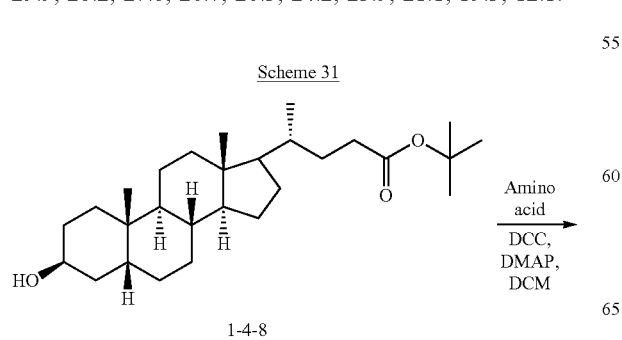

1-4-8

-continued

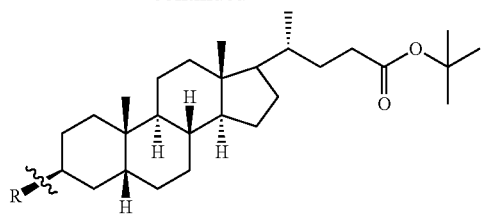

1-4-9

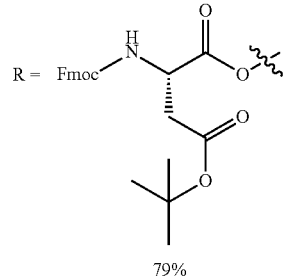

79%

1-4-12

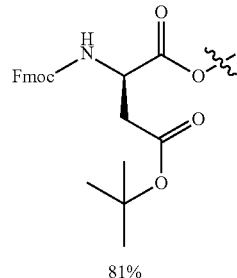

81%

1-4-15

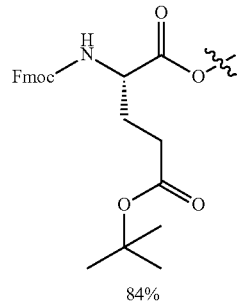

84%

1-4-18

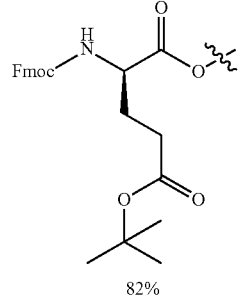

82%

Scheme 32
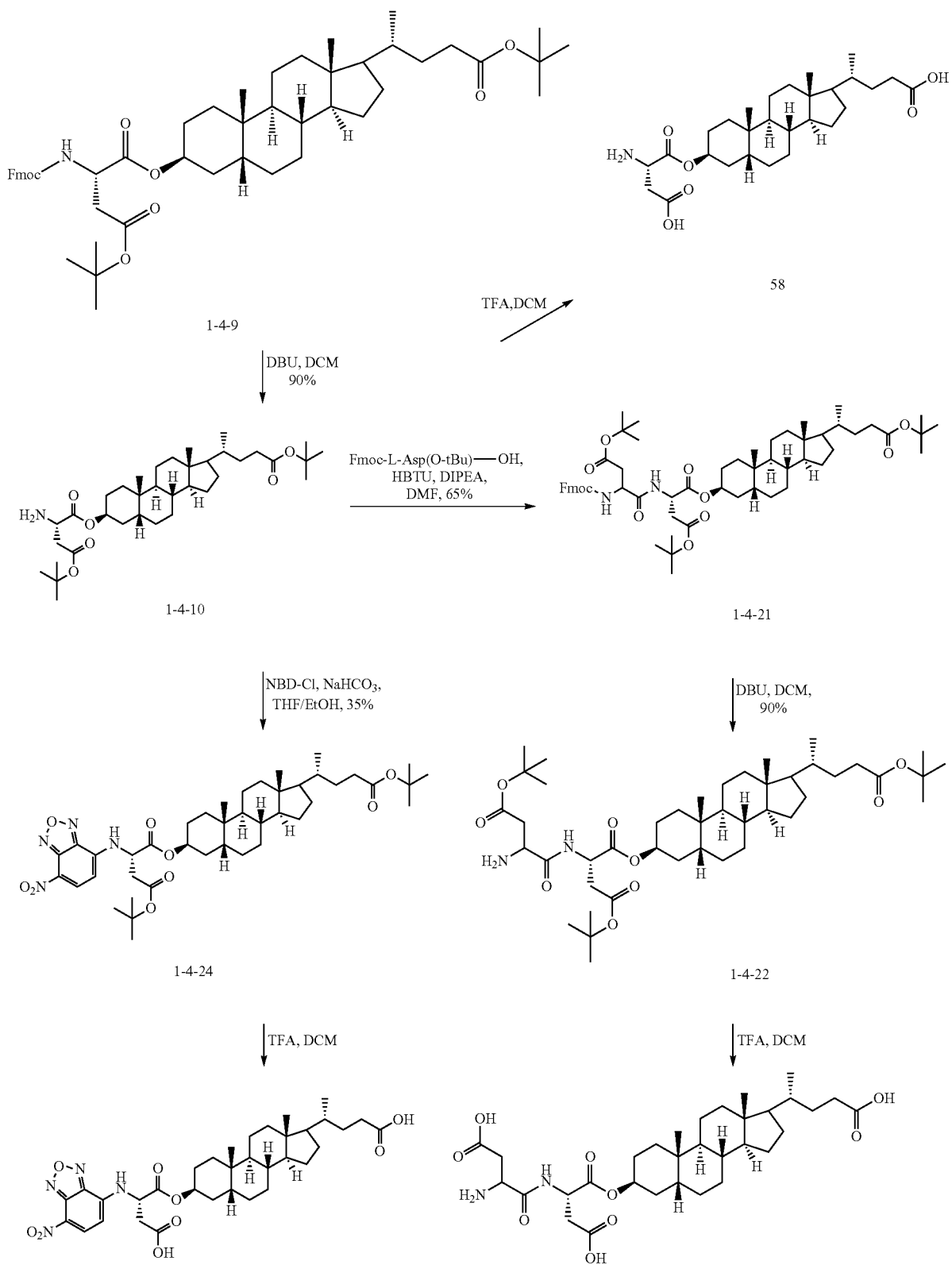

Scheme 33
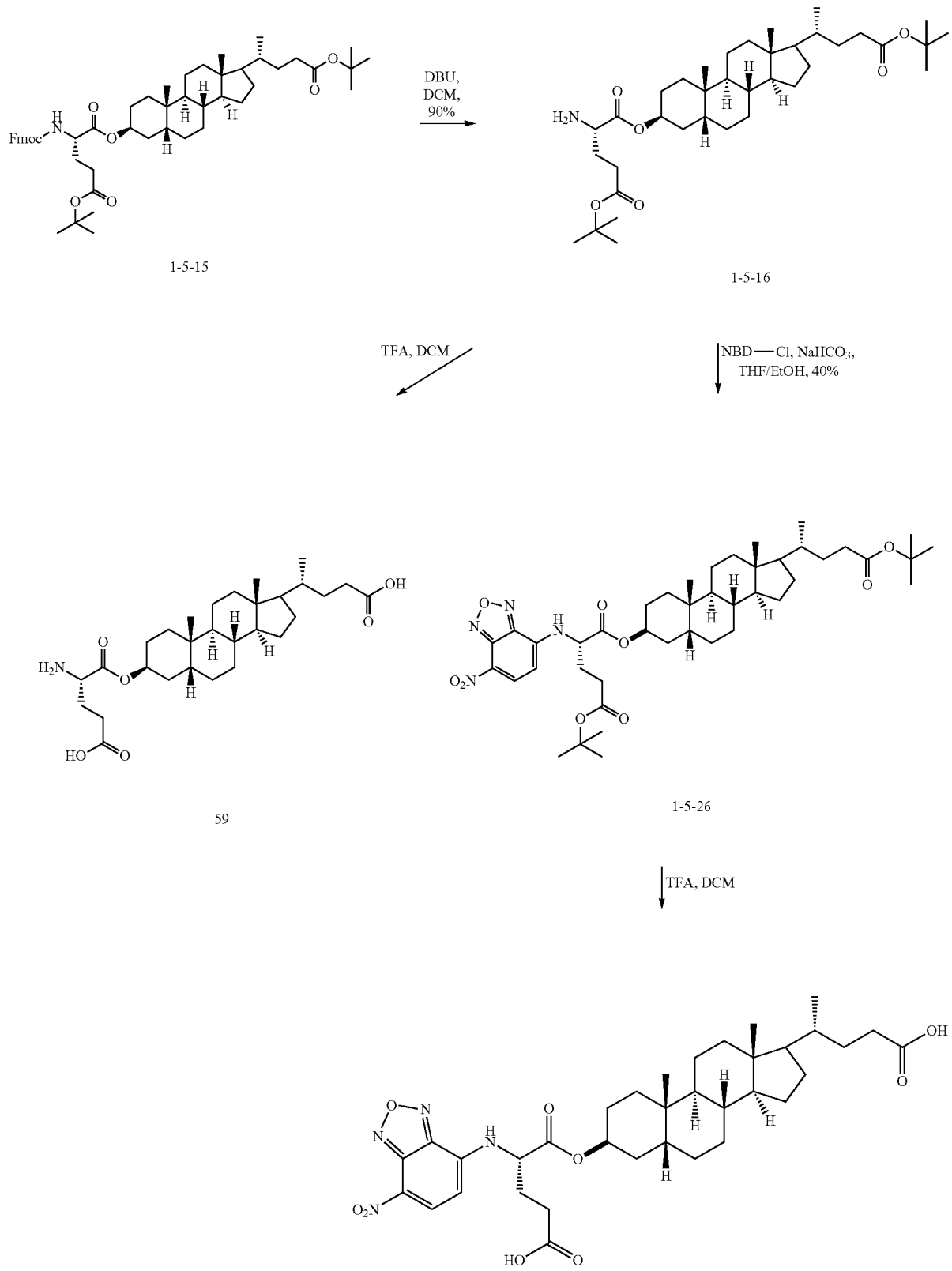

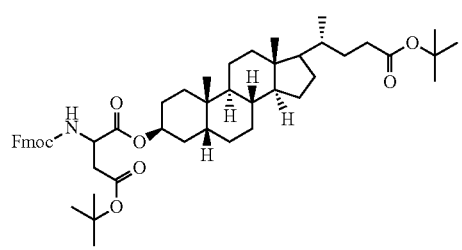
1-5-12
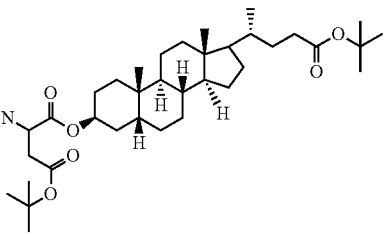
1-5-13
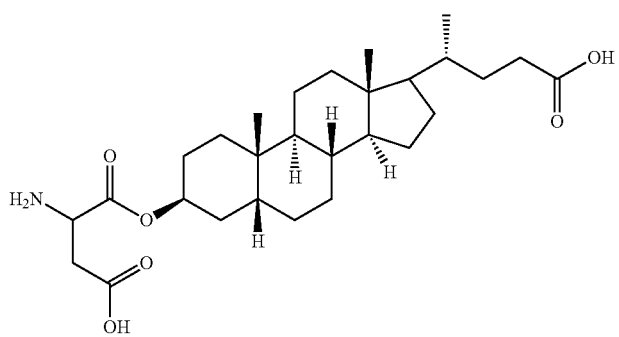
60
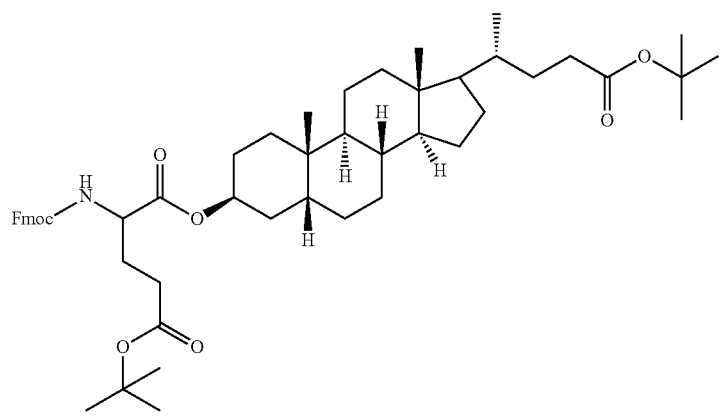
1-5-18
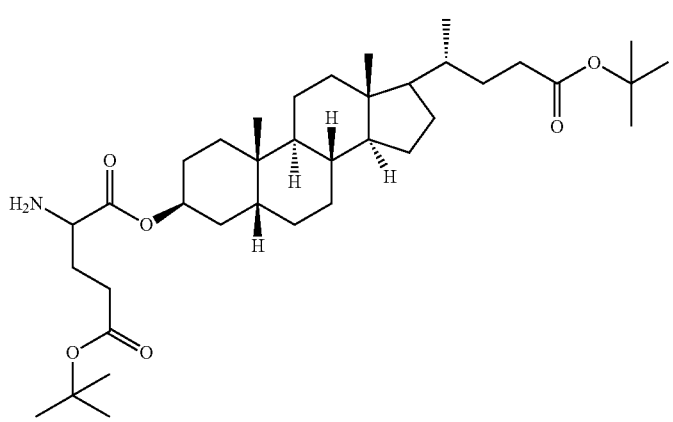
1-5-19

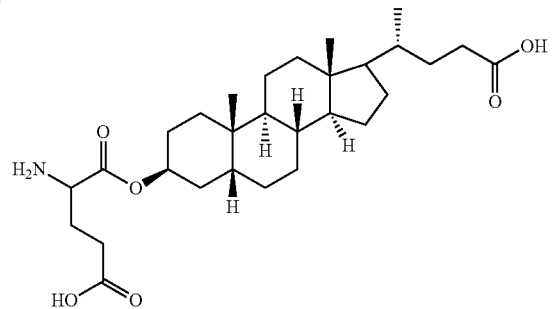

61

Synthesis of Compound 1-4-9

In a round ended flask, mixed and dissolved compound 1-4-8 (500 mg, 1.155 mmol) in methylene dichloride (25 mL), then added Fmoc-L-Asp-tert-butyl (620 mg, 1.5 mmol), DCC (240 mg, 2.671 mmol), and DMAP (45 mg, 0.347 mmol), allowed the mixture to react at room temp for 1 hr.

Filtered the solution, discarded the precipitate, and extracted the filtrate with distilled water twice, collected and combined the organic layers, dried with $Na_2SO_4$, then subjected it to column chromatography (ethyl acetate/hexane=1:9), a white, non-crystallined solid or compound 1-4-9 was obtained (760 mg, 79%). TLC (Ethyl acetate/Hexane=2:8): $R_f$=0.45.

Compound 1-4-9: $^1$H NMR (400 MHz, $CDCl_3$): δ 7.74 (d, J=7.5 Hz, 2H), 7.58 (t, J=6.4 Hz, 2H), 7.38 (t, J=7.4 Hz, 2H), 7.30 (t, J=7.4 Hz, 2H), 5.84 (d, J=8.5 Hz, 1H), 5.14 (s, 1H), 4.55 (m, 1H), 4.34 (m, 2H), 4.22 (m, 1H), 2.86 (m, 1H), 2.21 (m, 1H), 2.10 (m, 1H), 1.94 (m, 2H), 1.82 (m, 2H), 1.71 (s, 1H), 1.58 (m, 5H), 1.43 (s, 9H), 1.41 (s, 9H), 1.34 (d, J=5.7 Hz, 3H), 1.27 (s, 4H), 1.23 (s, 3H), 1.20 (s, 2H), 1.14 (m, 2H), 1.02 (m, 3H), 0.96 (s, 1H), 0.92 (s, 3H), 0.89 (s, 2H), 0.84 (s, 1H), 0.62 (s, 3H); $^{13}$C NMR (100 MHz, $CDCl_3$): δ 173.8, 170.3, 170.2, 156.2, 144.1, 144.1, 143.9, 141.4, 141.4, 127.8, 127.8, 127.2, 127.2, 125.3, 125.3, 120.1, 120.1, 81.9, 80.0, 72.8, 67.4, 56.7, 56.2, 50.9, 47.3, 42.9, 40.3, 40.1, 37.8, 37.6, 35.8, 35.4, 35.0, 32.7, 31.2, 31.0, 30.5, 28.3, 28.3, 28.3, 28.2, 28.2, 28.2, 26.6, 26.3, 25.1, 24.3, 24.1, 21.2, 18.4, 12.1. HRMS (ESI) calculated for $C_{51}H_{71}NO_8Na$ (M+Na)$^+$ 848.5077; found 848.5079.

Synthesis of Compound 58

In a 100 mL round ended flask, mixed and dissolved compound 1-4-9 (200 mg, 0.242 mmol) in methylene dichloride (20 mL), then added DBU (40 μL, 0.242 mmol), allowed the mixture to react at room temp for 0.5 hr.

Concentrated, and purified the product by flash column chromatograpy (eluted the column with hexan to hexane/EA=3:7), a white, non-crystallined solid of compound 1-4-10 was obtained (130 mg, 90%). TLC (Ethyl acetate/Hexane=4:6): $R_f$=0.45.

In a 50 mL round ended flask, mixed and dissolved compound 1-4-10 (100 mg, 0.165 mmol) in TFA (3 mL), then added deionized water (60 μL), allowed the mixture to react at room temp for 3 hrs. Concentrated the product to remove residual TFA, and a crude compound 58 was obtained (60 mg, 70%), which was further purified by HPLC to give a white, non-crystallized solid of compound 58. M.P.=143-145° C.

Compound 58: $^1$H NMR (400 MHz, MeOH-$d_4$): δ 5.21 (s, 1H), 4.30 (t, J=5.2 Hz, 1H), 2.99 (m, 2H), 2.26 (m, 2H), 2.05 (m, 2H), 1.92 (m, 2H), 1.80 (m, 1H), 1.64 (m, 5H), 1.45 (m, 6H), 1.29 (m, 4H), 1.18 (m, 3H), 1.08 (m, 3H), 0.99 (s, 3H), 0.95 (d, J=6.4 Hz, 3H), 0.70 (s, 3H); $^{13}$C NMR (100 MHz, MeOH-$d_4$): δ 174.2, 172.8, 169.0, 75.8, 57.9, 57.6, 50.8, 44.0, 41.5, 41.2, 38.8, 37.1, 36.8, 36.0, 35.0, 32.4, 32.1, 31.9, 31.4, 29.3, 27.6, 27.9, 25.9, 25.3, 24.3, 22.3, 18.9, 12.6. HRMS (ESI) calculated for $C_{28}H_{46}NO_6$ (M+H)$^+$492.3325; found 492.3323.

Synthesis of Compound 1-4-12

In a 100 mL round ended flask, mixed and dissolved compound 1-4-8 (500 mg, 1.155 mmol) in methylene dichloride (25 mL), then added Fmoc-D-Asp-tert-butyl (620 mg, 1.5 mmol), DCC (240 mg, 2.671 mmol) and DMAP (45 mg, 0.347 mmol), allowed the mixture to react at room temperature for 1 hr.

Filtered the solution, discarded the precipitate, and extracted the filtrate with distilled water twice, collected and combined the organic layers, dried with $Na_2SO_4$, then subjected it to column chromatography (eluted the column with a gradient of hexane to ethyl acetate/hexane (1:9)), a white, non-crystallined solid or compound 1-4-12 was obtained (780 mg, 82%). TLC (Ethyl acetate/Hexane=2:8): $R_f$=0.45.

Compound 1-4-12: $^1$H NMR (400 MHz, $CDCl_3$): δ 7.73 (d, J=7.5 Hz, 2H), 7.58 (t, J=6.0 Hz, 2H), 7.38 (t, 2H), 7.29 (m, 2H), 5.85 (d, J=8.5 Hz, 1H), 5.15 (s, 1H), 4.56 (t, J=4.2 Hz, 1H), 4.38 (m, 2H), 4.22 (d, J=7.2 Hz, 1H), 2.85 (m, 2H), 2.15 (m, 2H), 1.84 (m, 6H), 1.57 (m, 4H), 1.44 (s, 9H), 1.41 (s, 9H), 1.36 (m, 3H), 1.24 (m, 6H), 1.12 (m, 3H), 1.01 (m, 4H), 0.93 (s, 3H), 0.88 (d, J=6.4 Hz, 3H), 0.62 (s, 3H). $^{13}$C NMR (100 MHz, $CDCl_3$): δ 173.8, 170.3, 170.2, 156.2, 144.1, 143.9, 143.9, 141.4, 141.4, 127.8, 127.8, 127.2, 127.2, 125.4, 125.4, 125.3, 125.3, 120.1, 120.1, 81.9, 80.0, 72.8, 67.4, 56.2, 56.2, 50.9, 47.3, 42.9, 40.0, 37.9, 37.6, 35.8, 35.4, 34.0, 32.7, 31.2, 30.6, 28.3, 28.3, 28.3, 28.2, 28.2, 28.2, 26.5, 26.2, 24.9, 24.3, 24.1, 21.2, 18.4, 12.2. HRMS (ACPI) calculated for $C_{51}H_{71}NO_8Na$ (M+Na)$^+$848.5077; found 848.5081.

Synthesis of Compound 60

In a 100 mL round ended flask, mixed and dissolved compound 1-4-12 (200 mg, 0.242 mmol) in methylene dichloride (20 mL), then slowly added DBU (40 μL, 0.242 mmol), allowed the mixture to react at room temperature for 0.5 hr. Concentrated, and purified the product by flash column chromatograpy (eluted the column with a gradient of hexane to ethyl acetate/hexane (3:7)), vacuum dried to produce a white, non-crystallined solid of compound 1-4-13 (130 mg, 90%). TLC (Ethyl acetate/Hexane=4:6): $R_f$=0.45.

In a 50 mL round ended flask, mixed and dissolved compound 1-4-13 (100 mg, 0.165 mmol) in TFA (3 mL), then added deionized water (60 μL), allowed the mixture to react at room temp for 3 hrs. Concentrated the product to remove any residual TFA, and a crude compound 60 was obtained (60 mg, 70%), which was further purified by HPLC to give a white, non-crystallized solid of compound 60. Melting point=184-186° C.

Compound 60: $^1$H NMR (400 MHz, MeOH-d$_4$): δ 5.21 (s, 1H), 4.31 (t, J=4.9 Hz, 1H), 3.00 (m, 2H), 2.26 (m, 2H), 2.06 (m, 2H), 1.86 (m, 3H), 1.64 (m, 5H), 1.46 (m, 6H), 1.31 (m, 4H), 1.13 (m, 6H), 1.00 (s, 3H), 0.95 (d, J=6.6 Hz, 3H), 0.70 (s, 3H); $^{13}$C NMR (100 MHz, MeOH-d$_4$): δ 178.2, 172.8, 169.0, 75.7, 57.9, 57.6, 50.8, 44.0, 41.5, 41.2, 38.8, 37.1, 36.8, 36.0, 35.0, 32.4, 32.1, 31.8, 31.6, 29.3, 27.6, 27.3, 25.7, 25.3, 24.3, 22.3, 18.9, 12.6; HRMS (ESI) calculated for $C_{28}H_{46}NO_6$ (M+H)$^+$492.3325; found 492.3333.

Synthesis of Compound 1-4-15

In a 100 mL round ended flask, mixed and dissolved compound 1-4-8 (200 mg, 0.242 mmol) in methylene dichloride (25 mL), then added Fmoc-L-Glu-tert-butyl (640 mg, 1.5 mmol), DCC (240 mg, 2.671 mmol) and DMAP (45 mg, 0.347 mmol), allowed the mixture to react at room temperature for 1 hr.

Filtered the solution, discarded the precipitate, and extracted the filtrate with distilled water twice, collected and combined the organic layers, dried with Na$_2$SO$_4$, then subjected it to column chromatography (eluted the column with a gradient of hexane to ethyl acetate/hexane (1:9)), a white, non-crystallined solid or compound 1-4-15 was obtained (800 mg, 84%). TLC (Ethyl acetate/Hexane=2:8): R$_f$=0.45.

Compound 1-4-15: $^1$H NMR (400 MHz, CDCl$_3$): δ 7.72 (d, J=7.3 Hz, 2H), 7.56 (m, 2H), 7.36 (t, J=7.4 Hz, 2H), 7.27 (t, J=7.46 Hz, 2H), 5.55 (d, J=7.9 Hz, 1H), 5.10 (s, 1H), 4.35 (t, J=7.0 Hz, 2H), 4.18 (t, J=7.0 Hz, 1H), 2.23 (m, 4H), 1.94 (m, 3H), 1.83 (m, 3H), 1.70 (m, 2H), 1.56 (m, 5H), 1.42 (s, 9H), 1.41 (s, 9H), 1.35 (t, J=4.4 Hz, 3H), 1.31 (d, J=4.0 Hz, 1H), 1.24 (d, 5H), 1.10 (m, 4H), 1.00 (d, J=8.3 Hz, 3H), 0.92 (s, 3H), 0.84 (d, J=11.7 Hz, 3H), 0.61 (s, 3H); $^{13}$C NMR (100 MHz, CDCl$_3$): δ 173.7, 172.0, 171.4, 156.0, 143.9, 143.7, 143.7, 141.2, 141.2, 127.7, 127.7, 127.0, 127.0, 125.1, 125.1, 119.9, 119.9, 80.7, 76.7, 72.6, 67.0, 56.6, 56.5, 56.0, 53.7, 47.1, 42.7, 40.1, 39.9, 37.5, 36.5, 35.6, 35.2, 34.8, 33.5, 32.5, 31.0, 29.7, 28.1, 28.1, 28.1, 28.0, 28.0, 28.0, 26.4, 26.1, 24.9, 24.1, 23.8, 21.0, 18.3, 12.0; HRMS (ESI) calculated for $C_{52}H_{73}NO_8Na$ (M+Na) 862.5234; found 862.5229.

Synthesis of Compound 59

In a 100 mL round ended flask, mixed and dissolved compound 1-4-15 (200 mg, 0.238 mmol) in methylene dichloride (20 mL), then slowly added DBU (40 μL, 0.238 mmol), allowed the mixture to react at room temperature for 0.5 hr. Concentrated, and purified the product by flash column chromatograpy (eluted the column with a gradient of hexane to ethyl acetate/hexane (3:7)), vacuum dried to produce a white, non-crystallined solid of compound 1-4-16 (140 mg, 90%). TLC (Ethyl acetate/Hexane=4:6): R$_f$=0.45.

In a 50 mL round ended flask, mixed and dissolved compound 1-4-16 (100 mg, 0.161 mmol) in TFA (3 mL), then added deionized water (60 μL), allowed the mixture to react at room temp for 3 hrs. Concentrated the product to remove any residual TFA, and a crude compound 59 was obtained (60 mg, 70%), which was further purified by HPLC to give a white, non-crystallized solid of compound 59. Melting point=145-147° C.

Compound 59: H NMR (400 MHz, MeOH-d$_4$): δ 5.23 (s, 1H), 4.09 (t, J=6.6 Hz, 1H), 2.55 (m, 2H), 2.32 (m, 1H), 2.15 (m, 4H), 2.02 (m, 1H), 1.92 (m, 2H), 1.80 (d, J=6.8 Hz, 1H), 1.65 (m, 4H), 1.54 (s, 1H), 1.48 (m, 6H), 1.32 (m, 4H), 1.20 (m, 3H), 1.09 (m, 3H), 1.00 (s, 3H), 0.94 (d, J=6.5 Hz, 3H), 0.69 (s, 3H); 13C NMR (100 MHz, MeOH-d$_4$): δ 178.3, 175.4, 170.0, 75.7, 57.9, 57.6, 53.4, 44.0, 41.5, 41.2, 39.0, 37.1, 36.8, 36.1, 32.4, 32.1, 31.9, 31.6, 30.4, 29.3, 27.6, 27.3, 26.9, 25.9, 25.3, 24.3, 22.3, 18.8, 12.6; HRMS (ESI) calculated for $C_{29}H_{48}NO_6$ (M+H)$^+$506.3482; found 506.3481.

Synthesis of Compound 1-4-18

In a 100 mL round ended flask, mixed and dissolved compound 1-4-8 (500 mg, 1.155 mmol) in methylene dichloride (25 mL), then added Fmoc-D-Glu-tert-butyl (640 mg, 1.5 mmol), DCC (240 mg, 2.671 mmol) and DMAP (45 mg, 0.347 mmol), allowed the mixture to react at room temperature for 1 hr.

Filtered the solution, discarded the precipitate, and extracted the filtrate with distilled water twice, collected and combined the organic layers, dried with Na$_2$SO$_4$, then subjected it to column chromatography (eluted the column with a gradient of hexane to ethyl acetate/hexane (1:9)), a white, non-crystallined solid or compound 1-4-18 was obtained (780 mg, 82%). TLC (Ethyl acetate/Hexane=2:8): R$_f$=0.45.

Compound 1-4-18: $^1$H NMR (400 MHz, CDCl$_3$): δ 7.73 (d, J=7.5 Hz, 2H), 7.55 (d, J=7.2 Hz, 2H), 7.36 (t, J=7.4 Hz, 2H), 7.27 (t, J=7.4 Hz, 2H), 5.57 (d, J=8.2 Hz, 1H), 5.11 (s, 1H), 4.35 (m, 2H), 4.18 (t, J=7.0 Hz, 1H), 2.33 (s, 2H), 2.21 (m, 2H), 2.09 (m, 2H), 1.94 (d, J=12.7 Hz, 4H), 1.82 (m, 2H), 1.72 (m, 2H), 1.63 (d, J=12.8 Hz, 2H), 1.54 (m, 3H), 1.43 (s, 9H), 1.41 (s, 9H), 1.34 (s, 3H), 1.27 (d, J=3.3 Hz, 2H), 1.21 (s, 2H), 1.12 (d, J=11.8 Hz, 3H), 1.06 (d, J=9.8 Hz, 1H), 1.00 (d, J=7.8 Hz, 3H), 0.92 (s, 3H), 0.87 (d, J=6.3 Hz, 3H), 0.61 (s, 3H); $^{13}$C NMR (100 MHz, CDCl$_3$): δ 173.6, 172.0, 171.4, 156.0, 143.9, b143.7, 143.7, 141.2, 141.2, 127.7, 127.7, 127.0, 127.0, 125.1, 125.1, 119.9, 119.9, 80.7, 76.8, 72.5, 67.0, 56.6, 56.5, 56.0, 53.7, 47.1, 42.7, 40.1, 39.9, 37.3, 36.5, 35.6, 35.2, 34.8, 33.5, 32.5, 31.0, 29.7, 28.1, 28.1, 28.1, 28.0, 28.0, 28.0, 26.4, 26.1, 24.9, 24.1, 23.8, 21.1, 18.3, 12.0; HRMS (ESI) calculated for $C_{52}H_{73}NO_8Na$ (M+Na)$^+$ 862.5234; found 862.5229.

Synthesis of Compound 61

In a 100 mL round ended flask, mixed and dissolved compound 1-4-18 (200 mg, 0.238 mmol) in methylene dichloride (20 mL), then slowly added DBU (40 μL, 0.238 mmol), allowed the mixture to react at room temperature for 0.5 hr. Concentrated, and purified the product by flash column chromatograpy (eluted the column with a gradient of hexane to ethyl acetate/hexane (3:7)), vacuum dried to produce a white, non-crystallined solid of compound 1-4-19 (140 mg, 90%). TLC (Ethyl acetate/Hexane=4:6): R$_f$=0.45.

In a 50 mL round ended flask, mixed and dissolved compound 1-4-19 (100 mg, 0.161 mmol) in TFA (3 mL), then added deionized water (60 μL), allowed the mixture to react at room temp for 3 hrs. Concentrated the product to remove any residual TFA, and a crude compound 61 was obtained (60 mg, 70%), which was further purified by HPLC to give a white, non-crystallized solid of compound 61. Melting point=159-161° C.

Compound 61: $^1$H NMR (400 MHz, MeOH-d$_4$): δ 5.24 (s, 1H), 4.11 (t, J=6.8 Hz, 1H), 2.57 (m, 2H), 2.32 (m, 1H), 2.15 (m, 4H), 1.90 (m, 4H), 1.64 (m, 5H), 1.47 (m, 6H), 1.31 (m, 4H), 1.13 (m, 6H), 1.00 (s, 3H), 0.94 (d, J=6.4 Hz, 3H), 0.70 (s, 3H); 13C NMR (100 MHz, MeOH-d$_4$): δ 178.3, 175.5, 170.0, 75.7, 57.9, 57.6, 53.4, 44.0, 41.5, 41.2, 38.9, 37.1, 36.8, 36.1, 32.4, 32.1, 31.9, 31.6, 30.5, 29.3, 27.6, 27.3, 27.0, 25.9, 25.3, 24.3, 22.3, 18.8, 12.6; HRMS (ESI) calculated for $C_{29}H_{48}NO_6$ (M+H)$^+$ 506.3482; found 506.3485.

Synthesis of Compound 62

In a 100 mL round ended flask, mixed and dissolved compound 1-4-13 (200 mg, 0.331 mmol) in methylene dichloride (25 mL), then added Fmoc-D-Asp-tert-butyl (160 mg, 0.37 mmol), HBTU (165 mg, 0.431 mmol) and DiPEA (180 µL, 0.993 mmol), allowed the mixture to react at room temperature for 2 hrs.

Concentrated to remove any residual DMF, dissolved the concentrated product in methylene dichloride, then extracted the solution with NaHCO$_3$ twice, collected and combined the organic layers, dried with Na$_2$SO$_4$, then subjected it to column chromatography (eluted the column with a gradient of hexane to ethyl acetate/hexane (3:7)), a white, non-crystallined solid or compound 1-4-21 was obtained (220 mg, 65%). TLC (Ethyl acetate/Hexane=3:7): R$_f$=0.45.

Compound 1-4-21: $^1$H NMR (400 MHz, CDCl$_3$): δ 7.72 (d, J=7.5 Hz, 2H), 7.55 (d, J=7.3 Hz, 2H), 7.42 (d, J=8.1 Hz, 1H), 7.36 (t, J=7.4 Hz, 2H), 7.27 (t, J=7.4 Hz, 2H), 5.98 (d, J=8.3 Hz, 1H), 5.11 (s, 1H), 4.72 (m, 1H), 4.57 (d, J=6.6 Hz, 1H), 4.36 (d, J=7.2 Hz, 2H), 4.20 (t, J=7.1 Hz, 1H), 2.90 (m, 2H), 2.74 (m, 1H), 2.63 (m, 1H), 2.21 (m, 1H), 2.09 (m, 1H), 1.92 (m, 2H), 1.81 (m, 2H), 1.70 (m, 1H), 1.55 (m, 4H), 1.43 (s, 9H), 1.41 (s, 9H), 1.38 (s, 9H), 1.36 (s, 2H), 1.32 (s, 3H), 1.23 (m, 5H), 1.11 (m, 3H), 0.99 (m, 4H), 0.91 (s, 3H), 0.87 (d, J=6.4 Hz, 3H), 0.60 (s, 3H).

In a 100 mL round ended flask, mixed and dissolved compound 1-4-21 (200 mg, 0.203 mmol) in methylene dichloride (20 mL), then slowly added DBU (30 µL, 0.203 mmol), allowed the mixture to react at room temperature for 0.5 hr. Concentrated, and purified the product by flash column chromatograpy (eluted the column with methylene dichloride/methanol (9:1)), vacuum dried to produce a white, non-crystallined solid of compound 1-4-22 (145 mg, 90%). TLC (methylene dichloride/methanol=8:2): R$_f$=0.70.

In a 50 mL round ended flask, mixed and dissolved compound 1-4-22 (100 mg, 0.129 mmol) in TFA (3 mL), then added deionized water (60 µL), allowed the mixture to react at room temp for 3 hrs. Concentrated the product to remove any residual TFA, and a crude compound 62 was obtained (60 mg, 70%), which was further purified by HPLC to give a white, non-crystallized solid of compound 62. Melting point=155-157° C.

Compound 62: H NMR (400 MHz, MeOH-d$_4$): δ 5.11 (s, 1H), 4.81 (t, J=5.5 Hz, 1H), 4.26 (m, 1H), 2.87 (m, 3H), 2.33 (m, 1H), 2.19 (m, 1H), 2.03 (m, 2H), 1.91 (m, 2H), 1.78 (m, 1H), 1.63 (m, 5H), 1.46 (m, 6H), 1.31 (m, 5H), 1.12 (m, 6H), 1.00 (s, 3H), 0.94 (d, J=6.5 Hz, 3H), 0.69 (s, 3H); $^{13}$C NMR (100 MHz, MeOH-d$_4$): δ 178.2, 173.7, 172.9, 171.2, 169.3, 74.3, 57.9, 57.5, 51.0, 50.7, 44.0, 41.6, 41.3, 38.9, 37.1, 36.8, 36.3, 36.0, 32.4, 32.1, 32.0, 31.7, 31.5, 29.3, 27.6, 27.4, 25.9, 25.3, 24.4, 22.3, 18.9, 12.6; HRMS (MALDI) calculated for C$_{32}$H$_{50}$N$_2$O$_9$Na (M+Na)$^+$ 629.3414; found 629.3431.

Synthesis of Compound 63

In a 100 mL round ended flask, mixed and dissolved compound 1-4-10 (200 mg, 0.331 mmol) in THF/ethanol=1:1 (20 mL), then added NBD-Cl (73 mg, 0.365 mmol), NaHCO$_3$ (42 mg, 0.497 mmol), allowed the mixture to react at room temperature for 24 hrs.

Concentrated the product, and then dissolved the concentrated product in methylene dichloride, extracted twice with water, collected and combined the organic layers, dried with Na$_2$SO$_4$, then subjected it to column chromatography (eluted the column with a gradient of hexane to ethyl acetate/hexane (1:9)), a white, non-crystallined solid or compound 1-4-24 was obtained (90 mg, 35%). TLC (Ethyl acetate/Hexane=2:8): R$_f$=0.45.

In a 50 mL round ended flask, mixed and dissolved compound 1-4-24 (90 mg, 0.129 mmol) in TFA (3 mL), then added deionized water (60 µL), allowed the mixture to react at room temp for 3 hrs. Concentrated the product to remove any residual TFA, and a crude compound 63 was obtained (60 mg, 70%), which was further purified by HPLC to give a white, non-crystallized solid of compound 63. Melting point=138-140° C.

Compound 63:
$^1$H NMR (400 MHz, Methanol-d$_4$): δ 8.57 (d, J=8.7 Hz, 1H), 6.60 (d, J=8.7 Hz, 1H), 5.15 (s, 2H), 3.12 (m, 2H), 2.27 (m, 4H), 2.00 (m, 2H), 1.79 (m, 2H), 1.59 (m, 3H), 1.46 (m, 4H), 1.33 (m, 8H), 1.17 (m, 2H), 1.04 (m, 3H), 0.93 (m, 3H), 0.70 (d, J=5.5 Hz, 3H), 0.66 (s, 3H); $^{13}$C NMR (100 MHz, Methanol-d$_4$): δ 176.7, 172.2, 170.5, 169.2, 144.5, 136.3, 75.7, 73.1, 73.0, 68.8, 56.3, 56.0, 42.4, 41.9, 39.9, 39.6, 37.3, 35.5, 35.2, 34.3, 34.2, 30.8, 30.5, 30.2, 30.0, 27.7, 25.9, 25.7, 24.3, 23.7, 22.6, 22.3, 20.7, 17.3; HRMS (MALDI) calculated for C$_{34}$H$_{46}$N$_4$O$_9$Na (M+Na)$^+$ 677.3162; found 677.3181.

Synthesis of Compound 64

In a 100 mL round ended flask, mixed and dissolved compound 1-4-16 (200 mg, 0.323 mmol) in THF/ethanol=1:1 (20 mL), then added NBD-Cl (72 mg, 0.356 mmol), NaHCO$_3$ (41 mg, 0.485 mmol), allowed the mixture to react at room temperature for 24 hrs, at which time, the solution was yellow in color.

Concentrated the product, and then dissolved the concentrated product in methylene dichloride, extracted it twice with water, collected and combined the organic layers, dried with Na$_2$SO$_4$, then subjected the product to column chromatography (eluted the column with a gradient of hexane to ethyl acetate/hexane (1:9)), a yellow, non-crystallined solid or compound 1-4-26 was obtained (100 mg, 40%). TLC (Ethyl acetate/Hexane=2:8): R$_f$=0.45.

$^1$H NMR (400 MHz, CDCl$_3$): δ 8.53 (d, J=8.2 Hz, 1H), 6.32 (d, J=8.2 Hz, 1H), 5.21 (m, 1H), 4.57 (m, 1H), 2.57 (s, 2H), 2.31 (m, 3H), 2.06 (m, 4H), 1.80 (m, 5H), 1.59 (m, 8H), 1.44 (t, J=10.0 Hz, 18H), 1.28 (t, J=26.0 Hz, 18H), 1.07 (m, 8H), 0.86 (m, 11H), 0.66 (s, 3H)

In a 50 mL round ended flask, mixed and dissolved compound 1-4-26 (100 mg, 0.1495 mmol) in TFA (3 mL), then added 2% deionized water (60 µL), allowed the mixture to react at room temp for 3 hrs. Concentrated the product to remove any residual TFA, and a crude compound 64 was obtained (60 mg, 70%), which was further purified by HPLC to give a yellow, non-crystallized solid of compound 64. Melting point=195-197° C.

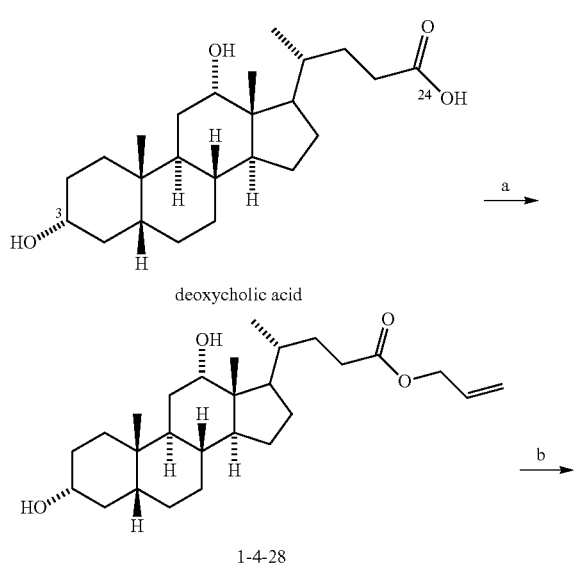

Scheme 34

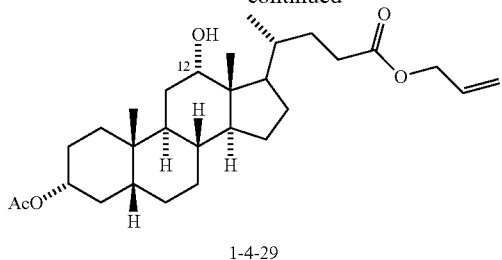
1-4-29
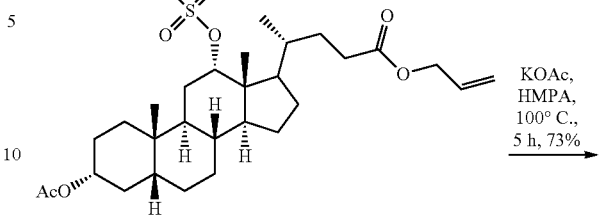
1-4-30
Scheme 35
KOAc, HMPA, 100° C., 5 h, 73%
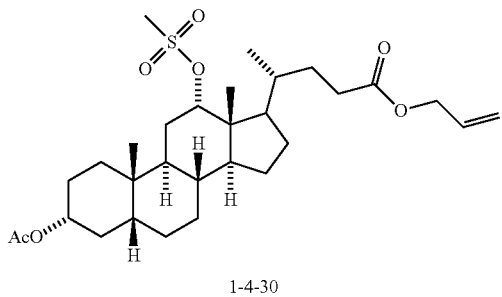
1-4-30
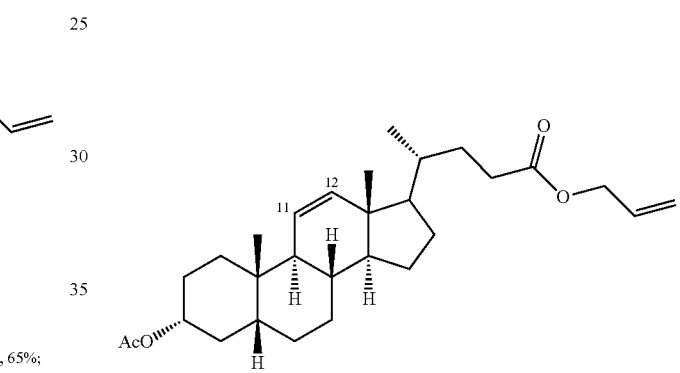
1-4-40
Reagents and conditions:
(a) allyl bromide, Cs$_2$CO$_3$, DMF, rt, 6 h, 96%; (b) Ac$_2$O, pyridine, DCM, rt, 17 h, 65%;
(c) MsCl, pyridine, 0° C.-rt, 5 h, 74%; and (d) KOAc, DMPU, 125° C., 4 h, 80%.
1-4-31
Scheme 36
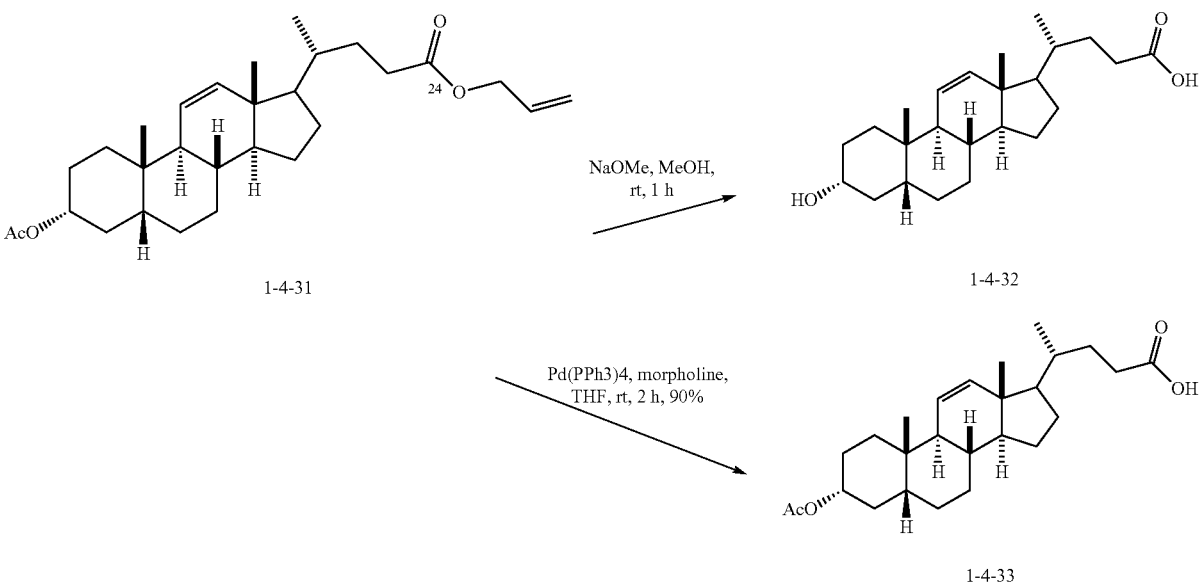
1-4-31
NaOMe, MeOH, rt, 1 h
1-4-32
Pd(PPh$_3$)$_4$, morpholine, THF, rt, 2 h, 90%
1-4-33

-continued
Scheme 37

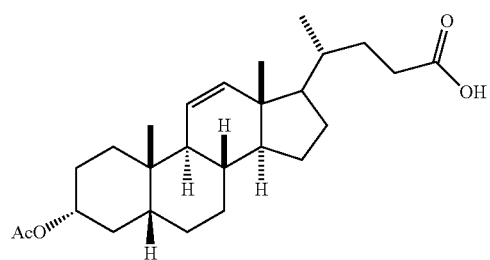

1-4-33

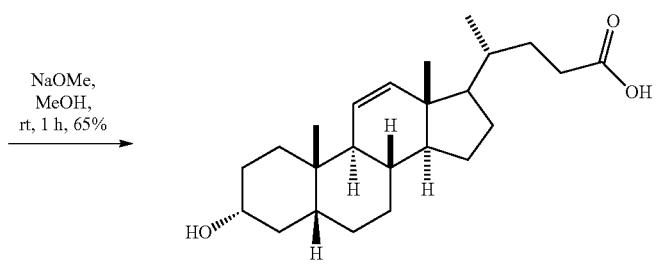

EY-22

Synthesis of Compound 1-4-30

In a 100 mL double-necked flask, mixed and dissolved deoxycholic acid (2.00 g, 5.09 mmol) in dry DMF (8 ml), then $Cs_2CO_3$ (1.66 g, 5.09 mmol) and ally bromide (3.1 mL, 35.87 mmol) were added, and allowed the mixture to react at room temperature for 6 hrs or until the color of the pH indicator, Bromocresol Green, turned into blue, indicating the reaction had completed. Removed any of the residues by filtering, collected the filtrate and removed the residual DMF by vacuum. Dissolved the product in ethyl acetate (EA), then extracted twice with double distilled water. Harvested and combined the organic layers, dried with $Na_2SO_4$, then subjected it to column chromatography (eluted the column with a gradient of EA/hexane, from 1:6 to 1:1), a white, non-crystallined solid or compound 1-4-28 was obtained (2.11 g, 95%). TLC (Ethyl acetate/Hexane=5:5): R=0.75.

In a 100 mL double-necked flask, mixed and dissolved compound 1-4-31 (2.00 g, 4.63 mmol) in dry DCM (15 ml), then acetic anhydride (1.75 mL, 18.55 mmol) was added, followed by the addition of pyridine (1.5 mL, 18.60 mmol) in dropwise manner, allowed the mixture to react at room temperature for 17 hrs. Vacuums removed any residual pyridine and/or acetic anhydride, redissolved the product in DCM, extracted it twice with 6% HCl. Harvested and combined the organic layers, then extracted it twice with $NaHCO_3$, collected and combined the organic layers, dried with $Na_2SO_4$, then subjected it to flash column chromatography (eluted the column with a gradient of EA/hexane, from 1:5 to 3:7), a sticky liquid of compound 1-4-29 was obtained (1.43 g, 65%). TLC (Ethyl acetate/Hexane=2:8): $R_f$=0.55.

In a 100 mL double-necked flask, mixed and dissolved compound 1-4-29 (1.50 g, 3.16 mmol) in pyridine (10 ml), placed the entire system in an iced bath, then slowly added methanesulfonyl chloride (0.74 mL, 9.56 mmol), at which time the temperature of the reacting mixture would rise from 0° C. to room temperature, allowed the mixture to react at room temperature for about 5 hrs. Once the reaction was completed, vacuums removed any residual pyridine, redissolved the product in DCM, extracted it twice with 6% HCl. Harvested and combined the organic layers, then extracted it twice with $NaHCO_3$, collected and combined the organic layers, dried with $Na_2SO_4$, then subjected it to flash column chromatography (eluted the column with a gradient of EA/hexane, from 1:5 to 3:7), a sticky liquid of compound 1-4-30 was obtained (1.43 g, 65%). TLC (Ethyl acetate/Hexane=2:8): $R_f$=0.55. Melting point=95-97° C.

Compound 1-4-30: $^1H$ NMR (400 MHz, $CDCl_3$): δ 5.88 (m, 1H), 5.28 (dd, J=17.2, 1.6 Hz, 1H), 5.20 (dd, J=10.4, 1.6 Hz, 1H), 5.08 (s, 1H), 4.67 (m, 1H), 4.54 (d, J=6.0 Hz, 2H), 3.03 (s, 3H), 2.40-2.15 (m, 2H), 1.99 (s, 3H), 1.97-1.60 (m, 9H), 1.59-1.39 (m, 8H), 1.35-0.99 (m, 7H), 0.96 (d, J=6.4 Hz, 3H), 0.89 (s, 3H), 0.73 (s, 3H); $^{13}C$ NMR (100 MHz, $CDCl_3$): δ 173.9, 170.8, 132.5, 118.4, 85.3, 74.3, 65.2, 48.9, 47.4, 46.2, 42.0, 39.9, 36.0, 35.4, 35.0, 34.4, 34.2, 32.6, 31.3, 31.0, 27.7, 27.3, 27.2, 26.6, 26.0, 23.7, 23.3, 21.7, 17.9, 12.6; HRMS-ESI: calculated for $C_{30}H_{48}O_7SNa$ $(M+Na)^+$, 575.3018; found, 575.3022.

Synthesis of Compound 1-4-31

In a 100 mL double-necked flask, mixed and dissolved compound of 1-4-30 (2.00 g, 3.62 mmol) in hexamethylphosphoramine (HMPA) (15 ml), then potassium acetate (5.33 g, 54.3 mmol) was added. The mixture was then heated to about 100° C., then allowed it to react for 5 hrs. Dissolved the product in EA, then extracted the solution twice with 6% HCl. Harvested and combined the organic layers, dried with $MgSO_4$, then subjected it to column chromatography (eluted the column with a gradient of EA/hexane (1:25)), an oil compound 1-4-31 was obtained (1.2 g, 73%). TLC (Ethyl acetate/Hexane=1:9): $R_f$=0.60.

Synthesis of EY-22

In a 100 mL double-necked flask, mixed and dissolved compound 1-4-31 (1.5 g, 3.32 mmol) in dry THF (15 ml), added $Pd(Ph_3)_4$ (0.12 g, 0.10 mmol), followed by the addition of morpholine (5.74 mL, 66.40 mmol) in dropwise manner. Allowed the mixture to react at room temperature for 2 hrs or until the color of the mixture turned into golden yellow, indicating the reaction had completed. Vacuumed removed the residual DMF. Dissolved the product in DCM, then extracted the solution twice with 6% HCl. Harvested and combined the organic layers, dried with $Na_2SO_4$, then subjected it to column chromatography (eluted the column with a gradient of EA/hexane, from 1:20 to 3:7), an oil compound 1-4-33 was obtained (1.2 g, 90%). TLC (Ethyl acetate/Hexane=3:7): $R_f$=0.50.

In a 50 mL flask, mixed and dissolved compound 1-4-33 (0.2 g, 0.48 mmol) in methanol (8 mL), then NaOMe (0.13 g, 2.40 mmol) was added, allowed the mixture to react at room temperature for 1 hr. Vacuumed removed residual methanol once the reaction was completed, re-dissolved the product in DCM, then extracted the solution twice with double distilled water. Harvested and combined the organic layers, dried with $Na_2SO_4$, then subjected it to column chromatography (eluted the column with a gradient of EA/hexane, from 1:9 to 2:1), a white, non-crystallined solid or compound EY-22 was obtained (117 mg, 65%). TLC (Ethyl acetate/Hexane=1:1): $R_f$=0.50.

Compound EY-22 was further purified by HPLC, then freezed dried to produce a white solid of compound EY-22.

Melting point=155-157° C.

Compound EY-22: $^1$H NMR (400 MHz, CDCl$_3$): δ 6.07 (dd, J=10.4, 2.8 Hz, 1H), 5.40 (d, J=10.4 Hz, 1H), 3.62 (m, 1H), 2.4-2.18 (m, 3H), 1.96-1.62 (m, 7H), 1.60-1.38 (m, 6H), 1.37-1.10 (m, 8H), 0.99 (d, J=6.4 Hz, 3H), 0.86 (s, 3H), 0.71 (s, 3H); $^{13}$C NMR (100 MHz, CDCl$_3$): δ 179.8, 138.9, 125.8, 72.0, 53.8, 52.1, 45.2, 43.4, 41.4, 37.2, 36.1, 35.4, 35.2, 34.6, 31.2, 30.9, 30.6, 28.6, 28.3, 25.7, 23.9, 23.2, 18.5, 16.9; HRMS-ESI: calculated for $C_{24}H_{37}O_3(M-H)^-$, 373.2743: found, 373.2750.

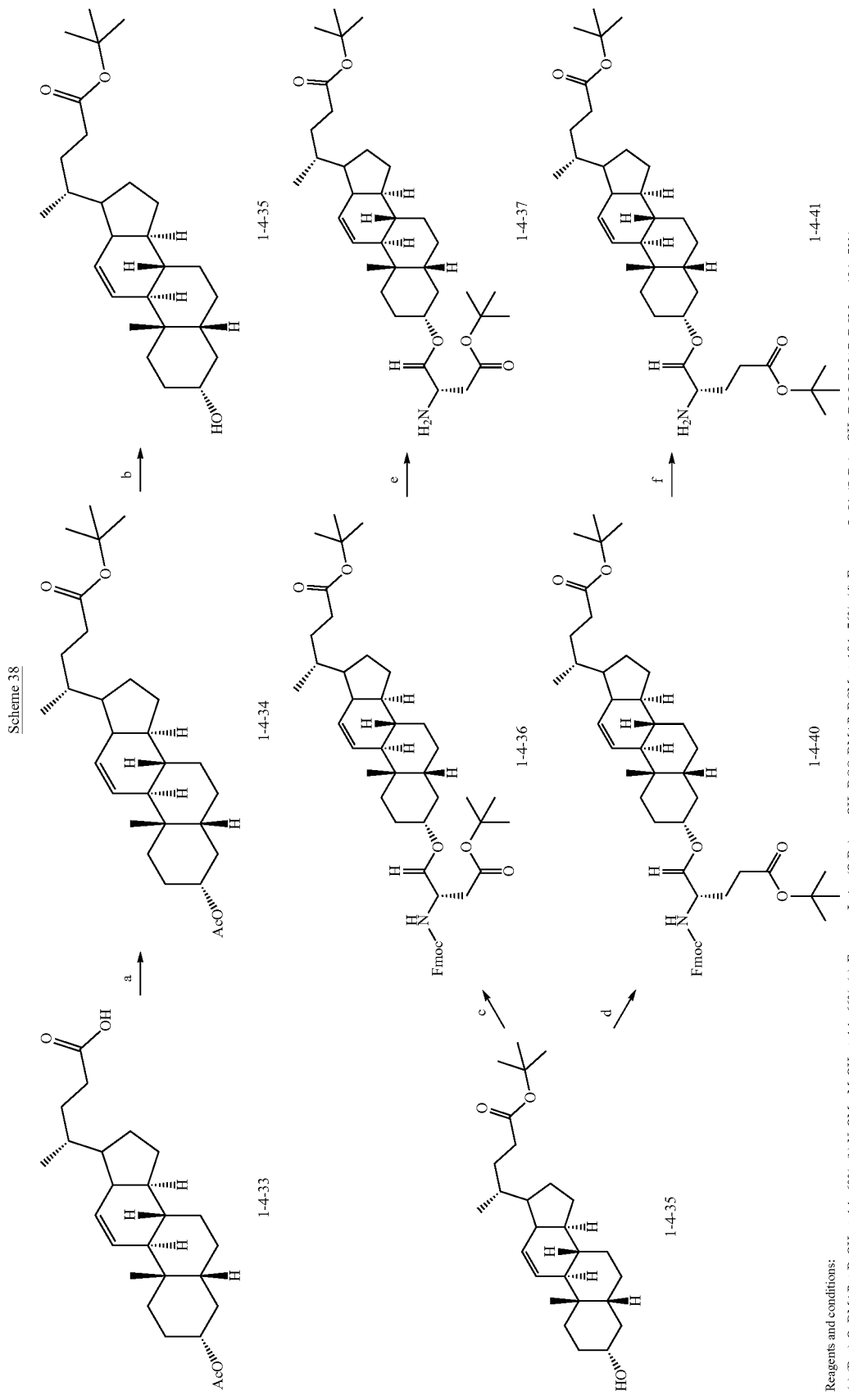
Scheme 38
Reagents and conditions:
(a) (Boc)₂O, DMAP, t-BuOH, rt, 1 h, 60%; (b) NaOMe, MeOH, rt, 1 h, 66%; (c) Fmoc—L-Asp(OtBu)—OH, DCC, DMAP, DCM, rt, 18 h, 76%; (d) Fmoc—L-Glu(OtBu)—OH, DCC, DMAP, DCM, rt, 18 h, 73%; (e) DBU, DCM, rt, 1 h, 91%; and (f) DBU, DCM, rt, 1 h, 75%.

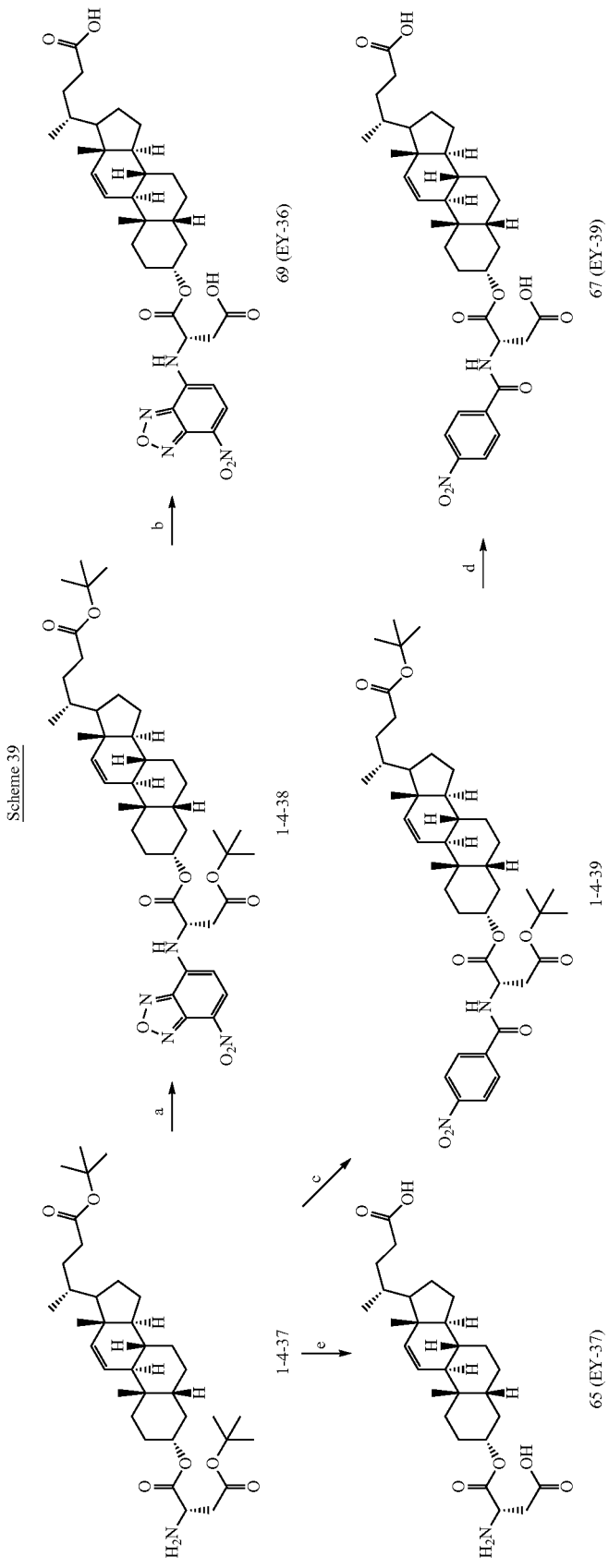
Scheme 39
Reagents and conditions:
(a) NBD—Cl, NaHCO₃, THF:EtOH (1:1), rt, 48 hr, 26%; (b) TFA, dd H₂O, DCM, rt, 4 hr, 90%; (c) 4-nitrobenzoic acid, HBTU, DiPEA, dry DMF, rt, 24 hr, 95%; (e) TFA, dd H₂O, DCM, rt, 4 hr, 85%; (f) TFA, dd H₂O, DCM, rt, 4 hr, 88%.

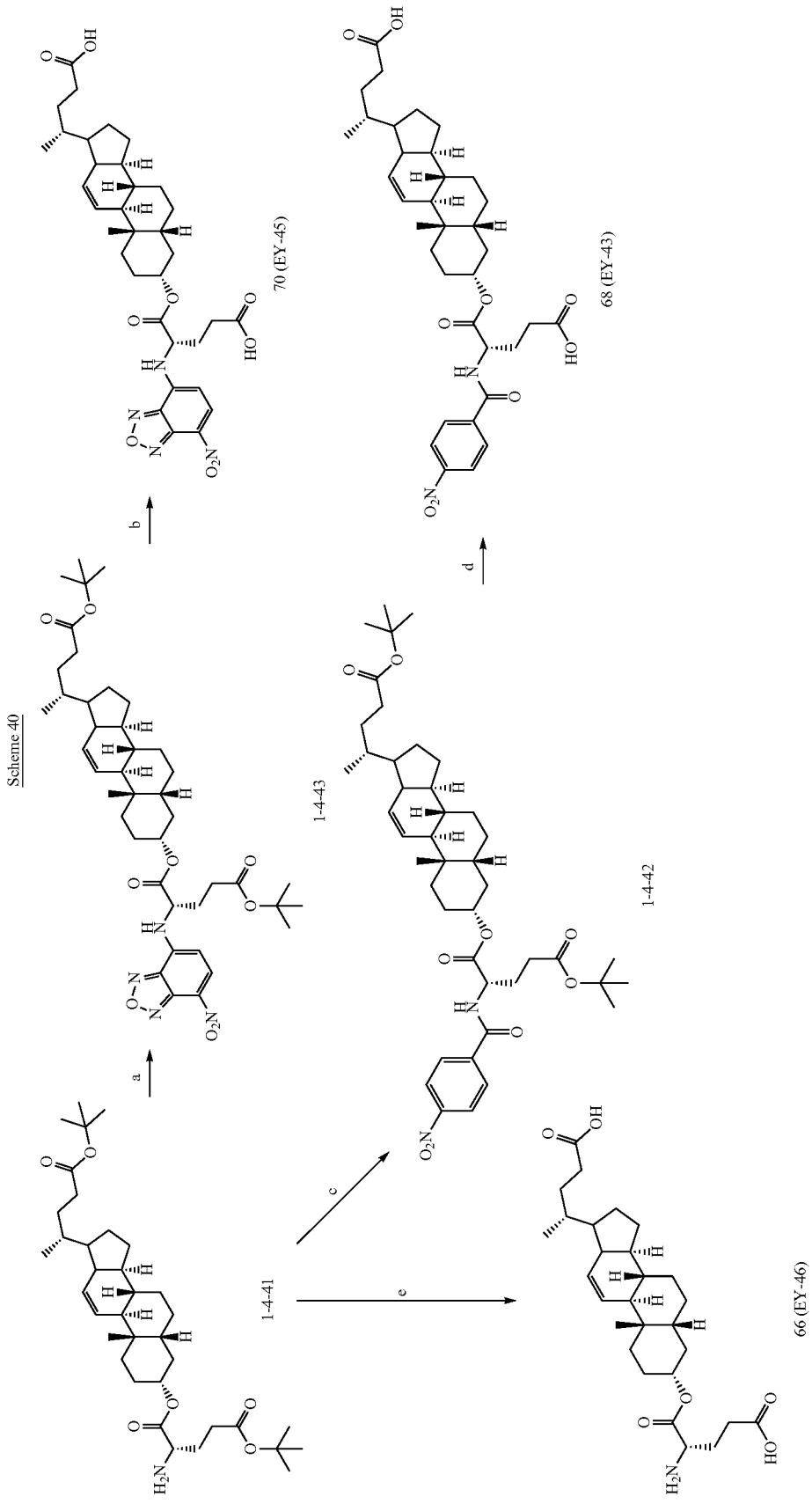
Scheme 40
Reagents and conditions:
(a) NBD—Cl, NaHCO₃, THF; EtOH (1:1), rt, 48 hr, 68%; (b) TFA, dd H₂O, DCM, rt, 4 hr, 91%; (c) 4-nitrobenzoic acid, HBTU, DiPEA, dry DMF, rt, 24 hr, 815%; (e) TFA, dd H₂O, DCM, rt, 4 hr, 93%; (f) TFA, dd H₂O, DCM, rt, 4 hr, 84%.

Synthesis of Compound 1-4-36

In a 100 mL double-necked flask, mixed and dissolved compound 1-4-33 (1.5 g, 3.6 mmol) in t-BuOH (10 ml), added (Boc₂)O (1.54 mL, 7.2 mmol), followed by the addition of DMAP (0.13 g, 1.08 mmol). Allowed the mixture to react at room temperature for 1 hr. Vacuumed removed the residual t-BuOH once the reaction was completed. Dissolved the product in DCM, then extracted the solution twice with double distilled water. Harvested and combined the organic layers, dried with $Na_2SO_4$, then subjected it to column chromatography (eluted the column with a gradient of hexane to EA/hexane (1:25)), a white solid compound 1-4-34 was obtained (1.0 g, 60%). TLC (Ethyl acetate/Hexane=1:7): $R_f$=0.70.

In a 100 mL flask, mixed and dissolved compound 1-4-34 (0.2 g, 0.48 mmol) in methanol (10 mL), then NaOMe (0.57 g, 10.60 mmol) was added, allowed the mixture to react at room temperature for 1 hr. Vacuumed removed residual methanol once the reaction was completed, re-dissolved the product in DCM, then extracted the solution twice with double distilled water. Harvested and combined the organic layers, dried with $Na_2SO_4$, then subjected it to column chromatography (eluted the column with a gradient of EA/hexane, from 1:25 to 1:10), a white solid of compound 1-4-35 was obtained (0.6 g, 66%). TLC (Ethyl acetate/Hexane=1:9): $R_f$=0.30

In a 100 mL flask, mixed and dissolved Fmoc-L-Asp(OtBu)-OH (0.63 g, 1.53 mmol) in a mixture of 10 mL of DCM and 2% THF, then compound 1-4-35 (0.60 g, 1.39 mmol) and DCC (0.57 g, 2.78 mmol) were added, followed by the addition of DMAP (54 mg, 0.42 mmol), allowed the mixture to react at room temperature for 18 hrs.

Filtered and removed the residual, collected the filtrate, and extracted the filtrate twice with double distilled water. Harvested and combined the organic layers, dried with $Na_2SO_4$, then subjected it to column chromatography (eluted the column with a gradient of EA/hexane, from 1:30 to 1:15), a white solid of compound 1-4-36 was obtained (0.87 g, 76%). TLC (Ethyl acetate/Hexane=2:8): $R_f$=0.55

Synthesis of Compound 69 (EY-36)

In a 100 mL double-necked flask, mixed and dissolved compound 1-4-36 (0.65 g, 0.793 mmol) in DCM (8 ml), then DBU (0.12 mL, 0.79 mmol), allowed the mixture to react at room temperature for 1 hr, at which time the solution appeared to have a light yellow color. Vacuums removed any residual solvent once the reaction was completed, then subjected it to flash column chromatography (eluted the column with a gradient of EA/hexane, from 1:0 to 1:1), a white solid of compound 1-4-37 was obtained (430 mg, 91%). TLC (Ethyl acetate/Hexane=3:7): $R_f$=0.35.

In a 100 mL flask, mixed and dissolved compound 1-4-37 (0.43 g, 0.71 mmol) in a mixture of 8 mL THF/ethanol (1:1), then $NaHCO_3$ (119 mg, 1.42 mmol) and NBD-Cl (156 mg, 0.78 mmol) were added, allowed the mixture to react at room temperature for 48 hrs, at which time the color of the reacting mixture would turn into golden yellow. Concentrated and subjected the concentrated product to flash column chromatography (eluted the column with a gradient of hexane to EA/hexane (1:10)), a yellow solid of compound 1-4-38 was obtained (140 mg, 26%). TLC (Ethyl acetate/Hexane=3:7): $R_f$=0.70.

In a 50 mL flask, mixed and dissolved compound 1-4-38 (0.14 g, 0.18 mmol) in DCM (10 mL), then TFA (2 mL) and 2% double distilled water were added, allowed the mixture to react at room temperature for 4 hrs. Vacuumed removed residual TFA once the reaction was completed, a solid of compound 69 (EY-36) was obtained (106 mg, 90%). TLC (Ethyl acetate/Hexane=3:7): $R_f$=0.30.

Compound 69 (EY-36) was further purified by HPLC, then freezed dried to produce a white solid of compound 69 or EY-36.

Melting point=188-190° C.

Compound 69 (EY-36): ¹H NMR (400 MHz, CD₃OD): δ 8.52 (d, J=8.8 Hz, 1H), 6.51 (d, J=8.8 Hz, 1H), 6.07 (dd, J=10.4, 2.8 Hz, 1H), 5.37 (d, J=10.4 Hz, 1H), 4.80 (m, 2H), 3.08 (m, 2H), 2.40-2.15 (m, 3H), 2.0-1.67 (m, 7H), 1.67-1.40 (m, 5H), 1.39-1.24 (m, 6H), 1.20-1.06 (m, 3H), 1.00 (d, J=6.4 Hz, 3H), 0.89 (s, 3H), 0.71 (s, 3H); ¹³C NMR (100 MHz, (CD₃)₂CO): δ 175.4, 172.4, 170.0, 145.6, 145.1, 145.0, 139.7, 137.5, 126.1, 124.9, 101.7, 76.9, 54.5, 54.4, 52.9, 45.8, 44.0, 41.8, 36.8, 36.4, 35.8, 35.4, 35.2, 33.5, 31.8, 31.3, 29.1, 28.7, 27.2, 26.2, 24.0, 23.7, 18.8, 17.1; HRMS-ESI: calculated for $C_{34}H_{44}N_4O_9Na$ $(M+Na)^+$, 675.3006: found, 675.3008.

Synthesis of Compound 65 (EY-37)

In a 50 mL flask, mixed and dissolved compound 1-4-37 (0.20 g, 0.24 mmol) in DCM (5 ml), then TFA (2 mL) and 2% double distilled water were added, allowed the mixture to react at room temperature for 4 hrs. Vacuumed removed residual TFA once the reaction was completed, a solid of compound 65 (EY-37) was obtained (103 mg, 88%). TLC (Ethyl acetate/Hexane=3:7): $R_f$=0.25.

Compound 65 (EY-37) was further purified by HPLC, then freezed dried to produce a white solid of compound 65 or EY-37.

Melting point=164-166° C.

Compound 65: ¹H NMR (400 MHz, CD₃OD): δ 6.14 (dd, J=10.4, 2.8 Hz, 1H), 5.44 (d, J=10.4 Hz, 1H), 4.85 (s, 1H), 4.28 (dd, J=6.0, 4.4 Hz, 1H), 3.04 (dd, J=18.0, 6.0 Hz, 1H), 2.96 (dd, J=18.0, 4.4 Hz, 1H), 2.40-2.18 (m, 3H), 2.06-1.74 (m, 7H), 1.71-1.45 (m, 6H), 1.43-1.10 (m, 8H), 1.03 (d, J=6.4 Hz, 3H), 0.93 (s, 3H), 0.77 (s, 3H); ¹³C NMR (100 MHz, CD₃OD): δ 178.2, 172.9, 169.1, 140.3, 126.2, 78.6, 55.2, 53.6, 50.8, 46.4, 44.6, 42.5, 37.4, 36.2, 35.9, 35.8, 35.0, 33.8, 32.3, 32.1, 29.6, 29.2, 27.5, 26.7, 24.2, 24.1, 19.0, 17.2; HRMS-ESI: calculated for $C_{28}H_{44}NO_6$ $(M+H)^+$, 490.3169: found, 490.3176.

Synthesis of Compound 67 (EY-39)

In a 50 mL flask, mixed and dissolved 4-nitrobenzoic acid (57 mg, 0.34 mmol) in dry DMF (10 ml), then HBTU (129 mg, 0.34 mmol) and DiPEA (0.15 mL, 0.84 mmol) were added, followed by the addition of compound 1-4-37, allowed the mixture to react at room temperature for 24 hrs. Vacuumed removed residual TFA once the reaction was completed, re-dissolved the product in EA, then extracted the solution twice with ddH₂O and NaCl solution, harvested and combined the organic layers, dried with $Na_2SO_4$, then subjected it to column chromatography (eluted the column with a gradient of EA/hexane, from 1:9 to 2:8), a white solid of compound 1-4-39 was obtained (0.2 g, 95%). TLC (Ethyl acetate/Hexane=2:8): $R_f$=0.50

In a 50 mL flask, mixed and dissolved compound 1-4-39 (0.20 g, 0.27 mmol) in DCM (5 ml), then TFA (2 mL) and 2% double distilled water were added, allowed the mixture to react at room temperature for 4 hrs. Vacuumed removed residual TFA once the reaction was completed, a solid of compound 67 (EY-39) was obtained (150 mg, 85%). TLC (Ethyl acetate/Hexane=3:7): $R_f$=0.35.

Compound 67 (EY-39) was further purified by HPLC, then freezed dried to produce a white solid of compound 67 or EY-39.

Melting point=127-129° C.

Compound 67: $^1$H NMR (400 MHz, CDCl$_3$): δ 8.29 (d, J=8.4 Hz, 2H), 7.96 (d, J=8.4 Hz, 2H), 7.26 (s, 1H), 6.08 (dd, J=10.4, 2.4 Hz, 1H), 5.36 (d, J=10.4 Hz, 1H), 4.96 (m, 1H), 4.80 (m, 1H), 3.19 (dd, J=17.6, 4.0 Hz, 1H), 3.03 (dd, J=17.6, 4.4 Hz, 1H), 2.50-2.15 (m, 3H), 2.0-1.65 (m, 7H), 1.64-1.40 (m, 6H), 1.39-1.05 (m, 8H), 0.99 (d, J=6.4 Hz, 3H), 0.88 (s, 3H), 0.72 (s, 3H); $^{13}$C NMR (100 MHz, CDCl$_3$): δ 180.6, 176.2, 170.0, 165.7, 150.1, 139.2, 139.1, 128.7, 128.7, 125.4, 124.1, 124.1, 77.0, 53.8, 52.1, 49.5, 45.2, 43.3, 41.1, 36.3, 36.1, 35.2, 34.8, 34.5, 32.8, 31.2, 30.8, 28.6, 28.0, 26.4, 25.6, 23.8, 23.2, 18.5, 16.8; HRMS-ESI: calculated for C$_{35}$H$_{46}$N$_2$O$_9$Na (M+Na)$^+$, 661.3101; found, 661.3093.

Synthesis of Compound 1-4-40

In a 100 mL flask, mixed and dissolved Fmoc-L-Glu (OtBu)-OH (1.0 g, 2.35 mmol) in a mixture of 10 mL of DCM and 2% THF, then compound 1-4-35 (0.93 g, 1.97 mmol) and DCC (0.65 g, 3.15 mmol) were added, followed by the addition of DMAP (72 mg, 0.59 mmol), allowed the mixture to react at room temperature for 18 hrs.

Filtered and removed the residual, collected the filtrate, and extracted the filtrate twice with double distilled water. Harvested and combined the organic layers, dried with Na$_2$SO$_4$, then subjected it to column chromatography (eluted the column with a gradient of EA/hexane, from 1:40 to 1:15), a white solid of compound 1-4-40 was obtained (1.2 g, 73%). TLC (Ethyl acetate/Hexane=2:8): $R_f$=0.65

Synthesis of Compound 68 (EY-43)

In a 50 mL flask, mixed and dissolved compound 1-4-40 (0.22 g, 0.26 mmol) in DCM (8 ml), then slowly added DBU (39 μL, 0.26 mmol), allowed the mixture to react at room temperature for 1 hr, at which time the color of the reacting solution appeared to be light yellow. Vacuumed removed any residual DCM once the reaction was completed, then subjected it to flash column chromatography (eluted the column with a gradient of EA/hexane, from 1:10 to 1:1), a white solid of compound 1-4-41 was obtained (120 m g, 75%). TLC (Ethyl acetate/Hexane=2:8): $R_f$=0.20

In a 50 mL flask, mixed and dissolved 4-nitrobenzoic acid (38 mg, 0.23 mmol) in DCM (8 ml), then HBTU (87 mg, 0.23 mmol) and DiPEA (0.1 mL, 0.57 mmol) were added, followed by the addition of compound 1-4-41, allowed the mixture to react at room temperature for 24 hrs. Vacuumed removed residual TFA once the reaction was completed, extracted the product solution twice with ddH$_2$O and DCM, harvested and combined the organic layers, dried with Na$_2$SO$_4$, then subjected it to column chromatography (eluted the column with a gradient of EA/hexane, from 1:10 to 1:8), a white solid of compound 1-4-42 was obtained (118 mg, 81%). TLC (Ethyl acetate/Hexane=2:8): $R_f$=0.45

In a 50 mL flask, mixed and dissolved compound 1-4-42 (118 mg, 0.15 mmol) in DCM (5 ml), then TFA (2 mL) and 2% double distilled water were added, allowed the mixture to react at room temperature for 4 hrs. Vacuumed removed residual TFA once the reaction was completed, a solid of compound 68 (EY-43) was obtained (91 mg, 93%). TLC (Ethyl acetate/Hexane=3:7): $R_f$=0.40. Compound 68 (EY-43) was further purified by HPLC, then freezed dried to produce a white solid of compound 68 or EY-43.

Melting point=110-112° C.

Compound 68: $^1$H NMR (400 MHz, CDCl$_3$): δ 8.28 (d, J=8.4 Hz, 2H), 7.96 (d, J=8.4 Hz, 2H), 7.11 (d, J=7.2 Hz, 1H), 6.09 (dd, J=10.4, 2.4 Hz, 1H), 5.38 (d, J=10.4 Hz, 1H), 4.80 (m, 2H), 2.06-2.03 (m, 7H), 2.00-1.66 (m, 7H), 1.65-1.40 (m, 7H), 1.35-1.05 (m, 7H), 1.00 (d, J=6.4 Hz, 3H), 0.89 (s, 3H), 0.72 (s, 3H); $^{13}$C NMR (100 MHz, CDCl$_3$): δ 180.3, 178.3, 171.5, 165.8, 150.0, 139.2, 139.2, 128.6, 128.6, 125.4, 124.0, 124.0, 76.7, 53.8, 52.9, 52.0, 45.2, 43.3, 41.1, 36.1, 35.2, 34.9, 34.5, 32.9, 31.1, 30.9, 30.4, 28.6, 28.0, 27.2, 26.7, 25.6, 23.7, 23.1, 18.5, 16.8; HRMS-ESI: calculated for C$_{36}$H$_{48}$N$_2$O$_9$Na (M+Na)$^+$, 675.3258; found, 675.3255.

Synthesis of Compound 70

In a 100 mL flask, mixed and dissolved compound 1-4-37 (0.43 g, 0.71 mmol) in a mixture of 8 mL THF/ethanol (1:1), then NaHCO$_3$ (100 mg, 1.2 mmol) and NBD-Cl (140 mg, 0.70 mmol) were added, allowed the mixture to react at room temperature for 48 hrs, at which time the color of the reacting mixture would turn into golden yellow. Concentrated and subjected the concentrated product to flash column chromatography (eluted the column with a gradient of hexane to EA/hexane (1:10)), a yellow solid of compound 1-4-43 was obtained (310 mg, 68%). TLC (Ethyl acetate/Hexane=3:7): $R_f$=0.75.

In a 50 mL flask, mixed and dissolved compound 1-4-43 (0.31 g, 0.40 mmol) in DCM (8 ml), then TFA (2 mL) and 2% double distilled water were added, allowed the mixture to react at room temperature for 4 hrs. Vacuumed removed residual TFA once the reaction was completed, a solid of compound 70 (EY-45) was obtained (245 mg, 91%). TLC (Ethyl acetate/Hexane=3:7): $R_f$=0.30.

Compound 70 (EY-45) was further purified by HPLC, then freezed dried to produce a white solid of compound 70 or EY-45.

Melting point=214-216° C.

Compound 70: $^1$H NMR (400 MHz, (CD$_3$)$_2$CO): δ 8.55 (d, J=8.8 Hz, 1H), 8.19 (d, J=8.0 Hz, 1H), 6.51 (d, J=8.8 Hz, 1H), 6.11 (dd, J=10.4, 2.8 Hz, 1H), 5.42 (d, J=10.4 Hz, 1H), 4.83 (m, 2H), 2.64 (t, J=7.2 Hz, 2H), 2.50-2.17 (m, 5H), 2.02-1.70 (m, 7H), 1.68-1.37 (m, 7H), 1.36-1.10 (m, 7H), 1.02 (d, J=6.8 Hz, 3H), 0.91 (s, 3H), 0.75 (s, 3H); $^{13}$C NMR (100 MHz, (CD$_3$)$_2$CO): δ 175.1, 174.3, 170.9, 145.6, 145.2, 145.1, 139.7, 137.5, 126.1, 125.0, 101.4, 76.8, 57.2, 54.5, 53.0, 45.9, 44.0, 41.8, 36.8, 35.8, 35.4, 35.2, 33.6, 31.8, 31.3, 30.4, 29.1, 28.7, 27.4, 27.3, 26.2, 24.0, 23.7, 18.8, 17.1; HRMS-ESI: calculated for C$_{35}$H$_{45}$N$_4$O$_9$ (M−H)$^-$, 665.3187; found, 665.3190.

Synthesis of Compound 66

In a 50 mL flask, mixed and dissolved compound 1-4-41 (157 mg, 0.25 mmol) in DCM (5 ml), then TFA (2 mL) and 2% double distilled water were added, allowed the mixture to react at room temperature for 4 hrs. Vacuumed removed residual TFA once the reaction was completed, a solid of compound 66 (EY-46) was obtained (108 mg, 84%). TLC (Ethyl acetate/Hexane=3:7): $R_f$=0.30.

Compound 66 (EY-46) was further purified by HPLC, then freezed dried to produce a white solid of compound 66 or EY-46.

Melting point=233-235° C.

Compound 66: $^1$H NMR (400 MHz, CD$_3$OD): δ 6.15 (dd, J=10.4, 2.8 Hz, 1H), 5.45 (d, J=10.4 Hz, 1H), 4.85 (s, 1H), 4.07 (t, J=6.8 Hz, 1H), 2.54 (m, 2H), 2.40-2.08 (m, 5H), 2.07-1.73 (m, 7H), 1.72-1.43 (m, 7H), 1.40-1.12 (m, 7H), 1.03 (d, J=6.4 Hz, 3H), 0.94 (s, 3H), 0.77 (s, 3H); $^{13}$C NMR (100 MHz, CD$_3$OD): δ 178.2, 176.0, 170.0, 140.3, 126.3, 78.5, 55.1, 53.6, 53.6, 46.4, 44.6, 42.5, 37.4, 36.3, 35.9, 35.9, 33.9, 32.3, 32.2, 30.9, 29.6, 29.2, 27.6, 27.0, 26.7, 24.2, 24.1, 19.0, 17.2; HRMS-ESI: calculated for C$_{29}$H$_{46}$NO$_6$ (M+H)+, 504.3325; found, 504.3316.

1.8 Synthesis of Compounds 71 to 87

Compounds 71 to 87 (or compounds of formula (1-6)) were synthesized in accordance with procedures set forth in Schemes 41 to 49.

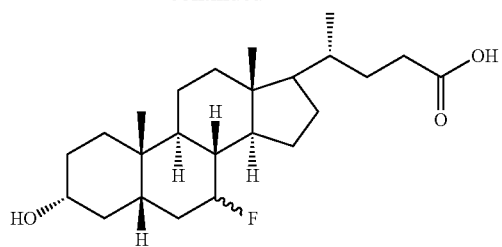

71, 72

Reagents and conditions:
(a) H$_2$SO$_4$, MeOH, 97%, (b) Ac$_2$O, pyridine, CH$_2$Cl$_2$, 30%, (c) DAST, CH$_2$Cl$_2$, -78° C., 45%, (d) KOH, MeOH, 80° C., 86%.

Scheme 41:

Scheme 42:

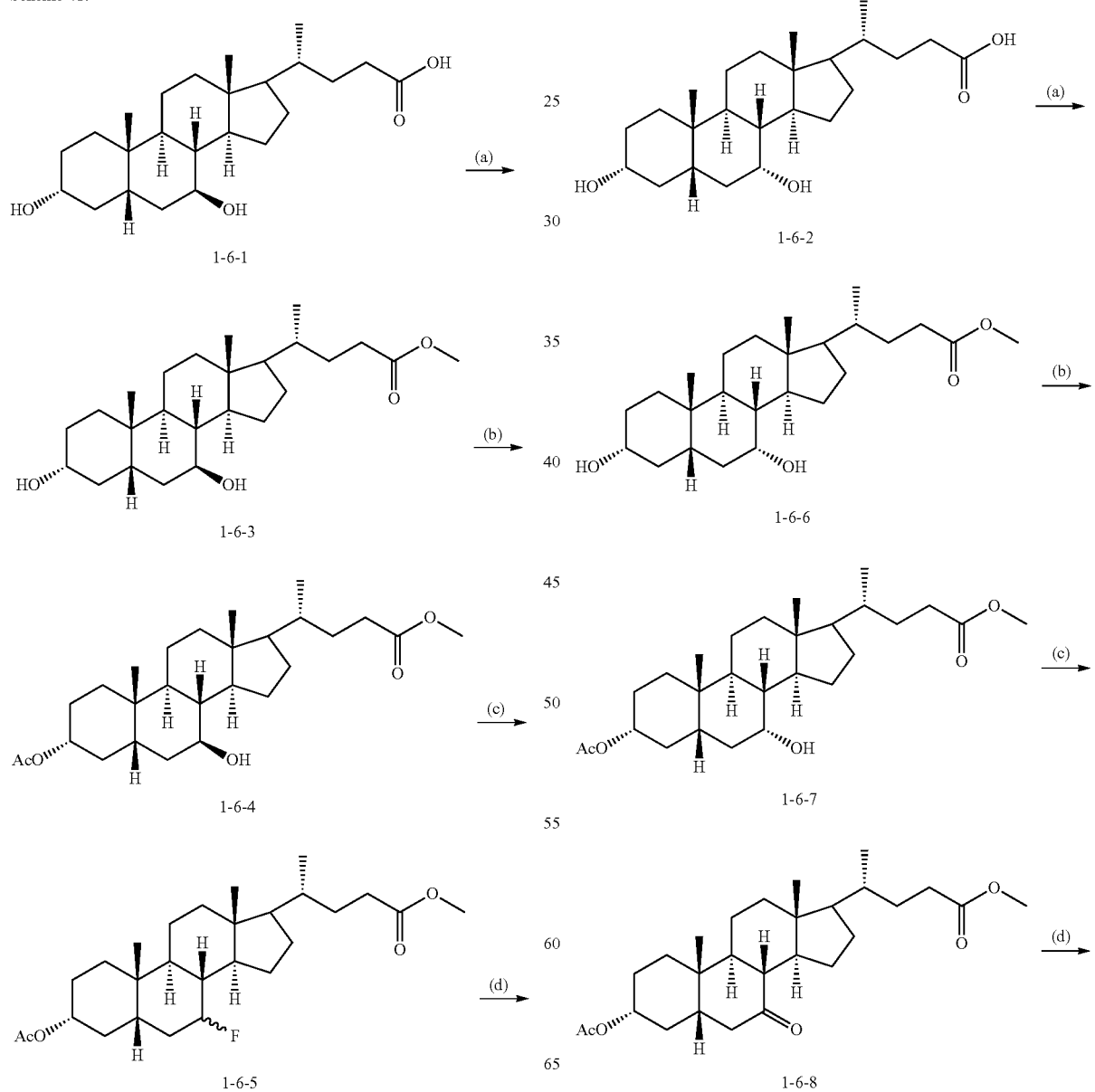

-continued
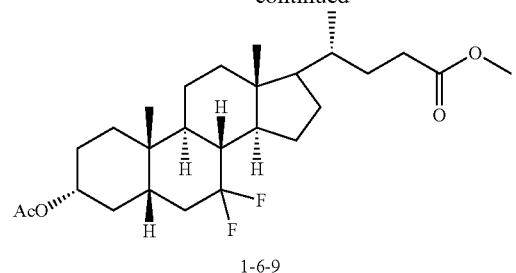
1-6-9
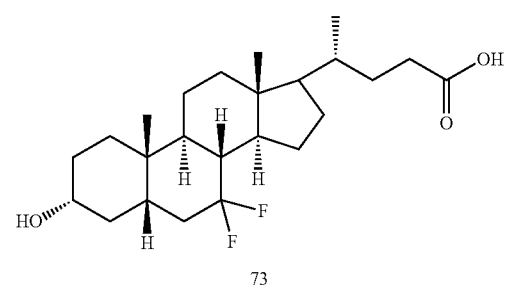
73
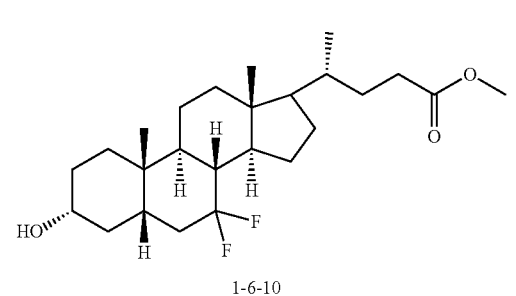
1-6-10
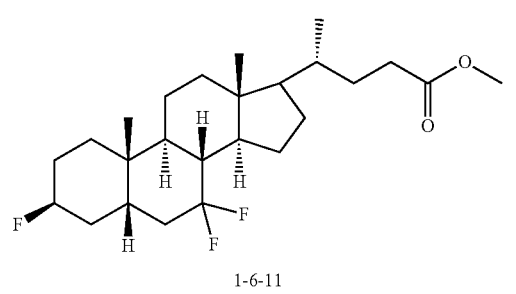
1-6-11
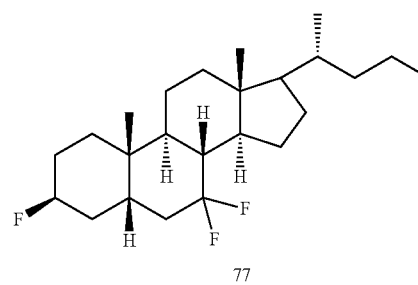
77
Reagents and conditions: (a) $H_2SO_4$, MeOH, 96%, (b) $Ac_2O$, pyridine, $CH_2Cl_2$, 53%, (c) $CrO_3$, AcOH, 83%, (d) DAST, 80° C., 55%, (e) KOH, MeOH, 80° C., 80%, (f) $H_2SO_4$, MeOH, 99%, (g) DAST, $CH_2Cl_2$, -78° C., 46%, (h) KOH, MeOH, 80° C., 83%.
Scheme 43:
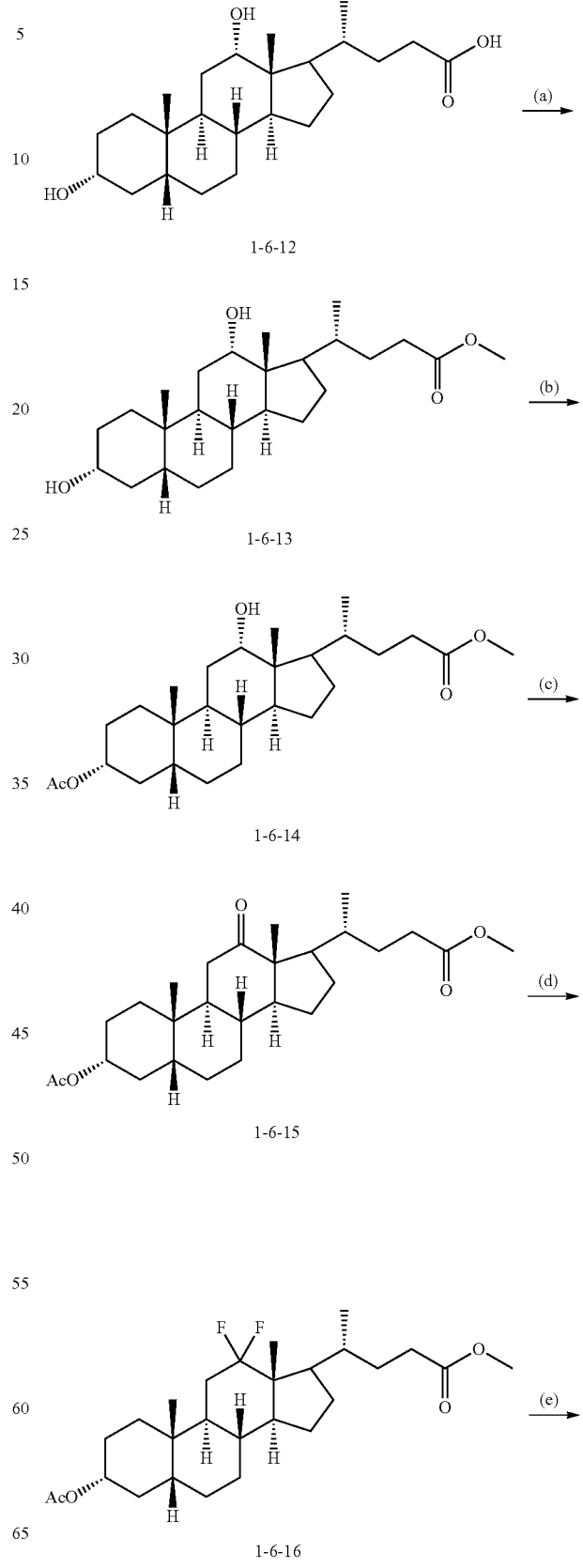

195
-continued
196
-continued
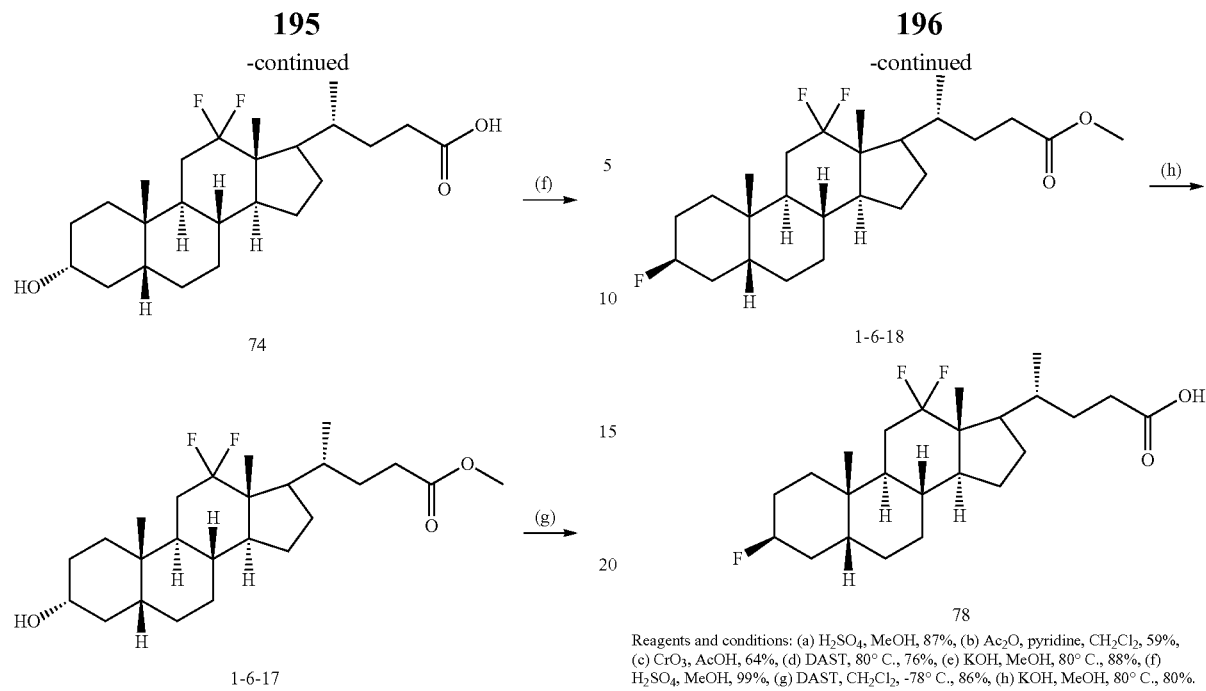
Reagents and conditions: (a) H₂SO₄, MeOH, 87%, (b) Ac₂O, pyridine, CH₂Cl₂, 59%, (c) CrO₃, AcOH, 64%, (d) DAST, 80° C., 76%, (e) KOH, MeOH, 80° C., 88%, (f) H₂SO₄, MeOH, 99%, (g) DAST, CH₂Cl₂, -78° C., 86%, (h) KOH, MeOH, 80° C., 80%.
Scheme 44:
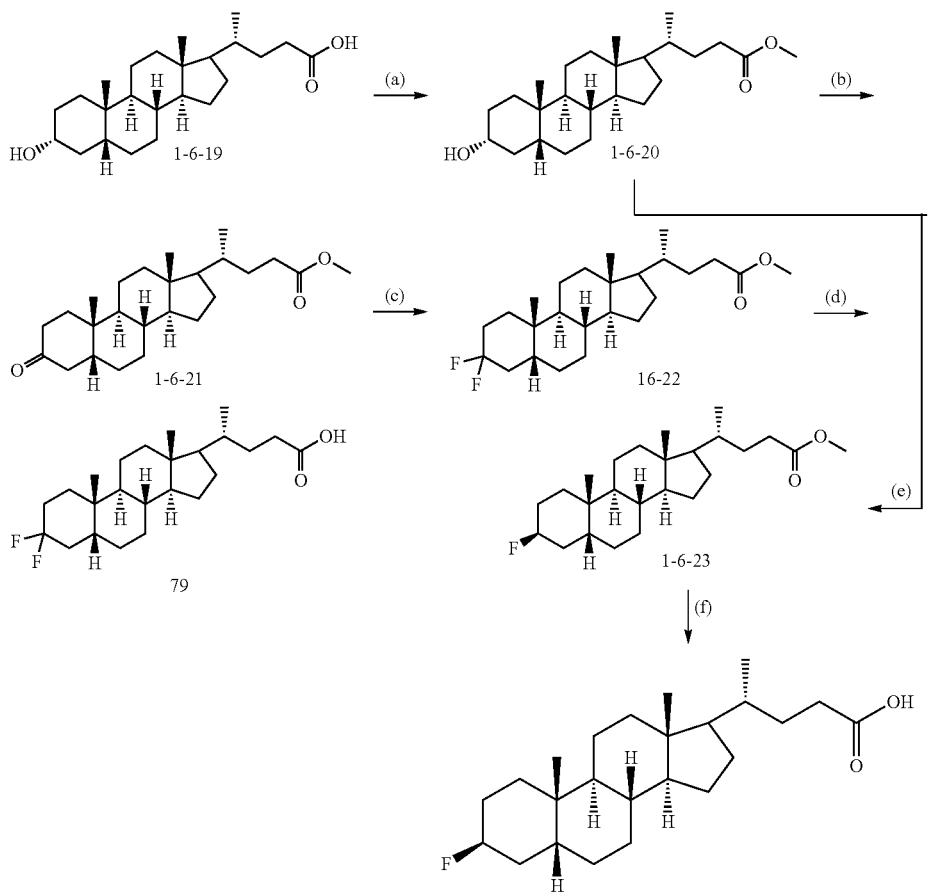
Reagents and conditions: (a) H₂SO₄, MeOH, 99%, (b) CrO₃, AcOH, 40%, (c) DAST, 80° C., 76%, (d) KOH, MeOH, 80° C., 90%, (e) DAST, CH₂Cl₂, -78° C., 37%, (f) KOH, MeOH, 80° C., 95%

Scheme 45:
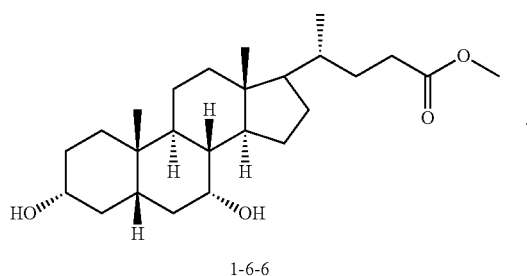
1-6-6
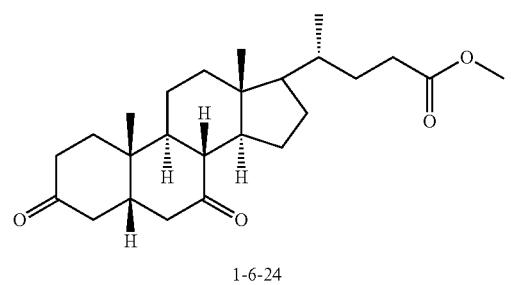
1-6-24
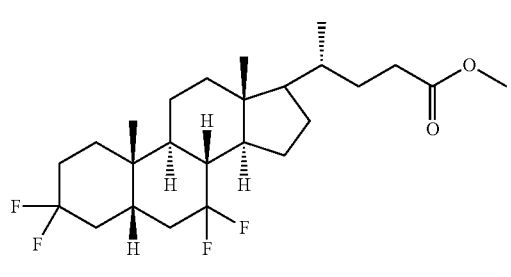
1-6-25
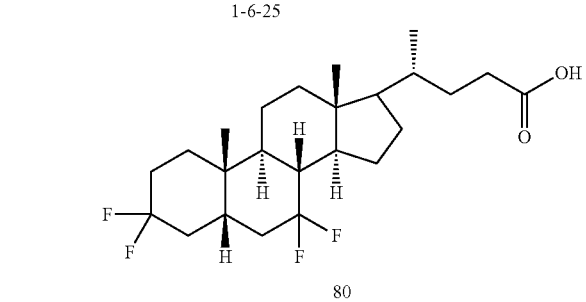
80
Reagents and conditions: (a) CrO₃, AcOH, 58%, (b) DAST, 80° C., 34%, (c) KOH, MeOH, 80° C., 93%.
Scheme 46:
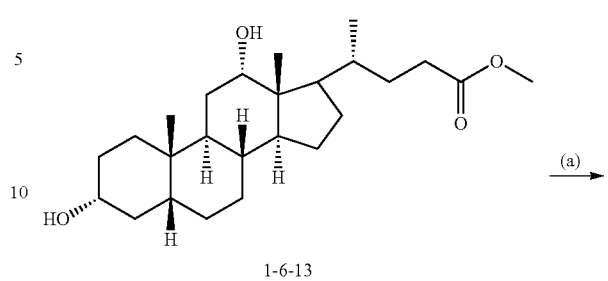
1-6-13
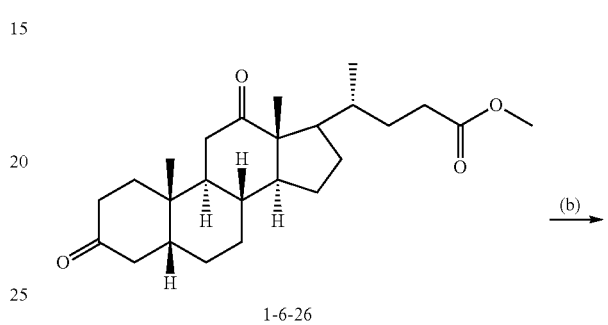
1-6-26
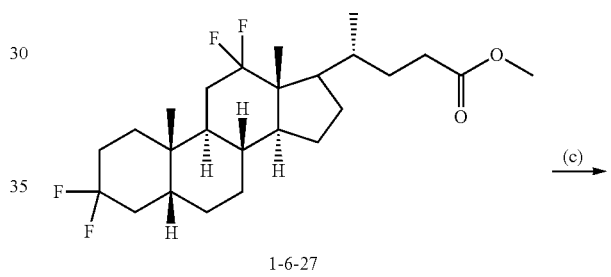
1-6-27
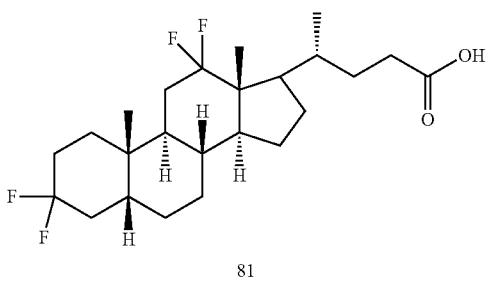
81
Reagents and conditions:
(a) CrO₃, AcOH, 63%, (b) DAST, 80° C., 70%, (c) KOH, MeOH, 80° C., 90%.
Scheme 47:
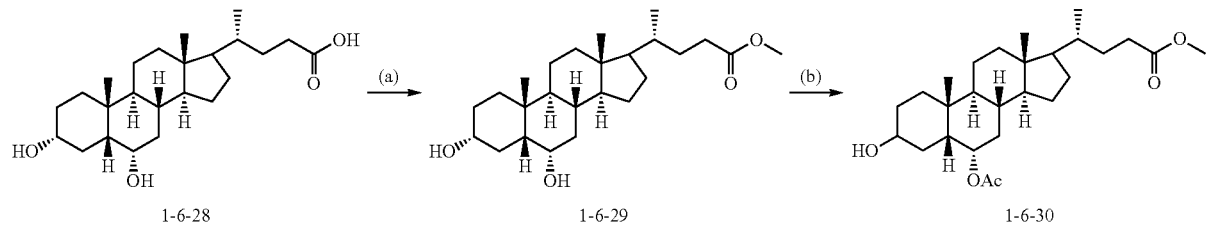
1-6-28      1-6-29      1-6-30
+

-continued
199 200
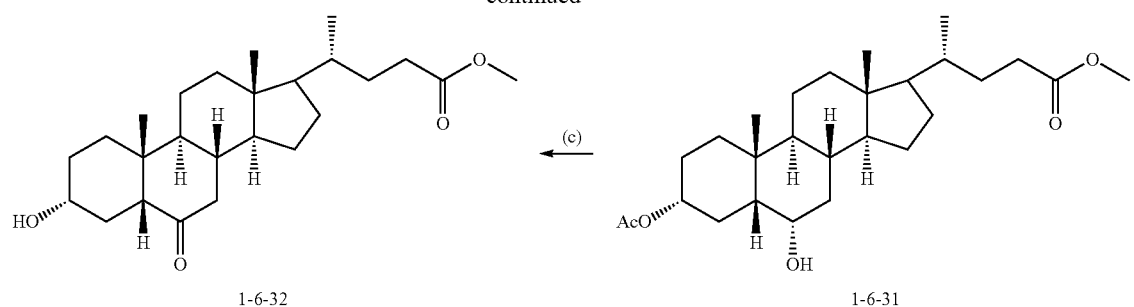
1-6-32   1-6-31
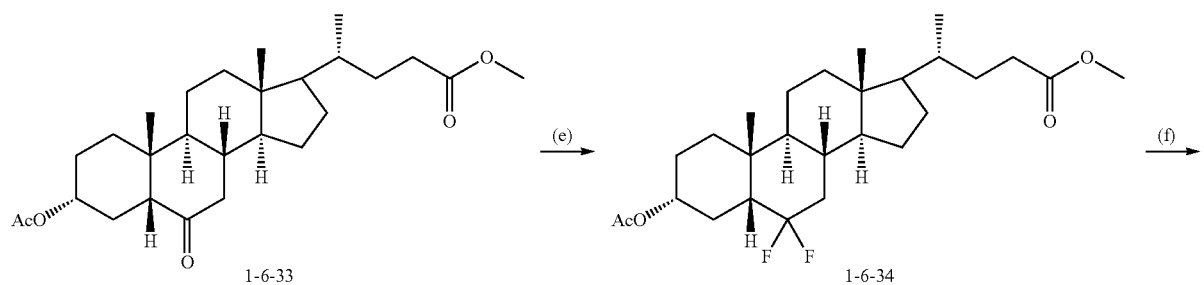
1-6-33   1-6-34
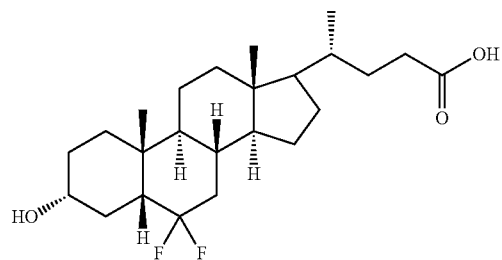
73
Reagents and conditions: (a) H₂SO₄, MeOH, 98%, (b) Ac₂O, pyridine, CH₂Cl₂, 30%, (c) PCC, CH₂Cl₂, 69%, (d) Ac₂O, pyridine, CH₂Cl₂, 53%, (e) DAST, 80° C., 53%, (f) KOH, MeOH, 80° C., 89%.

Scheme 48:
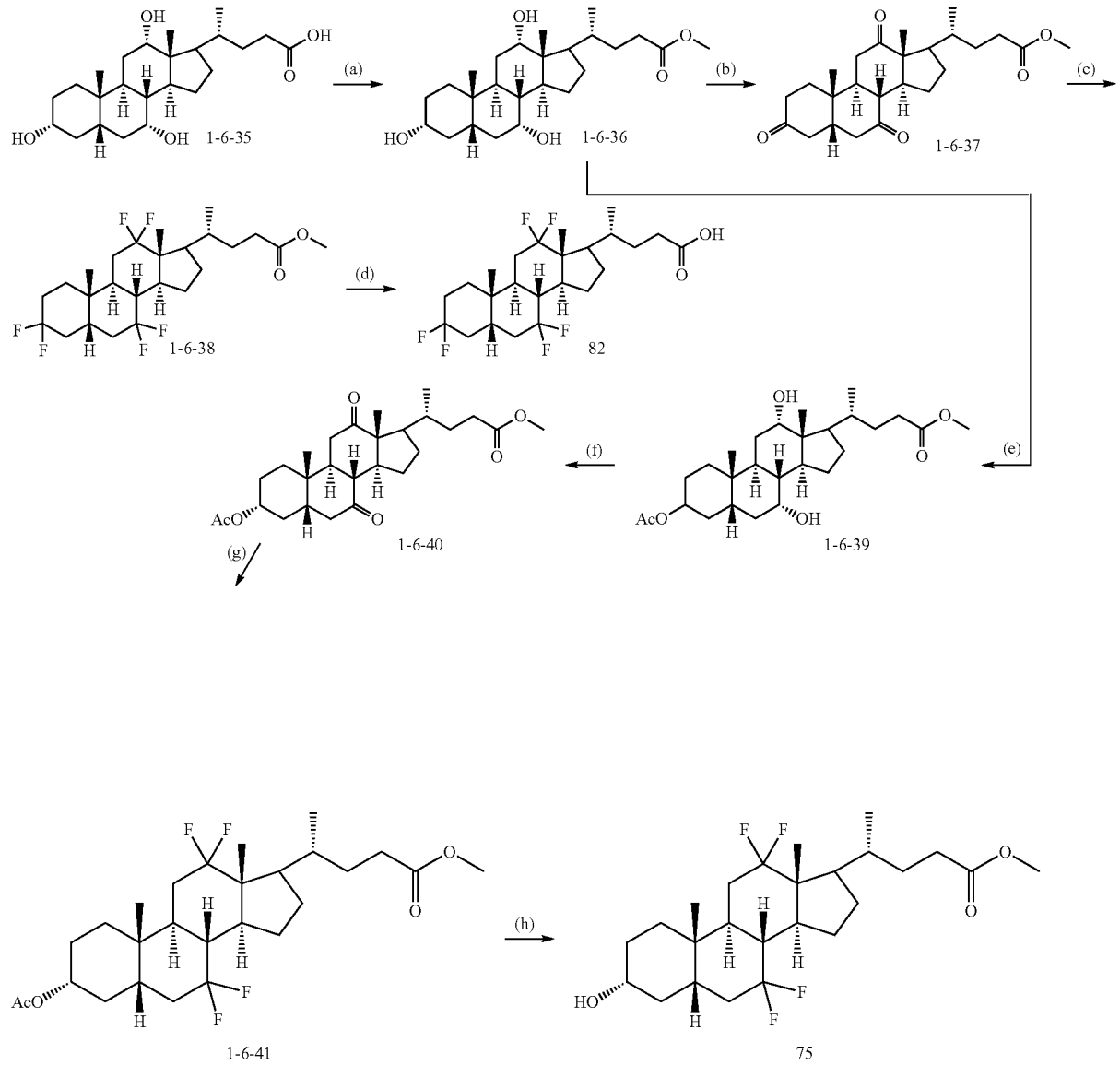
Reagents and conditions: (a) H₂SO₄, MeOH, 99%, (b) PDC, CH₂Cl₂, 72%, (c) DAST, 80° C., 25%, (d) KOH, MeOH, 80° C., 72%, (e) Ac₂O, pyridine, CH₂Cl₂, 22%, (f) PDC, CH₂Cl₂, 77%, (g) DAST, 80° C., 56%, (h) KOH, MeOH, 80° C., 92%.
Scheme 49:
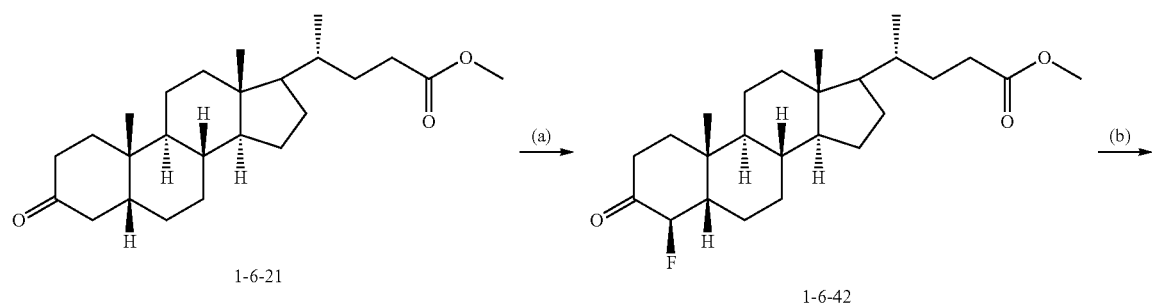

-continued
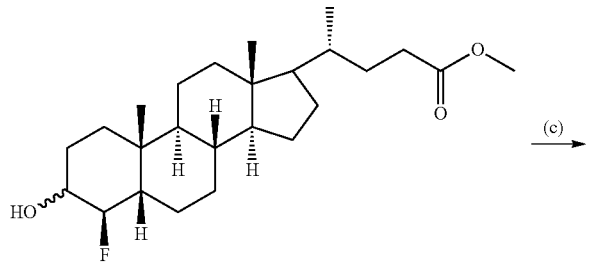
1-6-43
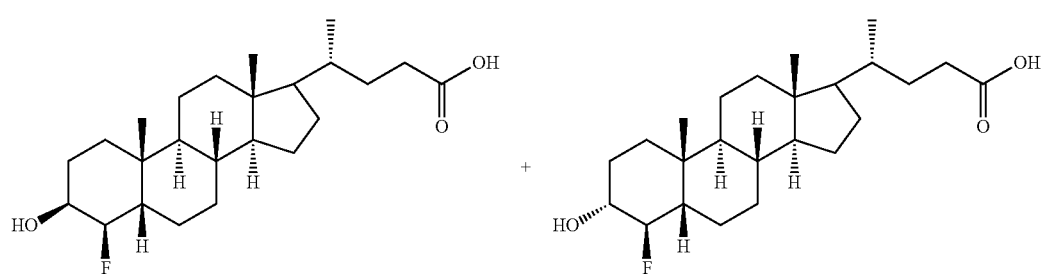
1-6-44      84
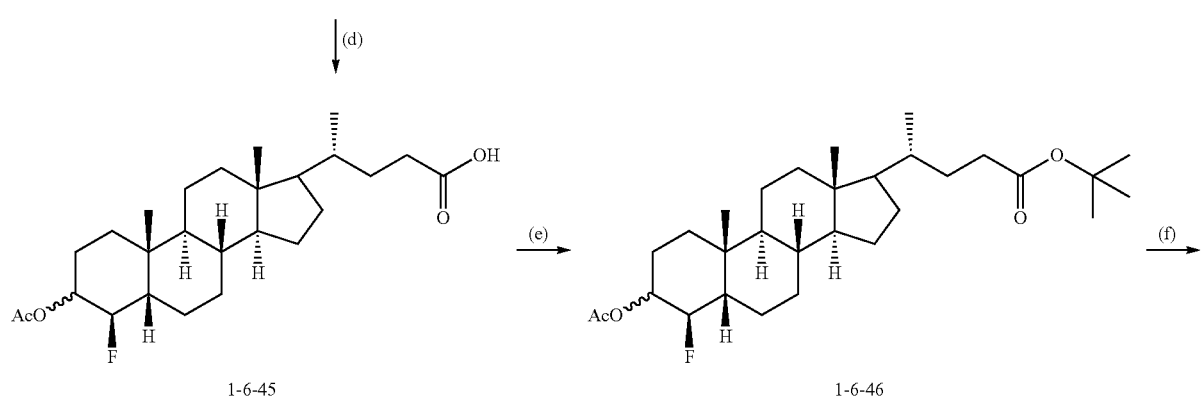
1-6-45      1-6-46
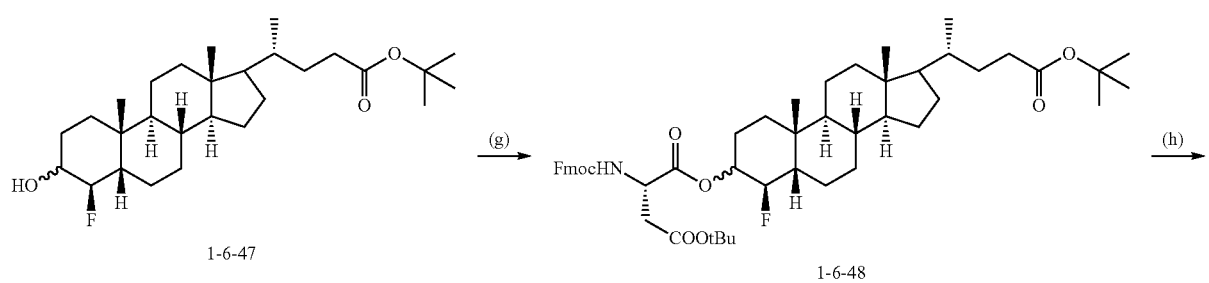
1-6-47      1-6-48
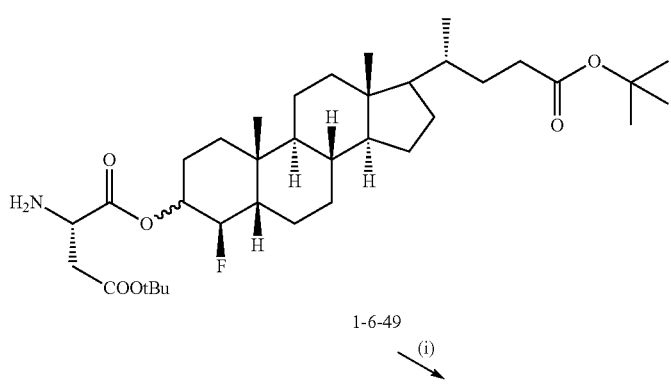
1-6-49

-continued

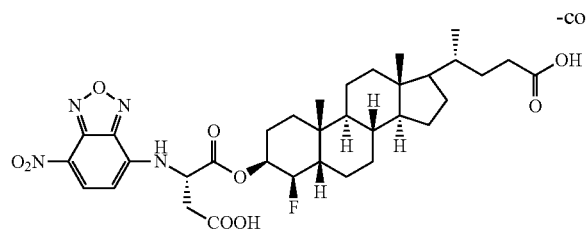

87

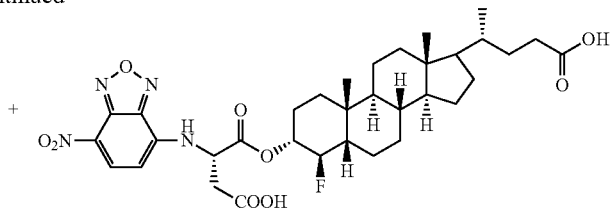

85

Reagents and conditions: (a) selectfluor, 85° C., 24 h, (b) LiAl(OtBu)₃, THF, rt, 1 h, (c) KOH, MeOH, H₂O, (d) Ac₂O, pyridine, CH₂Cl₂, rt, 24 h, (e) (Boc)₂O, DMAP, t-BuOH, rt, 4 h 80%, (f) NaOMe, MeOH, 60° C., 6 h, 92%, (g) Fmoc—L-Asp(OtBu)—OH, DCC, DMAP, CH₂Cl₂, rt. 6 h. 85%, (h) DBU, CH₂Cl₂, rt, 1 h, 87%, (i) 1. NBD—Cl, NaHCO₃, THF, EtOH, rt, 48 h, 2. TFA, H₂O, CH₂Cl₂, rt, 2 h, 24% (two steps).

Compound 71172: 1H NMR (400 MHz, CDCl$_3$): δ4.58, 4.40 (dm, dm, 2JF$_7$H$_{7\beta}$=48 Hz, 2JF$_7$H$_{7\alpha}$=48 Hz, 1H), 3.59-3.48 (m, m, isomer1+isomer2, 1H), 2.41-2.33 (m, m, isomer 1+isomer 2, 1H), 2.27-2.19 (m, m, isomer 1+isomer 2, 1H), 1.99-1.79 (m, m, isomer 1+isomer 2, 7H), 1.71-1.62 (m, m, isomer 1+isomer 2, 4H), 1.53-1.41 (m, m, isomer 1+isomer 2, 5H), 1.36-1.26 (m, m, isomer 1+isomer 2, 5H), 1.19-1.02 (m, m, isomer 1+isomer 2, 5H), 0.94, 0.87 (s, s, isomer 1+isomer2, 3H), 0.91 (d, J=6.3 Hz, isomer 1+isomer 2, 3H), 0.65, 0.63 (s, s, isomer 1+isomer 2, 3H); 13C NMR (100 MHz, CDCl$_3$): δ 179.2, 93.8 [d, 1J (19F, 13C)=171 Hz], 91.2 [d, 1J (19F, 13C)=171 Hz], 71.9, 71.4, 55.7, 55.2, 50.1, 43.2, 42.7, 42.5, 42.4, 41.8, 41.6, 40.9, 39.9, 39.5, 39.2, 39.0, 38.7, 38.6, 37.2, 35.3, 35.2, 35.1, 34.6, 34.1, 33.8, 33.7, 33.6, 32.6, 32.4, 30.9, 30.8, 30.4, 30.2, 28.3, 28.1, 25.9, 23.5, 23.3, 22.5, 21.0, 20.6, 18.3, 12.0, 11.7 (two isomer); 19F NMR (376 MHz, CDCl$_3$): δ−172.49 (s, 1F), −186.53 (s, 1F) (two isomer); HRMS-ESI: calculated for C$_{24}$H$_{38}$FO$_3$ (M−H)−, 393.2805: found, 393.2797.

Compound 73: 1H NMR (400 MHz, CDCl$_3$): δ3.55-3.50 (m, 1H), 2.43-2.35 (m, 1H), 2.27-2.25 (m, 1H), 2.16-1.97 (m, 3H), 1.83-1.75 (m, 4H), 1.70-1.67 (m, 5H), 1.57-1.45 (m, 4H), 1.34-1.27 (m, 3H), 1.24-1.05 (m, 5H), 0.93 (s, 3H), 0.92 (d, J=7.1 Hz, 3H), 0.65 (s, 3H); 13C NMR (100 MHz, CDCl$_3$): δ 179.2, 124.6 [t, 1J (19F, 13C)=243.2 Hz], 71.3, 55.0, 48.6, 43.1, 41.8 [t, 2J (19F, 13C)=22.6 Hz], 41.2 [d, 3J (19F, 13C)=10.5 Hz], 39.4, 37.2, 37.0 [d, 3J (19F, 13C)=8.9 Hz], 36.2 [t, 2J (19F, 13C)=23.1 Hz], 35.3, 34.7, 34.3, 30.9, 30.8, 30.1, 28.3, 25.3, 22.6, 20.9, 18.3, 11.8; 19F NMR (376 MHz, CDCl$_3$): δ−84.39 (d, 2J (19F, 19F)=236.9 Hz, 1F), −101.21 (d, 2J (19F, 19F)=240.6 Hz, 1F); HRMS-FAB: calculated for C$_{24}$H$_{38}$F$_2$O$_3$Na (M+Na)+, 435.2686; found, 435.2687.

Compound 77: 1H NMR (400 MHz, CDCl$_3$): δ 4.82 (dm, 2JF$_{3\alpha}$H$_{3\beta}$=48.8 Hz, 1H), 2.42-2.34 (m, 1H), 2.28-2.20 (m, 1H), 2.25-1.92 (m, 3H), 1.92-1.76 (m, 6H), 1.72-1.57 (m, 3H), 1.56-1.44 (m, 5H), 1.44-1.32 (m, 5H), 1.27-1.10 (m, 4H), 0.98 (s, 3H), 0.92 (d, J=6.4 Hz, 3H), 0.66 (s, 3H); 13C NMR (125 MHz, CDCl$_3$): δ 179.8, 124.9 [t, 1J (19F, 13C)=243.8 Hz], 89.3 [t, 1J (19F, 13C)=166.3 Hz], 55.0, 48.7, 43.2, 41.8 [t, 2J (19F, 13C)=22.5 Hz], 39.5, 36.5 [d, 3J (19F, 13C)=8.8 Hz], 36.3 [d, 3J (19F, 13C)=10.5 Hz], 35.6 [t, 2J (19F, 13C)=22.9 Hz], 35.2, 34.5, 32.5[d, 3J (19F, 13C)=4.4 Hz], 32.3[d, 3J (19F, 13C)=4.1 Hz], 30.8 [t, 2J (19F, 13C)=20.0 Hz], 29.6, 28.3, 25.7 [t, 2J (19F, 13C)=21.1 Hz], 25.3 [d, 3J (19F, 13C)=3.4 Hz], 23.0, 21.2, 18.3, 11.8; 19F NMR (376 MHz, CDCl$_3$): δ −83.99 (d, 2J (19F, 19F)=240.6 Hz, 1F), −101.15 (d, 2J (19F, 19F)=240.6 Hz, 1F), −184.9 (s, 1F); HRMS-FAB: calculated for C$_{24}$H$_{38}$F$_3$O$_2$(M+H)+, 415.2820: found, 415.2824.

Compound 74: 1H NMR (400 MHz, CDCl$_3$): δ 3.65-3.57 (m, 1H), 2.44-2.40 (m, 2H), 2.32-2.24 (m, 1H), 1.99-1.70 (m, 5H), 1.67-1.53 (m, 6H), 1.53-1.36 (m, 5H), 1.36-1.18 (m, 5H), 1.18-1.02 (m, 3H), 0.98 (d, J=6.0 Hz, 3H), 0.90 (s, 3H), 0.79 (s, 3H); 13C NMR (125 MHz, CDCl$_3$): δ 178.3, 126.5[t, 1J (19F, 13C)=249.0 Hz], 71.6, 52.5 [d, 3J (19F, 13C)=7.1 Hz], 49.2 [t, 2J (19F, 13C)=20.5 Hz], 47.8, 41.6, 37.2 [d, 3J (19F, 13C)=9.4 Hz], 36.2, 35.1, 34.7, 34.1, 33.2, 31.3 [t, 2J (19F, 13C)=25.3 Hz], 31.2, 30.1 [d, 3J (19F, 13C)=9.4 Hz], 26.9, 26.3, 25.5, 23.1, 23.0, 18.9, 18.8, 10.5; 19F NMR (376 MHz, CDCl$_3$): δ−90.8 (d, 2J (19F, 19F) =229.4 Hz, 1F), −111.9 (d, 2J (19F, 19F)=229.4 Hz, 1F); HRMS-ESI: calculated for C$_{24}$H$_{37}$F$_2$O$_3$(M−H)−, 411.2711; found, 411.2714.

Compound 78: 1 H NMR (400 MHz, CDCl$_3$): δ 4.86 (dm, 2JF$_{3\alpha}$H$_{3\beta}$=48.8 Hz, 1H), 2.44-2.32 (m, 1H), 2.32-2.24 (m, 1H), 1.92-1.83 (m, 5H), 1.83-1.70 (m, 5H), 1.62-1.47 (m, 7H), 1.47-1.22 (m, 6H), 1.19-0.99 (m, 3H), 0.99-0.95 (m, 6H), 0.80 (s, 3H); 13C NMR (125 MHz, CDCl$_3$): δ 179.3, 126.5 [t, 1J (19F, 13C)=245.1 Hz], 89.8 [t, 1J (19F, 13C)= 165 Hz], 52.7, 49.3 [t, 2J (19F, 13C)=21.3 Hz], 47.8, 36.6[d, 3J (19F, 13C)=9.3 Hz], 36.5, 34.4, 34.4[d, 3J (19F, 13C)=7.6 Hz], 33.2, 31.6 [t, 2J (19F, 13C)=25.8 Hz], 31.5, 31.3, 30.2, 30.0, 26.4, 26.0, 25.8 [t, 2J (19F, 13C)=21.3 Hz], 25.2, 23.3, 23.0, 18.9 [d, 3J (19F, 13C)=10.9 Hz], 10.5; 19F NMR (376 MHz, CDCl$_3$): δ −90.93 (d, 2J (19F, 19F)=229.4 Hz, 1F), −111.97 (d, 2J (19F, 19F)=229.4 Hz, 1F), −182.70 (s, 1F); HRMS-FAB: calculated for C$_{24}$H$_{39}$F$_3$O$_2$Na (M+Na)+, 437.2643; found, 437.2658.

Compound 79: 1H NMR (400 MHz, CDCl$_3$): 2.42-2.34 (m, 1H), 2.28-2.20 (m, 1H), 2.15-1.94 (m, 2H), 1.85-1.45 (m, 5H), 1.66-1.56 (m, 3H), 1.46-1.34 (m, 5H), 1.29-1.23 (m, 5H), 1.17-1.05 (m, 5H), 0.95 (s, 3H), 0.90 (d, J=6.4 Hz, 3H), 0.64 (s, 3H); 13C NMR (100 MHz, CDCl$_3$): δ 180.1, 124.6 [t, 1J (19F, 13C)=238.5 Hz], 56.4, 55.9, 42.8, 40.0, 39.9, 35.2, 35.3, 34.5, 34.5 [t, 2J (19F, 13C)=18.5 Hz], 33.1, 33.0, 31.0, 30.7, 29.3 [t, 2J (19F, 13C)=24.5 Hz], 28.1, 26.1, 26.0, 24.1, 22.8, 21.1, 18.2, 12.1; 19F NMR (376 MHz, CDCl$_3$): δ−88.24 (d, 2J (19F, 19F)=233.1 Hz, 1F), −99.4 (d, 2J (19F, 19F)=233.1 Hz, 1F); HRMS-ESI calculated for C$_{24}$H$_{37}$F$_2$O$_2$ (M−H)−, 395.2762: found, 395.2768.

Compound 76: 1H NMR (400 MHz, CDCl$_3$): δ 4.85 (dm, 2JF$_{3\alpha}$H$_{3\beta}$=49.2 Hz, 1H), 2.41-2.33 (m, 1H), 2.23-2.19 (m, 1H), 1.96-1.87 (m, 2H), 1.82-1.72 (m, 3H), 1.69-1.57 (m, 4H), 1.39-1.32 (m, 7H), 1.23-1.11 (m, 3H), 1.11-1.01 (m, 4H), 1.19-1.13 (m, 3H), 0.94 (s, 3H), 0.90 (d, J=6.4 Hz, 3H), 0.63 (s, 3H); 13C NMR (125 MHz, CDCl$_3$): δ 179.6, 90.2 [d, 1 J (19F, 13C)=165.4 Hz], 56.6, 56.0, 42.8, 40.2, 39.9, 36.9, 35.6, 35.3, 34.8, 31.7, 31.5, 30.9, 30.8, 30.2, 28.2, 26.3, 26.1, 24.2, 23.7, 21.1, 18.3, 12.1; 19F NMR (376 MHz, CDCl$_3$): δ−182.1 (s, 1F); HRMS-FAB: calculated for C$_{24}$H$_{40}$FO$_2$ (M+H)+, 379.3016; found, 379.3012.

Compound 78: 1H NMR (400 MHz, CDCl$_3$): δ 2.42-2.35 (m, 1H), 2.29-2.21 (m, 1H), 2.18-1.98 (m, 3H), 1.90-1.73 (m, 8H), 1.73-1.58 (m, 3H), 1.48-1.36 (m, 4H), 1.36-1.06 (m, 7H), 0.99 (s, 3H), 0.92 (d, J=6.4 Hz, 3H), 0.66 (s, 3H); 13C NMR (125 MHz, CDCl$_3$): δ179.3, 124.3; [t, 1J (19F, 13C)=243.1 Hz], 123.5 [t, 1J (19F, 13C)=240 Hz], 55.0, 48.5, 43.2, 41.7 [t, 2J (19F, 13C)=22.4 Hz], 39.3, 39.2 [t, 2J (19F, 13C)=11.6 Hz], 36.5 [d, 3J (19F, 13C)=8.7 Hz], 35.3[t, 2J (19F, 13C)=23.3 Hz], 35.2, 34.3, 32.4 [d, 3J (19F, 13C)=9.0 Hz], 30.8, 30.7, 29.1 [t, 2J (19F, 13C)=22.9 Hz], 28.3, 25.3, 25.3, 22.1, 21.2, 18.3, 11.8; 19F NMR (376 MHz, CDCl$_3$): δ−87.7 (d, 2J (19F, 19F)=240.6 Hz, 1F), −89.7 (d, 2J (19F, 19F)=231.88 Hz, 1F), −101.27 (d, 2J (19F, 19F)=169.2 Hz, 1F), −101.9 (d, 2J (19F, 19F)=157.9 Hz, 1F); HRMS-ESI: calculated for C$_{24}$H$_{35}$F$_4$O$_2$(M−H)−, 431.2573: found, 431.2586.

Compound 81: 1H NMR (400 MHz, CDCl$_3$): 2.44-2.40 (m, 1H), 2.28-2.24 (m, 1H), 2.12-1.91 (m, 1H), 1.90-1.83 (m, 4H), 1.75-1.67 (m, 5H), 1.63-1.56 (m, 4H), 1.48-1.40 (m, 5H), 1.34-1.07 (m, 5H), 0.98 (d, J=6.8 Hz, 3H), 0.95 (s, 3H), 0.80 (s, 3H); 13C NMR (125 MHz, CDCl$_3$): δ 179.9, 126.2[t, 1J (19F, 13C)=246.1 Hz], 124.11 [t, 1J (19F, 13C)=239.4 Hz], 52.5, 52.4, 49.2 [t, 2J (19F, 13C)=20.4 Hz], 47.8, 39.6 [d, 3J (19F, 13C)=8.8 Hz], 36.6 [d, 3J (19F, 13C)=9.1 Hz], 34.4 [t, 2J (19F, 13C)=22.3 Hz], 34.1, 33.2, 32.8 [d, 3J (19F, 13C)=9.1 Hz], 31.5 [t, 2J (19F, 13C)=25.8 Hz], 31.4, 30.2, 29.1 [t, 2J (19F, 13C)=23.6 Hz], 26.3, 25.8, 25.1, 23.0, 22.4, 18.9 [d, 3J (19F, 13C)=10.6 Hz], 10.5; 19F NMR (376 MHz, CDCl$_3$): δ−88.8 (d, 2J (19F, 19F)=233.1 Hz, 1F), −91.0 (d, 2J (19F, 19F)=233.1 Hz, 1F), −99.7 (d, 2J (19F, 19F)=233.1 Hz, 1F), −111.9 (d, 2J (19F, 19F)=233.1 Hz, 1F); HRMS-ESI: calculated for C$_{24}$H$_{35}$F$_4$O$_2$(M−H)−, 431.2573; found, 431.2568.

Compound 73: 1H NMR (400 MHz, CDCl$_3$): δ3.65-3.57 (m, 1H), 2.41-2.34 (m, 1H), 2.28-2.20 (m, 1H), 1.98-1.91 (m, 2H), 1.90-1.74 (m, 5H), 1.73-1.42 (m, 6H), 1.41-1.31 (m, 4H), 1.30-1.20 (m, 2H), 1.19-1.01 (m, 5H), 0.94 (d, J=4.6 Hz, 3H), 0.91 (d, J=6.37 Hz, 3H), 0.65 (s, 3H); 13C NMR (125 MHz, CDCl$_3$): δ 179.5, 125.0[t, 1J (19F, 13C)=244.5 Hz], 70.4, 55.8[d, 3J (19F, 13C)=11.7 Hz], 49.1 [t, 2J (19F, 13C)=18.5 Hz], 42.8, 39.8, 39.6, 35.7 [d, 3J (19F, 13C)=5.5 Hz], 35.2, 35.2 [t, 2J (19F, 13C)=20.5 Hz], 33.0 [d, 3J (19F, 13C)=9.5 Hz], 32.8, 31.0, 30.7, 29.8, 28.0, 27.9, 24.1 [d, 3J (19F, 13C)=7.17 Hz], 24.0, 22.5, 20.4, 18.2, 11.9; 19F NMR (376 MHz, CDCl$_3$): δ−87.5 (d, J=210.6 Hz, 1F), −91.1 (d, J=240.6 Hz, 1F).

Compound 82: 1H NMR (400 MHz, CDCl$_3$): δ 2.40-2.33 (m, 1H), 2.32-2.25 (m, 1H), 2.18-1.90 (m, 5H), 1.89-1.86 (m, 5H), 1.83-1.74 (m, 4H), 1.74-1.53 (m, 3H), 1.44-1.24 (m, 5H), 1.00 (s, 3H), 0.98 (dm, 3H), 0.84 (s, 3H); 13C NMR (100 MHz, CDCl$_3$): δ 180.1, 125.3 [t, 1J (19F, 13C)=245.0 Hz], 123.7 [t, 1J (19F, 13C)=243.8 Hz], 123.1 [t, 1J (19F, 13C)=240 Hz], 49.4 [t, 2J (19F, 13C)=20.5 Hz], 46.7, 45.2, 40.7 [t, 2J (19F, 13C)=21.8 Hz], 39.0 [t, 2J (19F, 13C)=10.2 Hz], 23.3 [t, 2J (19F, 13C)=23.3 Hz], 33.9, 33.7 [(d, 3J (19F, 13C)=9.2 Hz], 33.0, 32.2 [d, 3J (19F, 13C)=9.2 Hz], 31.5, 31.4 [t, 2J (19F, 13C)=26.5 Hz], 30.0, 28.9 [t, 2J (19F, 13C)=23.1 Hz], 26.0, 24.1, 24.0, 21.8, 19.1 [d, 3J (19F, 13C)=10.2 Hz], 10.5; 19F NMR (376 MHz, CDCl$_3$): δ −85.4 (d, J=244.4 Hz, 1F), −90.2 (d, J=244.4 Hz, 1F), −93.1 (d, J=244.4 Hz, 1F), −101.4 (d, J=244.4 Hz, 1F), −102.1 (d, J=236.9 Hz, 1F), −111.74 (d, J=236.9 Hz, 1F); HRMS-FAB: calculated for C$_{24}$H$_{34}$F$_6$O$_2$Na (M+Na)+, 491.2361; found, 491.2376.

Compound 75: 1H NMR (400 MHz, CDCl$_3$): δ 3.58-3.48 (m, 1H), 2.46-2.37 (m, 1H), 2.34-3.24 (m, 1H), 2.21-1.96 (m, 3H), 1.92-1.83 (m, 4H), 1.79-1.61 (m, 7H), 1.61-1.43 (m, 3H), 1.38-1.09 (m, 5H), 0.98 (d, J=6.0 Hz, 3H), 0.95 (s, 3H), 0.83 (s, 3H); 13C NMR (100 MHz, CDCl$_3$): δ 177.8, 125.5[t, 1J (19F, 13C)=248.7 Hz], 124.0 [t, 1J (19F, 13C)=248.7 Hz], 71.1, 49.4 [t, 2J (19F, 13C)=20.4 Hz], 46.7, 45.2, 40.9 [d, 3J (19F, 13C)=16.7 Hz], 40.8 [t, 2J (19F, 13C)=21.5 Hz], 37.1, 36.1 [t, 2J (19F, 13C)=21.6 Hz], 34.5, 34.2 [t, 2J (19F, 13C)=10.2 Hz], 33.9, 33.0, 31.2 [t, 2J (19F, 13C)=22.5 Hz], 30.1 [d, 3J (19F, 13C)=12.5 Hz], 30.0, 29.7, 26.0, 24.1, 22.3, 19.1° C. [d, 3J (19F, 13C)=10.9 Hz], 10.5; 19F NMR (376 MHz, CDCl$_3$): δ−85.1 (d, J=244.4 Hz, 1F), −93.0 (d, J=244.4 Hz, 1F), −101.3 (d, J=244.4 Hz, 1F), −111.8 (d, J=244.4 Hz, 1F); HRMS-ESI: calculated for C$_{24}$H$_{35}$F$_4$O$_3$ (M−H)−, 447.2522; found, 447.2515.

Compound 86: 1H NMR (500 MHz, DMSO): δ 4.71 (ddd, J=4.7 Hz, 1H), 3.97 (m, 1H), 2.26-2.05 (m, 2H), 1.89 (d, J=10.0 Hz, 1H), 1.83-1.74 (m, 2H), 1.71-1.49 (m, 4H), 1.49-1.29 (m, 8H), 1.29-0.98 (m, 9H), 0.93 (s, 3H), 0.86 (d, 3H), 0.61 (s, 3H); 13C NMR (125 MHz, DMSO): δ 175.3, 91.7, 90.3, 66.2, 66.1, 56.2, 56.0, 42.6, 41.3, 41.2, 41.1, 37.4, 37.3, 35.5, 35.2, 31.2, 31.1, 29.1, 28.1, 26.2, 26.1, 25.9, 24.2, 23.7, 21.2, 20.3, 18.5, 12.3.

Compound 84: 1 H NMR (500 MHz, DMSO): δ 4.99 (d, J=4.8 Hz, 1H), 4.47 (td, J=51.1 Hz, 1H), 3.47-3.30 (m, 1H), 2.27-2.05 (m, 2H), 1.94-1.87 (d, J=12.0 Hz, 1H), 1.85-1.75 (m, 1H), 1.73-1.51 (m, 6H), 1.47-0.98 (m, 16H), 0.92 (s, 3H), 0.86 (d, J=6.6 Hz, 3H), 0.61 (s, 3H); 13C NMR (125 MHz, DMSO): δ 175.3, 95.5, 94.1, 73.0, 72.8, 56.2, 55.9, 47.0, 46.9, 42.6, 42.1, 37.5, 37.4, 35.4, 35.2, 34.3, 31.2, 31.1, 28.1, 28.0, 27.9, 26.0, 24.2, 23.3, 20.8, 18.5, 12.3.

Compound 87: 1H NMR (500 MHz, DMSO): δ 8.59 (d, J=8.5 Hz, 1H), 8.19 (d, J=9.23 Hz, 1H), 6.70 (d, J=8.8 Hz, 1H), 5.44-5.32 (br, 1H), 5.39-5.21 (br, 1H), 5.02-4.84 (ddd, J=46.9 Hz, 1H), 3.24 (d, J=2.3 Hz, 2H), 2.36-2.25 (m, 2H), 2.24-2.13 (m, 2H), 1.98-1.91 (d, J=9.87 Hz, 1H), 1.85-1.70 (m, 3H), 1.68-1.33 (m, 10H), 1.32-1.04 (m, 9H), 0.91 (d=J=6.7 Hz, 3H), 0.73 (s, 3H), 0.65 (s, 3H); 13C NMR (125 MHz, DMSO): δ 174.1, 171.0, 168.7, 144.6, 144.1, 136.3 124.0, 101.3, 88.3, 86.9, 71.8, 71.7, 56.1, 56.0, 42.7, 42.6, 42.4, 41.2, 39.8, 36.8, 36.7, 35.3, 35.1, 35.0, 30.8, 30.2, 27.8, 25.2, 23.7, 23.0, 22.9, 22.4, 20.9, 19.7, 17.7, 11.4.

Compound 85: 1H NMR (500 MHz, DMSO): δ 9.03 (d, J=9.05 Hz, 1H), 8.58-8.45 (m, 1H), 7.11 (d, J=8.8 Hz, 1H), 5.71-5.58 (m, 1H), 5.47-5.31 (m, 1H), 5.38-5.18 (td, J=51.3 Hz, 1H), 3.70 (d, J=5.7 Hz, 2H), 2.85-2.74 (m, 2H), 2.71-2.60 (m, 2H), 2.46-2.39 (m, 1H), 2.38-2.13 (m, 7H), 2.13-1.80 (m, 9H), 1.86-1.52 (m, 11H), 1.48 (s, 3H), 1.39 (d, J=6.4 Hz, 3H), 1.14 (s, 3H); 13C NMR (125 MHz, DMSO): 174.1, 170.8, 169.1, 144.6, 144.1, 136.4, 124.2, 100.9, 91.0, 89.6, 77.7, 77.5, 56.1, 56.0, 53.1, 47.2, 47.1, 42.3, 42.0, 39.8, 37.0, 35.3, 35.2, 33.4, 30.8, 30.2, 27.8, 25.5, 23.8, 22.2, 20.6, 20.3, 17.7, 11.4.

1.9 Synthesis of Compounds 88 to 94

Compounds 88 to 94 (or compounds of formula (1-7), (1-8) and (1-9)) were synthesized in accordance with procedures set forth in Schemes 50 to 52.

Scheme 50:

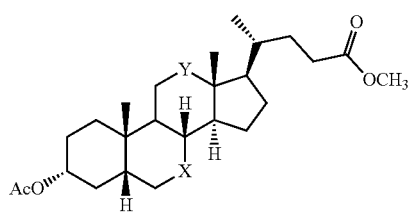

1-7-1: X = CO, Y = CH₂.
1-8-1: X = CH₂, Y = CO.
1-7-4: X = CHOAc, Y = CO.

CF₃COOOH, DCM
0-rt, 6 h
(251 mg, 82.5%)

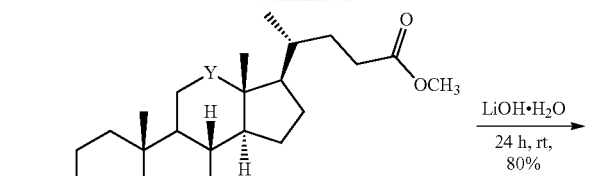

1-7-7: X = —CONH—, Y = CH₂.
1-8-4: X = CH₂, Y = CONH.
1-7-8: X = CHOAc, Y = —CONH—.

LiOH·H₂O
24 h, rt, 80%

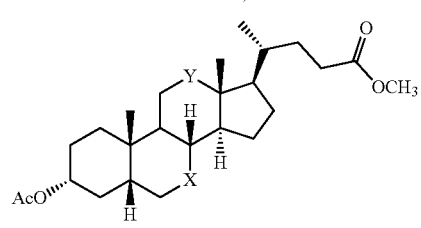

1-7-2: X = COO, Y = CH₂.
1-8-2: X = CH₂, Y = COO.
1-7-5: X = CHOAc, Y = COO.

Ba(OH)₂·8H₂O, MeOH
r.t., 3 d, 90%.

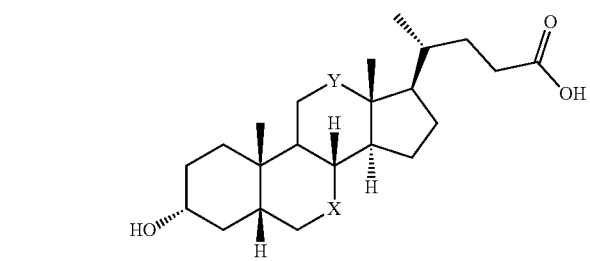

89: X = —CONH—, Y = CH₂.
91: X = CH₂, Y = —CONH—.
93: X = CHOH, Y = —CONH—.

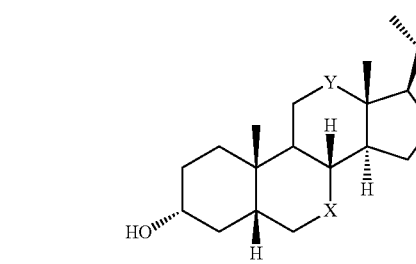

88: X = —COO—, Y = CH₂.
90: X = CH₂, Y = —COO—.
92: X = CHOH, Y = —COO—.

Scheme 51:

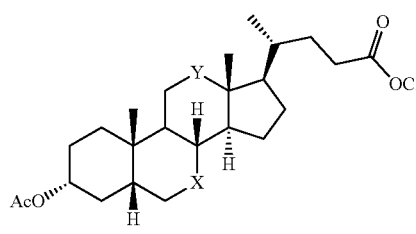

1-7-1: X = CO, Y = CH₂.
1-8-1: X = CH₂, Y = CO.
1-7-4: X = CHOAc, Y = CO.

NH₂OH·HCl, AcONa
MeOH, reflux, 6 h 90%

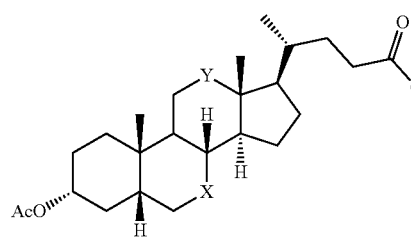

1-7-3: X = CH=NOH, Y = CH₂.
1-8-3: X = CH₂, Y = CH=NOH,
1-7-6: X = CHOAc, Y = CH=NOH,

SOCl₂, THF
0° C. to rt, 4 h, 80%

Scheme 52:

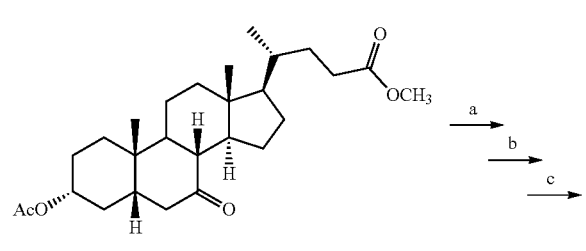

1-7-1 a
b
c

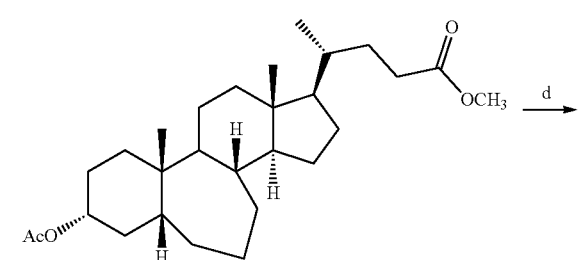

1-9-1 d

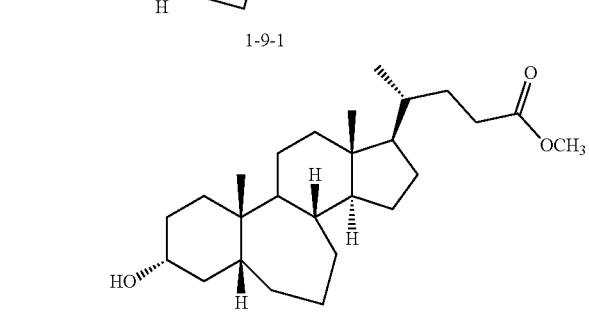

94

(a) (1) 2.8 equiv. of TMSCHN₂, 4.2 equiv. of BF₃·Et₂O, CH₂Cl₂, -15 oc, 3 h, (2) 2N HCl, SiO₂, Et₂O, rt, 6 h.
(b) TsNHNH₂, MeOH, rt, 24 h.
(c) (1) catecholborane, CHCl₃, (2) NaOAc, reflux. 33% yield (3 steps)
(d) 20% KOH, EtOH, reflux, 4 h. 70% yield

Synthesis of Compounds 88, 90 and 92

Homolactones (compds. 88, 90 and 92; scheme 37) were synthesized by Bayer-Viliger oxidation of the known ketocholanes (compounds 1-7-1, 1-8-1, and 1-7-4), using trifluoroperacetic acid. Baeyer-Villiger oxidation of ketocholanes was chosen for the ring expansion to incorporate an additional oxygen atom to give lactone. This reaction proceeds with complete retention of the configuration and regioselectivity, thus offering possibilities for a reliable synthetic design. Hence, Baeyer-Villiger oxidation of ketocholanes furnished the lactones 1-7-2, 1-8-2, 1-7-5 which was purified by rapid column chromatography. The lactones were saponified with methanolic barium hydroxide in analogy to a reported procedure (Peterson et al., Tetrahedron, 51, 9467-9486 (1995)) and subsequently acidified with concentrated hydrochloric acid, extracted with ethyl acetate, washed with brine, dried and evaporated under vacuum to afford the title compounds 88, 90, and 92.

General Procedure for Baeyer-Villiger Oxidation

The Methyl ketocholanate (0.66 mmol) in dichloromethane (12 mL) was added at 0° C. to a solution of trifluoroperacetic acid in dichloromethane prepared by adding trifluoroacetic anhydride (4.5 mL) to 30% aqueous hydrogen peroxide (0.75 mL) in dichloromethane (12 mL) at 0° C. The mixture was stirred at this temperature for 2 h then was warmed to room temperature and maintained for 4 h. The reaction mixture was diluted with dichloromethane (30 mL), and the resulting solution was washed with saturated sodium bicarbonate solution, brine solution, dried over anhydrous sodium sulfate, and concentrated. The residue was chromatographed (eluting with ethyl acetate/hexane; 2/1) to afford the lactone in 82%.

General Procedure for Saponification of Lactone

A mixture of lactone (0.11 mmol) and barium hydroxide octahydrate (powdered 3.5 g) in MeOH (5 mL) was stirred at room temperature for 97 h. The heavy white suspension was diluted with brine (3 ml) and acidified with 1 M HCl to give a clear solution of pH=3-4. This aqueous solution was extracted with EtOAc (2×50+2×20) and the combined organic extracts washed with brine (20 mL), dried, concentrated in vacuo, washed with chloroform to give 80-90% yield.

Methyl 3α-acetoxy-8-oxa-7-oxo-B-homo-5β-cholanate (1-7-2)

$R_f$=0.25 (hexane/EtOAc, 2:1). $^1$H NMR (400 MHz, CDCl$_3$) 4.62-4.58 (m, H-3 ax.), 4.11 (dd, J=9.2 and 10.0 Hz, H-8 ax), 3.55 (s, CH$_3$O), 2.95 (br. d, J=15.0 Hz, H-6), 2.30-2.05 (m, 3H), 1.95-1.07 (m, 24H, steroidal CH and CH$_2$), 0.98 (s, CH$_3$-19), 0.81 (d, J=6.8 Hz, CH$_3$-21), 0.56 (s, CH$_3$-18). $^{13}$C NMR (75 MHz, CDCl$_3$) 35.2 (C-1), 26.2 (C-2), 72.3 (C-3), 31.4 (C-4), 41.2 (C-5), 35.2 (C-6), 173.6 (C-7), 79.2 (C-8), 39.7 (C-9), 37.2 (C-10), 22.6 (C-11), 38.1 (C-12), 42.9 (C-13), 54.1 (C-14), 24.7 (C-15), 27.4 (C-16), 55.4 (C-17), 11.2 (C-18), 23.1 (C-19), 34.7 (C-20), 17.9 (C-21), 30.5 (C-22), 30.6 (C-23), 174.0 (C-24), 51.1 (CH$_3$—O), 170.0 (AcO).

Methyl 3α-acetoxy-13-oxa-12-oxo-C-homo-5β-cholanate (1-8-2)

$R_f$=0.30 (hexane/EtOAc, 2:1). $^1$H NMR (400 MHz, CDCl$_3$) 4.67-4.59 (m, H-3 ax.), 3.57 (s, CH$_3$O), 2.52 (br. d, J=12.0 Hz, H-11), 2.37-2.25 (m, 3H), 1.92 (s, 3H, CH$_3$CO), 1.84-1.02 (m, 24H, steroidal CH and CH$_2$), 0.95 (d, J=6.5 Hz, CH$_3$-21), 0.8 (s, CH$_3$-18). $^{13}$C NMR (75 MHz, CDCl$_3$) 14.3, 17.0, 20.3, 20.5, 21.0, 22.1, 23.8, 25.5, 25.8, 26.2, 26.3, 29.9, 30.5, 31.6, 33.9, 34.5, 35.2, 36.2, 37.3, 38.8, 40.8, 51.2, 54.9, 55.1, 73.4 (C-3), 87.2 (C-13), 170.5 (AcO), 174.2 (C-12), 175.2 (C-24).

Methyl 3α, 7α-diacetoxy-13-oxa-12-oxo-B-homo-5β-cholanate (1-7-5)

$R_f$=0.30 (hexane/EtOAc, 2:1). $^1$H NMR (400 MHz, CDCl$_3$) 4.60 (br. d, J=2.0 Hz, H-7) 4.46-4.39 (m, 1H, H-3 ax.), 3.49 (s, CH$_3$O), 2.52 (br. d, J=13.2 Hz, H-11), 2.37-2.25 (m, 4H), 2.10-0.99 (m, 30H, steroidal CH and CH$_2$, 2 Ac), 0.88 (d, J=6.6 Hz, CH$_3$-21), 0.76 (s, CH$_3$-18). $^{13}$C NMR (75 MHz, CDCl$_3$) 14.2, 17.0, 21.0, 21.7, 23.7, 24.7, 26.3, 29.9, 30.4, 30.6, 32.7, 33.8, 34.2, 34.7, 35.1, 35.6, 39.8, 40.6, 49.8, 51.1, 55.0, 71.0 (C-3), 73.1 (C-3), 86.2 (C-13), 169.7 (AcO), 170.1 (C-12), 173.9 (C-24).

3α-Hydroxy-8-oxa-7-oxo-B-homo-5β-cholanoic acid (88)

90% yield, $R_f$=0.23 (dichloromethane/MeOH, 5:1). Mp. 212-213° C. $^1$H NMR (400 MHz, acetone-d6) 4.40 (dd, J=9.2 and 10.0 Hz, H-8 ax), 3.59-3.54 (m, H-3 ax.), 3.20 (br. d, J=14.8 Hz, H-6), 2.35-2.19 (m, 3H), 1.99-1.26 (m, 22H, steroidal CH and CH$_2$), 1.12 (s, CH$_3$-19), 0.96 (d, J=6.4 Hz, CH$_3$-21), 0.72 (s, CH$_3$-18). $^{13}$C NMR (100 MHz, acetone-d6) 36.3 (C-1), 28.4 (C-2), 70.9 (C-3), 35.8 (C-4), 41.1 (C-5), 31.7 (C-6), 173.9 (C-7), 79.5 (C-8), 39.4 (C-9), 37.0 (C-10), 23.2 (C-11), 38.4 (C-12), 42.6 (C-13), 55.7 (C-14), 25.7 (C-15), 28.4 (C-16), 56.7 (C-17), 11.9 (C-18), 23.9 (C-19), 36.3 (C-20), 18.6 (C-21), 31.2 (C-22), 31.3 (C-23), 175.0 (C-24). HRMS calcd for C$_{24}$H$_{37}$O$_5$(M−H)$^-$, 405.2641; found, 405.2635.

3α-Hydroxy-13-oxa-12-oxo-C-homo-5β-cholanoic acid (90)

80% yield, $R_f$=0.21 (dichloromethane/MeOH, 5:1). Mp. 102-103° C. $^1$H NMR (400 MHz, MeOH-d4) 3.56-3.50 (m, H-3 ax.), 2.37-2.17 (m, 4H), 2.00-1.20 (m, 20H, steroidal CH and CH$_2$), 1.05 (d, J=5.6 Hz, CH$_3$-21), 0.93 (s, CH$_3$-19), 0.82 (s, CH$_3$-18). $^{13}$C NMR (100 MHz, MeOH-d4) 17.8, 20.3, 23.9, 25.8, 26.6, 28.1, 31.7, 31.9, 32.0, 35.7, 36.5, 37.2, 37.6, 43.2, 52.9, 54.4, 72.4 (C-3), 82.2 (C-13), 178.3 (C-12), 179.0 (C-24). HRMS calcd for C$_{24}$H$_{37}$O$_5$(M+Na)$^+$, 429.2617; found, 429.2613.

3α, 7α-Dihydroxy-13-oxa-12-oxo-C-homo-5β-cholanoic acid (92)

85% yield, $R_f$=0.2 (dichloromethane/MeOH, 5:1). Mp. 99-101° C. $^1$H NMR (400 MHz, MeOH-d4) 3.70 (d, J=2.4 Hz, H-7) 3.44-3.39 (m, H-3 ax.), 2.7-2.5 (m, 2H), 2.40-1.26 (m, 26H, steroidal CH and CH$_2$, CH$_3$-19), 1.05 (d, J=6.4 Hz, CH$_3$-21), 0.91 (s, CH$_3$-18). $^{13}$C NMR (100 MHz, MeOH-d4) 14.7, 17.8, 22.6, 25.1, 26.0, 26.5, 31.3, 31.9, 32.3, 33.7, 35.5, 36.3, 37.3, 40.4, 42.5, 43.7, 51.7, 57.0, 68.7 (C-7), 72.5 (C-3), 88.9 (C-13), 178.1 (C-12 and C-24). HRMS calcd for C$_{24}$H$_{38}$O$_6$(M−H)$^-$, 421.2590; found, 421.2583.

Synthesis of Compounds 89, 91, and 93

Compounds 1-7-1, 1-8-1, and 1-7-4 (Scheme 38) were transformed into the corresponding oximes 1-7-3, 1-8-3, and 1-7-6 under standard reaction conditions (Iuliano et al., Tetrahedron: Asymmetry 2001, 12, 2811-2825). Compounds 1-8-3 and 1-7-6 underwent Beckmann rearrangement with $SOCl_2$/THF at 0° C. to corresponding lactams 1-7-7, 1-8-4, and 1-7-8, then converted to compounds 89, 91 and 93 by reacting with LiOH at room temperature for 24 hrs.

General Procedure for Oxime Synthesis (1-7-3, 1-8-3, and 1-7-6)

Sodium acetate (1.03 g, 13.42 mmol, 5.75 equiv.) and hydroxylamine hydrochloride (0.288 g, 4.13 mmol, 2 equiv) were added to a solution of ketone (1.0 g, 1 equiv) in methanol (20 mL). The reaction mixture was stirred at reflux for 6 h. The solvent was removed under vacuum and the residue dissolved in $CH_2Cl_2$. The organic solution was washed with water then dried over $Na_2SO_4$. The solvent was evaporated under reduced pressure and the crude product recrystallized from aqu. Ethanol to afford chemically pure oxime in 90% yield.

General Procedure for Beckmann Rearrangement (1-7-7, 1-8-4, 1-7-8)

Freshly distilled thionyl chloride (1.5 mL) in 4 mL dry THF was added dropwise to a solution of oxime (1-7-3, 1-8-3 or 1-7-6, 355 mg, 0.77 mmol) in 12 mL dry THF cooled to 0° C., while maintaining the temperature at 0° C. After this addition, the reaction mixture was stirred at 0-10° C. for 1 h and then at room temperature for 4 h under argon atmosphere. The mixture was then poured into ice-water, neutralized with a solution of $NH_3$, and extracted with dichloromethane. The organic layer was washed with water and saturated brine, dried over anhydrous $Na_2SO_4$. Evaporation of the solvent under reduced pressure gave a solid residue, which was chromatographed over silica gel using hexane/EtOAc (1:2) as the eluent to give 347 mg (80%) as a white solid.

General Procedures for the Hydrolysis of the Ester: (89, 91, and 93)

LiOH (91 mg, 2.2 mmol, 10 equiv.) in water (1 ml) was added to a solution of 1-7-7, 1-8-4, or 1-7-8 (100 mg, 0.21 mmol) in THF-methanol 1:2 (7 mL) and the mixture was stirred at room temperature for 24 h. Then acidified with 10% aqueous HCl. The solvents were removed at reduced pressure and ethyl acetate (20 mL was added. The organic solution was washed with brine then dried ($MgSO_4$), evaporated. The solid residue was recrystallized from ethyl acetate to furnish the target compounds (89, 91 or 93) 70 to 80%.

Methyl 3α-acetoxy-7-oximino-5β-cholan-24-oate (1-7-3)

$R_f$=0.43 (hexane/EtOAc, 5:1). $^1$H NMR (400 MHz, $CDCl_3$): 7.35 (br. S, 1H. NOH), 4.75-4.65 (m, 1H, H-3 ax.), 3.65 (s, $CH_3O$), 3.08 (dd, J=2.0 and 12.8 Hz, H-6), 2.34-2.15 (m, 4H), 2.05-1.10 (m, 24H, steroidal CH and $CH_2Ac$), 1.07 (s, $CH_3$-19), 0.91 (d, J=6.4 Hz, $CH_3$-21), 0.66 (s, $CH_3$-18). $^{13}$C NMR (100 MHz, $CDCl_3$, 5): 12.2, 18.5, 21.2, 21.5 ($CH_3CO$), 23.3, 25.4, 26.4, 27.5, 28.2, 31.1, 31.2, 32.8, 34.3, 35.4, 35.6, 39.2, 42.4, 42.9, 43.1, 44.6, 49.5, 51.6 ($CH_3O$), 55.0, 73.4 (C3), 161.0 (C=NOH), 170.7 ($CH_3\underline{C}$=O); 174.8 (24 C=O).

Methyl 3α-acetoxy-8-aza-7-oxo-B-homo-5β-cholanate (1-7-7)

$R_f$=0.16 (hexane/EtOAc, 1:1). $^1$H NMR (400 MHz, $CDCl_3$) 5.37 (br. s., 1H, NH), 4.79-4.72 (m, H-3 ax.), 3.65 (s, $CH_3O$), 3.31 (dd, J=6.0 and 9.6 Hz, H-8 ax), 2.92 (br. d, J=14.4 Hz, H-6), 2.34-2.13 (m, 3H), 1.97 (s, 3H, Ac), 1.97-1.08 (m, 24H, steroidal CH and $CH_2$), 1.06 (s, $CH_3$-19), 0.91 (d, J=6.4 Hz, $CH_3$-21), 0.66 (s, $CH_3$-18). $^{13}$C NMR (100 MHz, $CDCl_3$, 5): 11.6, 18.3, 21.4, 21.9, 23.2, 25.2, 26.6, 27.7, 29.8, 30.9, 31.1, 31.5, 35.2, 36.3, 36.8, 38.5, 38.841.0, 41.7, 42.7, 51.6, 51.9, 54.7, 55.7, 73.1 (C3), 170.5 ($CH_3\underline{C}$=O); 174.5 (C7), 175.5 (24 C=O). HRMS calcd for $C_{27}H_{43}NO_5$ (M+Na)$^+$, 484.3039; found, 484.3036.

Methyl 3α-acetoxy-13-aza-12-oxo-C-homo-5β-cholanate (1-8-4)

$R_f$=0.16 (hexane/EtOAc, 1:1). $^1$H NMR (400 MHz, $CDCl_3$) 6.00 (br. s., 1H, NH), 4.79-4.72 (m, H-3 ax.), 3.65 (s, $CH_3O$), 2.38-2.22 (m, 3H), 1.98-1.14 (m, 29H, steroidal CH and $CH_2$, $CH_3$, $CH_3CO$), 1.03 (d, J=6.4 Hz, $CH_3$-21), 0.86 (s, $CH_3$-18). $^{13}$C NMR (1100 MHz, $CDCl_3$) 15.0, 18.0, 21.4, 22.7, 25.9, 26.6, 26.8, 26.83, 27.0, 29.8, 30.3, 30.9, 32.1, 34.8, 35.1, 35.7, 37.0, 37.0, 40.0, 41.4, 51.6, 56.5, 58.6, 58.6, 60.7, 74.0 (C-3), 170.7 (AcO), 174.2 (C-12), 176.6 (C-24). HRMS calcd for $C_{27}H_{43}NO_5$ (M+Na)$^+$, 484.3039; found, 484.3031.

Methyl 3α, 7α-diacetoxy-13-aza-12-oxo-C-homo-5-cholanate (1-7-8)

$R_f$=0.14 (hexane/EtOAc, 1:1). $^1$H NMR (400 MHz, $CDCl_3$) 6.00 (br. s., 1H, NH), 4.89 (br. d, J=2.8 Hz, H-7) 4.60-4.53 (m, 1H, H-3 ax.), 3.65 (s, $CH_3O$), 2.45-2.19 (m, 4H), 2.05-1.10 (m, 36H, steroidal CH and $CH_2$, $CH_3$, 2 Ac), 0.87 (d, J=6.4 Hz, $CH_3$-21), 0.83 (s, $CH_3$-18). $^{13}$C NMR (100 MHz, $CDCl_3$) 14.6, 18.0, 21.4, 21.6, 22.3, 25.8, 26.3, 26.8, 29.8, 30.3, 30.6, 30.9, 31.1, 32.9, 34.8, 35.3, 35.6, 35.8, 36.2, 40.4, 41.9, 51.7, 53.1, 56.7, 60.2, 71.9 (C-3), 73.8 (C-7), 170.2 (AcO), 170.2 (AcO), 170.7 (AcO), 174.1 (C-12), 176.2 (C-24). HRMS calcd for $C_{29}H_{45}NO_7$ (M+Na)$^+$, 542.3094; found, 542.3099.

3α-Hydroxy-8-aza-7-oxo-B-homo-5(3-cholanoic acid (Compound 89)

79.5% yield, $R_f$=0.45 (dichloromethane/MeOH, 10:1). Mp. 285-286° C. $^1$H NMR (400 MHz, MeOH-d4) 3.61-3.58 (m, H-3 ax.), 3.44 (dd, J=10.0 and 10.4 Hz, H-8 ax), 3.10 (br. d, J=14.0 Hz, H-6), 2.36-2.17 (m, 2H), 2.03-1.18 (m, 21H, steroidal CH and $CH_2$), 1.10 (s, $CH_3$-19), 0.97 (d, J=6.4 Hz, $CH_3$-21), 0.73 (s, $CH_3$-18). $^{13}$C NMR (100 MHz, MeOH-d4) 36.4 (C-1), 28.6 (C-2), 71.6 (C-3), 36.3 (C-4), 41.5 (C-5), 31.9 (C-6), 178.0 (C-7), 53.4 (C-8), 39.9 (C-9), 37.4 (C-10), 23.5 (C-11), 39.6 (C-12), 42.8 (C-13), 55.0 (C-14), 25.9 (C-15), 28.6 (C-16), 56.9 (C-17), 11.8 (C-18), 25.9 (C-19), 37.44 (C-20), 18.7 (C-21), 30.9 (C-22), 28.6 (C-23), 178.7 (C-24). HRMS calcd for $C_{24}H_{39}NO_4$ (M–H)$^{-1}$, 404.2801; found, 404.2805.

3α-Hydroxy-13-aza-12-oxo-C-homo-5β-cholanoic acid (Compound 91)

70% yield, $R_f$=0.42 (dichloromethane/MeOH, 10:1). Mp. 154-156° C. $^1$H NMR (400 MHz, MeOH-d4) 3.59-3.50 (m, H-3 ax.), 2.56-2.24 (m, 4H), 2.04-1.20 (m, 25H, steroidal CH and $CH_2$, $CH_3$-19), 1.08 (d, J=6.4 Hz, $CH_3$-21), 0.91 (s, $CH_3$-18). $^{13}$C NMR (100 MHz, MeOH-d4) 15.0, 17.8, 23.1, 25.8, 26.8, 27.7, 27.9, 31.4, 31.6, 36.1, 36.4, 36.7, 36.9, 37.4, 39.1, 41.2, 42.9, 56.8, 59.6, 62.0, 72.1 (C-3), 179.7 (C-12 and C-24). HRMS calcd for $C_{24}H_{39}NO_4$ (M–H)$^{-1}$, 404.2801; found, 404.2803.

3α, 7α-Dihydroxy-13-aza-12-oxo-C-homo-5β-cholanoic acid (Compound 93)

80% yield, $R_f$=0.25 (dichloromethane/MeOH, 10:1). Mp. 263-264° C. $^1$H NMR (400 MHz, MeOH-d4) 3.86 (d, J=2.8

Hz, H-7) 3.43-3.37 (m, H-3 ax.), 2.56 (t, J=12.8 Hz, H-11), 2.39-1.28 (m, 25H, steroidal CH and $CH_2$, $CH_3$-19), 1.08 (d, J=6.4 Hz, $CH_3$-21), 0.91 (s, $CH_3$-18). 13C NMR (100 MHz, MeOH-d4) 14.7, 17.8, 22.6, 26.7, 27.2, 31.5, 31.8, 33.3, 35.9, 36.1, 36.7, 37.3, 40.4, 42.6, 44.5, 54.1, 57.0, 61.6 (C-13), 69.0 (C-7), 72.6 (C-3), 177.7 (C-12 and C-24). HRMS calcd for $C_{24}H_{39}NO_5$ $(M+H)^{+-}$, 422.2906; found, 422.2902.

Synthesis of Compound 1-7-9

A 2 M solution of $TMSCHN_2$ in hexane (0.65 mL, 1.31 mmol) was added dropwise at −20° C. to a stirred solution of 1-7-1 (211 mg, 0.474 mmol) and $BF_3.Et_2O$ (250 μL, 1.98 mmol) in dry $CH_2Cl_2$ (20 mL). The mixture was stirred at −15° C. for 3 h. The reaction mixture was poured into ice-water and extracted with AcOEt. The extract was washed with brine, dried over $Na_2SO_4$, and evaporated, thus giving a pale yellow residue. The residue was dissolved into $Et_2O$ (70 mL), to which silica gel (1.2 g) and 2N HCl (0.3 mL) was added. The heterogeneous solution was stirred at room temperature for 3 h, and $Na_2SO_4$ (500 mg) was added. After filtration through a glass-filter and evaporation, the residue was dissolved in methanol (10 ml) and reacted directly with p-toluenesulfonhydrazide (71 mg, 0.474 mmol, 1 equiv.) under nitrogen and at room temperature with stirring for 10 h. The resultant mixture was filtered and the solid washed with cold methanol. Evaporation under reduced pressure afforded tosylhydrazone. This was dissolved in chloroform (15 ml) under argon and was cooled to 0° C. Catecholborane (4.5 mL, 1.0 M solution in THF, 4.43 mmol, 10 equiv.) was added dropwise. The resultant mixture was stirred for 10 h at 0° C. Sodium acetate (1.2 g, 8.86 mmol) was added in portions. The mixture was allowed to warm to room temperature over 30 min and then heated under reflux for 8 h. The reaction mixture was cooled to room temperature and filtered. The solid material was washed with dichloromethane (10 mL), and the combined filtrates were evaporated under reduced pressure to dryness. The remaining residue was purified by chromatography on a silica gel column with 5% ethyl acetate in hexane to give compound 1-7-9 as a white solid (130 mg, 33%, 3 steps).

Methyl 3α-acetoxy-8-carba-B-homo-5β-cholanoate (1-7-9)

$R_f$=0.52 (hexane/EtOAc, 10:1). 1H NMR (400 MHz, $CDCl_3$): 4.75-4.67 (m, 1H, H-3 ax.), 3.63 (s, $CH_3O$), 2.37-2.15 (m, 2H), 2.00 (s, 3H, Ac), 1.98-1.00 (m, 28H, steroidal CH and $CH_2$), 0.89 (s, $CH_3$-19), 0.86 (d, J=6.4 Hz, $CH_3$-21), 0.62 (s, $CH_3$-18). $^{13}C$ NMR (100 MHz, $CDCl_3$, 5): 11.8, 18.3, 21.3, 21.5 23.6, 23.9, 26.1, 27.3, 27.6, 29.7, 30.0, 30.9, 31.0, 32.8, 33.6, 35.4, 37.1, 37.5, 38.7, 40.1, 42.3, 43.1, 45.9, 51.4 ($CH_3O$), 56.0, 56.4, 74.2 (C3), 170.6 (Ac), 174.7 (24 C=O).

Synthesis of Compound 94

Compound 1-7-9 (130 mg, 0.29 mmol) was dissolved in ethanol (10 mL) and refluxed with 20% aqueous KOH (10 mL) for 6 h. After cooling to room temperature, the solution was acidified with 6 N HCl until a precipitate was formed. The resulting suspension was then extracted with $CH_2Cl_2$ (20 mL×3). The organic extracts were combined, and the solvent was removed in vacuo. the product was recrystallized from ethyl acetate/hexane to yield compound 94 (80 mg, 70%) as a white solid 3α-Hydroxy-8-carba-B-homo-5β-cholanoic acid (Compound 94)

$R_f$=0.62 (hexane/EtOAc, 1:2). Mp. 204-206° C. $^1H$ NMR (400 MHz, $CDCl_3$): 3.59-3.54 (m, 1H, H-3 ax.), 2.35-2.10 (m, 2H), 2.05-1.11 (m, 28H, steroidal CH and $CH_2$), 0.87 (s, 6H, $CH_3$-19 and $CH_3$-21). $^{13}C$ NMR (100 MHz, $CDCl_3$, 5): 12.3, 18.9, 22.5, 24.5, 24.7, 27.1, 28.6, 31.3, 31.9, 33.1, 34.2, 34.4, 37.0, 38.5, 38.56, 39.0, 39.7, 41.5, 43.4, 44.4, 47.6, 57.6 57.7, 72.4 (C3), 181.1 (24 C=O).

Example 2 Characterization of the Compounds of Example 1

2.1 Compounds 1-5 Selectively Suppress α2,3(N)-sialyltransferase ST3GALIII or α2,6(N)-sialyltransferases ST6GALI, but not α2,3(O)-sialyltransferase ST3GALI Effects of the present compounds on the activity of sialyltransferase, including α2,3(N)-sialyltransferase ST3GALIII, α2,6(N)-sialyltransferases ST6GALI, and α2,3 (O)-sialyltransferase ST3GALI, were determined in accordance with procedures described in the "Materials and Methods" section, and results are summarized in Table 1.

As evidenced from the data presented in Table 1, compounds 1-5, 6-10 and 11-15, exhibited a comparative inhibitory activity against ST6GALI with $IC_{50}$ values in the range 3-7 μM (Table 1). Similarly, the results reveal that compounds 2aA-2eA were also potent inhibitors of ST3GALIII with $IC_{50}$ values in the range 0.77-1.74 μM. It is surprising that none of the compounds 1-5 displayed inhibitory activity toward ST3GALI, at concentrations as high as 500 μM, with modest inhibitory activity being observed at the highest concentration (1 mM). The inhibition constants of compounds 1-5 indicate up to 287- to 649-fold (or 575- to 1299-fold) selectivity in favor of for ST3GALIII versus ST3GALI. The three series LA analogues (i.e., compounds 1-5; 6-10, and 11-15) also exhibited approximately 2 orders of magnitude improvement over ST6GALI versus ST3GALI. These results suggest that compounds 1-5, 6-10 and 11-15, possessing the respective EG or PEG linker units, are thus the first known inhibitors with potency and selectivity for the ST3GALIII and ST6GALI rather than ST3GALI to modify the α2,3- and α2,6-sialylated proteins with only N-linked glycans.

TABLE 1

Inhibitory potency and specificity of the present sialytransferase inhibitors

| Compound | α2,3-N-link ST3GALIII | α2,6-N-link ST6GALI | α2,3-O-link ST3GALI | selectivity ratio ST3GALI/ST3GALIII | selectivity ratio ST3GALI/ST6GALI |
|---|---|---|---|---|---|
| | IC$_{50}$ (µM) | | | | |
| 1 | 0.80 ± 0.11 | 4.20 ± 0.26 | 0%$^a$ | >625$^d$ | >119 |
| 1 | 0.77 ± 0.02 | 4.33 ± 0.04 | 0%$^a$ (74%)$^b$ | >649$^d$ (<299)$^e$ | >116 |
| 3 (FCW34) | 1.74 ± 0.09 | 3.59 ± 0.38 | 0%$^a$ (60%)$^b$ | >287$^d$ (<575)$^e$ | >139 |
| 4 (FCW66) | 1.01 ± 0.07 | 4.90 ± 0.08 | 0%$^a$ (50%)$^b$ | >495$^d$ (≤990)$^e$ | >102 |
| 5 | 0.97 ± 0.14 | 5.03 ± 0.20 | 0%$^a$ | >516$^d$ | >99 |
| 6 | $^c$ | 7.21 ± 0.10 | 0%$^a$ | $^c$ | >70 |
| 7 | $^c$ | 6.72 ± 0.30 | 0%$^a$ | $^c$ | >74 |
| 8 | $^c$ | 5.35 ± 0.46 | 0%$^a$ | $^c$ | >94 |
| 9 | $^c$ | 5.70 ± 0.36 | 0%$^a$ | $^c$ | >88 |
| 10 | $^c$ | 7.45 ± 0.36 | 0%$^a$ | $^c$ | >67 |
| 11 | $^c$ | 5.59 ± 0.24 | 0%$^a$ | $^c$ | >89 |
| 12 | $^c$ | 5.14 ± 0.11 | 0%$^a$ | $^c$ | >97 |
| 13 | $^c$ | 4.61 ± 0.35 | 0%$^a$ | $^c$ | >109 |
| 14 | $^c$ | 4.95 ± 0.37 | 0%$^a$ | $^c$ | >101 |
| 15 | $^c$ | 5.69 ± 0.40 | 0%$^a$ | $^c$ | >88 |
| Lith-O-Asp | 12 | 15.78 ± 0.13 | 38.95 ± 1.26 | 3 | 3 |
| AL10 | 0.88 ± 0.07 | 1.50 ± 0.46 | 13.21 ± 0.59 | 15 | 9 |

$^a$inhibition percentage was measured at 500 µM.
$^b$Inhibition percentage was measured at 1 mM.
$^c$Not determined.
$^d$The selectivity ratio was calculated based on the concentration, 500 µM, of ST inhibitor used toward α2,3-O-ST3GALI.
$^e$The selectivity ratio was calculated based on the concentration, 1 mM, of ST inhibitor used toward α2,3-O-ST3GALI.

2.2 FCW34 and FCW66 Respectively Suppress the Migration of Breast Cancer Cells In this example, effects of the present compounds, particularly, FCW34 and FCW66, on cancer cell motilities were investigated by Transwell analysis.

Briefly, breast cancer cells were first treated with 2-30 µM FCW34 or FCW66 prior to transwell migration assay, and then allowed the cells to invade to the lower side of the chamber for 16 hours. The IC$_{50}$ of the compound 3 (FCW34) and 4 (FCW66) on migration were 10.64±0.09 µM and 12.01±0.13 µM, respectively (data not shown).

To find out the mediator of the inhibitory effects of the compounds 3 or 4 on the migration of breast cancer cells, the gene of ST3GAL(III) was knocked out in MDA-MD-231 cells in accordance with the procedures set forth in the "Materials and Methods" section. Quantified results are summarized in FIG. 1.

As depicted in FIG. 1, knock down the expression of ST3GAL(III) significantly inhibited the migration activity of MDA-MD-231 cells, such effect was seen when MDA-MD-231 cells were treated with FCW34 or FCW66 (20 µM). Taken together, the results suggest that FCW34 or FCW66 inhibited the migration of MDA-MD-231 cells via inhibiting sialyltransferase, particularly ST3GAL(III).

2.3 FCW34 Suppresses the Genesis of Breast Cancer

The effects of the sialyltransferase inhibitor in tumor growth and metastasis were investigated in a nude mice model of human MDA-MB-231 breast cancer established in accordance with procedures set forth in the "Materials and Methods" section. The MDA-MB-231/Luc cells (5×10$^6$ cells) were orthotopically injected into the mammary fat pad of nude mice. Then the mice were given FCW34 and vehicle, respectively, on day 20, and the tumor volume were evaluated by bioluminescence every 3 days using IVIS image analysis. Results are illustrated in FIGS. 2A and 2B.

Figure 2A:
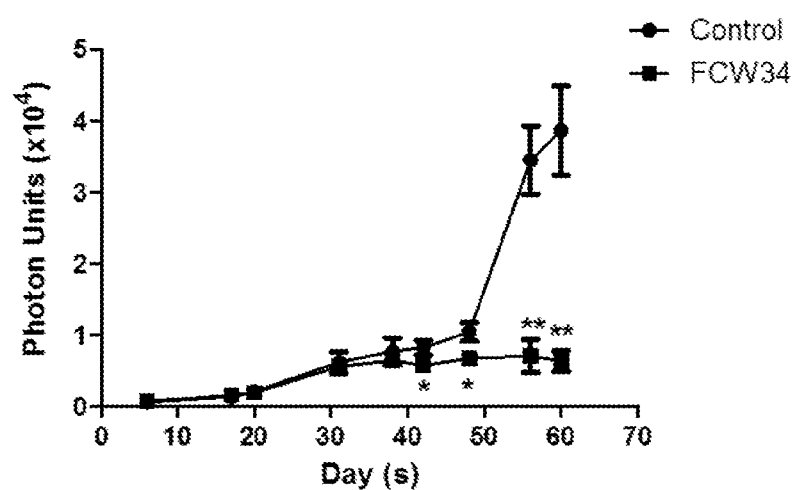
FIG. 2A is a line graph illustrating the quantified results of FCW34 suppressing the migration of MDA-MB-231 cells injected intraperitoneally in the test animal in accordance with one embodiment of the present disclosure.
Figure 2B:
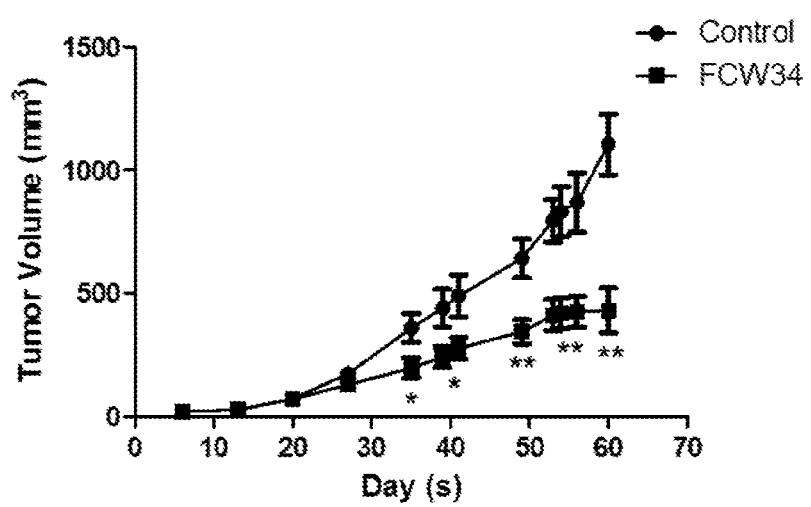
FIG. 2B is a line graph illustrating the effect of FCW34 on the tumor volume in the test animals of FIG. 2A.

As evidenced in FIG. 2A, the level of bioluminescence continued to rise throughout the entire time course of the experiment, indicating continued growth of tumor in the control mice or the mice treated with vehicle; whereas in mice treated with FCW34 (10 mg/Kg/mouse/3 days), bioluminescence remained at a relatively low level, indicating the growth of the tumor was suppressed. This finding was confirmed afterwards, when the test animals were sacrificed on day 60, and the respective tumors were harvested and weighted. Results in FIG. 2B confirmed that administering FCW34 to mice bearing MDA-MB-231 breast cancer cells, may suppresses the growth of the cancer cells. Further, the biochemistry tests of blood and the body weight assessment indicated that FCW34 had limited toxic effects on the treated mice (data not shown).

2.4 FCW34 Suppresses the Invasion and/or Migration of Pancreatic Cancer Cells In this example, the ability of the FCW34 in suppressing the migration and/or invasion of pancreatic cancer cells was investigated using in vitro transwell analysis and in vivo mice model bearing pancreatic cancer.

Figure 3:
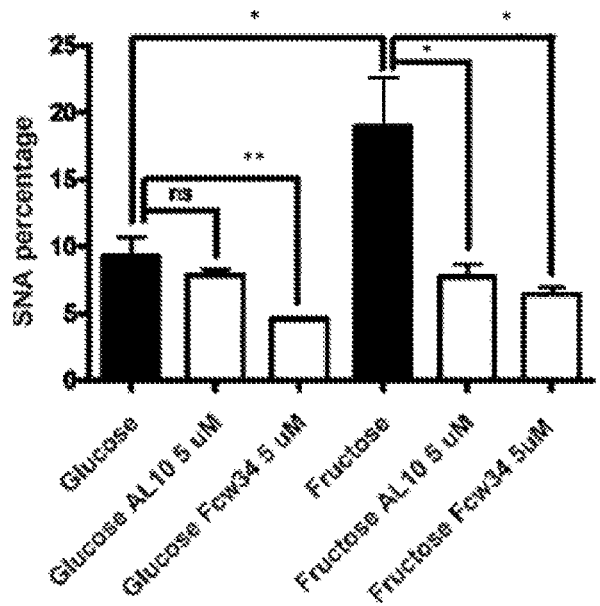
FIG. 3 is a bar graph illustrating the effects of FCW34 on sialyltransferas detected by SNA lectin staining in PANC-1 cells grown in glucose or fructose medium in accordance with one embodiment of the present disclosure.

PANC-1 cells were first grown in glucose-containing or fructose-containing medium treated with or without the presence of the test compound (i.e., FCW34 or AL10, which was used as a positive control), then the cells were stained with SNA lectin to measure 2,6-sialylation level by FACS analysis. It was found that PANC-1 cells exhibited a significantly higher expression of the 2,6-sialylation if they were grown in fructose-containing medium, and the level of 2,6-sialylation was greatly reduced by the treatment of either the compound 3 or AL10 (FIG. 3).

Figure 4:
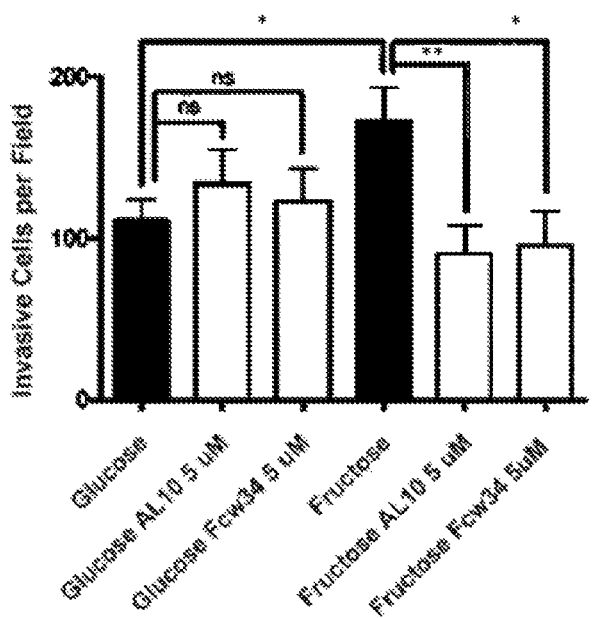
FIG. 4 is a bar graph illustrating the effects of FCW34 in suppressing the migrating PANC-1 cells grown in glucose or fructose medium in accordance with one embodiment of the present disclosure.

According to the results from the in vitro transwell analysis, PANC-1 cells grown in fructose-containing medium possessed higher invasion ability, and treatment of FCW34 significantly inhibited its invasion ability promoted by replacing the culturing medium from glucose to fructose (FIG. 4).

Figure 5:
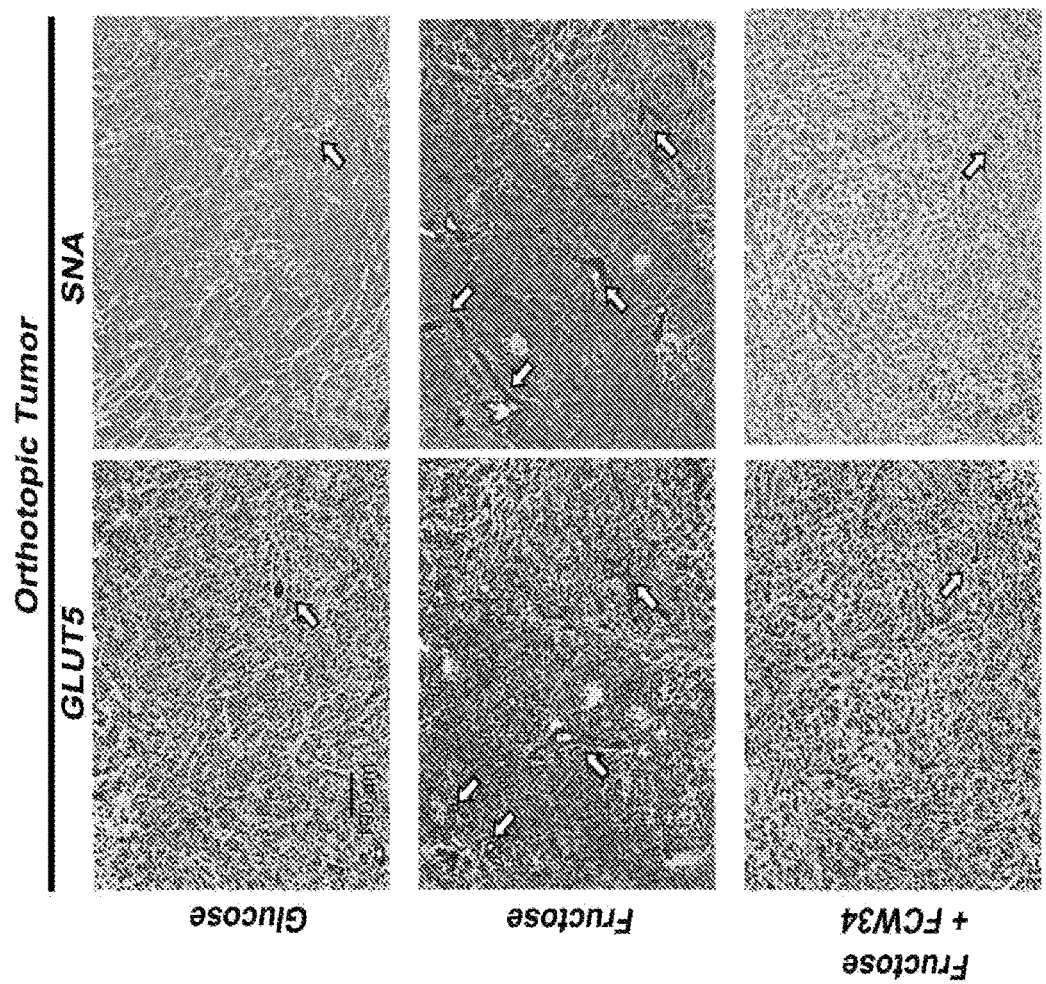
FIG. 5 illustrates the effect of FCW34 on test animals injected with PANC-1 cells grown in glucose or fructose-containing medium in accordance with one embodiment of the present disclosure, in which (A) are representative bioluminescence IVIS images of the test animals, and (B) are histological staining of liver section taken from tumor lesions resulted from PANC-1 cells grown in glucose or fructose-containing medium in accordance with one embodiment of the present disclosure.
Figure 5:
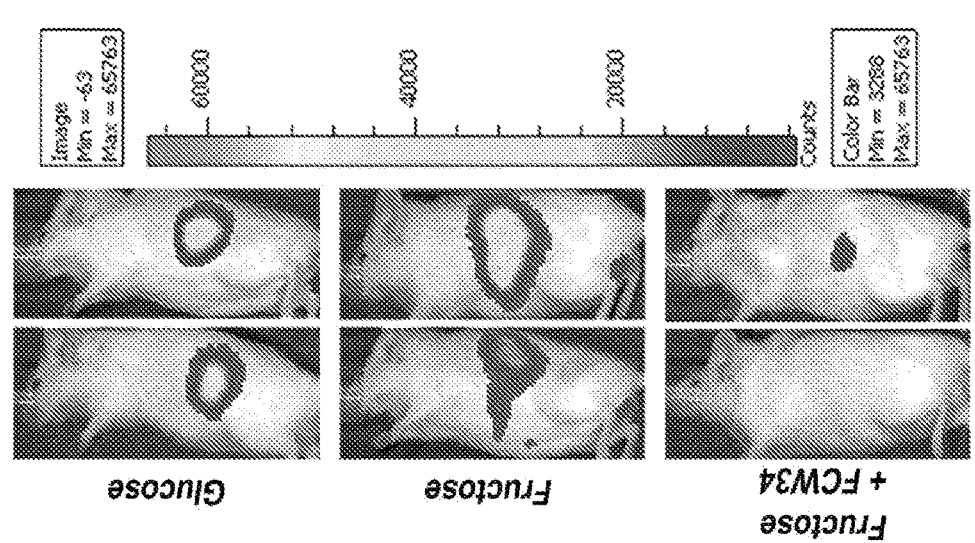

According to results from mice bearing pancreatic tumor, mice injected with PANC-1 cells grown in fructose-containing medium developed more advanced tumor than those injected with PANC-1 cells grown in glucose-containing medium, and if the PANC-1 cells were pre-treated with FCW34, the progression of the tumor would be halted significantly (FIG. 5). In addition, histological analysis of the liver sections taken from the test animals also indicated that PANC-1 cells grown in fructose-containing medium caused metastatic lesions in livers, which was suppressed by the treatment of FCW34 (Table 2).

TABLE 2

Liver lesions in mice bearing pancreatic cancer

|  | Incidence | P value |
| --- | --- | --- |
| Glucose medium | 0/4 |  |
| Fructose medium | 3/4 | 0.028 |
| Treated with FCW34 | 0/3 | N/A |

2.5 FCW551 Possesses No Significant Cytotoxicity Toward PANC-1 and LN Cells

The cytotoxicity of FCW551 on PANC-1 and LN cells were determined by MTT assay in according to procedures described in the "Materials and Methods" section. Results are presented in FIG. 6.

Figure 6:
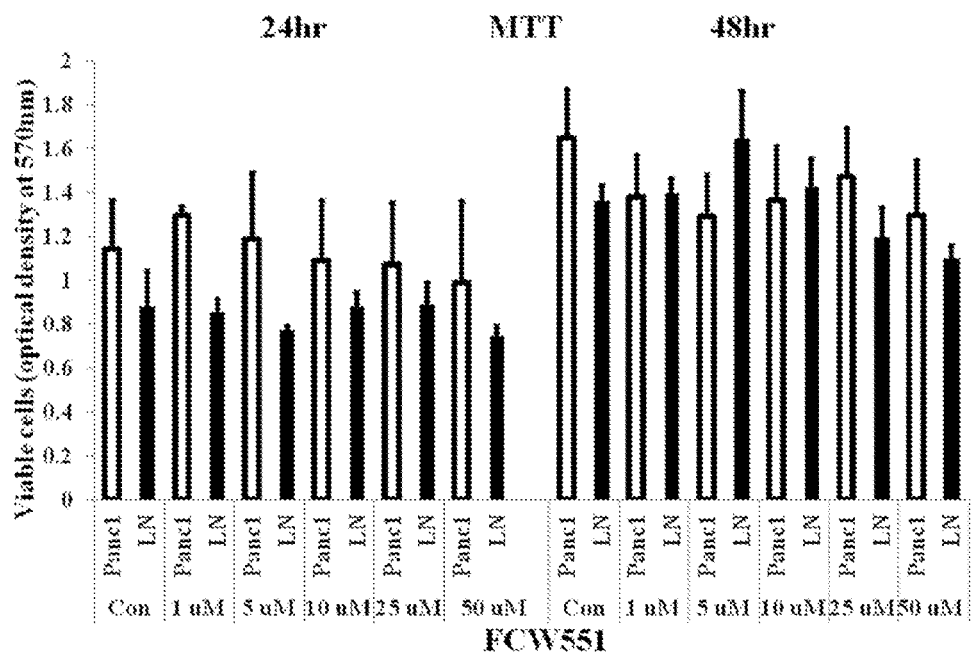
FIG. 6 illustrates the cytotoxicity of FCW551 on PANC-1 and LN cells in accordance with one embodiment of the present disclosure.

As evidenced in FIG. 6, no significant cytotoxicity was found for PANC-1 and LN cells, respectively treated with various doses of FCW551 (1, 5, 10, 25 and 50 µM) for 24 and 48 hours.

2.6 FCW551 Inhibits the Invasion and/or Migration of PANC-1 and LN Cells

In this example, the ability of the FCW551 in suppressing the migration and/or invasion of pancreatic cancer cells was investigated. Briefly, PANC-1 and LN cells were respectively treated with 1 and 20 µM FCW551 for 24 and 48 hours before subjecting to the migration and invasion analysis. Results are illustrated in FIG. 7.

Figure 7:
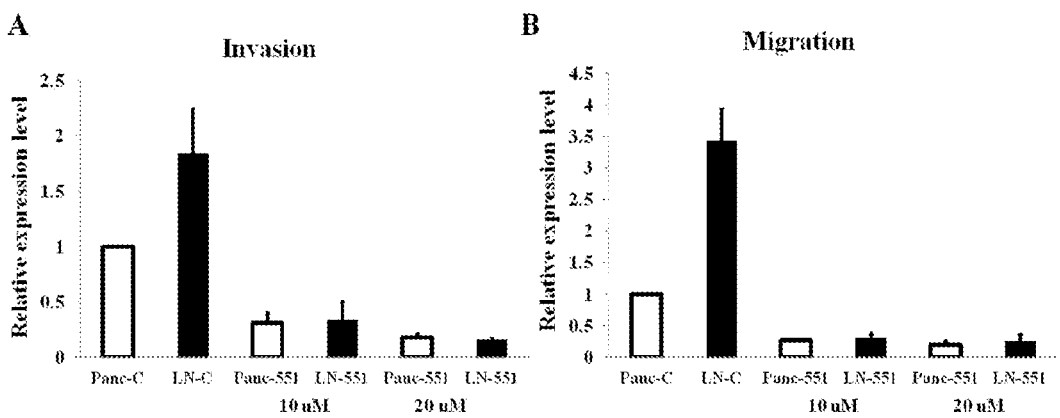
FIG. 7 are bar graphs illustrating the effects of FCW551 on (A) the invasion of PANC-1 and LN cells; and (B) the migration of PANC-1 and LN cells in accordance with one embodiment of the present disclosure.

As evidenced in FIG. 7, LN cells possessed much higher capability in terms of migrating and invading, as compared to those of PANC-1 cells; and both the migration and invasion abilities were greatly suppressed by the treatment of FCW551.

Example 3 Effects of FCW393 on Melanoma

In this example, effects of FCW393 (or compound 16) on animals implanted with primary melanoma cells were investigated, in which the body weight; the size of the tumor; the respective weights of lymph nodes, thymus, and spleen; the respective functions of liver, kidney, and vascular system; as well as the levels of inflammation and/or stress markers were determined. Results are illustrated in FIGS. 8-15.

3.1 Effects of FCW393 on Primary Melanoma-Bearing Mice

Figure 8A:
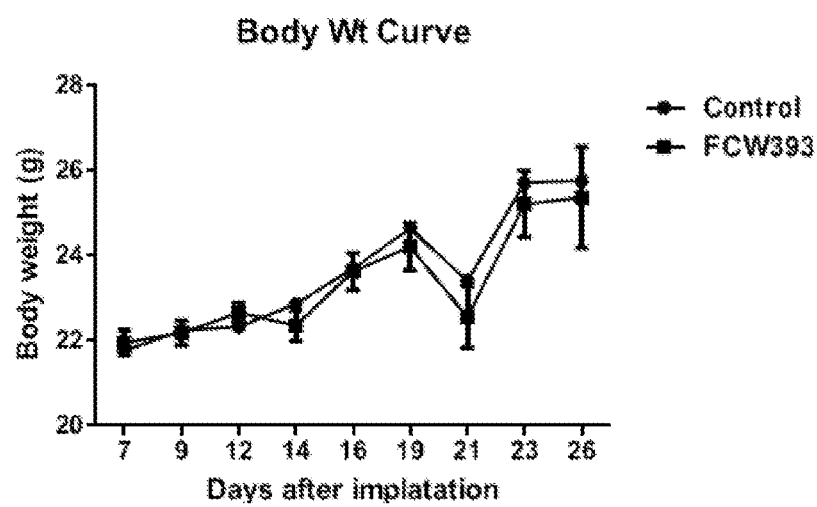
FIG. 8A is a line graph illustrating the effect of FCW393 on the body weight of the test animals implanted with primary melanoma cells in accordance with one embodiment of the present disclosure.
Figure 8B:
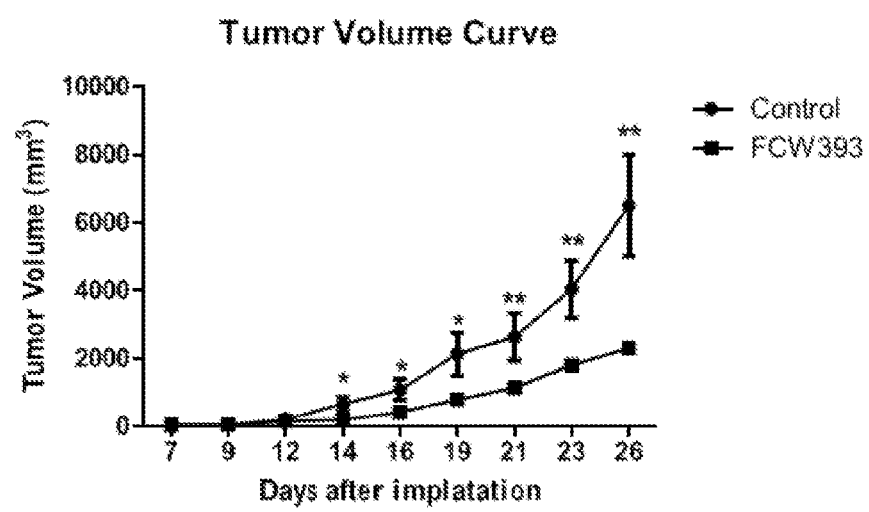
FIG. 8B is a line graph illustrating the effect of FCW393 on the the tumor volume in the test animals of FIG. 8A.
Figure 9:
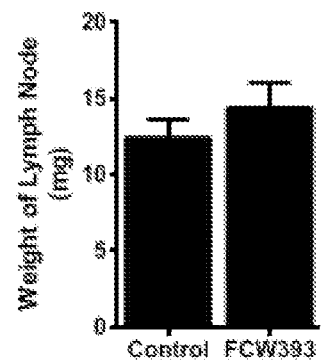
FIG. 9 are bar graphs illustrating the effect of FCW393 on the weights of (A) lymph noew, (B) thymus, and (C) spleen of the the test animals of FIG. 8A.
Figure 9:
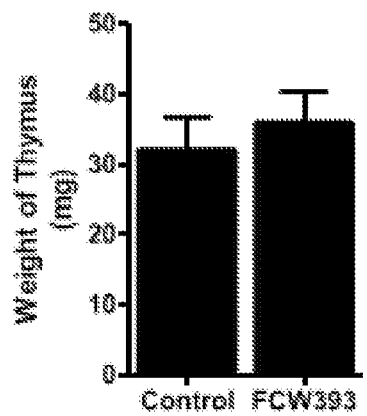
Figure 9:
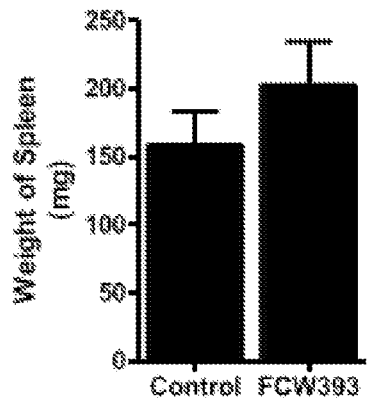

As evidenced in FIGS. 8A and 8B, FCW393 was able to suppress the growth of tumor by reducing the tumor volume to about 1/3 as compared with that of the control animal (FIG. 8A), while at the same time, without significantly affecting the body weights of the test animals (FIG. 8B). Similarly, FCW393 had no effects on the weight of lymph node, thymus or spleen of the test animals either (FIG. 9).

Figure 10:
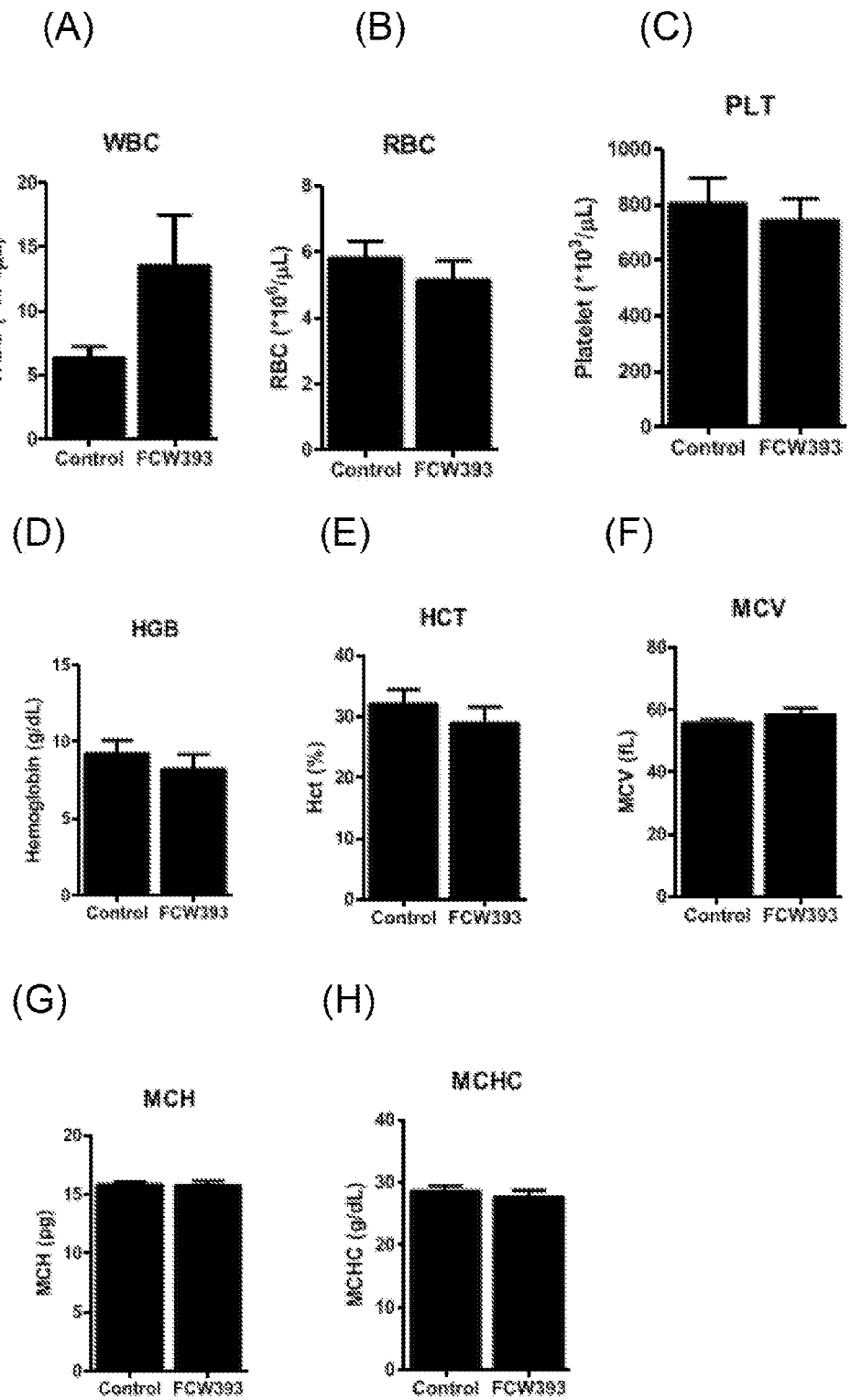
FIG. 10 are bar graphs illustrating the effect of FCW393 on the counts or levels of (A) white blood cells (WBC), (B) red blood cells (RBC), (C) platelets, (D) hemoglobin (HGB), (E) hematocrit (HCT), (F) mean corpuscular volume (MCV), (G) mean corpuscular hemoglobin (MCH), and (H) mean corpuscular hemoglobin concentration (MCHC) of the the test animals of FIG. 8A.

Further, except the counts of white blood cells (WBC), which exhibited a 2-fold increases after FCW393 treatment (FIG. 10, panel A), FCW393 had no effects on the levels of red blood cells (RBC), platelets (PLT), hemoglobin (HGB), hematocrit (HCT), mean corpuscular volume (MCV), mean corpuscular hemoglobin (MCH), and mean corpuscular hemoglobin concentration (MCHC) (FIG. 10, panels B to H).

Figure 11:
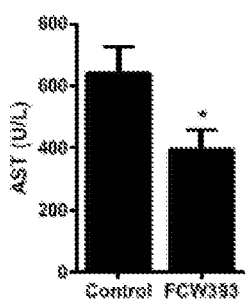
FIG. 11 are bar graphs illustrating the effect of FCW393 on the levels of (A) aspartate aminotransferase (AST), (B) alanine aminotransferase (ALT), (C) albumin, (D) triglyceride, (E) blood urea nitrogen (BUN), (F) creatinine, and (G) uric acid of the the test animals of FIG. 8A.
Figure 11:
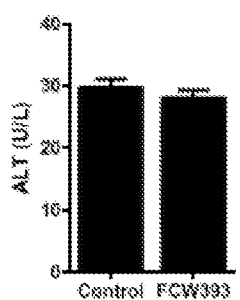
Figure 11:
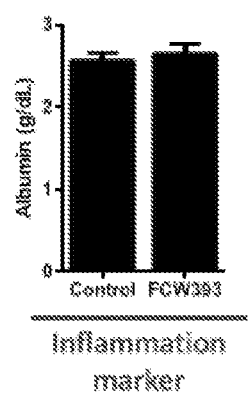
Figure 11:
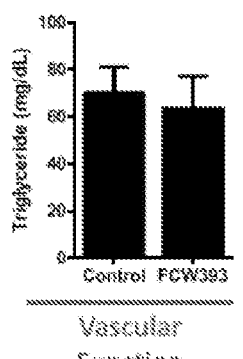
Figure 11:
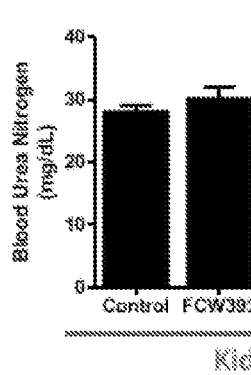
Figure 11:
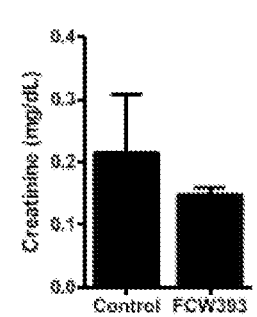
Figure 11:
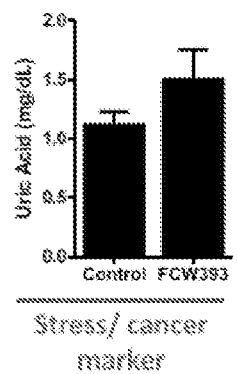

FCW393 also had no effect on the level of inflammation marker (i.e., albumin), (FIG. 11, panel C), nor did FCW393 affect the vascular and kidney functions either (FIG. 11, panels D, E and F). Regarding the liver function, while FCW393 did not affect the level of analine aminotransferase (ALT), yet it did reduce the level of aspartate aminotransferase (AST) (FIG. 11, panels A and B). In addition, the level of the stress marker (i.e., uric acid) was slightly increased after FCW393 treatment (FIG. 11, panel G).

3.2 Effects of FCW393 on Metastatic Melanoma-Bearing Mice

In this example, effects of FCW393 on mice bearing metastatic melanoma were investigated, and results are provided in FIGS. 12 to 15.

Figure 12:
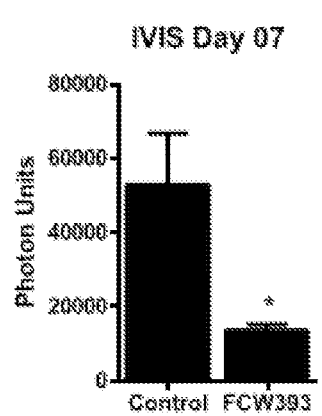
FIG. 12 are bar graphs illustrating the effect of FCW393 in suppressing the growth of metastatic melanoma based on quantified results of bioluminescence IVIS images of test animals bearing metastatic melanoma taken at (A) day 7, and (B) day 14 in accordance with one embodiment of the present disclosure, panel (C) is a bar graph depicting the effect of FCW393 on luciferase activity.
Figure 12:
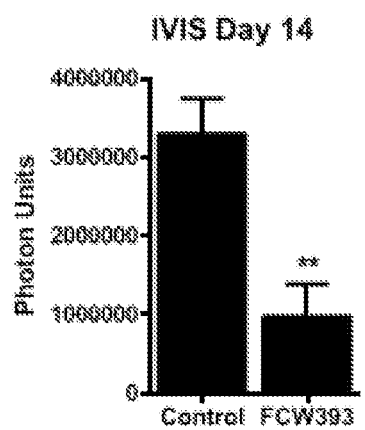
Figure 12:
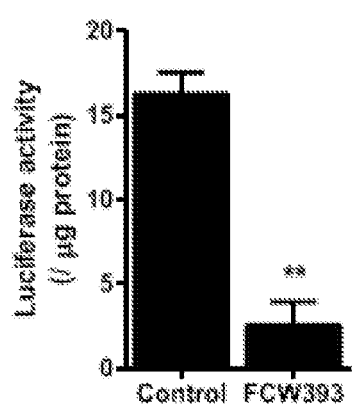
Figure 13:
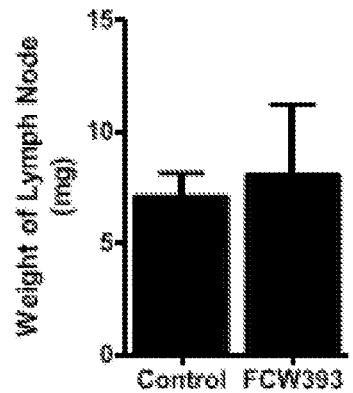
FIG. 13 are bar graphs illustrating the effect of FCW393 on the weights of (A) lymph node, (B) thymus, and (C) spleen of the the test animals of FIG. 12.
Figure 13:
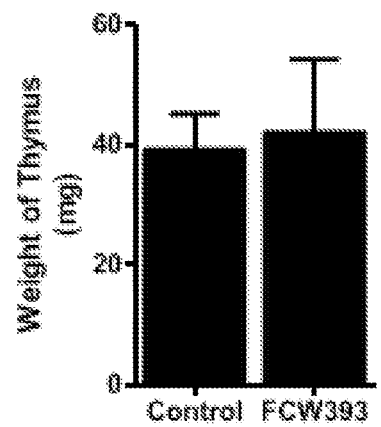
Figure 13:
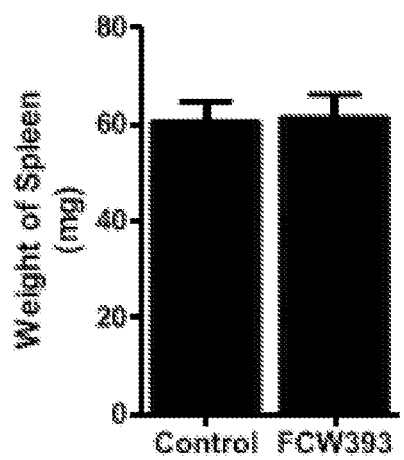
Figure 14:
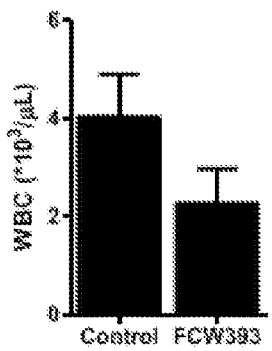
FIG. 14 are bar graphs illustrating the effect of FCW393 on the counts or levels of (A) white blood cells (WBC), (B) red blood cells (RBC), (C) platelets, (D) hemoglobin (HGB), (E) hematocrit (HCT), (F) mean corpuscular volume (MCV), (G) mean corpuscular hemoglobin (MCH), and (H) mean corpuscular hemoglobin concentration (MCHC) of the the test animals of FIG. 12.
Figure 14:
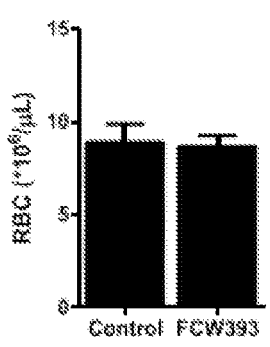
Figure 14:
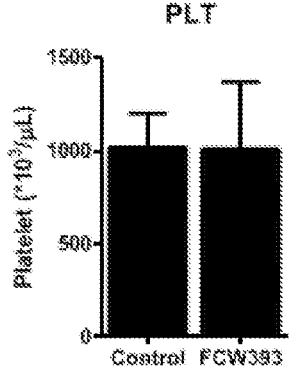
Figure 14:
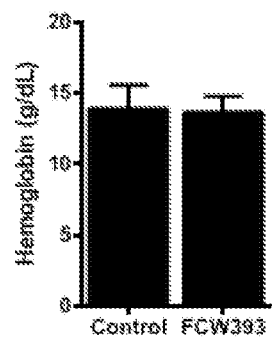
Figure 14:
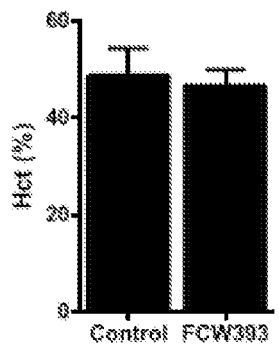
Figure 14:
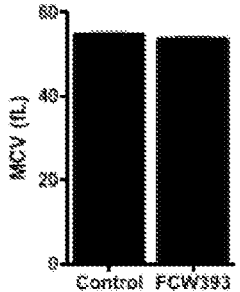
Figure 14:
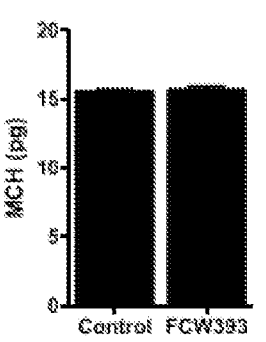
Figure 14:
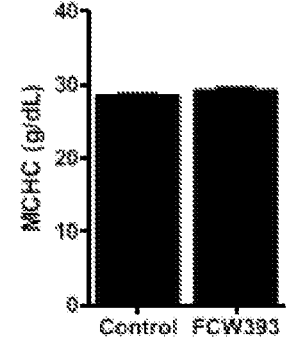

According to the quantified results of bioluminescence IVIS images of test animals bearing metastatic melanoma taken at days 7 and 14, respectively, it was evident that FCW393 may suppress the growth of tumor (FIG. 12, panels A and B). This observation was further confirmed by direct measurement of the luciferase activity (FIG. 12, panel C).

Similar to the findings in Example 3.1, FCW393 did not affect the weight of lymph node, thymus, or spleen of the the test animals (FIG. 13); nor did it possess any significant effects on the levels of WBC, RBC, platelets, HGB, HCT, MCV, MCH, and MCHC (FIG. 14) of the test animals.

Figure 15:
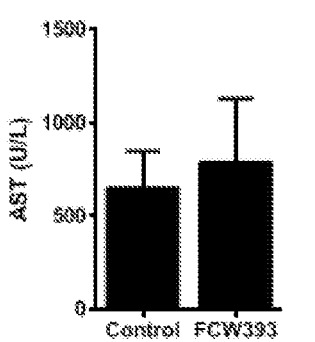
FIG. 15 are bar graphs illustrating the effect of FCW393 on the levels of (A) aspartate aminotransferase (AST), (B) analine aminotransferase (ALT), (C) albumin, (D) triglyceride, (E) blood urea nitrogen (BUN), (F) creatinine, and (G) uric acid of the the test animals of FIG. 12.
Figure 15:
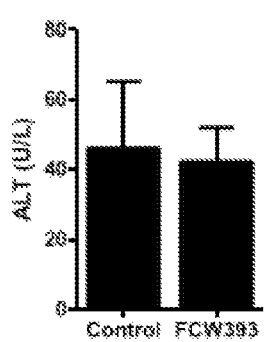
Figure 15:
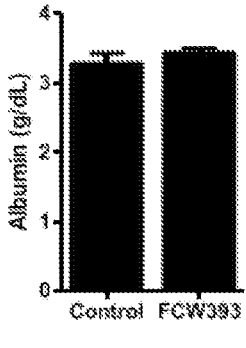
Figure 15:
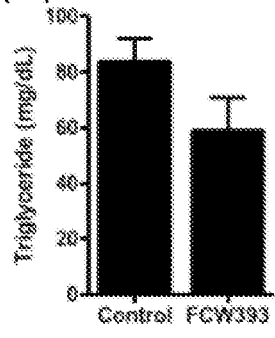
Figure 15:
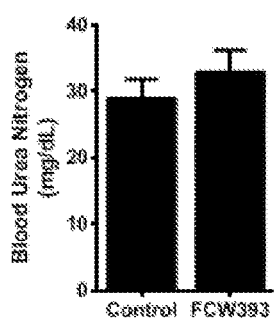
Figure 15:
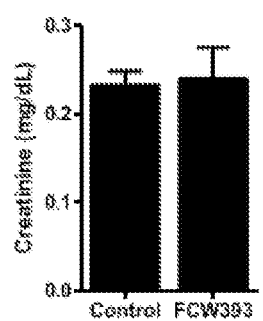
Figure 15:
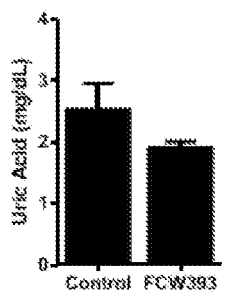

Further, FCW393 did not affect the level of inflammation marker or stress marker, nor did it affect the function of liver, kidney or vascular system (FIG. 15).

Taken together, the findings in the examples presented above suggest that the compounds of the present application are sialyltransferase (ST) inhibitors, and some of them are selective toward α2,3(N)-sialyltransferase ST3GALIII or α2,6(N)-sialyltransferases ST6GALI, but not α2,3(O)-sialyltransferase ST3GALI. In addition, the identified ST inhibitors are potent anticancer agents for the treatment of cancers, particularly the metastatic cancers.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

SEQUENCE LISTING

<160> NUMBER OF SEQ ID NOS: 6

<210> SEQ ID NO 1
<211> LENGTH: 25
<212> TYPE: RNA
<213> ORGANISM: Artificial Sequence
<220> FEATURE:
<223> OTHER INFORMATION: ST3GALIII _HSS143938_primer 1

<400> SEQUENCE: 1
ggacgcacaa uauccagcga gagaa                                           25

<210> SEQ ID NO 2
<211> LENGTH: 25
<212> TYPE: RNA
<213> ORGANISM: Artificial Sequence
<220> FEATURE:
<223> OTHER INFORMATION: ST3GALIII _HSS143938_primer2

<400> SEQUENCE: 2
uucucucgcu ggauauugug cgucc                                           25

<210> SEQ ID NO 3
<211> LENGTH: 25
<212> TYPE: RNA
<213> ORGANISM: Artificial Sequence
<220> FEATURE:
<223> OTHER INFORMATION: HSS143939_primer1

<400> SEQUENCE: 3
ggaagcuggu gaaagcucgc gucau                                           25

<210> SEQ ID NO 4
<211> LENGTH: 25
<212> TYPE: RNA
<213> ORGANISM: Artificial Sequence
<220> FEATURE:
<223> OTHER INFORMATION: ST3GALIII _HSS143939_primer2

<400> SEQUENCE: 4
augacgcgag cuuucaccag cuucc                                           25

<210> SEQ ID NO 5
<211> LENGTH: 25
<212> TYPE: RNA
<213> ORGANISM: Artificial Sequence
<220> FEATURE:
<223> OTHER INFORMATION: ST3GALIII _HSS143940_primer1

<400> SEQUENCE: 5
gggacucuug guauuugugc gcaau                                           25

<210> SEQ ID NO 6
<211> LENGTH: 25
<212> TYPE: RNA
<213> ORGANISM: Artificial Sequence
<220> FEATURE:
<223> OTHER INFORMATION: ST3GALIII _HSS143940_primer2

<400> SEQUENCE: 6
auugcgcaca aauaccaaga guccc                                           25

What is claimed is:

1. A compound having the structure of formula (1)

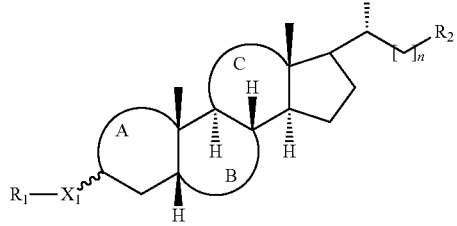

and pharmaceutically acceptable salts and solvates thereof, wherein, n is an integral from 1 to 4;

A, B, and C are independently a 6-membered saturated or unsaturated carbon cyclic ring, in which the saturated or unsaturated carbon cyclic ring is optionally substituted with one or more fluoro or hydroxy;

$X_1$ is O, or N;

$R_1$ is

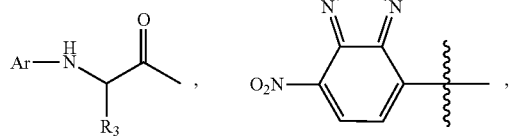

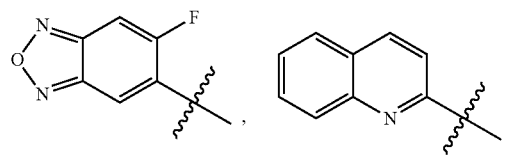

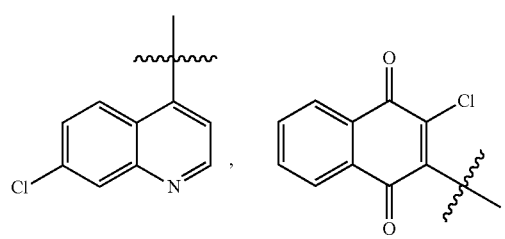

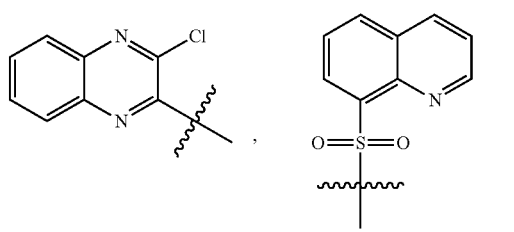

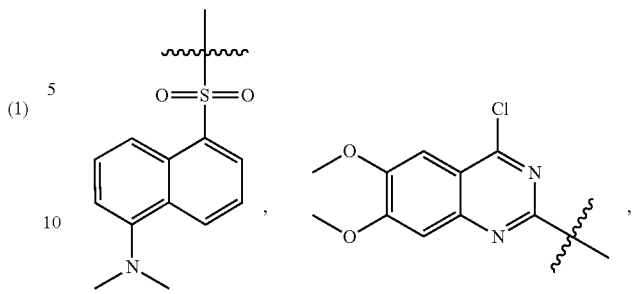

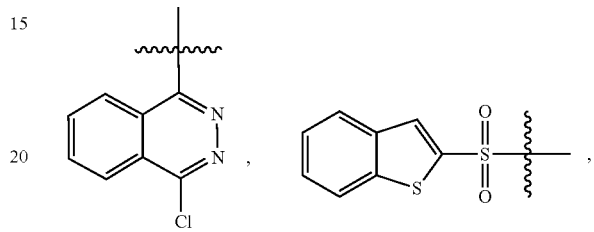

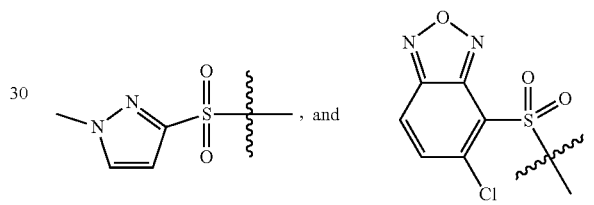

$R_3$ is selected from the group consisting of methyl, methoxy, $R_aCOOH$, $R_aNH_2$, $R_aNHC(NH_2)=NH$, $R_aSR_b$,

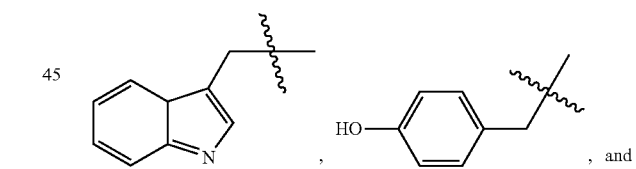

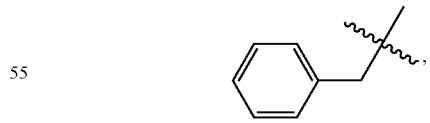

or $R_3$ and the neighboring carbon and nitrogen atoms are taken together to form a 5-membered heterocyclic ring;

$R_a$ and $R_b$ are independently H or $C_{1-6}$ alkyl;

$R_2$ is COOH, CH(COOH)COOH, or $COX_2(CH_2CH_2O)_m CH_2CH_2N_3$, $X_2$ is O or N, and m is an integral from 1 to 4; and
Ar is selected from the group consisting of H,

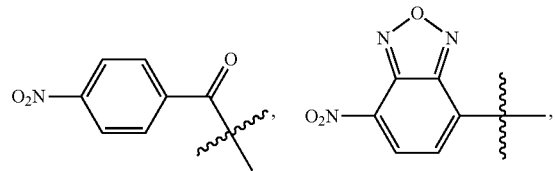

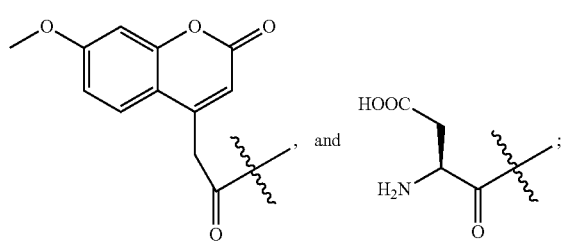

Provided that when $R_2$ is COOH, $R_1$ is not

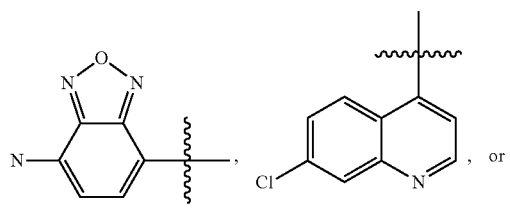, or

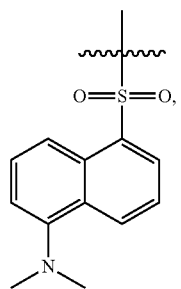

2. The compound of claim 1, wherein the compound has the structure of formula (1-1)

wherein, p is an integral from 1 to 4; and

Ar is selected from the group consisting of,

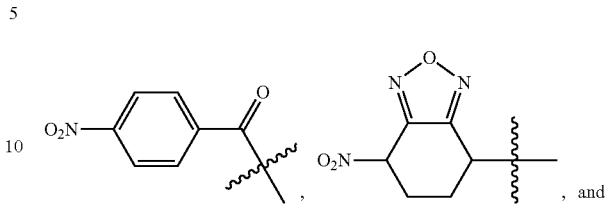, and

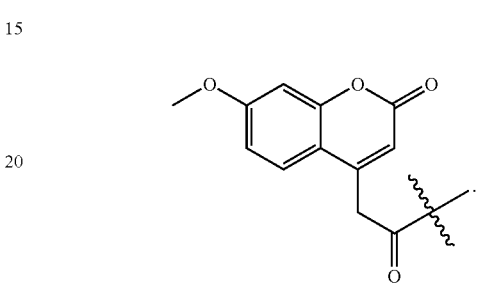

3. The compound of claim 2, wherein in formula (1-1), p is 2, and Ar is

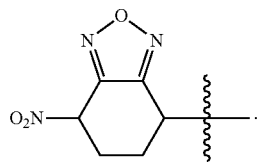

4. The compound of claim 2, wherein in formula (1-1), p is 3, and Ar is

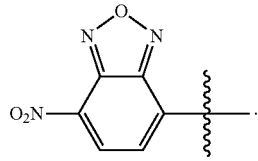

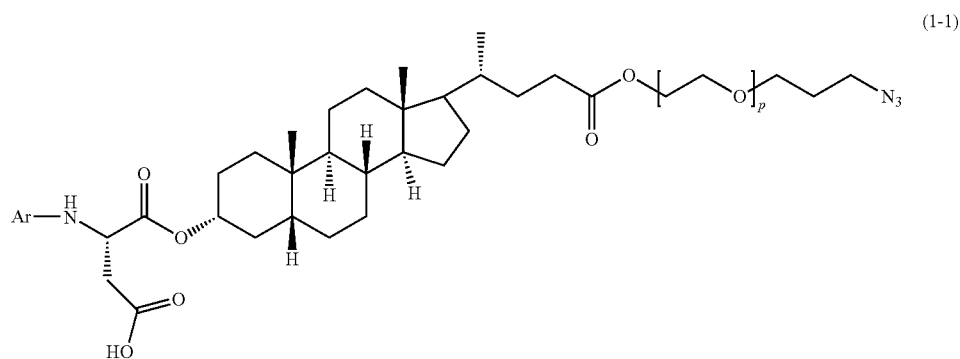

(1-1)

5. The compound of claim 1, wherein the compound has the structure of formula (1-2)

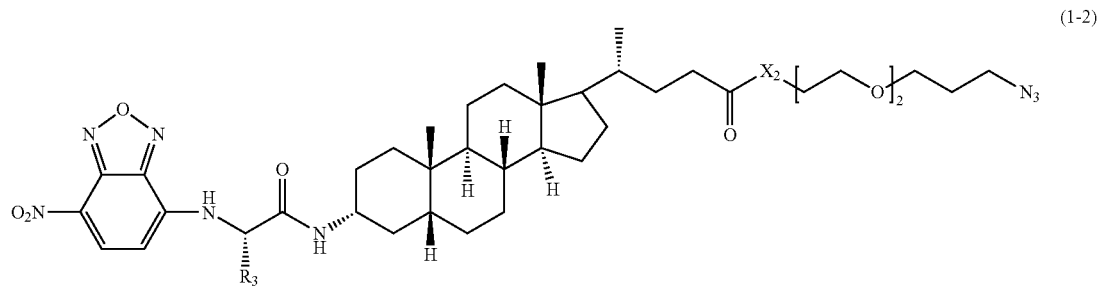
(1-2)

wherein, $X_2$ is O or N; and $R_3$ is selected from the group consisting of $CH_3$, $R_aCOOH$, $R_aNH_2$, $R_aNHC(NH_2)=NH$, $R_aSR_b$,

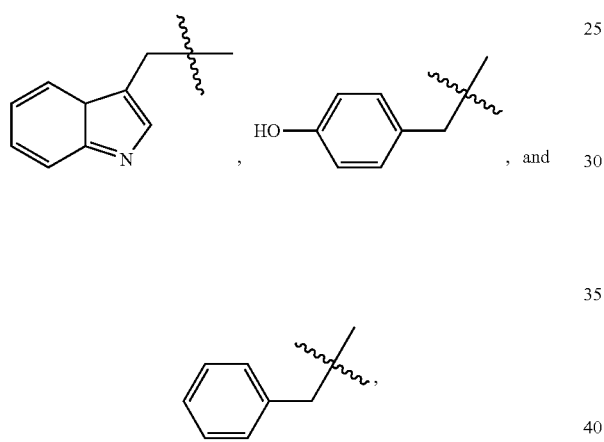
, and or $R_3$ and the neighboring carbon and nitrogen atoms are taken together to form a 5-membered heterocyclic ring;

$R_a$ and $R_b$ are independently H or $C_{1-6}$ alkyl.

6. The compound of claim 5, wherein in formula (1-2), $X_2$ is O, $R_3$ is $R_aCOOH$, and $R_a$ is H.

7. The compound of claim 5, wherein in formula (1-2), $X_2$ is N, $R_3$ is $R_aCOOH$, and $R_a$ is H.

8. The compound of claim 1, wherein the compound has the structure of formula (1-3)

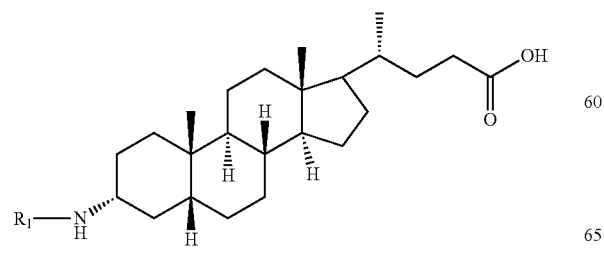
(1-3)

wherein, $R_1$ is selected from the group consisting of,

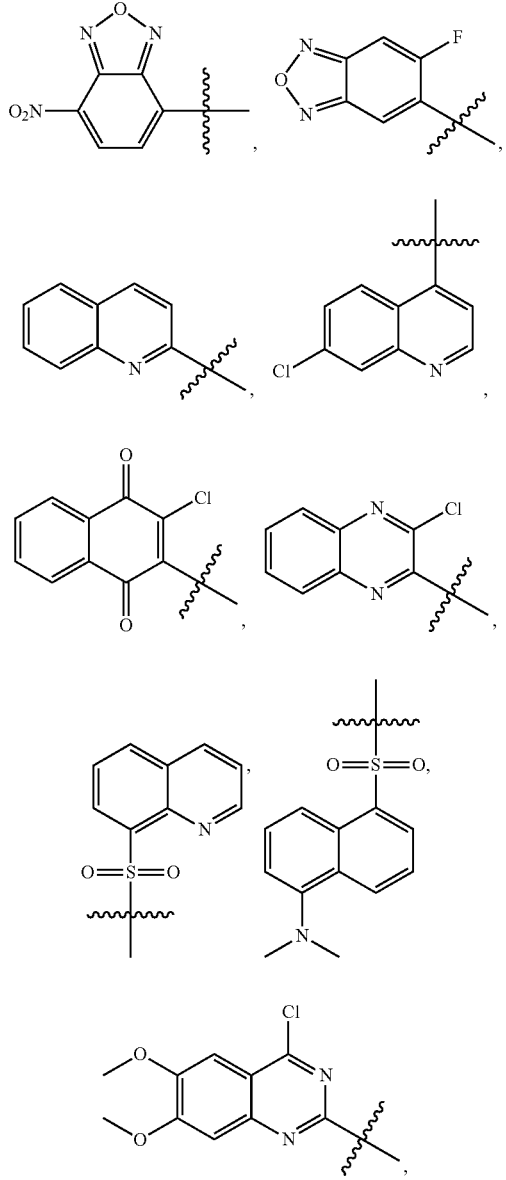

229

-continued

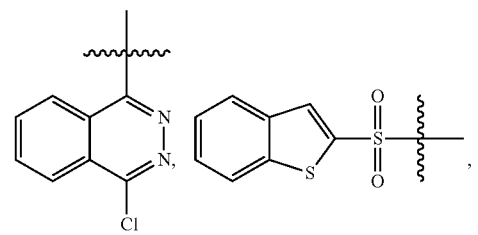

, and

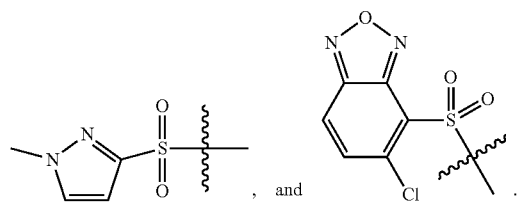

, and  .

9. The compound of claim 1, wherein the compound has the structure of formula (1-4)

(1-4)

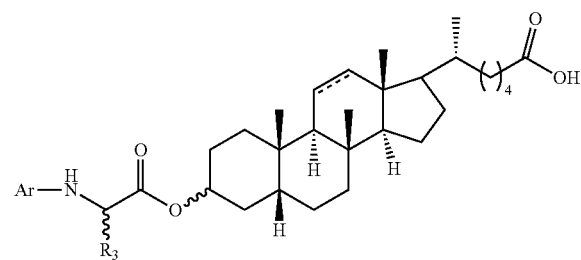

wherein,

⸺ is a single or a double bond;

$R_3$ is selected from the group consisting of, $CH_2OH$, $R_aCOOH$, $R_aNH_2$, $R_aNHC(NH_2)=NH$, $R_aSR_b$

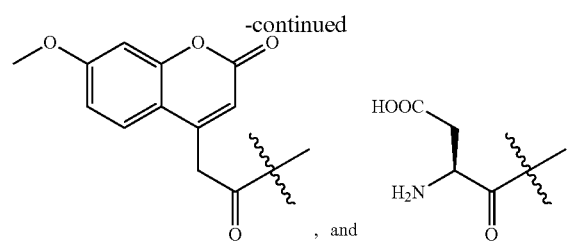

, and

;

and

Ar is selected from the group consisting of H,

230

-continued

, and .

10. The compound of claim 2, wherein the compound has the structure of formula (1-5)

(1-5)

wherein, $R_3$ is $CH_2COOH$, or $CH_2CH_2COOH$; and

Ar is H,

, and .

11. The compound of claim 1, wherein the compound has the structure of formula (1-6), (1-6)

wherein,

A, B, and C are independently a 6-membered saturated carbon cyclic ring substituted with at least one fluoro;

$X_1$ is O, and

;

and

R₃ is CH₂COOH or

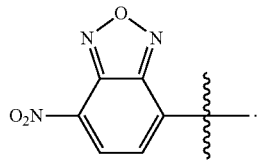

12. The compound of claim 1, wherein the compound of formula (1-1) to (1-3) is an inhibitor of α2,3(N)-sialyltransferase ST3GALIII or α2,6(N)-sialyltransferases ST6GALI, but not α2,3(O)-sialyltransferase ST3GALI.

13. A pharmaceutical composition comprising an effective amount of a compound of claim 1, a salt or a solvate thereof; and a pharmaceutically acceptable excipient.

14. A method of treating a disease associated with the activation of sialyltransferase of a subject, comprising administering to the subject the pharmaceutical composition of claim 13, so as to alleviate or ameliorate the symptoms of the disease, wherein the disease is a cancer, an inflammatory disease or an immune disease.

15. The method of claim 14, wherein the cancer is metastatic.

16. The method of claim 14, wherein the cancer is any of breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratocarcinoma, neuroblastoma, glioma, glioblastoma, keratoacanthomas, analplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL).

17. The method of claim 16, wherein the hematopoietic tumors of lymphoid lineage is any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma.

18. The method of claim 16, wherein the tumor of mesenchymal origin is fibrosarcomas or rhabdomyosarcomas.

19. The method of claim 14, wherein the immune disease is any of rheumatoid arthritis, psoriatic arthritis, systemic lupus erythematosus, myasthenia gravis, Type I diabetes mellitus, glomerulonephritis, autoimmune throiditis, ankylosing spondylitis, systemic sclerosis, multiple sclerosis, systemic anaphylaxia, drug allergies, insect sting allergies, graft rejection, Sjogren's syndrome, or human immunodeficiency virus infection.

20. The method of claim 14, wherein the inflammatory disease is any of diabetic retinopathy, proliferative retinopathy, dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, eosinophilic fasciitis, Crohn's disease, ulcerative colitis, hypersensitivity pneumonitis, eosinophilic pneumonia, delayed-type hypersensitivity, interstitial lung disease (ILD), idiopathic pulmonary fibrosis, and ILD associated with rheumatoid arthritis, macular edema, asthma, or allergic rhinitis.

21. The method of claim 14, wherein the pharmaceutical composition comprises a compound of formula (1-1):

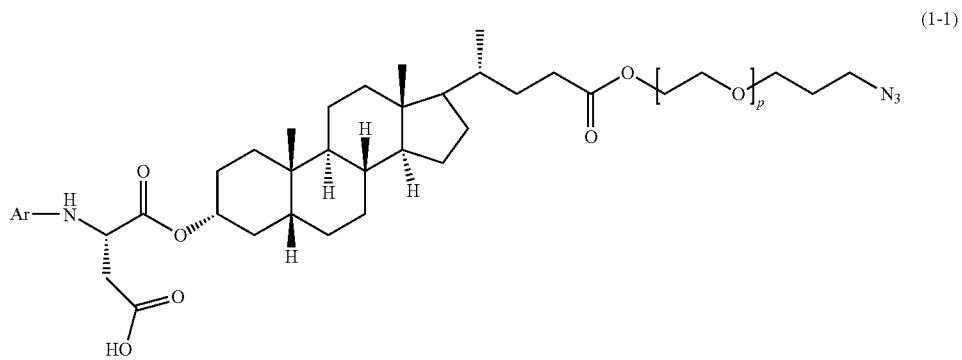

(1-1)

wherein formula (1-1), p is 2, and Ar is

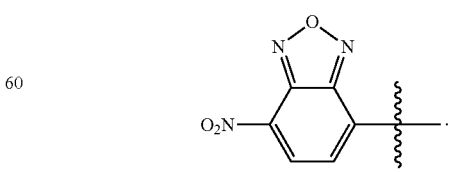

22. The method of claim 14, wherein the pharmaceutical composition comprises a compound of formula (1-1):

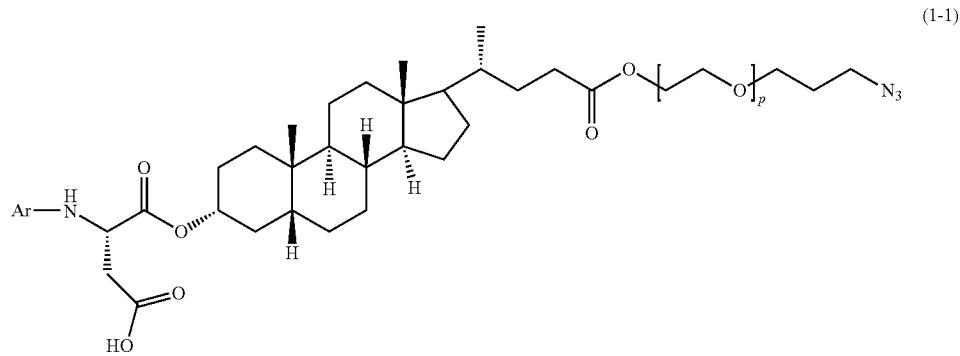
(1-1)
wherein formula (1-1), p is 3, and Ar is
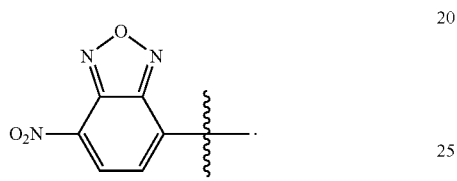
23. The method of claim 14, wherein the pharmaceutical composition comprises a following compound of formula (1-2):
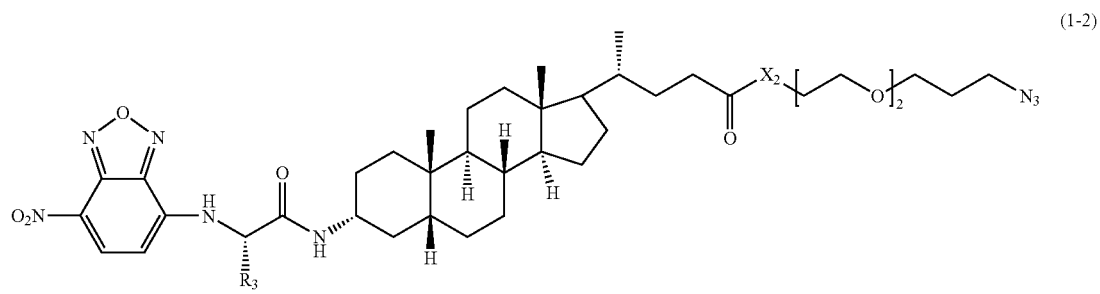
(1-2)
wherein formula (1-2), $X_2$ is O, $R_3$ is $R_a$COOH, and $R_a$ is H.
24. The method of claim 14, wherein the pharmaceutical composition comprises a following compound of formula (1-2):
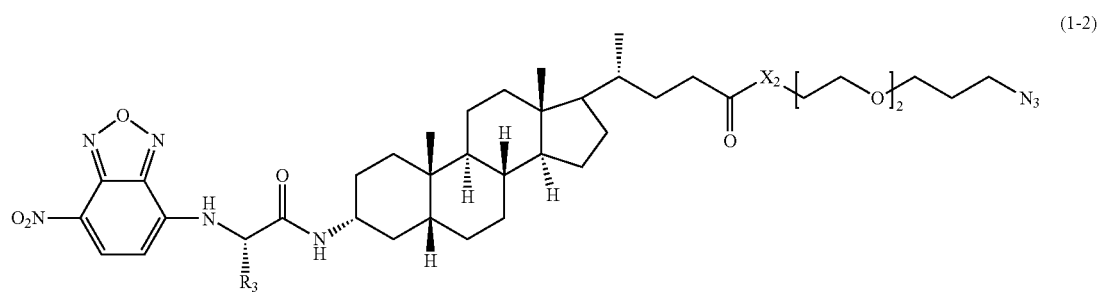
(1-2)
wherein formula (1-2) $X_2$ is N, $R_3$ is $R_a$COOH, and $R_a$ is H.
* * * * *